United States Patent
Hoffman

(10) Patent No.: US 9,857,328 B2
(45) Date of Patent: Jan. 2, 2018

(54) CHEMICALLY-SENSITIVE FIELD EFFECT TRANSISTORS, SYSTEMS AND METHODS FOR MANUFACTURING AND USING THE SAME

(71) Applicant: Agilome, Inc., La Jolla, CA (US)

(72) Inventor: Paul Hoffman, La Jolla, CA (US)

(73) Assignee: Agilome, Inc., San Diego, CA (US)

( * ) Notice: Subject to any disclaimer, the term of this patent is extended or adjusted under 35 U.S.C. 154(b) by 0 days.

(21) Appl. No.: 15/239,800

(22) Filed: Aug. 17, 2016

(65) Prior Publication Data
US 2017/0102358 A1    Apr. 13, 2017

Related U.S. Application Data

(63) Continuation-in-part of application No. 15/182,533, filed on Jun. 14, 2016, which is a continuation-in-part
(Continued)

(51) Int. Cl.
*H01L 29/66* (2006.01)
*G01N 27/414* (2006.01)
(Continued)

(52) U.S. Cl.
CPC ..... *G01N 27/4148* (2013.01); *G01N 27/3276* (2013.01); *H01L 29/1606* (2013.01);
(Continued)

(58) Field of Classification Search
CPC ....... H01L 2924/00014; H01L 29/7869; H01L 2924/00; H01L 29/66969; H01L 27/1225;
(Continued)

(56) References Cited

U.S. PATENT DOCUMENTS 3,377,893 A    4/1968  Shorb
3,466,874 A    9/1969  Holl
(Continued)

FOREIGN PATENT DOCUMENTS

CN    102703594 A    10/2012
CN    202854094 U     4/2013
(Continued)

OTHER PUBLICATIONS

Basu et al. Recent Advances in Carbon Nanotubes Based Biosensors, Sensors, 8:1-x manuscripts, downloaded from: ittp://www.mdpi.org/sensorstaccepted/sensors-util-24-21-malhorta-in-PRE-PUBLISHED-VERSION-0422.pdf (Jan. 31, 2008). 34 pages.
(Continued)

*Primary Examiner* — Robert Bachner
(74) *Attorney, Agent, or Firm* — Mintz Levin Cohn Ferris Glovsky and Popeo, P.C.

(57) ABSTRACT

This invention concerns chemically-sensitive field effect transistors (FETs) are preferably fabricated using semiconductor fabrication methods on a semiconductor wafer, and in preferred embodiments, on top of an integrated circuit structure made using semiconductor fabrication methods. The instant chemically-sensitive FETs typically comprise a conductive source, a conductive drain, and a channel composed of a one-dimensional (1D) or two-dimensional (2D) transistor material, which channel extends from the source to the drain and is fabricated using semiconductor fabrication techniques on top of a wafer. Such chemically-sensitive FETs, preferably configured in independently addressable arrays, may be employed to detect a presence and/or concentration changes of various analyte types in chemical and/or biological samples, including nucleic acid hybridization and/or sequencing reactions.

20 Claims, 99 Drawing Sheets

Related U.S. Application Data of application No. 15/065,744, filed on Mar. 9, 2016, now Pat. No. 9,618,474, and a continuation-in-part of application No. 14/963,253, filed on Dec. 9, 2015, application No. 15/239,800, which is a continuation-in-part of application No. 14/963,253, filed on Dec. 9, 2015.

(60) Provisional application No. 62/175,351, filed on Jun. 14, 2015, provisional application No. 62/130,621, filed on Mar. 10, 2015, provisional application No. 62/206,228, filed on Aug. 17, 2015, provisional application No. 62/199,987, filed on Aug. 1, 2015, provisional application No. 62/130,594, filed on Mar. 9, 2015, provisional application No. 62/094,016, filed on Dec. 18, 2014, provisional application No. 62/130,598, filed on Mar. 9, 2015, provisional application No. 62/130,601, filed on Mar. 9, 2015, provisional application No. 62/206,372, filed on Aug. 18, 2015, provisional application No. 62/206,814, filed on Aug. 18, 2015, provisional application No. 62/206,224, filed on Aug. 17, 2015, provisional application No. 62/205,803, filed on Aug. 17, 2015, provisional application No. 62/205,808, filed on Aug. 17, 2015, provisional application No. 62/206,166, filed on Aug. 17, 2015.

(51) Int. Cl.
*H01L 29/16* (2006.01)
*H01L 29/417* (2006.01)
*G01N 27/327* (2006.01)
*H01L 29/786* (2006.01)

(52) U.S. Cl.
CPC .... *H01L 29/4175* (2013.01); *H01L 29/41733* (2013.01); *H01L 29/78603* (2013.01); *H01L 29/78684* (2013.01)

(58) Field of Classification Search
CPC ............... H01L 29/24; H01L 29/78696; H01L 29/1606; H01L 29/78606; H01L 2224/03; H01L 2224/11; H01L 2224/131
See application file for complete search history.

(56) References Cited

U.S. PATENT DOCUMENTS

| | | |
|---|---|---|
| 3,564,151 A | 2/1971 | Shlesinger, Jr. |
| 3,605,428 A | 9/1971 | Smith et al. |
| 3,691,109 A | 9/1972 | Larsen |
| 3,772,069 A | 11/1973 | Daniel |
| 3,828,094 A | 8/1974 | Widdig et al. |
| 3,892,139 A | 7/1975 | Harris |
| 3,931,401 A | 1/1976 | Prasad et al. |
| 5,397,863 A | 3/1995 | Afzali-Ardakani et al. |
| 5,556,899 A | 9/1996 | Afzali-Ardakani et al. |
| 5,571,852 A | 11/1996 | Afzali-Ardakani et al. |
| 5,591,285 A | 1/1997 | Afzali-Ardakani et al. |
| 5,639,660 A | 6/1997 | Kinet et al. |
| 5,701,256 A | 12/1997 | Marr et al. |
| 5,958,784 A | 9/1999 | Benner |
| 6,001,611 A | 12/1999 | Will |
| 6,377,893 B1 | 4/2002 | Benner |
| 6,466,874 B1 | 10/2002 | Eisenberg et al. |
| 6,564,151 B1 | 5/2003 | Pellegrini et al. |
| 6,605,428 B2 | 8/2003 | Kilger et al. |
| 6,691,109 B2 | 2/2004 | Bjornson et al. |
| 6,772,069 B1 | 8/2004 | Eisenberg et al. |
| 6,828,094 B2 | 12/2004 | Kilger et al. |
| 6,892,139 B2 | 5/2005 | Eisenberg et al. |
| 6,931,401 B2 | 8/2005 | Gibson et al. |
| 7,008,764 B1 | 3/2006 | Honold et al. |
| 7,247,877 B2 | 7/2007 | Hakey et al. |
| 7,253,431 B2 | 8/2007 | Afzali-Ardakani et al. |
| 7,333,980 B2 | 2/2008 | Bjornson et al. |
| 7,462,468 B1 | 12/2008 | Williams et al. |
| 7,484,423 B2 | 2/2009 | Hakey et al. |
| 7,492,015 B2 | 2/2009 | Chen et al. |
| 7,504,132 B2 | 3/2009 | Afzali-Ardakani et al. |
| 7,514,063 B1 | 4/2009 | Tulevski et al. |
| 7,544,546 B2 | 6/2009 | Afzali-Ardakani et al. |
| 7,612,270 B1 | 11/2009 | Zhu |
| 7,670,810 B2 | 3/2010 | Gunderson et al. |
| 7,727,505 B2 | 6/2010 | Afazali-Ardakani et al. |
| 7,732,119 B2 | 6/2010 | Afzali-Ardakani et al. |
| 7,745,118 B2 | 6/2010 | Green et al. |
| 7,750,908 B2 | 7/2010 | Kincaid et al. |
| 7,761,462 B2 | 7/2010 | Bjornson et al. |
| 7,771,695 B2 | 8/2010 | Afzali-Ardakani et al. |
| 7,855,133 B2 | 12/2010 | Afzali-Ardakani et al. |
| 7,867,469 B2 | 1/2011 | Afzali-Ardakani et al. |
| 7,879,307 B2 | 2/2011 | Afzali-Ardakani et al. |
| 7,883,685 B1 | 2/2011 | Afzali-Ardakani et al. |
| 7,888,528 B2 | 2/2011 | Afzali-Ardakani et al. |
| 7,917,299 B2 | 3/2011 | Buhler et al. |
| 7,932,029 B1 | 4/2011 | Lok |
| 7,948,015 B2 | 5/2011 | Rothberg et al. |
| 7,951,424 B2 | 5/2011 | Afzali-Ardakani et al. |
| 7,955,585 B2 | 6/2011 | Afzali-Ardakani et al. |
| 7,955,931 B2 | 6/2011 | Appenzeller et al. |
| 7,982,274 B2 | 7/2011 | Afzali-Ardakani et al. |
| 7,993,842 B2 | 8/2011 | McKernan et al. |
| 8,017,934 B2 | 9/2011 | Appenzeller et al. |
| 8,032,305 B2 | 10/2011 | Shibuya |
| 8,039,334 B2 | 10/2011 | Furukawa et al. |
| 8,039,909 B2 | 10/2011 | Afzali-Ardakani et al. |
| 8,057,984 B2 | 11/2011 | Afzali-Ardakani et al. |
| 8,084,012 B2 | 12/2011 | Afzali-Ardakani et al. |
| 8,095,508 B2 | 1/2012 | Chamberlain et al. |
| 8,124,463 B2 | 2/2012 | Chen et al. |
| 8,138,102 B2 | 3/2012 | Afzali-Ardakani et al. |
| 8,138,491 B2 | 3/2012 | Appenzeller et al. |
| 8,138,492 B2 | 3/2012 | Afzali-Ardakani et al. |
| 8,143,030 B2 | 3/2012 | Maxham et al. |
| 8,153,375 B2 | 4/2012 | Travers et al. |
| 8,182,989 B2 | 5/2012 | Bignell et al. |
| 8,182,993 B2 | 5/2012 | Tomaney et al. |
| 8,209,130 B1 | 6/2012 | Kennedy et al. |
| 8,211,735 B2 | 7/2012 | Graham et al. |
| 8,211,741 B2 | 7/2012 | Appenzeller et al. |
| 8,217,433 B1 | 7/2012 | Fife |
| 8,227,171 B2 | 7/2012 | Afzali-Ardakani et al. |
| 8,244,479 B2 | 8/2012 | Kain et al. |
| 8,283,453 B2 | 10/2012 | Afzali-Ardakani et al. |
| 8,283,703 B2 | 10/2012 | Solomon |
| 8,293,607 B2 | 10/2012 | Afzali-Ardakani et al. |
| 8,296,075 B2 | 10/2012 | Den Hartog |
| 8,306,757 B2 | 11/2012 | Rothberg et al. |
| 8,309,330 B2 | 11/2012 | Travers et al. |
| 8,329,400 B2 | 12/2012 | Lok |
| 8,383,345 B2 | 2/2013 | Shendure et al. |
| 8,383,369 B2 | 2/2013 | Maxham et al. |
| 8,394,727 B1 | 3/2013 | Afzali-Ardakani et al. |
| 8,395,774 B2 | 3/2013 | Afzali et al. |
| 8,445,945 B2 | 5/2013 | Rothberg et al. |
| 8,455,193 B2 | 6/2013 | Travers et al. |
| 8,455,297 B1 | 6/2013 | Avouris et al. |
| 8,455,311 B2 | 6/2013 | Solomon |
| 8,463,555 B2 | 6/2013 | Zhang |
| 8,465,647 B2 | 6/2013 | Bol et al. |
| 8,471,249 B2 | 6/2013 | Chiu et al. |
| 8,481,413 B2 | 7/2013 | Afzali-Ardakani et al. |
| 8,486,630 B2 | 7/2013 | Pan et al. |
| 8,491,769 B2 | 7/2013 | Afzali-Ardakani et al. |
| 8,492,293 B1 | 7/2013 | Afzali-Ardakani et al. |
| 8,492,748 B2 | 7/2013 | Chang et al. |
| 8,512,458 B2 | 8/2013 | Holmes et al. |
| 8,515,682 B2 | 8/2013 | Buhler et al. |
| 8,518,829 B2 | 8/2013 | Dang et al. |
| 8,524,487 B2 | 9/2013 | Fife |

(56) References Cited

U.S. PATENT DOCUMENTS

| | | |
|---|---|---|
| 8,535,882 B2 | 9/2013 | Christians et al. |
| 8,546,246 B2 | 10/2013 | Lin et al. |
| 8,554,492 B2 | 10/2013 | Ahn et al. |
| 8,557,097 B2 | 10/2013 | Afzali-Ardakani et al. |
| 8,558,288 B2 | 10/2013 | Rothberg et al. |
| 8,574,892 B2 | 11/2013 | Su |
| 8,587,065 B2 | 11/2013 | Chen et al. |
| 8,594,951 B2 | 11/2013 | Homer |
| 8,598,569 B2 | 12/2013 | Afzali-Ardakani et al. |
| 8,603,792 B2 | 12/2013 | Nikiforov et al. |
| 8,604,559 B2 | 12/2013 | Afzali-Ardakani et al. |
| 8,609,481 B1 | 12/2013 | Franklin et al. |
| 8,610,989 B2 | 12/2013 | Avouris et al. |
| 8,614,436 B2 | 12/2013 | Solomon |
| 8,617,941 B2 | 12/2013 | Farmer et al. |
| 8,620,881 B2 | 12/2013 | Chamberlain et al. |
| 8,628,940 B2 | 1/2014 | Sorenson et al. |
| 8,637,374 B2 | 1/2014 | Appenzeller et al. |
| 8,642,432 B2 | 2/2014 | Afzali-Ardakani et al. |
| 8,674,412 B2 | 3/2014 | Franklin et al. |
| 8,688,388 B2 | 4/2014 | Dzakula et al. |
| 8,698,226 B2 | 4/2014 | Jain et al. |
| 8,700,341 B2 | 4/2014 | Rava et al. |
| 8,716,029 B1 | 5/2014 | Kim et al. |
| 8,716,597 B2 | 5/2014 | Mann et al. |
| 8,725,422 B2 | 5/2014 | Halpern et al. |
| 8,738,300 B2 | 5/2014 | Porreca et al. |
| 8,741,678 B2 | 6/2014 | Chen et al. |
| 8,741,751 B2 | 6/2014 | Cao et al. |
| 8,741,756 B2 | 6/2014 | Franklin et al. |
| 8,751,166 B2 | 6/2014 | Friedlander et al. |
| 8,751,452 B2 | 6/2014 | Chamberlain et al. |
| 8,753,816 B2 | 6/2014 | Rigatti et al. |
| 8,753,912 B2 | 6/2014 | Graham et al. |
| 8,754,393 B2 | 6/2014 | Cao et al. |
| 8,765,547 B2 | 7/2014 | Farmer et al. |
| 8,766,345 B2 | 7/2014 | Farmer et al. |
| 8,772,141 B2 | 7/2014 | Afzali-Ardakani et al. |
| 8,772,910 B2 | 7/2014 | Afzali-Ardakani et al. |
| 8,779,414 B2 | 7/2014 | Chang et al. |
| 8,785,262 B2 | 7/2014 | Farmer et al. |
| 8,785,911 B2 | 7/2014 | Chen et al. |
| 8,786,018 B2 | 7/2014 | Farmer et al. |
| 8,795,961 B2 | 8/2014 | Rank et al. |
| 8,796,642 B2 | 8/2014 | Boday et al. |
| 8,796,668 B2 | 8/2014 | Lin et al. |
| 8,797,059 B2 | 8/2014 | Boday et al. |
| 8,803,129 B2 | 8/2014 | Chang et al. |
| 8,803,131 B2 | 8/2014 | Lin et al. |
| 8,803,132 B2 | 8/2014 | Farmer et al. |
| 8,805,148 B2 | 8/2014 | Avouris et al. |
| 8,809,153 B2 | 8/2014 | Afzali-Ardakani et al. |
| 8,809,837 B2 | 8/2014 | Farmer et al. |
| 8,816,328 B2 | 8/2014 | Chang et al. |
| 8,816,787 B2 | 8/2014 | Jenkins et al. |
| 8,828,762 B2 | 9/2014 | Chu et al. |
| 8,834,967 B2 | 9/2014 | Afzali-Ardakani et al. |
| 8,835,686 B2 | 9/2014 | Afzali-Ardakani et al. |
| 8,852,342 B2 | 10/2014 | Dimitrakopoulos et al. |
| 8,852,985 B2 | 10/2014 | Cai et al. |
| 8,853,034 B2 | 10/2014 | Afzall-Ardakani et al. |
| 8,859,048 B2 | 10/2014 | Afzali-Ardakani et al. |
| 8,859,439 B1 | 10/2014 | Avouris et al. |
| 8,877,340 B2 | 11/2014 | Chu et al. |
| 8,878,193 B2 | 11/2014 | Avouris et al. |
| 8,890,116 B2 | 11/2014 | Chen et al. |
| 8,890,121 B1 | 11/2014 | Han et al. |
| 8,895,372 B2 | 11/2014 | Guo et al. |
| 8,895,417 B2 | 11/2014 | Afzali-Ardakani et al. |
| 8,900,538 B2 | 12/2014 | Abou-Kandil et al. |
| 8,900,918 B2 | 12/2014 | Avouris et al. |
| 8,901,680 B2 | 12/2014 | Cal et al. |
| 8,901,689 B1 | 12/2014 | Avouris et al. |
| 8,911,972 B2 | 12/2014 | Chaisson et al. |
| 8,912,525 B2 | 12/2014 | Afzali-Ardakani et al. |
| 8,916,451 B2 | 12/2014 | Bayram et al. |
| 8,927,057 B2 | 1/2015 | Bol et al. |
| 8,932,919 B2 | 1/2015 | Farmer et al. |
| 8,936,763 B2 | 1/2015 | Rothberg et al. |
| 8,951,727 B2 | 2/2015 | Jaramillo-Botero et al. |
| 8,952,258 B2 | 2/2015 | Plucinski et al. |
| 8,957,405 B2 | 2/2015 | Adkisson et al. |
| 8,957,463 B2 | 2/2015 | Afzali-Ardakani et al. |
| 8,963,215 B2 | 2/2015 | Afzali-Ardakani et al. |
| 8,968,582 B2 | 3/2015 | Franklin et al. |
| 8,969,090 B2 | 3/2015 | Sun et al. |
| 8,969,115 B2 | 3/2015 | Chen et al. |
| 8,969,118 B2 | 3/2015 | Afzali-Ardakani et al. |
| 8,975,095 B2 | 3/2015 | Han et al. |
| 8,987,740 B2 | 3/2015 | Avouris et al. |
| 9,000,499 B2 | 4/2015 | Franklin et al. |
| 9,000,594 B2 | 4/2015 | Ott et al. |
| 9,014,989 B2 | 4/2015 | McMillen et al. |
| 9,017,813 B2 | 4/2015 | El-Ashry et al. |
| 9,029,841 B2 | 5/2015 | Farmer et al. |
| 9,040,364 B2 | 5/2015 | Farmer et al. |
| 9,045,796 B2 | 6/2015 | Gunderson et al. |
| 9,045,842 B2 | 6/2015 | Han et al. |
| 9,051,611 B2 | 6/2015 | Christians et al. |
| 9,059,188 B1 | 6/2015 | Dimitrakopoulos et al. |
| 9,062,389 B2 | 6/2015 | Han et al. |
| 9,064,698 B1 | 6/2015 | Khakifirooz et al. |
| 9,064,776 B2 | 6/2015 | Lin et al. |
| 9,064,842 B2 | 6/2015 | Bol et al. |
| 9,068,221 B2 | 6/2015 | Merriman et al. |
| 9,068,936 B2 | 6/2015 | Guo et al. |
| 9,076,873 B2 | 7/2015 | Chen et al. |
| 9,082,856 B2 | 7/2015 | Chen et al. |
| 9,085,802 B2 | 7/2015 | Liu et al. |
| 9,087,691 B2 | 7/2015 | Zhu et al. |
| 9,091,648 B2 | 7/2015 | Afzali-Ardakani et al. |
| 9,093,507 B2 | 7/2015 | Cohen et al. |
| 9,093,631 B2 | 7/2015 | Davis |
| 9,097,658 B2 | 8/2015 | Afzali-Ardakani et al. |
| 9,099,542 B2 | 8/2015 | Franklin et al. |
| 9,102,118 B2 | 8/2015 | Afzali-Ardakani et al. |
| 9,102,540 B2 | 8/2015 | Afzali-Ardakani et al. |
| 9,103,776 B2 | 8/2015 | Afzali-Ardakani et al. |
| 9,105,702 B2 | 8/2015 | Franklin et al. |
| 9,105,853 B2 | 8/2015 | Afzali-Ardakani et al. |
| 9,123,454 B2 | 9/2015 | Franklin et al. |
| 9,142,471 B2 | 9/2015 | Abou-Kandil et al. |
| 9,145,295 B2 | 9/2015 | Peng |
| 9,146,209 B2 | 9/2015 | Johnson et al. |
| 9,150,918 B2 | 10/2015 | Turner et al. |
| 9,157,887 B2 | 10/2015 | Guo et al. |
| 9,162,883 B2 | 10/2015 | El-Ashry et al. |
| 9,174,413 B2 | 11/2015 | Avouris et al. |
| 9,174,414 B2 | 11/2015 | Avouris et al. |
| 9,177,688 B2 | 11/2015 | Bol et al. |
| 9,179,579 B2 | 11/2015 | Hada et al. |
| 9,281,305 B1 | 3/2016 | Yang et al. |
| 9,618,474 B2 | 4/2017 | van Rooyen et al. |
| 2002/0164588 A1 | 11/2002 | Eisenberg et al. |
| 2002/0194173 A1 | 12/2002 | Bjornson et al. |
| 2003/0033279 A1 | 2/2003 | Gibson et al. |
| 2003/0200033 A1 | 10/2003 | Segal et al. |
| 2003/0224384 A1 | 12/2003 | Sayood et al. |
| 2003/0228618 A1 | 12/2003 | Levanon et al. |
| 2004/0072204 A1 | 4/2004 | Shibuya |
| 2004/0110227 A1 | 6/2004 | Levanon et al. |
| 2004/0142347 A1 | 7/2004 | Stockwell et al. |
| 2004/0143571 A1 | 7/2004 | Bjornson et al. |
| 2004/0152108 A1 | 8/2004 | Keith et al. |
| 2004/0241730 A1 | 12/2004 | Yakhini et al. |
| 2004/0248189 A1 | 12/2004 | Bulaj et al. |
| 2005/0009771 A1 | 1/2005 | Levanon et al. |
| 2005/0038609 A1 | 2/2005 | Benner |
| 2005/0039123 A1 | 2/2005 | Kuchinsky et al. |
| 2005/0107961 A1 | 5/2005 | Uemura et al. |
| 2005/0131649 A1 | 6/2005 | Larsen et al. |
| 2005/0188294 A1 | 8/2005 | Kuchinsky et al. |
| 2005/0197783 A1 | 9/2005 | Kuchinsky et al. |
| 2005/0240352 A1 | 10/2005 | Liang |

(56) References Cited

U.S. PATENT DOCUMENTS

| | | |
|---|---|---|
| 2006/0028471 A1 | 2/2006 | Kincaid et al. |
| 2006/0064247 A1 | 3/2006 | Yuan et al. |
| 2006/0100788 A1 | 5/2006 | Carrino et al. |
| 2006/0106545 A1 | 5/2006 | Balaji et al. |
| 2006/0141529 A1 | 6/2006 | Koleske et al. |
| 2006/0275794 A1 | 12/2006 | Carrino et al. |
| 2006/0294059 A1 | 12/2006 | Chamberlain et al. |
| 2007/0063304 A1 | 3/2007 | Matsumoto et al. |
| 2007/0067108 A1 | 3/2007 | Buhler et al. |
| 2007/0088510 A1 | 4/2007 | Li et al. |
| 2007/0134692 A1 | 6/2007 | Valmeekam et al. |
| 2007/0138463 A1 | 6/2007 | Herlogsson et al. |
| 2007/0152335 A1 | 7/2007 | Chun |
| 2007/0196816 A1 | 8/2007 | Schwartz et al. |
| 2007/0232060 A1 | 10/2007 | Niu |
| 2007/0259337 A1 | 11/2007 | Hully et al. |
| 2007/0277036 A1 | 11/2007 | Chamberlain et al. |
| 2008/0035494 A1 | 2/2008 | Gomez et al. |
| 2008/0063566 A1 | 3/2008 | Matsumoto et al. |
| 2008/0086274 A1 | 4/2008 | Chamberlain et al. |
| 2008/0104041 A1 | 5/2008 | Bjornson et al. |
| 2008/0154567 A1 | 6/2008 | Qiu et al. |
| 2008/0250016 A1 | 10/2008 | Farrar |
| 2008/0274912 A1 | 11/2008 | Johnson et al. |
| 2008/0283875 A1* | 11/2008 | Mukasa ............... B82Y 10/00 257/253 |
| 2009/0008629 A1 | 1/2009 | Matsumoto et al. |
| 2009/0014757 A1 | 1/2009 | Takulapalli et al. |
| 2009/0119313 A1 | 5/2009 | Pearce |
| 2009/0125248 A1 | 5/2009 | Shams et al. |
| 2009/0153130 A1 | 6/2009 | Shim et al. |
| 2009/0156431 A1 | 6/2009 | Lok |
| 2009/0171647 A1 | 7/2009 | Mannava et al. |
| 2009/0278556 A1 | 11/2009 | Man et al. |
| 2009/0292665 A1 | 11/2009 | Den Hartog |
| 2009/0325239 A1 | 12/2009 | Lok |
| 2010/0025660 A1 | 2/2010 | Jain et al. |
| 2010/0035254 A1 | 2/2010 | Williams |
| 2010/0069263 A1 | 3/2010 | Shendure et al. |
| 2010/0075309 A1 | 3/2010 | Maxham et al. |
| 2010/0075327 A1 | 3/2010 | Maxham et al. |
| 2010/0077267 A1 | 3/2010 | Perego et al. |
| 2010/0082805 A1 | 4/2010 | Orton et al. |
| 2010/0088040 A1 | 4/2010 | Johnson, Jr. |
| 2010/0105202 A1 | 4/2010 | Daamen |
| 2010/0121582 A1 | 5/2010 | Pan et al. |
| 2010/0227384 A1 | 9/2010 | Vann |
| 2010/0228496 A1 | 9/2010 | Leong et al. |
| 2010/0293167 A1 | 11/2010 | Biasci et al. |
| 2010/0304989 A1 | 12/2010 | Von Hoff et al. |
| 2010/0327847 A1 | 12/2010 | Leiber et al. |
| 2011/0003301 A1 | 1/2011 | Raymond et al. |
| 2011/0004413 A1 | 1/2011 | Carnevali et al. |
| 2011/0042673 A1 | 2/2011 | Yamabayashi et al. |
| 2011/0098193 A1 | 4/2011 | Kingsmore et al. |
| 2011/0121273 A1 | 5/2011 | Jo et al. |
| 2011/0177517 A1 | 7/2011 | Rava et al. |
| 2011/0195406 A1 | 8/2011 | Sorenson et al. |
| 2011/0201507 A1 | 8/2011 | Rava et al. |
| 2011/0212464 A1 | 9/2011 | Hagmann et al. |
| 2011/0224087 A1 | 9/2011 | Quake et al. |
| 2011/0227043 A1 | 9/2011 | Guo et al. |
| 2011/0230358 A1 | 9/2011 | Rava |
| 2011/0231446 A1 | 9/2011 | Buhler et al. |
| 2011/0237444 A1 | 9/2011 | Clancy et al. |
| 2011/0245085 A1 | 10/2011 | Rava et al. |
| 2011/0252008 A1 | 10/2011 | Chamberlain et al. |
| 2011/0257889 A1 | 10/2011 | Klammer et al. |
| 2011/0270533 A1 | 11/2011 | Zhang et al. |
| 2011/0281740 A1 | 11/2011 | Beechem et al. |
| 2011/0281768 A1 | 11/2011 | Travers et al. |
| 2011/0295514 A1 | 12/2011 | Breu et al. |
| 2011/0295858 A1 | 12/2011 | Ahn et al. |
| 2011/0295977 A1 | 12/2011 | Shibuya |
| 2011/0296543 A1 | 12/2011 | Chang et al. |
| 2012/0001615 A1 | 1/2012 | Levine |
| 2012/0010085 A1 | 1/2012 | Rava et al. |
| 2012/0011086 A1 | 1/2012 | Zhang et al. |
| 2012/0046175 A1 | 2/2012 | Rodesch et al. |
| 2012/0046877 A1 | 2/2012 | Hyland et al. |
| 2012/0053845 A1 | 3/2012 | Bruestle et al. |
| 2012/0089339 A1 | 4/2012 | Ganeshalingam et al. |
| 2012/0094849 A1 | 4/2012 | Rava et al. |
| 2012/0095697 A1 | 4/2012 | Halpern et al. |
| 2012/0100548 A1 | 4/2012 | Rava et al. |
| 2012/0102041 A1 | 4/2012 | Park et al. |
| 2012/0109849 A1 | 5/2012 | Chamberlain et al. |
| 2012/0110316 A1 | 5/2012 | Chamberlain et al. |
| 2012/0116688 A1 | 5/2012 | Mishra et al. |
| 2012/0149582 A1 | 6/2012 | Rava et al. |
| 2012/0156677 A1 | 6/2012 | Bitinaite et al. |
| 2012/0165203 A1 | 6/2012 | Quake et al. |
| 2012/0197623 A1 | 8/2012 | Homer |
| 2012/0203792 A1 | 8/2012 | Zhang et al. |
| 2012/0208706 A1 | 8/2012 | Downing et al. |
| 2012/0214172 A1 | 8/2012 | Chen et al. |
| 2012/0214678 A1 | 8/2012 | Rava et al. |
| 2012/0221249 A1 | 8/2012 | Lizardi et al. |
| 2012/0221432 A1 | 8/2012 | Yuan et al. |
| 2012/0237928 A1 | 9/2012 | Rava et al. |
| 2012/0264121 A1 | 10/2012 | Rava et al. |
| 2012/0270739 A1 | 10/2012 | Rava et al. |
| 2012/0271558 A1 | 10/2012 | Hur et al. |
| 2012/0289408 A1 | 11/2012 | Travers et al. |
| 2012/0289412 A1 | 11/2012 | Seitz et al. |
| 2012/0295260 A1 | 11/2012 | Pan et al. |
| 2012/0330559 A1 | 12/2012 | Jiang et al. |
| 2012/0330566 A1 | 12/2012 | Chaisson |
| 2013/0018599 A1 | 1/2013 | Peng |
| 2013/0029852 A1 | 1/2013 | Rava et al. |
| 2013/0034546 A1 | 2/2013 | Rava et al. |
| 2013/0054151 A1 | 2/2013 | Kermani et al. |
| 2013/0054508 A1 | 2/2013 | Kermani et al. |
| 2013/0059740 A1 | 3/2013 | Drmanac et al. |
| 2013/0085681 A1 | 4/2013 | Deciu et al. |
| 2013/0091121 A1 | 4/2013 | Galinsky |
| 2013/0091126 A1 | 4/2013 | Krishnaswami et al. |
| 2013/0091176 A1 | 4/2013 | Harris et al. |
| 2013/0096011 A1 | 4/2013 | Rava et al. |
| 2013/0096841 A1 | 4/2013 | Kermani et al. |
| 2013/0103320 A1 | 4/2013 | Dzakula et al. |
| 2013/0124100 A1 | 5/2013 | Drmanac et al. |
| 2013/0137588 A1 | 5/2013 | Shendure et al. |
| 2013/0137605 A1 | 5/2013 | Shendure et al. |
| 2013/0138355 A1 | 5/2013 | Inglis et al. |
| 2013/0138358 A1 | 5/2013 | Tang et al. |
| 2013/0140518 A1 | 6/2013 | Jain et al. |
| 2013/0150253 A1 | 6/2013 | Deciu et al. |
| 2013/0157870 A1 | 6/2013 | Pushkarev et al. |
| 2013/0164859 A1 | 6/2013 | Johnson et al. |
| 2013/0166221 A1 | 6/2013 | Inglis et al. |
| 2013/0184161 A1 | 7/2013 | Kingsmore et al. |
| 2013/0194882 A1 | 8/2013 | Ishii et al. |
| 2013/0204851 A1 | 8/2013 | Bhola et al. |
| 2013/0211729 A1 | 8/2013 | Sastry-Dent et al. |
| 2013/0230909 A1 | 9/2013 | Pan et al. |
| 2013/0237432 A1 | 9/2013 | Li et al. |
| 2013/0240378 A1 | 9/2013 | Lee et al. |
| 2013/0245958 A1 | 9/2013 | Forster et al. |
| 2013/0251726 A1 | 9/2013 | Mascola et al. |
| 2013/0261983 A1 | 10/2013 | Dzakula et al. |
| 2013/0273543 A1 | 10/2013 | Gudmundsson et al. |
| 2013/0288244 A1 | 10/2013 | Deciu et al. |
| 2013/0288901 A1 | 10/2013 | Kennedy et al. |
| 2013/0296175 A1 | 11/2013 | Rafnar et al. |
| 2013/0297221 A1 | 11/2013 | Johnson et al. |
| 2013/0304392 A1 | 11/2013 | Deciu et al. |
| 2013/0307029 A1 | 11/2013 | Xu et al. |
| 2013/0309666 A1 | 11/2013 | Deciu et al. |
| 2013/0309678 A1 | 11/2013 | Travers et al. |
| 2013/0310260 A1 | 11/2013 | Kim et al. |
| 2013/0311106 A1 | 11/2013 | White et al. |
| 2013/0316331 A1 | 11/2013 | Isakov et al. |
| 2013/0316915 A1 | 11/2013 | Halpern et al. |

(56) References Cited

U.S. PATENT DOCUMENTS

| | | |
|---|---|---|
| 2013/0316916 A1 | 11/2013 | Flusberg et al. |
| 2013/0324417 A1 | 12/2013 | Kennedy et al. |
| 2013/0324419 A1 | 12/2013 | Seshagiri |
| 2013/0325360 A1 | 12/2013 | Deciu et al. |
| 2013/0325666 A1 | 12/2013 | Carrino et al. |
| 2013/0332081 A1 | 12/2013 | Reese et al. |
| 2013/0338012 A1 | 12/2013 | Sulem et al. |
| 2013/0338933 A1 | 12/2013 | Deciu et al. |
| 2013/0338934 A1 | 12/2013 | Asadi et al. |
| 2013/0345066 A1 | 12/2013 | Brinza et al. |
| 2014/0024536 A1 | 1/2014 | Richards et al. |
| 2014/0024541 A1 | 1/2014 | Richards et al. |
| 2014/0024542 A1 | 1/2014 | Richards et al. |
| 2014/0025312 A1 | 1/2014 | Chin et al. |
| 2014/0031240 A1 | 1/2014 | Behlke et al. |
| 2014/0033125 A1 | 1/2014 | Merel |
| 2014/0034880 A1 | 2/2014 | Blouin et al. |
| 2014/0038830 A1 | 2/2014 | Srinivasan et al. |
| 2014/0045705 A1 | 2/2014 | Bustamante et al. |
| 2014/0051154 A1 | 2/2014 | Hyland et al. |
| 2014/0051588 A9 | 2/2014 | Drmanac et al. |
| 2014/0053294 A1 | 2/2014 | Gresshoff |
| 2014/0066317 A1 | 3/2014 | Talasaz |
| 2014/0067830 A1 | 3/2014 | Buhler et al. |
| 2014/0087961 A1 | 3/2014 | Sulem et al. |
| 2014/0100792 A1 | 4/2014 | Deciu et al. |
| 2014/0114582 A1 | 4/2014 | Mittelman et al. |
| 2014/0121116 A1 | 5/2014 | Richards et al. |
| 2014/0122509 A1 | 5/2014 | Pantaleoni et al. |
| 2014/0129201 A1 | 5/2014 | Kennedy et al. |
| 2014/0134629 A1 | 5/2014 | Turner et al. |
| 2014/0148346 A1 | 5/2014 | Spormann et al. |
| 2014/0149049 A1 | 5/2014 | Chen et al. |
| 2014/0152291 A1 | 6/2014 | Afzali-Ardakani et al. |
| 2014/0155298 A1 | 6/2014 | Von Hoff et al. |
| 2014/0156199 A1 | 6/2014 | Von Hoff et al. |
| 2014/0162278 A1 | 6/2014 | Richards et al. |
| 2014/0163900 A1 | 6/2014 | Erlich et al. |
| 2014/0166487 A1 | 6/2014 | Lieber et al. |
| 2014/0172319 A1 | 6/2014 | Von Hoff et al. |
| 2014/0173606 A1 | 6/2014 | Pantaleoni |
| 2014/0193938 A1 | 7/2014 | Fife |
| 2014/0200166 A1 | 7/2014 | Van Rooyen et al. |
| 2014/0209982 A1 | 7/2014 | Putnam et al. |
| 2014/0236490 A1 | 8/2014 | Van Rooyen et al. |
| 2014/0248692 A1 | 9/2014 | Lagace et al. |
| 2014/0249052 A1 | 9/2014 | Mehmet et al. |
| 2014/0260547 A1 | 9/2014 | Balandin |
| 2014/0274774 A1 | 9/2014 | Li et al. |
| 2014/0297196 A1 | 10/2014 | Olson |
| 2014/0309944 A1 | 10/2014 | van Rooyen et al. |
| 2014/0315199 A1 | 10/2014 | Rhodes et al. |
| 2014/0363808 A1 | 12/2014 | Gu et al. |
| 2014/0371109 A1 | 12/2014 | McMillen et al. |
| 2014/0371110 A1 | 12/2014 | Van Rooyen et al. |
| 2015/0065353 A1 | 3/2015 | Turner et al. |
| 2015/0069329 A1 | 3/2015 | Jeon et al. |
| 2015/0087534 A1 | 3/2015 | Gormley et al. |
| 2015/0101931 A1 | 4/2015 | Garaj et al. |
| 2015/0111759 A1 | 4/2015 | Ju et al. |
| 2015/0123080 A1 | 5/2015 | Yamaguchi |
| 2015/0137078 A1 | 5/2015 | Guo et al. |
| 2015/0159196 A1 | 6/2015 | Travers et al. |
| 2015/0159212 A1 | 6/2015 | Pantoja et al. |
| 2015/0160159 A1 | 6/2015 | Afzali-Ardakani et al. |
| 2015/0176071 A1 | 6/2015 | Fisher et al. |
| 2015/0211054 A1 | 7/2015 | Kostem et al. |
| 2015/0218630 A1 | 8/2015 | Sun et al. |
| 2015/0225785 A1 | 8/2015 | Zhao et al. |
| 2015/0232929 A1 | 8/2015 | Stephens et al. |
| 2015/0239947 A1 | 8/2015 | Brinkmann et al. |
| 2015/0243917 A1 | 8/2015 | Kim et al. |
| 2015/0259743 A1 | 9/2015 | Burgess et al. |
| 2015/0302143 A1 | 10/2015 | Ma et al. |
| 2015/0302144 A1 | 10/2015 | Chin et al. |
| 2015/0307936 A1 | 10/2015 | Goldsmith |
| 2015/0307947 A1 | 10/2015 | Basu et al. |
| 2015/0339437 A1 | 11/2015 | McMillen et al. |
| 2015/0368638 A1 | 12/2015 | Steemers et al. |
| 2016/0004298 A1 | 1/2016 | Mazed et al. |
| 2016/0122792 A1 | 5/2016 | Peterson et al. |
| 2016/0171153 A1 | 6/2016 | Van Rooyen et al. |
| 2016/0178569 A1 | 6/2016 | Hoffman et al. |
| 2016/0180019 A1 | 6/2016 | Van Rooyen et al. |
| 2016/0231251 A1 | 8/2016 | Ou et al. |
| 2016/0265047 A1 | 9/2016 | van Rooyen et al. |
| 2017/0018626 A1 | 1/2017 | Hoffman et al. |
| 2017/0053908 A1 | 2/2017 | Hoffman |
| 2017/0059514 A1 | 3/2017 | Hoffman |

FOREIGN PATENT DOCUMENTS

| | | |
|---|---|---|
| CN | 103293209 A | 9/2013 |
| CN | 104237352 A | 12/2014 |
| DE | 19813317 A1 | 9/1999 |
| EP | 2163646 A1 | 3/2010 |
| EP | 2334802 A1 | 6/2011 |
| EP | 2535429 A1 | 12/2012 |
| JP | 2004085392 A | 3/2004 |
| JP | 2010172290 A | 8/2010 |
| WO | WO-99/049403 A1 | 9/1999 |
| WO | WO-00/045322 A1 | 8/2000 |
| WO | WO-01/13432 A1 | 2/2001 |
| WO | WO-02/090978 A1 | 11/2002 |
| WO | WO-03/046220 A1 | 6/2003 |
| WO | WO-2004/029298 A2 | 4/2004 |
| WO | WO-2004/090100 A2 | 10/2004 |
| WO | WO-2004/104161 A2 | 12/2004 |
| WO | WO-2005/026925 A2 | 3/2005 |
| WO | WO-2005/029059 A1 | 3/2005 |
| WO | WO-2005/048134 A2 | 5/2005 |
| WO | WO-2005/090961 A1 | 9/2005 |
| WO | WO-2005/113812 A2 | 12/2005 |
| WO | WO-2006/015084 A2 | 2/2006 |
| WO | WO-2006/019892 A2 | 2/2006 |
| WO | WO-2006/096324 A2 | 9/2006 |
| WO | WO-2007/064758 A2 | 6/2007 |
| WO | WO-2007/076726 A1 | 7/2007 |
| WO | WO-2008/022036 A2 | 2/2008 |
| WO | WO-2008/098014 A2 | 8/2008 |
| WO | WO-2008/127213 A2 | 10/2008 |
| WO | WO-2008/143679 A2 | 11/2008 |
| WO | WO-2008/156773 A1 | 12/2008 |
| WO | WO-2009/035647 A1 | 3/2009 |
| WO | WO-2009/120372 A2 | 10/2009 |
| WO | WO-2009/143212 A1 | 11/2009 |
| WO | WO-2010/003316 A1 | 1/2010 |
| WO | WO-2010/027497 A2 | 3/2010 |
| WO | WO-2010/036287 A1 | 4/2010 |
| WO | WO-2010/036311 A2 | 4/2010 |
| WO | WO-2010/051773 A1 | 5/2010 |
| WO | WO-2010/072382 A1 | 7/2010 |
| WO | WO-2010/093465 A1 | 8/2010 |
| WO | WO-2010/127045 A2 | 11/2010 |
| WO | WO-2010/129019 A2 | 11/2010 |
| WO | WO-2010/129301 A2 | 11/2010 |
| WO | WO-2010/132814 A1 | 11/2010 |
| WO | WO-2011/025819 A1 | 3/2011 |
| WO | WO-2011/050341 A1 | 4/2011 |
| WO | WO-2011/056688 A2 | 5/2011 |
| WO | WO-2011/063210 A2 | 5/2011 |
| WO | WO-2011/071923 A2 | 6/2011 |
| WO | WO-2011/082178 A1 | 7/2011 |
| WO | WO-2011/090556 A1 | 7/2011 |
| WO | WO-2011/090557 A1 | 7/2011 |
| WO | WO-2011/090558 A1 | 7/2011 |
| WO | WO-2011/090559 A1 | 7/2011 |
| WO | WO-2011/091046 A1 | 7/2011 |
| WO | WO-2011/091063 A1 | 7/2011 |
| WO | WO-2011/095501 A1 | 8/2011 |
| WO | WO-2011/137368 A2 | 11/2011 |
| WO | WO-2011/139797 A2 | 11/2011 |
| WO | WO-2011/143525 A2 | 11/2011 |
| WO | WO-2011/145954 A1 | 11/2011 |

(56) References Cited

FOREIGN PATENT DOCUMENTS

| | | |
|---|---|---|
| WO | WO-2011/145955 A1 | 11/2011 |
| WO | WO-2012/006291 A2 | 1/2012 |
| WO | WO-2012/029080 A1 | 3/2012 |
| WO | WO-2012/051346 A1 | 4/2012 |
| WO | WO-2012/058459 A2 | 5/2012 |
| WO | WO-2012/065228 A1 | 5/2012 |
| WO | WO-2012/066582 A1 | 5/2012 |
| WO | WO-2012/085948 A1 | 6/2012 |
| WO | WO-2012/092336 A2 | 7/2012 |
| WO | WO-2012/092426 A1 | 7/2012 |
| WO | WO-2012/095872 A1 | 7/2012 |
| WO | WO-2012/101643 A1 | 8/2012 |
| WO | WO-2012/123972 A1 | 9/2012 |
| WO | WO-2012/142334 A2 | 10/2012 |
| WO | WO-2012/142531 A2 | 10/2012 |
| WO | WO-2012/168803 A2 | 12/2012 |
| WO | WO-2012/168815 A2 | 12/2012 |
| WO | WO-2012/170715 A1 | 12/2012 |
| WO | WO-2012/172575 A1 | 12/2012 |
| WO | WO-2012/177774 A2 | 12/2012 |
| WO | WO-2012/177792 A2 | 12/2012 |
| WO | WO-2013/043909 A1 | 3/2013 |
| WO | WO-2013/052907 A2 | 4/2013 |
| WO | WO-2013/052913 A2 | 4/2013 |
| WO | WO-2013/055817 A1 | 4/2013 |
| WO | WO-2013/058907 A1 | 4/2013 |
| WO | WO-2013/062856 A1 | 5/2013 |
| WO | WO-2013/065072 A1 | 5/2013 |
| WO | WO-2013/067167 A2 | 5/2013 |
| WO | WO-2013/080227 A1 | 6/2013 |
| WO | WO-2013/088457 A1 | 6/2013 |
| WO | WO-2013/109935 A1 | 7/2013 |
| WO | WO-2013/109981 A1 | 7/2013 |
| WO | WO-2013/119770 A1 | 8/2013 |
| WO | WO-2013/123330 A1 | 8/2013 |
| WO | WO-2013/128371 A2 | 9/2013 |
| WO | WO-2013/148400 A1 | 10/2013 |
| WO | WO-2013/166517 A1 | 11/2013 |
| WO | WO-2013/177086 A1 | 11/2013 |
| WO | WO-2013/177581 A2 | 11/2013 |
| WO | WO-2013/184643 A1 | 12/2013 |
| WO | WO-2013/192562 A1 | 12/2013 |
| WO | WO-2014/008447 A1 | 1/2014 |
| WO | WO-2014/012051 A1 | 1/2014 |
| WO | WO-2014/014497 A1 | 1/2014 |
| WO | WO-2014/014498 A1 | 1/2014 |
| WO | WO-2014/014950 A1 | 1/2014 |
| WO | WO-2014/015084 A2 | 1/2014 |
| WO | WO-2014/015319 A1 | 1/2014 |
| WO | WO-2014/018093 A1 | 1/2014 |
| WO | WO-2014/024041 A1 | 2/2014 |
| WO | WO-2014/026168 A1 | 2/2014 |
| WO | WO-2014/036488 A1 | 3/2014 |
| WO | WO-2014/039556 A1 | 3/2014 |
| WO | WO-2014/041380 A1 | 3/2014 |
| WO | WO-2014/052909 A2 | 4/2014 |
| WO | WO-2014/055774 A1 | 4/2014 |
| WO | WO-2014/060305 A1 | 4/2014 |
| WO | WO-2014/071070 A1 | 5/2014 |
| WO | WO-2014/071279 A2 | 5/2014 |
| WO | WO-2014/074246 A1 | 5/2014 |
| WO | WO-2014/078739 A1 | 5/2014 |
| WO | WO-2014/089241 A2 | 6/2014 |
| WO | WO-2014/142850 A1 | 9/2014 |
| WO | WO-2014/153188 A2 | 9/2014 |
| WO | WO-2014/166535 A1 | 10/2014 |
| WO | WO-2014/171969 A1 | 10/2014 |
| WO | WO-2014/172046 A2 | 10/2014 |
| WO | WO-2015/033229 A2 | 3/2015 |
| WO | WO-2015/123444 A2 | 8/2015 |
| WO | WO-2016/205253 A1 | 12/2016 |

OTHER PUBLICATIONS

Cooper et al., Experimental Review of Graphene, ISRN Condensed Matter Physics 2012: Art. ID 501686, 56 pages. (2012).

Definition of "Well", http://www.merriam-webster.com (2016). 1 page.

DeVolder et al., Carbon Nanotubes: Present and Future Commercial Applications, Science, 339: 535-539. (Feb. 1, 2013).

Fakih et al., Large area graphene ion sensitive field effect transistors with tantalum pentoxide sensing layers for pH measurement at the Nernstian limit, Applied Physics Letters 105: 083101 (Aug. 25, 2014). 6 pages.

Gao et al., The new age of carbon nanotubes: An updated review of functionalized carbon nanotubes in electrochemical sensors, Nanoscale 4:1948-1963. (2012).

Green et al., Interactions of DNA with graphene and sensing applications of graphene field-effect transistor devices: A review, Analytica Chimica Acta 853:127-142. (2015).

Kim. Lecture Notes, 2.76/2.760 Multiscale Systems Design & Manufacturing, downloaded from: http://ocw.mitedu/murses/mechanical-engineering/2-76-multi-scale-system-design-fall-2004/lecture-notes/lecture_15.pdf (Fall 2004). 49 pages.

Park et al., High-density integration of carbon nanotubes via chemical self-assembly, Nature Nanotechnology 7:787-791. (2012).

Schwierz, Frank; Graphene Transistors, Nature Nanotechnology 5:487-496 (May 30, 2010).

Tulevski et al., Toward High-Performance Digital Logic Technology with Carbon Nanotubes, ACS Nano 8(9):8730-8745. (Aug. 21, 2014).

Zhan et al., Graphene Field-Effect Transistor and Its Application for Electronic Sensing, Small 10(20):4042-4065. (Aug. 29, 2014).

Cheng, Zengguang et al. "Sensitivity Limits and Scaling of Bioelectronic Graphene Transducers.", *Nano Letters*, (2013), pp. 2902-2907, 13(6), ACS Publications.

Cheng, Zengguang et al. "Supporting Information for: Sensitivity Limits and Scaling of Bioelectronic Graphene Transducers.", (2013), 26 pages, pubs.acs.org. [retrieved from the Internet on Nov. 7, 2017].

Cheng, Zengguang et al. "Suspended Graphene Sensors with Improved Signal and Reduced Noise." *Nano Letters*, (2010), pp. 1864-1868, 10(5), pubs.acs.org.

Kim, Kihyun et al. "Electrical and pH Sensing Characteristics of Si Nanowire-Based Suspended FET Biosensors." *Proceedings of the 14th IEEE, International Conference on Nanotechnology*, IEEE, (Aug. 18-21, 2014), pp. 768-771.

Kim, Kihyun et al. "Suspended honeycomb nanowire ISFETs for improved stiction-free performance." *Nanotechnology*, (2014), pp. 345-501 (7 pages), 25(34), IOP Publishing, Bristol, GB.

Wang, Bei et al. "Oxide-on-graphene field effect bio-ready sensors." *Nano Research*, (2014), 7(9):pp. 1263-1270. Tsinghua University Press, CN.

\* cited by examiner

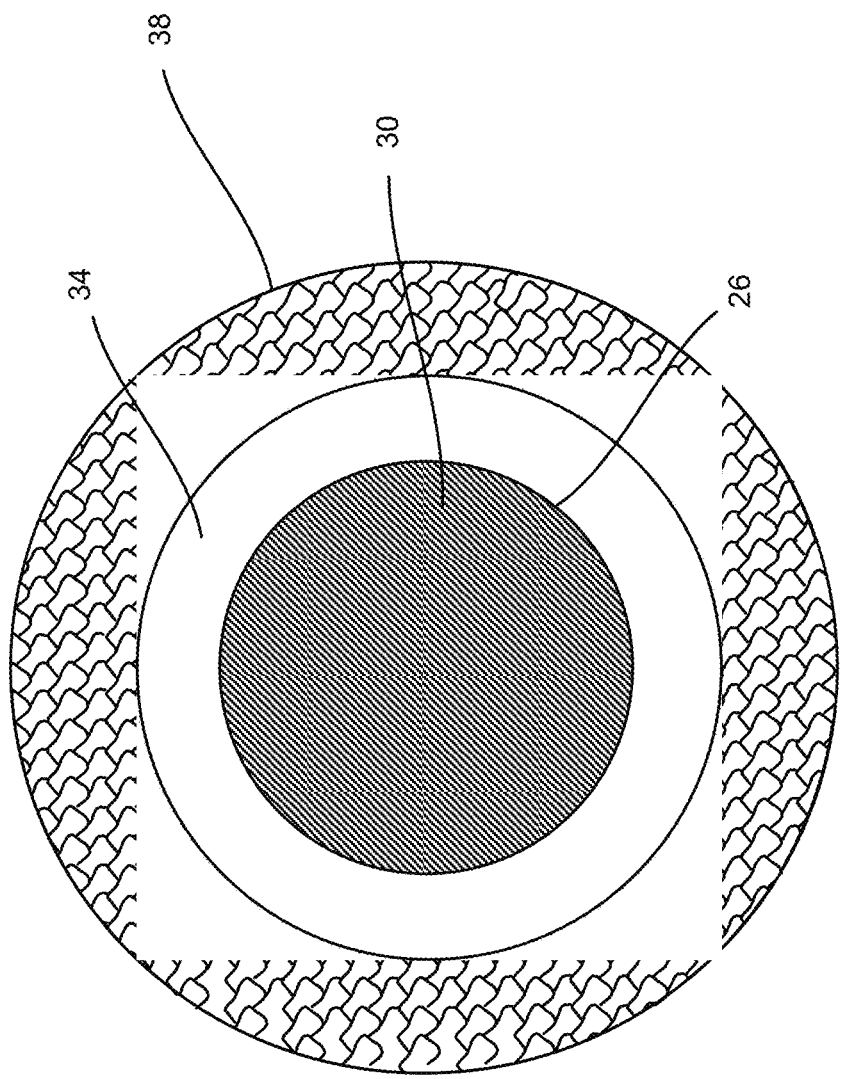

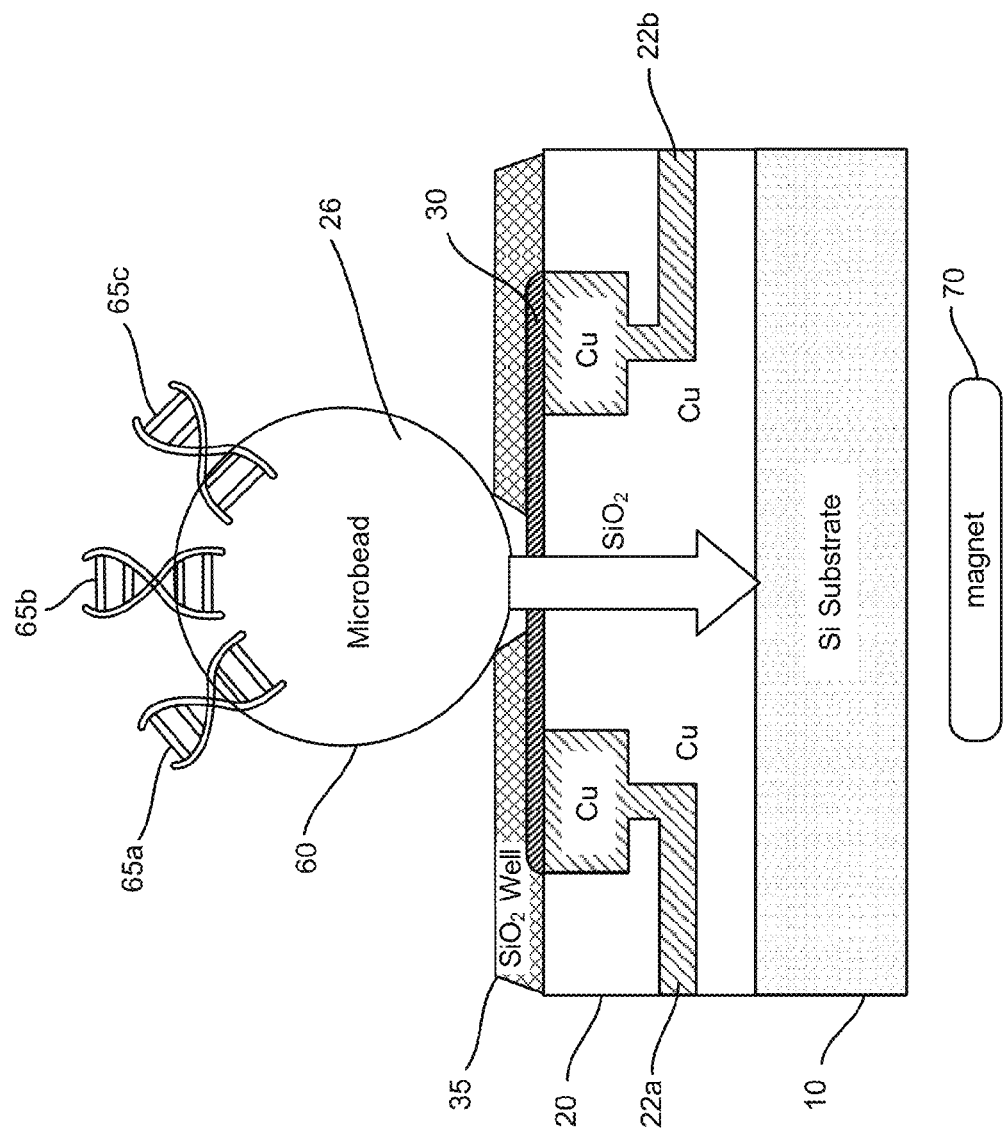

$$I1 = K + aV_g + bV_g^2 + cV_g^3...$$
$$I2 = K + xV_g + yV_g^2 + zV_g^3...$$

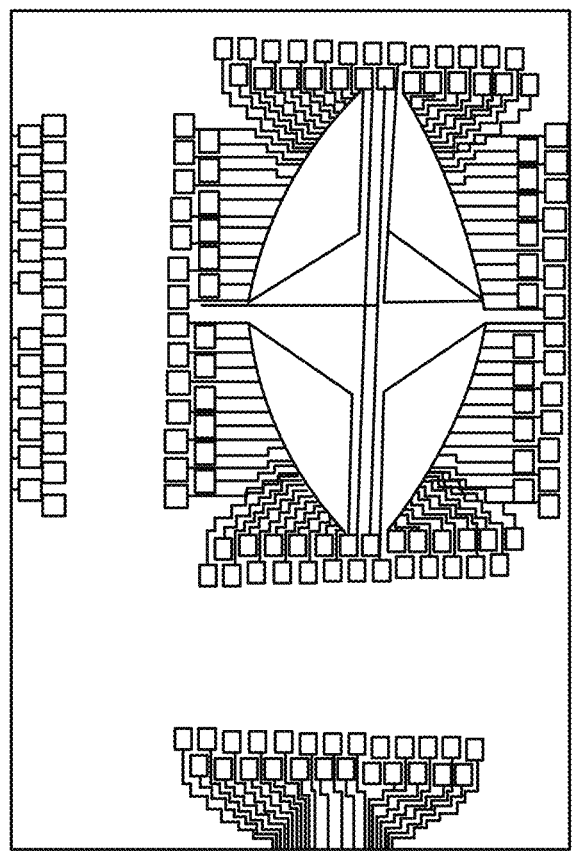
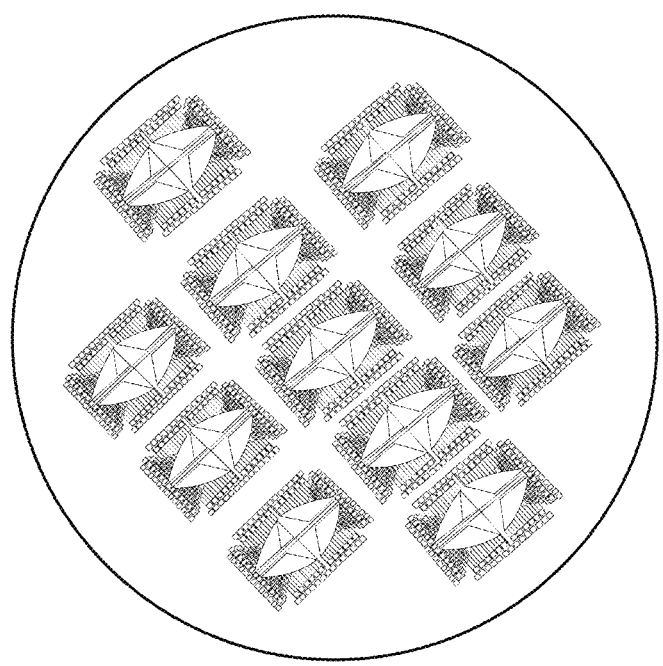
FIG. 10B

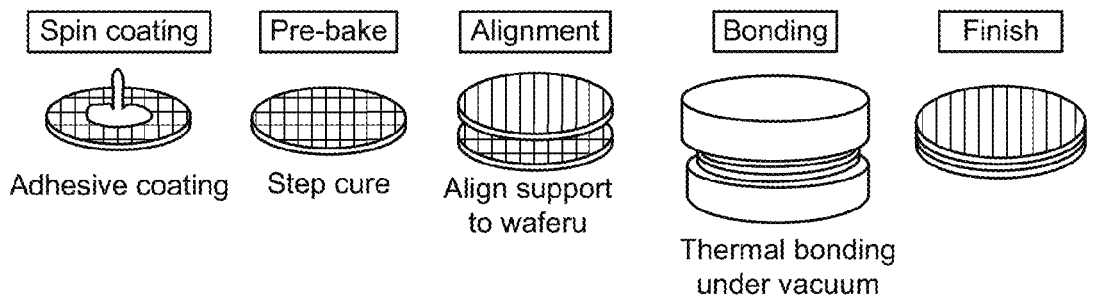
Adhesive spin coating ⟶ Bake ⟶ Bonding. A very simple process.
➢ Low Bonding pressure (0.12MPa)
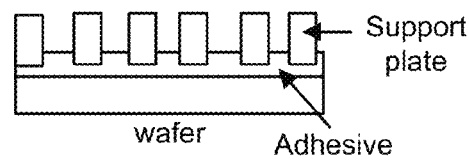
FIG. 22A
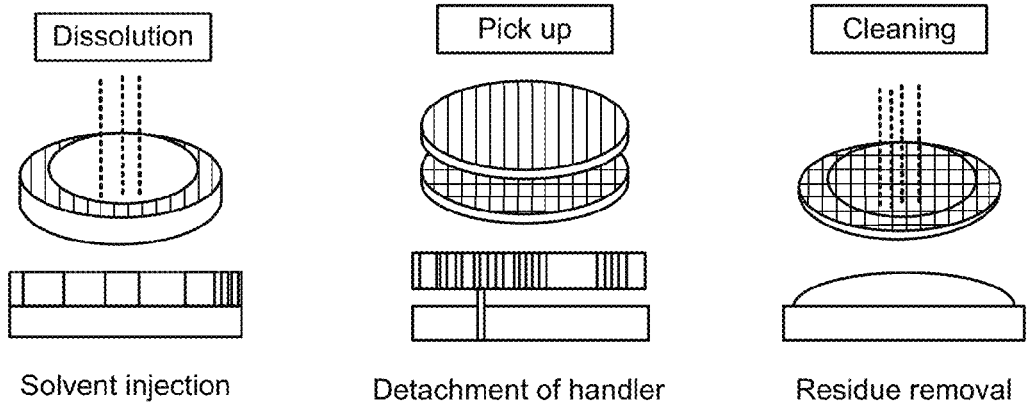
FIG. 22B

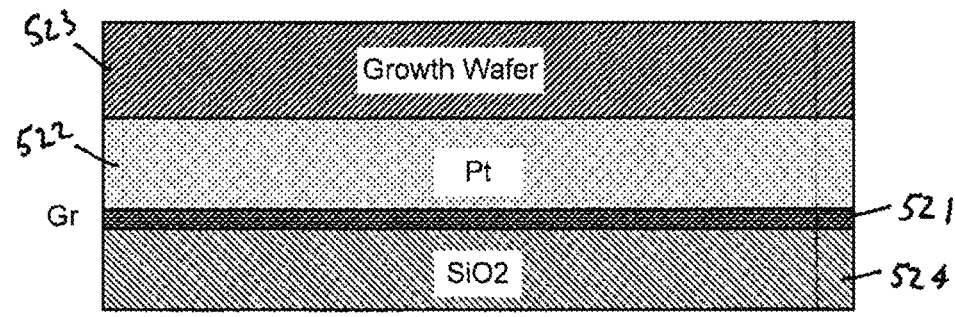
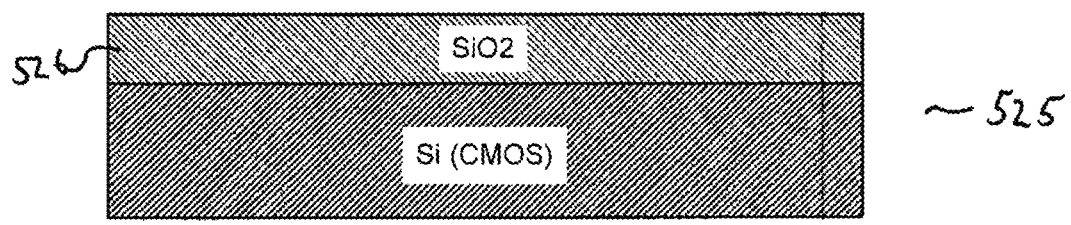
FIG. 25D
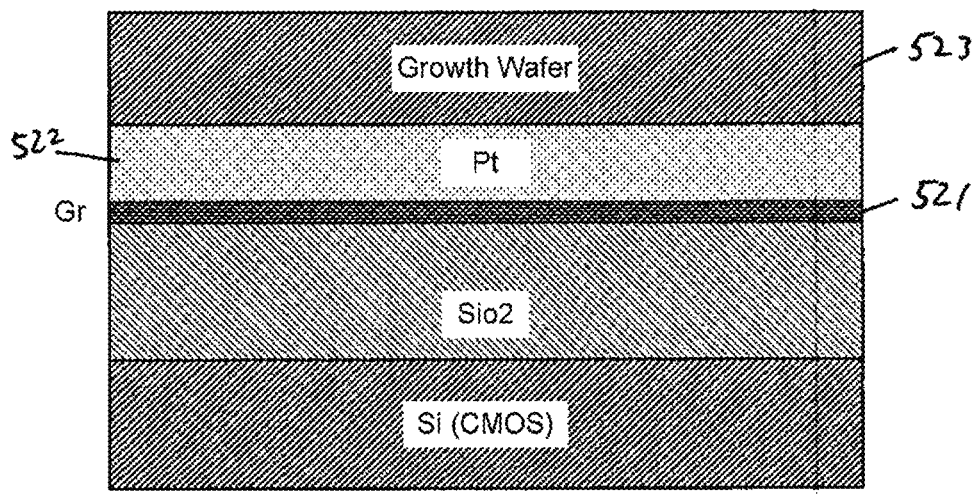
FIG. 25E

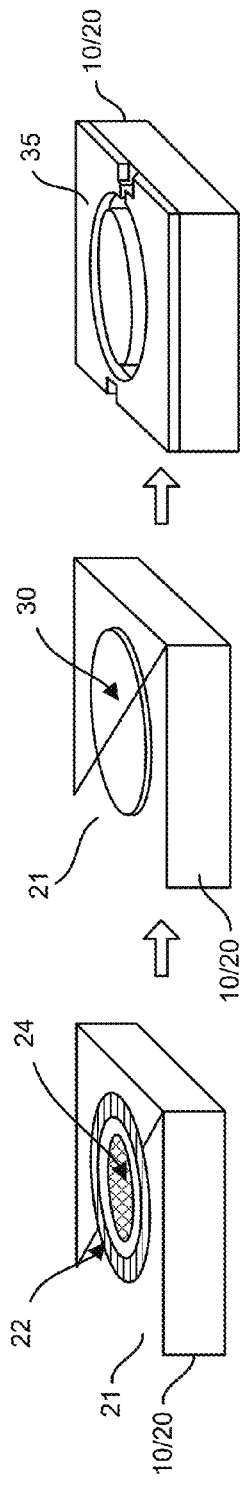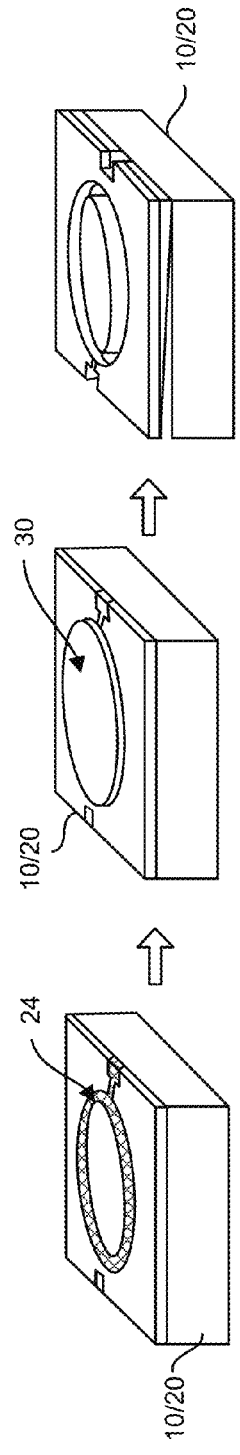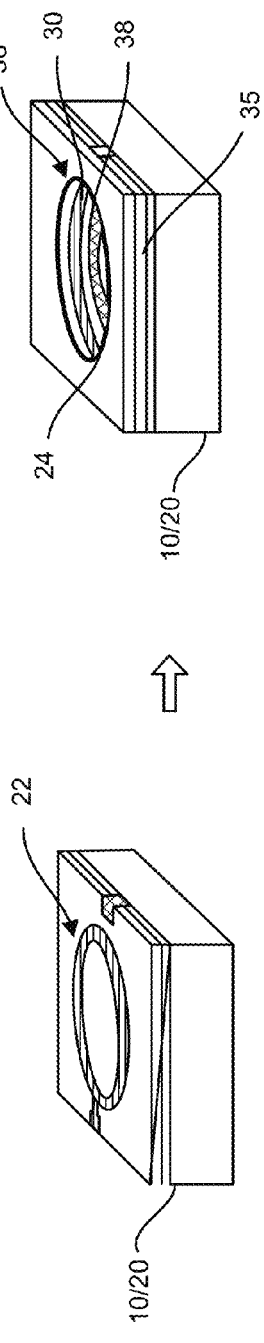

1) Thin inorganic layer on graphene

1) Thin inorganic layer on graphene

Etch oxide

Place graphene

Pattern graphene

1) Ion sensitive or other functional layer on graphene

2) Thin inorganic layer (etch stop layer) on the functional layer

1) Graphene deposited on exposed metal patterns

2) Photoresist patterns and etch under the graphene and Cu is channel (purple is ESL)

3) Etch Cu from beneath Graphene

Option with a functional layer over the graphene channel

CHEMICALLY-SENSITIVE FIELD EFFECT TRANSISTORS, SYSTEMS AND METHODS FOR MANUFACTURING AND USING THE SAME

CROSS REFERENCE TO RELATED APPLICATIONS

This application claims the benefit of priority to U.S. Provisional Application Ser. No. 62/206,228, filed on Aug. 17, 2015; U.S. Provisional Application Ser. No. 62/206,224, filed on Aug. 17, 2015; U.S. Provisional Application Ser. No. 62/205,803, filed on Aug. 17, 2015; U.S. Provisional Application Ser. No. 62/205,808, filed on Aug. 17, 2015; U.S. Provisional Application Ser. No. 62/206,166, filed on Aug. 17, 2015; U.S. Provisional Application Ser. No. 62/206,372, filed on Aug. 18, 2015; U.S. Provisional Application Ser. No. 62/206,814, filed on Aug. 18, 2015. This application is a continuation in part of U.S. application Ser. No. 15/225,764, filed on Aug. 1, 2016, which in turn claims benefit of U.S. Provisional Application Ser. No. 62/199,956, filed on Jul. 31, 2015 and U.S. Provisional Application Ser. No. 62/199,987, filed on Aug. 1, 2015. This application is a continuation in part of U.S. application Ser. No. 15/065,744, filed on Mar. 9, 2016, which in turn claims benefit of U.S. Provisional Application Ser. No. 62/130,598, filed on Mar. 9, 2015; U.S. Provisional Application Ser. No. 62/130,594, filed on Mar. 9, 2015; U.S. Provisional Application Ser. No. 62/130,601, filed on Mar. 9, 2015; U.S. Provisional Application Ser. No. 62/130,621, filed on Mar. 10, 2015; U.S. application Ser. No. 15/065,744 is a continuation in part of U.S. application Ser. No. 14/963,253, filed on Dec. 9, 2015, which in turn claims benefit of U.S. Provisional Application Ser. No. 62/094,016, filed on Dec. 18, 2014; U.S. Provisional Application Ser. No. 62/130,594, filed on Mar. 9, 2015; U.S. Provisional Application Ser. No. 62/199,987, filed on Aug. 1, 2015; and U.S. Provisional Application Ser. No. 62/206,228, filed on Aug. 17, 2015. This application is a continuation in part of U.S. application Ser. No. 15/182,533, filed on Jun. 14, 2016, which in turn claims benefit of U.S. Provisional Application Ser. No. 62/175,351, filed on Jun. 14, 2015. This application is a continuation in part of U.S. application Ser. No. 14/963,253, filed on Dec. 9, 2015, which in turn claims benefit of U.S. Provisional Application Ser. No. 62/094,016, filed on Dec. 18, 2014; U.S. Provisional Application Ser. No. 62/130,594, filed on Mar. 9, 2015; U.S. Provisional Application Ser. No. 62/199,987, filed on Aug. 1, 2015; and U.S. Provisional Application Ser. No. 62/206,228, filed on Aug. 17, 2015, the disclosures of which are incorporated herein in their entirety.

STATEMENT REGARDING FEDERALLY SPONSORED RESEARCH OR DEVELOPMENT

Not Applicable

BACKGROUND OF THE DISCLOSURE

Field of the Disclosure

The present disclosure generally relates to field effect transistors and methods of making and using the same for sequencing, diagnostics, and bioinformatics processing. More specifically, the present disclosure relates to one-dimensional and two-dimensional field effect transistors useful for chemical and biological analysis.

Description of the Related Art

The detection and sequencing of nucleic acids, such as deoxyribonucleic acid (DNA), is a fundamental part of biological discovery. Detection and/or sequencing are useful for a variety of purposes, and are often used in scientific research, drug discovery, medical diagnostics, and in the prevention, monitoring, and treatment of disease. For instance, the genomics and bioinformatics fields, which rely on nucleic acid detection and sequencing techniques, are concerned with the application of information technology and computer science to the field of molecular biology. In particular, bioinformatics techniques can be applied to process and analyze various genomic data, such as from an individual so as to determine qualitative and quantitative information about that data that can then be used by various practitioners in the development of diagnostic, prophylactic, and/or therapeutic methods and products for detecting, preventing, treating, or at least ameliorating disease states, thus improving the safety, quality, and effectiveness of health care. The need for such diagnostic, therapeutic, and prophylactic advancements has led to a high demand for low-cost nucleic acid detection and sequencing methods, devices, and reagents, which in turn have driven, for example, the development of high-throughput sequencing, termed as Next Generation Sequencing (NGS).

Generally, the approach to DNA analysis, such as for genetic diagnostics and/or sequencing, involves nucleic acid hybridization and detection. For example, various conventional hybridization and detection approaches include the following steps. For genetic analysis, an RNA or DNA sample obtained from a subject to be analyzed is isolated and immobilized on a substrate. A detectable probe of a known genetic sequence, e.g., having a nucleotide sequence that corresponds to a disease marker (e.g., a marker evidencing a bacterial, fungal, or viral infection, a single nucleotide polymorphism (SNP) associated with a particular disease such as cancer, an autoimmune disease, etc.) is then added to the substrate, typically in a reaction mixture containing the requisite reagents to allow the probe to interact with its target, if present in the sample. If the disease marker is present, a binding event, e.g., hybridization, will occur and because the probe is detectable (e.g., via the inclusion in the probe of a detectable label such as a fluorescent dye), the hybridization event can either be or not be detected, thereby indicating the presence or absence of the disease marker in the subject's sample.

For DNA/RNA sequencing and/or detection, first, an unknown nucleic acid sequence to be identified, e.g., a single-stranded sequence of DNA/RNA from a subject, is isolated, amplified, and immobilized on a substrate. Next, in the presence of a primer complementary to a portion of the isolated nucleic acid sequence to be sequenced and/or identified, (preferably labeled) nucleotides, and a suitable DNA polymerase, a nucleic acid sequencing and/or detection reaction may take place. In such an instance, where the primer recognizes a corresponding sequence of the isolated and/or bound nucleic acid sequence, the polymerase can begin to add one or more labeled nucleotides to extend the primer in the presence of the unknown nucleic acid sequence, using the unknown nucleic acid sequence as the template. When the primer is extended, the most recently added labeled nucleotide, which hybridizes via hydrogen-bonding to its complementary base in the unknown sequence immobilized on the surface of the substrate, the most recent nucleotide's addition can then be detected, e.g., optically or electrically. These steps are then repeated until the entire DNA/RNA molecule has been completely sequenced. Typically, these steps are performed on a Next Gen Sequencer wherein thousands to millions of DNA fragments can be sequenced concurrently in the NGS process.

As will be appreciated, a central challenge in DNA sequencing based on the sequencing of numerous short DNA fragments is assembling full-length genomic sequences, e.g., chromosomal sequences, from a sample of genetic material, as the sequencing methods used in NGC processes do not produce full-length gene or chromosomal sequences from the sample DNA that can then be used for a desired genetic analysis, e.g., SNP genotyping, assessment of genetic variation or identity between the subject's sample and a reference gene, genome, etc. Rather, sequence fragments, typically from 100-1,000 nucleotides in length, are produced without any indication as to where in the genome they reside. Therefore, in order to generate full-length gene or chromosomal genomic constructs, or determine variants with respect to a reference genomic sequence, such DNA sequence fragments need to be mapped, aligned, merged, and/or compared to a reference genomic sequence. Through such processes the variants of the sample genomic sequences from the reference genomic sequences may be determined by suitable bioinformatics approaches, such as by implementing a suitable variant calling application.

Even so, as the human genome comprises approximately 3.1 billion base pairs, and as each sequence fragment in an NGS process is typically only from 100 to 500 to 1,000 nucleotides in length, the time and effort that goes into building full-length genomic sequences and determining the genetic variants therein is quite extensive, often requiring the use of several different computer resources applying several different algorithms over prolonged periods of time. This is because in a given NGS analysis, thousands, millions, or even billions of DNA sequences are generated, which sequences must then be aligned and merged in order to construct a genomic sequence that approximates a chromosome or genome in size. A step in this process often includes comparing the DNA fragment sequences to a reference sequence to determine where in the genome the fragments reside.

In order to perform an NGS analysis, genetic material from a subject must be pre-processed. This preprocessing may be done manually or via an automated sequencer. Typically, preprocessing involves obtaining a biological sample from a subject, such as through venipuncture (blood, plasma, serum), buccal swab, urine, saliva, etc., and treating the sample to isolate the DNA therefrom. Once isolated, the DNA is then fragmented and denatured. The DNA (or portions thereof) may then be amplified, e.g., via polymerase chain reaction (PCR), so as to build a library of replicated strands that are now ready to be sequenced, such as by an automated sequencer. The sequencing machine is configured to sequence the amplified DNA strands, e.g., by synthesis of new, complementary strands that include labeled nucleotides, from which the nucleotide sequences that make up the DNA in the sample can be determined.

Further, in various instances, such as in building the library of amplified strands, it may be useful to provide for over-coverage or over-representation when preprocessing a given portion of the DNA. To provide this over-representation, increased sample preparation may be required, thus making the process more expensive, although such steps often yield an enhanced probability of the end result being more accurate.

Once a library of amplified DNA strands has been generated, the strands may be injected into an automated sequencer that can then determine the nucleotide sequences of the strands, such as by synthesis. For instance, amplified single-stranded DNA can be attached to a nano- or microbead and inserted into a test vessel, e.g., an array. All the necessary components for synthesis of its complementary strand, including labeled nucleotides (for adenine (A), cytosine (C), guanine (G), and thymine (T)), are also added to the vessel but in a sequential fashion. In some instances, one or more the nucleotides, e.g., "A", "C", "G", and "T's" that are added may be configured so as to be reversible terminators, e.g., such that once incorporated into a growing strand being synthesized cause the synthesis reaction for that particular strand to be terminated at that point of incorporation, thereby producing several strands of terminated sequences that collectively represent the entire template nucleic acid sequence. Hence, in performing a nucleic acid synthesis or detection reaction all of the necessary nucleotide reactants are added, either one at a time or all together, to see which of the nucleotides is used to extend a primer molecule.

Particularly, after each addition, unincorporated nucleotides are washed away and a light, e.g., a laser, is then shone on the array. If the reaction fluoresces, that fluorescence can be detected, thereby indicating which nucleotide has been added and, due to the nature of the genetic code, which complementary nucleotide was present in the template DNA fragment in the subject location. In processes where labeled nucleotides are added one at a time, if extension occurs, then it's indicative fluorescence will be observed. If extension does not occur, the test vessel may be washed and the procedure repeated until the appropriate one of the four nucleotides binds to its complement and is incorporated by the polymerase into the growing DNA strand at the subject location such that its indicative fluorescence can be detected.

Where all four reversible terminator nucleotides are added at the same time, each may be labeled with a different fluorescent indicator; when the complementary labeled nucleotide binds to its complement in the template DNA strand such that it is then added by the polymerase during the elongation step, the identity of the added, labeled nucleotide at the subject position can then be determined, such as by the color of its fluorescence. As will be appreciated, the use of all four labeled nucleotides in a given reaction greatly accelerates the synthesis process.

After each elongation reaction, the complex is then washed and the synthesis steps are repeated for the next position. This process of elongation and detection is then repeated for all nucleotides for as many positions as are present in the input DNA fragments or for so long as the sequencing machine directs (e.g., 100, 500, 1,000, or more cycles), thereby generating "sequence reads" of the over-sampled nucleic acid segments. The resulting sequence data is collected.

Usually a typical length of a sequence replicated in this manner is from about 100 to about 500 or about 1000 base pairs, such as between 150 to about 400 base pairs, including from about 200 to about 350 base pairs, such as about 250 base pairs to about 300 base pairs dependent on the sequencing protocol being employed. Further, the length of these segments may be predetermined, e.g., engineered, to accord with any particular sequencing machinery and/or protocol by which it is run. In any event, the end result is a readout, or "read", that is comprised of an extended DNA fragment synthesized from an input DNA fragment.

Extended DNA fragments typically range from about 100 to about 1,000 nucleotides in length, and each nucleotide is labeled in such a manner that every nucleotide in the sequence can be identified because of its label. Hence, since the human genome is comprised of about 3.1 billion base pairs, and various known sequencing protocols usually result in labeled replicated sequences, e.g., reads, from about 100 or 101 bases to about 250 or about 300 or about 400 bases, the total number of segments that need to be sequenced, and consequently the total number of reads generated for single read coverage can be anywhere from about 10,000,000 to about 40,000,000, such as about 15,000,000 to about 30,000,000, dependent on how long the label replicated sequences are.

Therefore, the sequencer may typically generate about 30,000,000 reads, such as where the read length is 100 nucleotides in length, so as to cover the genome once. However, to ensure the accuracy of a particular base call (e.g., A, C, G, or T) at a particular nucleotide position, it is desirable that copies of each fragment in a sample be sequenced 5, 10, 20, 30, or more times, in some cases up to 500 or more times. Such over-sampling thus results in even more reads, thereby requiring more analysis. Fragment amplification in the pre-processing phase helps to facilitate such redundancy.

However, in part, due to the need for the use of optically detectable, e.g., fluorescent, labels in the sequencing reactions being performed, the required instrumentation for performing such high throughput sequencing is bulky, costly, and not portable. For this reason, a number of new approaches for direct, label-free DNA sequencing have been proposed. For instance, among the new approaches are detection methods that are based on the use of various electronic analytic devices. Such direct electronic detection methods have several advantages over the conventional NGS platform. For example, the detector may be incorporated in the substrate itself, such as employing a biosystem-on-a-chip device, such as a complementary metal oxide semiconductor ("CMOS") device.

More particularly, in using a CMOS device in genetic detection, the output signal representative of a nucleotide's addition in a DNA sequencing reaction can be directly acquired and processed on a microchip. In such an instance, automatic recognition is achievable in real time and at a lower cost than is currently achievable using conventional NGS processes and equipment. Moreover, standard CMOS devices may be employed for such electronic detection, making the process simple, inexpensive, and portable.

Particularly, in order for NGS methods to become widely used for diagnostic and therapeutic applications in the healthcare industry, sequencing instrumentation will need to be mass produced with a high degree of quality and economy. One way to achieve this is to recast DNA sequencing in a format that fully leverages the manufacturing base created for computer chips, such as CMOS chip fabrication, which is the current pinnacle of high technology large scale, high quality, low-cost manufacturing. To achieve this, ideally, the entire sensory apparatus of the sequencing device should be embodied in a standard semiconductor chip, manufactured in the same fabrication ("Fab") facilities used for logic and memory chips. Recently, such a sequencing chip, and the associated sequencing platform, has been developed and commercialized by Ion Torrent, a division of Thermo-Fisher, Inc. The promise of this idea has not been realized commercially, however, due to the fundamental limits of applying a metal oxide semiconductor field effect transistor, or MOSFET, as a biosensor. In particular, when a MOSFET is used in solution as a biosensor, it is referred to as an ISFET (ion sensitive field effect transistor). Particular limitations of ISFET devices include a lack of sensor sensitivity and signal-to-noise characteristics as the semiconductor node scales down to lower geometries of the transistor (gate length).

As is known, a field effect transistor (FET) typically includes a gate, a channel region connecting source and drain electrodes, and an insulating barrier separating the gate from the channel. The operation of a conventional FET relies on the control of the channel's conductivity, and thus the drain current, by a voltage, designated $V_{GS}$, applied between the gate and source. For high-speed applications, and for the purposes of increasing sensor sensitivity, FETs should respond quickly to variations in $V_{GS}$. However, this requires short gates and fast carriers in the channel. Unfortunately, FETs with short gates frequently suffer from degraded electrostatics and other problems (collectively known as short channel effects), such as threshold-voltage roll-off, drain-induced barrier lowering, and impaired drain-current saturation, which result in a decrease in sensor sensitivity. Nevertheless, scaling theory predicts that a FET with a thin barrier and a thin gate-controlled region (measured in the vertical direction) should be robust against short-channel effects down to very short gate lengths (measured in the horizontal direction).

Accordingly, the possibility of having channels that are very thin in the vertical dimension would allow for high-speed transmission of carriers as well as for increased sensor sensitivity and accuracy. What is needed, therefore, is a FET device that is configured in such a manner as to include a shorter gate than is currently achievable in present FET applications. A solution that includes such a FET device designed for use in biological applications, such as for nucleic acid detection, sequencing, and/or other diagnostic applications, would be especially beneficial.

SUMMARY OF THE INVENTION

The present disclosure addresses the aforementioned mentioned shortcomings of conventional NGS systems and current ISFET-based sequencing approaches. This disclosure is directed to a patentable class of chemically-sensitive field-effect transistors (FETs) that resolve many of the current issues associated with chemical and biological analyses, for example, nucleic acid hybridization, NGS sequencing, hybridization detection, genetic diagnostics, genome identification, species identification, nucleic acid capture, etc., systems incorporating such chemically-sensitive FETs, and methods of making and using such chemically-sensitive FETs.

One aspect of the present disclosure is a chemically-sensitive field effect transistor (FET). These chemically-sensitive FETs are preferably fabricated using semiconductor fabrication methods on a semiconductor wafer used for semiconductor manufacturing, and in preferred embodiments, on top of an integrated circuit structure made using semiconductor fabrication methods. The instant chemically-sensitive FETs typically comprise a conductive source, a conductive drain, and a channel composed of a one-dimensional (1D) or two-dimensional (2D) and/or three-dimensional (3D) transistor material, which channel extends from the source to the drain and may be fabricated using semiconductor fabrication techniques on top of a wafer. For instance, a substrate, such as a silicon substrate may be provided, upon which a non-conductive layer, e.g., an oxide layer, may be positioned, within which the source and drain electrodes may be deposited, and a channel member formed there between, which channel member may additionally be at least partially covered or coated with another non-conductive layer, such as an oxide layer. Specifically, in various embodiments, a non-conductive, e.g., oxide, layer may be disposed on the channel member and/or across the channel region. In some embodiments, chemically-sensitive FET may also include a gate or gate region, e.g., a solution gate, and/or a reference electrode. A processor and associated circuitry may also be included or otherwise be functionally associated with a chemically-sensitive FET of the disclosure (array thereof) in order to process and analyze signals generated thereby.

In use, desired chemical reactions that occur in proximity to the chemically-sensitive FET result in a change in conductance that can be sensed. Particularly, changes in conductance through the 1D, 2D, and/or 3D channel member connecting the source and the drain electrodes may be detected. For instance, in some embodiments, sensing of a desired reaction produces an alteration, e.g., a shift, in an I-V curve, for example, an I-$V_g$ curve, or a parameter of an I-$V_g$ curve, e.g., the curve's slope or position relative to the horizontal axis, corresponding to the chemically-sensitive field effect transistor. A processor functionally associated with the chemically-sensitive FET may be used to compare a reference I-V curve (or parameter thereof) for the well (or other capture region or structure) and an I-V curve (or the corresponding parameter thereof) generated in connection with a chemical reaction in well (or other capture region or structure associated with the chemically-sensitive FET). If the processor detects a difference between the reference and reaction-associated curves that exceeds a predetermined threshold, a positive result can be indicated.

Another aspect of the present invention concerns biosensors based on a chemically-sensitive FET according to the invention. Such biosensors may include a CMOS structure comprising a substrate and a non-conductive, e.g., oxide, layer having a copper source and a copper drain, a 1D or 2D, e.g., graphene, or 3D channel extending from the source to the drain, and further including a well, chamber, or other structure suitable for analyte capture and analysis associated with an exterior surface of the first oxide layer and/or the channel material member. An additional non-conductive, e.g., oxide, layer may be disposed on and/or around the channel material and/or channel region, which oxide layer may be configured so as to form the well and/or chamber. The oxide layer may be comprised of an oxide, for example, an aluminum oxide or a silicon oxide. In some embodiments, the oxide layer may be a thin layer, such as a layer having a thickness of about 9 nanometers (nm), 7 nm, 4 nm, or less. The well (or other or configuration) structure defines an opening allowing for direct contact with the channel material, e.g., the graphene channel. In some embodiments, sensing the occurrence of a desired chemical reaction, e.g., detection of a target biological compound or reactant thereof, is detectable such as by detecting a change in the conductance through the channel material and/or the production of a shift in an I-V curve or an I-$V_g$ curve corresponding to that change in conductance as determined by the chemically-sensitive field effect transistor.

Yet another aspect of the present disclosure is a chemically-sensitive graphene field effect transistor (GFET). A GFET according to the disclosure may include a CMOS structure comprising a damascene copper source, a damascene copper drain, and a graphene channel extending from the source to the drain. An oxide layer may also be included and disposed on or around the channel. The oxide layer may be composed of an aluminum oxide or a silicon oxide. In some embodiments, the oxide layer may be a thin layer, such as a layer having a thickness of about 9 nanometers (nm), or 7 nm, or 4 nm, or less. In particular embodiments, sensing of a desired chemical reaction, e.g., detection of a target biological compound, produces a shift in an I-V curve or an I-$V_g$ curve corresponding to the GFET.

Another aspect of the invention relates to methods of making chemically-sensitive FETs, particularly chemically-sensitive GFETs, of the invention. In some embodiments, these methods involve well formation on a 2D material FET. Preferably, such methods include depositing a protective layer on a channel of a 2D material FET of a semiconductor device structure. These methods also include etching through the majority of the protective layer with a first etching method to create a majority of a well formed over the channel. These methods can also include a second etching of the remaining protective layer over the channel to expose the channel within the formed well. In preferred embodiments, the protective layer is comprised of an inorganic material, for example, an oxide, a nitride, a carbide, an oxy-nitride, a carbon-doped oxide, or a fluorine-doped oxide material. In others embodiments, the protective layer is composed of an organic material, such as a polymer. In yet other embodiments, the protective layer is composed of both inorganic and organic materials.

Other embodiments concern methods for manufacturing a well formation for a 2D material FET with an organic protective layer. The method includes depositing an organic protective layer on a channel of a 2D material FET of a semiconductor device structure. The method also includes patterning the organic protective layer to create well formation locations over the channel. The method also includes removing the protective layer over the channel to expose the channel within the well formation.

In a related manufacturing aspect, the methods of the disclosure include depositing a 1D or a 2D material, for example, graphene, or 3D material, to form a channel on an exposed conductive, e.g., metal, layer of an integrated circuit structure. The integrated circuit structure may include a semiconductor substrate, a dielectric layer and/or non-conductive layer, and the conductive, e.g., metal or electrode, layer. These methods may also include utilizing a patterned material to expose a portion of a channel area and one or more adjacent areas. These methods may also include etching the dielectric material, e.g., starting with the adjacent areas, thereby exposing a trench under the channel and exposing the metal in the channel area. Such methods may also include etching the metal from underneath the channel, e.g., graphene, material to create a chemically-sensitive FET.

Another aspect of the disclosure relates to methods for preparing a growth substrate that are useful to produce the chemically-sensitive FETs, particularly chemically-sensitive GFETs, of the disclosure. These methods may include depositing a metal catalyst layer, e.g., Ni, Ru, Cu or Pt, on a substrate and annealing the metal catalyst, wherein the annealing may occur in an environment that includes hydrogen such that the resulting metal catalyst layer is a predominantly single crystalline metal catalyst layer with a crystal orientation. Such methods also include activating the metal catalyst layer by a plasma method such as includes a hydrogen gas and a nitrogen-containing gas.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE DRAWINGS

This patent application contains at least one drawing executed in color. Copies of this patent or patent application publication with color drawing(s) will be provided by the Office upon request and payment of the necessary fee. In this description, like numbers refer to like elements in the figures.

FIG. 1AA shows a side sectional view of an integrated circuit with a second insulating dielectric layer during the process of forming a well proximate the integrated circuit.

FIG. 1BB illustrates a side sectional view of an integrated circuit with a patterned second insulating dielectric layer during the process of forming a well proximate the integrated circuit.

FIG. 2D is a top plan view of a chemically-sensitive FET with another configuration of a well structure.

FIG. 5A is an illustration of the substrate of FIG. 1A, having a silicon dioxide layer positioned above a graphene layered reaction zone, and utilizing a magnetic field for the positioning of a nano- or micro-bead to be associated therewith.

FIG. 10B is an illustration of an exemplary graphene field-effect transistor and chip.

FIG. 22A illustrates an adhesive temporary bond material process.

FIG. 22B illustrates an adhesive temporary bond material process.

FIG. 25B illustrates a deposit cover material and CMP or polish surface step of direct bond transfer via fusion bonding.

FIG. 25C illustrates a wafer-flipping step of direct bond transfer via fusion bonding.

FIG. 25D illustrates a ROIC preparation and ROIC alignment step of direct bond transfer via fusion bonding.

FIG. 25E illustrates a bonding a cover material to a ROIC wafer top insulator step of direct bond transfer via fusion bonding.

FIG. 25F illustrates a growth substrate removal from the ROIC wafer, leaving the graphene on the ROIC step of direct bond transfer via fusion bonding.

FIG. 26A illustrates a graphene on a ROIC wafer step of a CMOS integration method.

FIG. 26B illustrates a patterning a graphene layer to form channels step of a CMOS integration method.

FIG. 26C illustrates a depositing an etch stop layer over a graphene layer to step of a CMOS integration method.

FIG. 26D illustrates a deposit, pattern and etch a thick insulator layer step of a CMOS integration method.

FIG. 26E illustrates a wet etch ESL, pattern and DRIE oxide over interconnects step of a CMOS integration method.

FIG. 26F illustrates an optional addition of work function matching material prior to a via fill step of a CMOS integration method.

FIG. 26G illustrates a deposit a barrier, liner, copper plate, CMP step of a CMOS integration method.

Figure 26A:
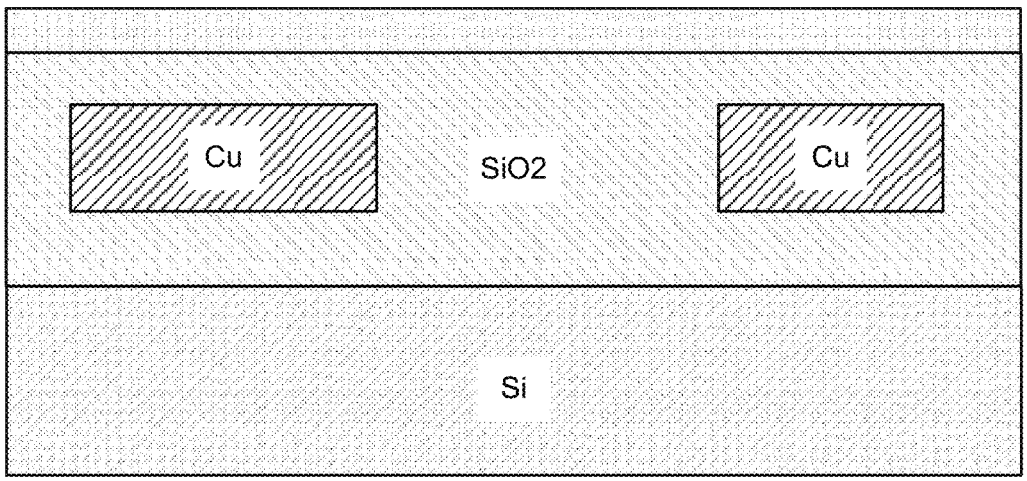
Figure 26B:
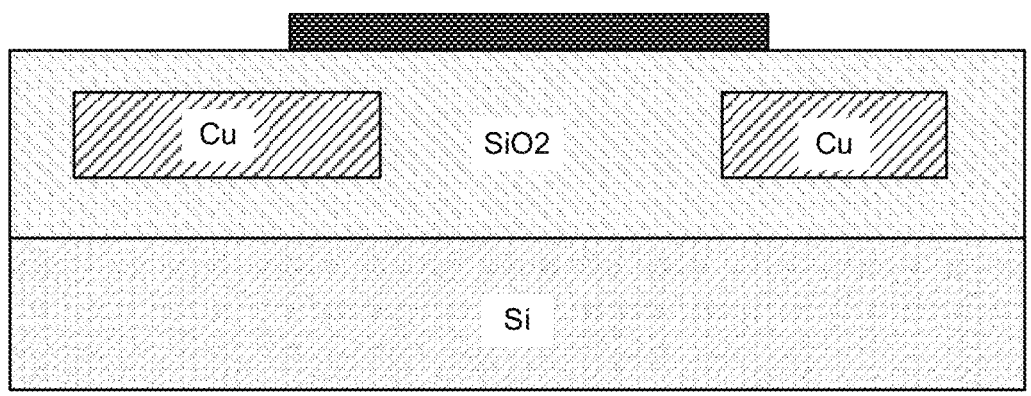
Figure 26C:
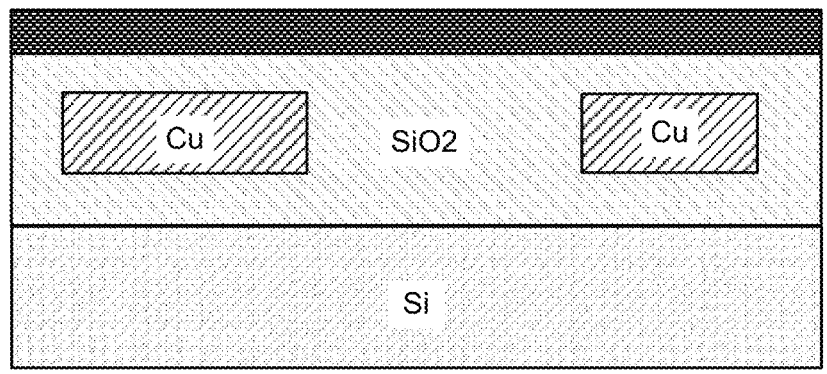
Figure 26D:
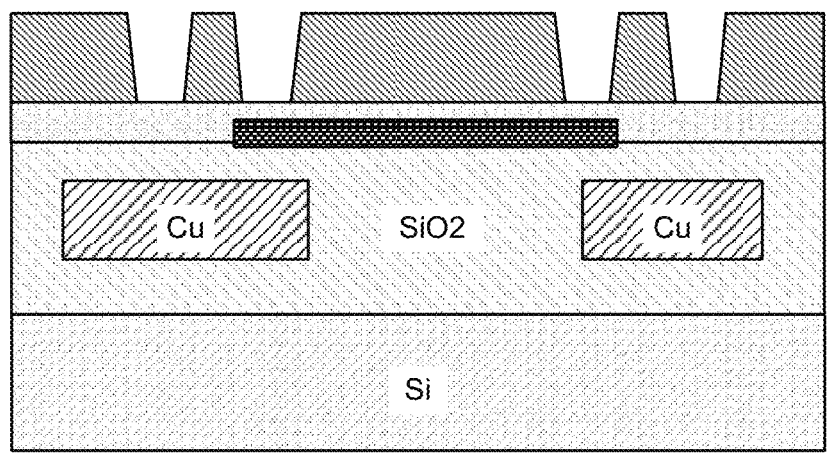
Figure 26E:
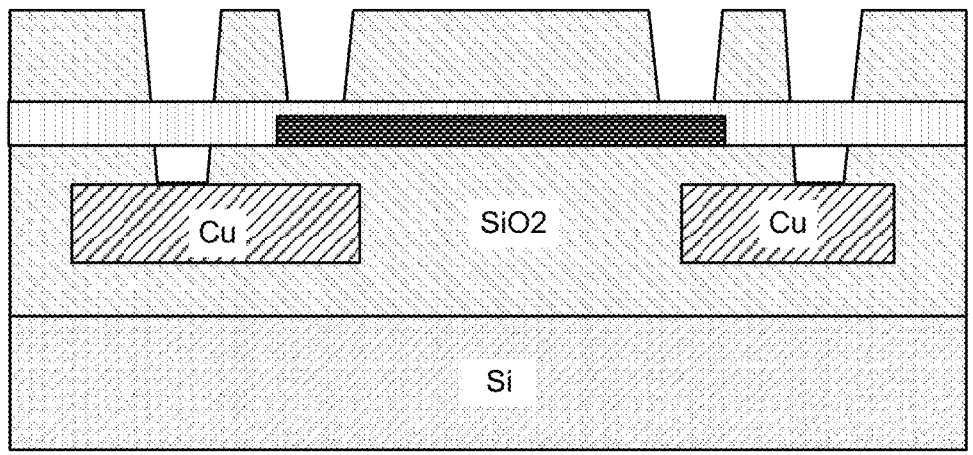
Figure 26F:
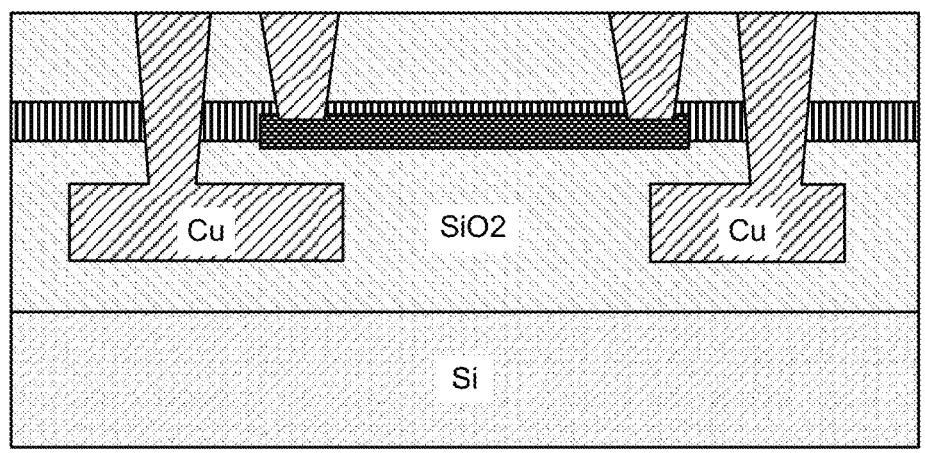
Figure 26G:
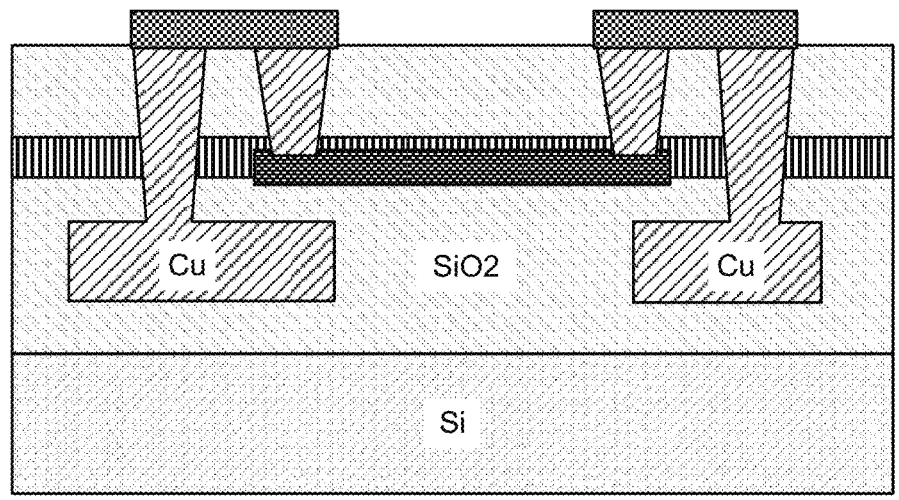
Figure 26H:
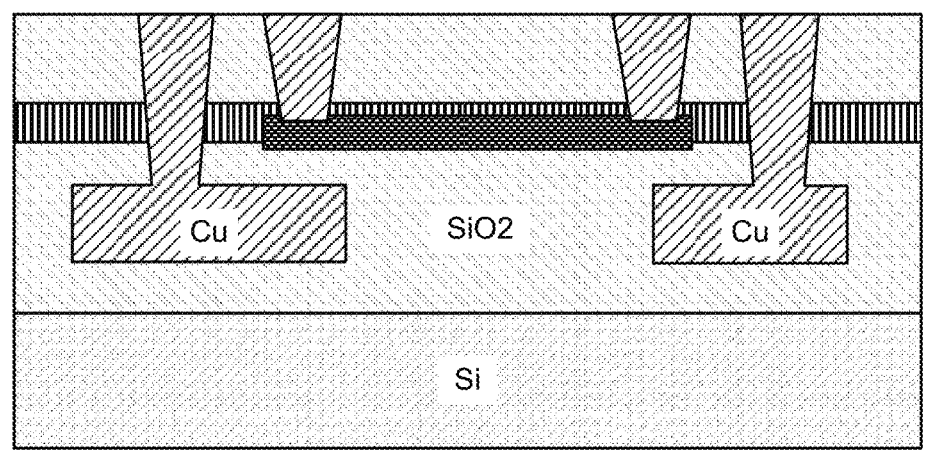

FIG. 26H illustrates a deposit a barrier, liner, copper plate, CMP step of a CMOS integration method.

Figure 26I:
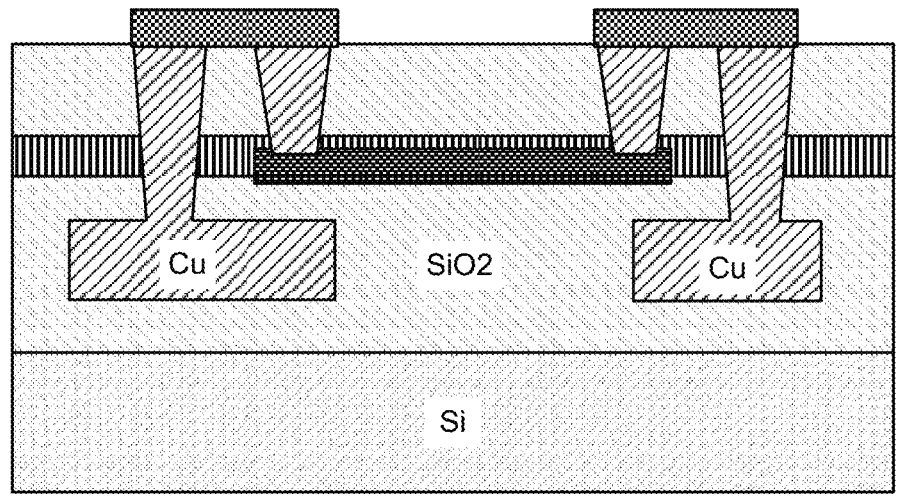

FIG. 26I illustrates a deposit a barrier/adhesion layer, deposit aluminum, pattern, etch aluminum interconnect and pad layer step of a CMOS integration method.

Figure 26J:
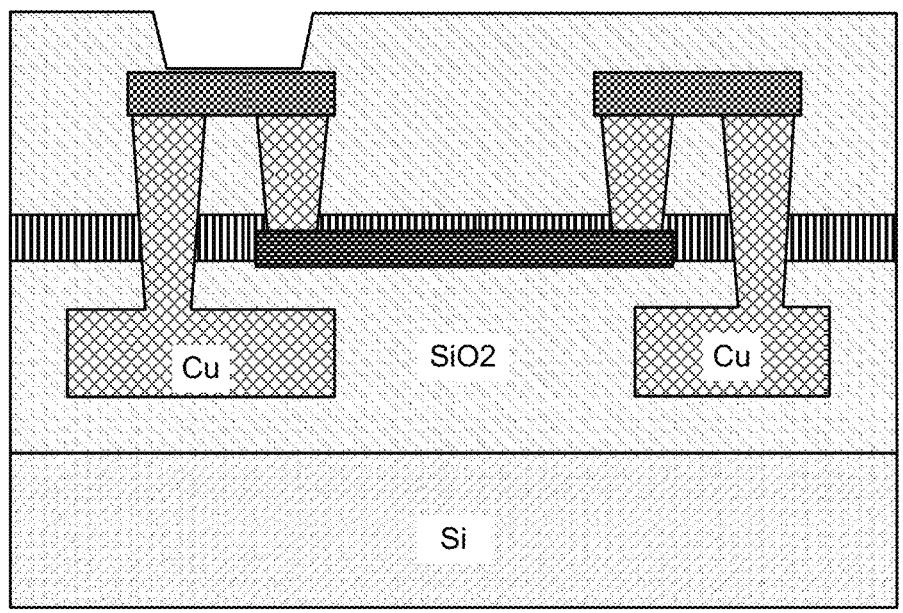

FIG. 26J illustrates a deposit $SiO_2$ (e.g. CVD), CMP, pad open etch step of a CMOS integration method.

Figure 26K:
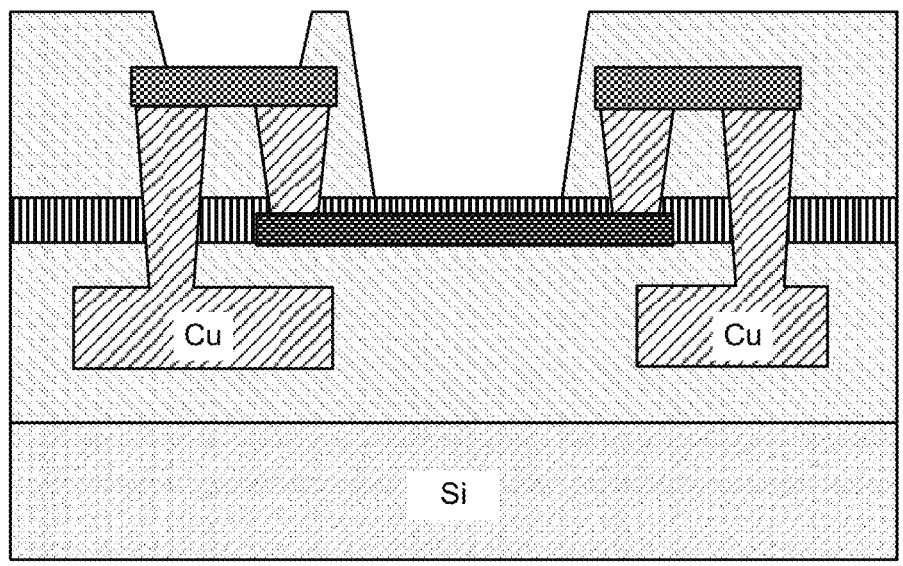

FIG. 26K illustrates a DRIE well insulator down to an etch stop layer step of a CMOS integration method.

Figure 26L:
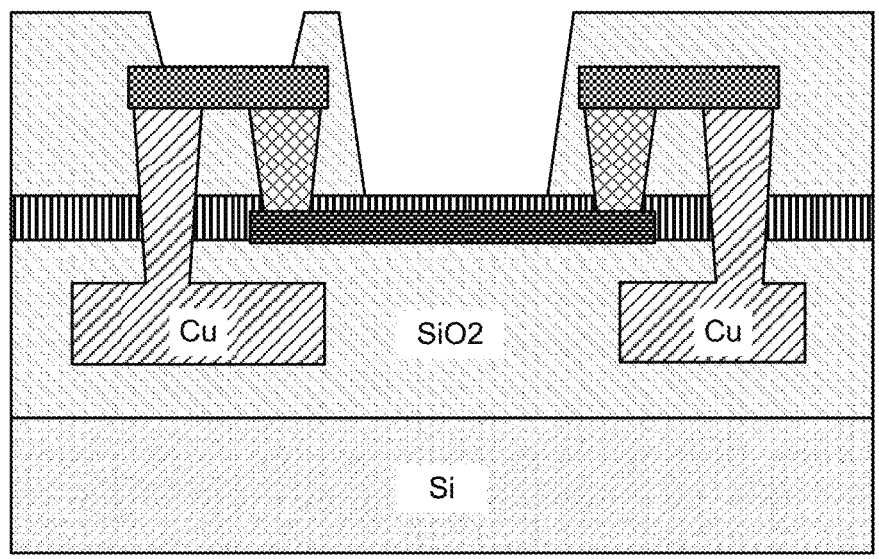

FIG. 26L illustrates a wet etch a thin etch stop layer step of a CMOS integration method.

Figure 26M:
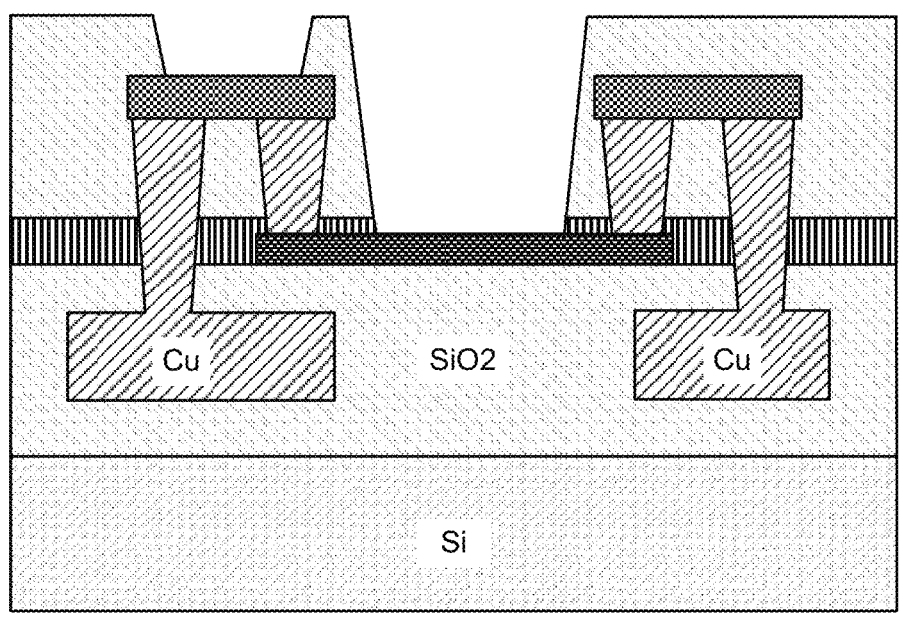

FIG. 26M illustrates a wet etch ESL open etch step of a CMOS integration method.

Figure 27:
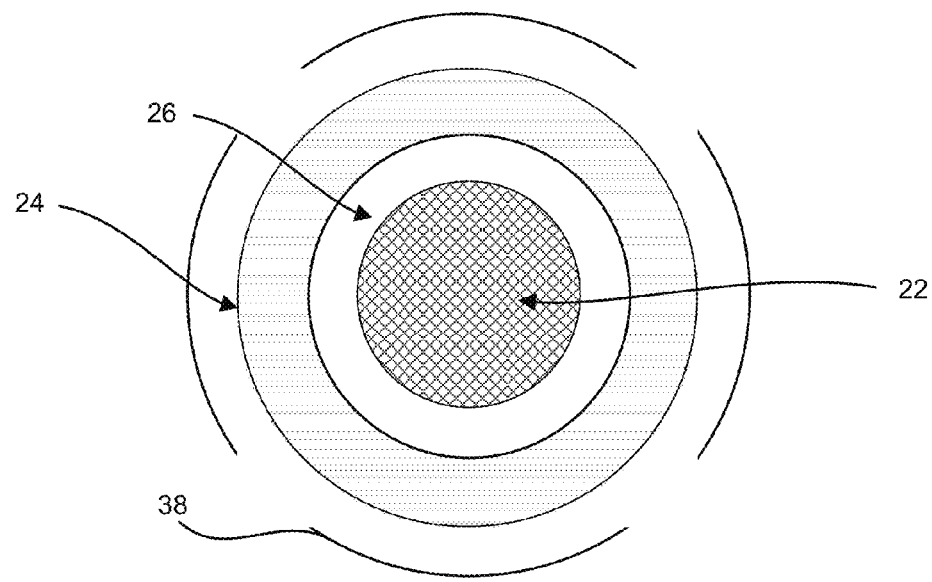

FIG. 27 is an illustration of a top plane view of a source and drain electrodes at the bottom of a well.

Figure 28:
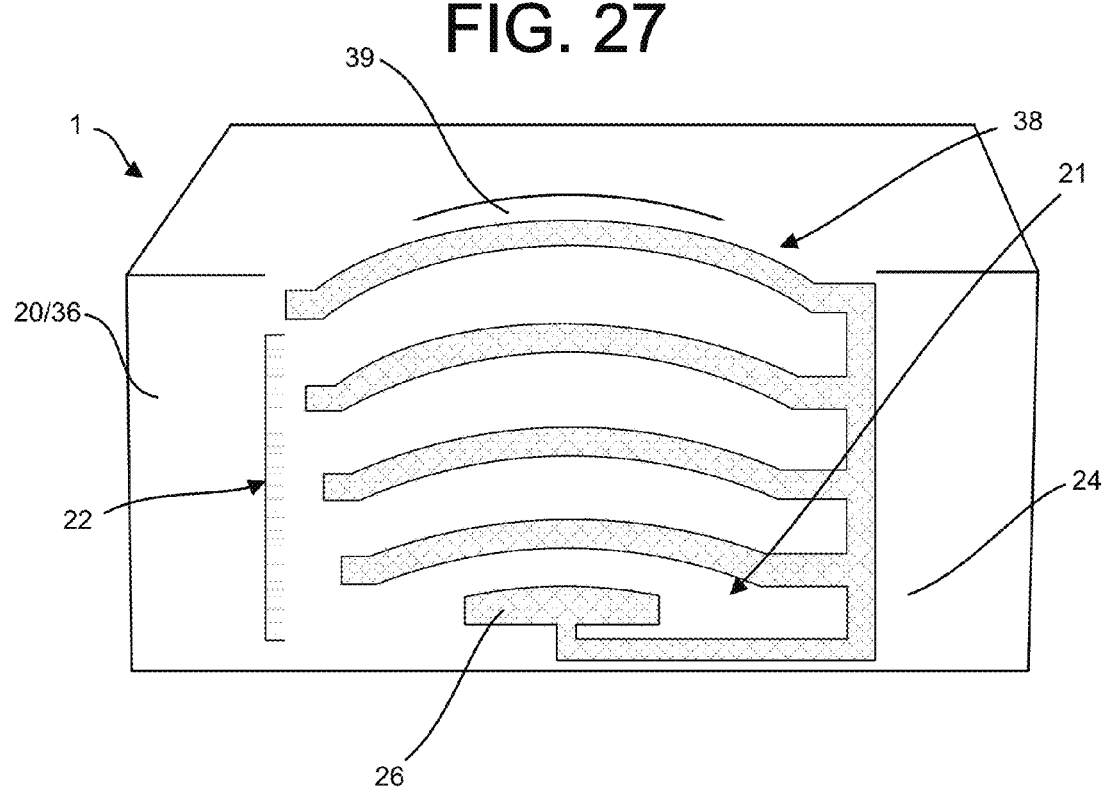

FIG. 28 is an illustration of using alternating vertical metal layers to create an interdigitated type of effect to maximize the of ratio channel width to channel length.

Figure 29:
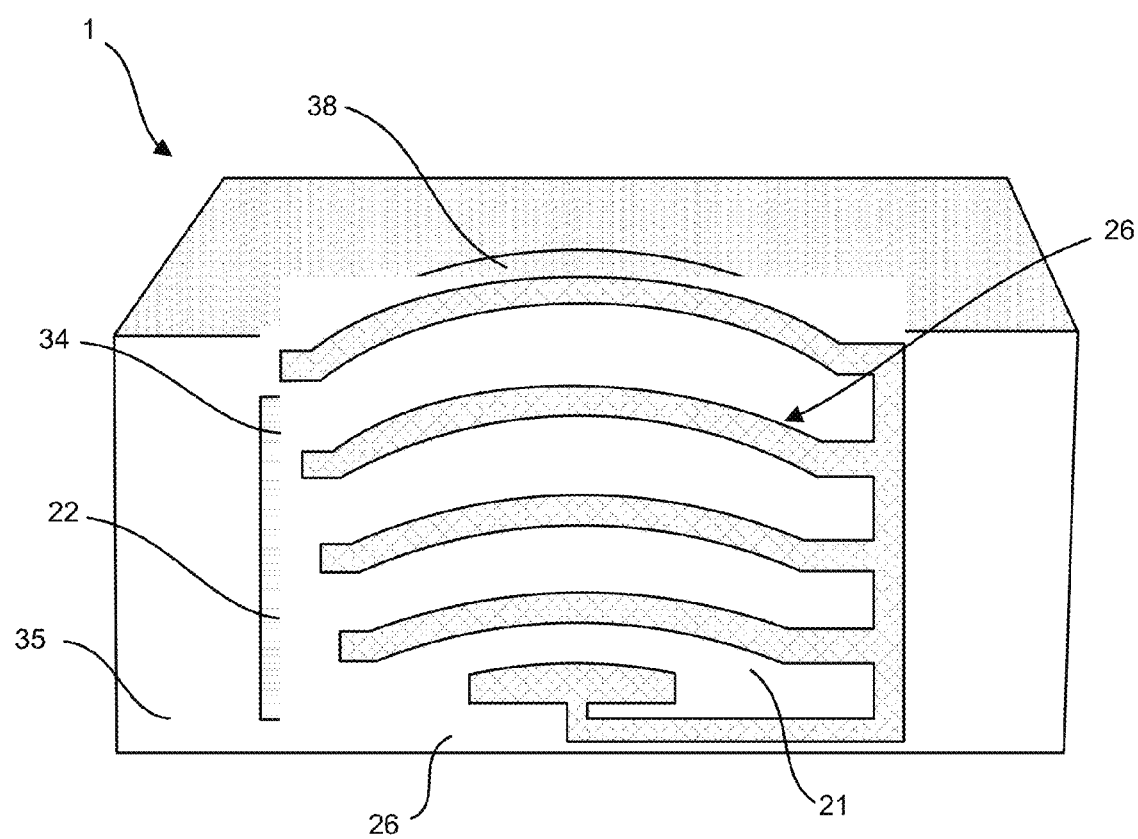

FIG. 29 is an illustration of the structure of FIG. 28 with a transistor material or an analyte-sensitive layer.

Figure 30:
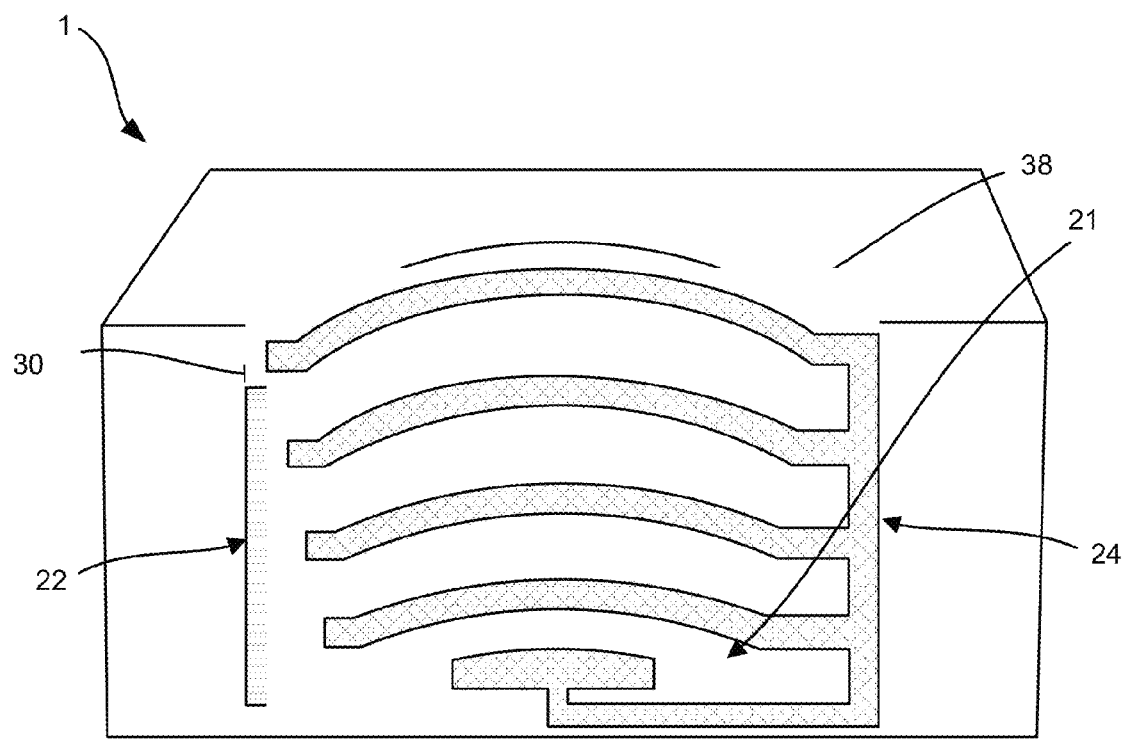

FIG. 30 is an illustration of using alternating vertical layers of metal and transistor material to create an interdigitated type of effect to maximize the ratio of channel width to channel length.

FIG. 31A-H illustrate a process steps that may be used to create the structure shown in FIG. 30.

Figures 32A, 32B:
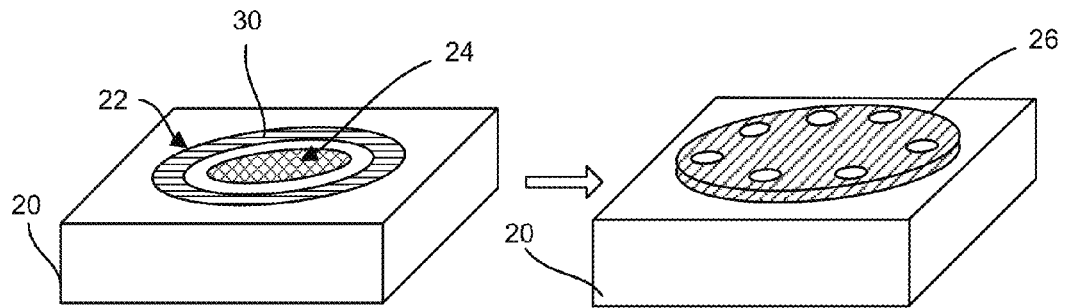

FIGS. 32A and B are an illustration of how vias or chambers in the transistor channel material may be formed thus allowing for edge contact to the channel material.

Figure 33:
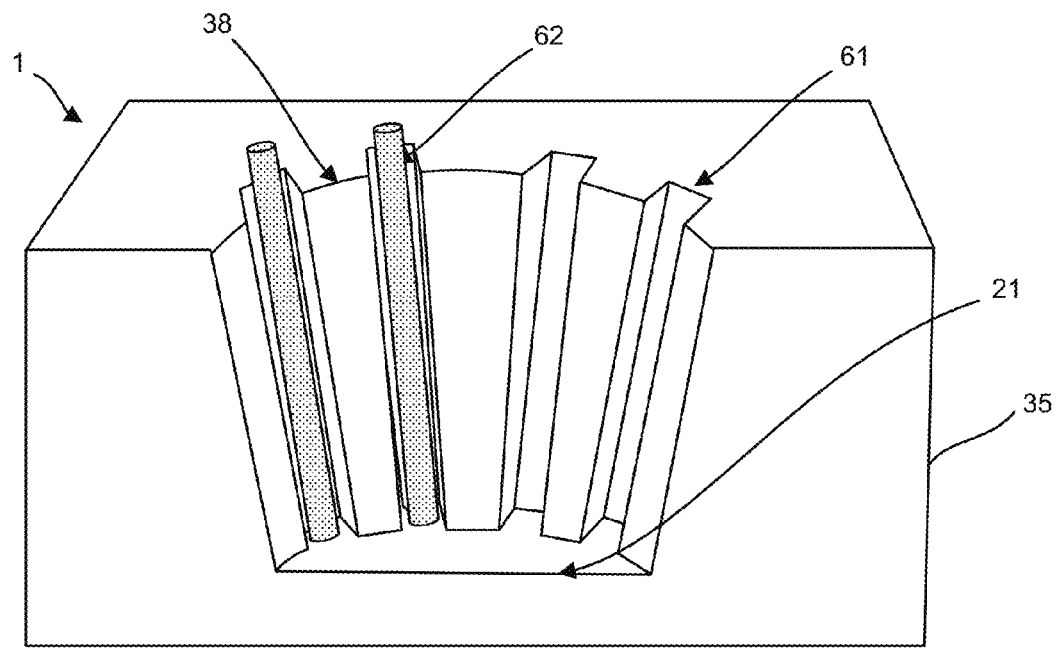

FIG. 33 is an illustration of a well that uses carbon nanotubes to create interdigitated transistors in a vertical direction.

Figure 34:
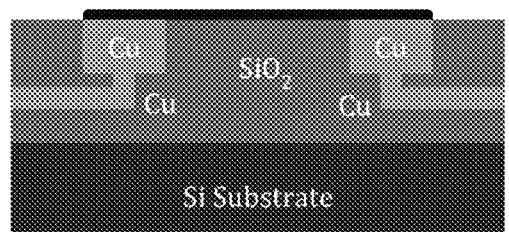

FIG. 34 is an illustration of a thin inorganic layer on a GFET according to the invention.

Figure 35:
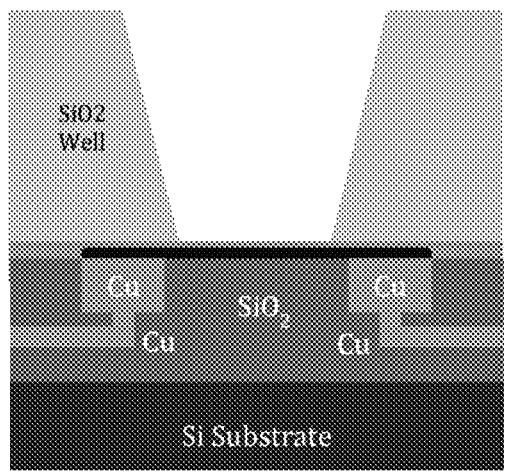

FIG. 35 is an illustration of a dry etched thick inorganic layer for well formation on a GFET according to the invention.

Figure 36:
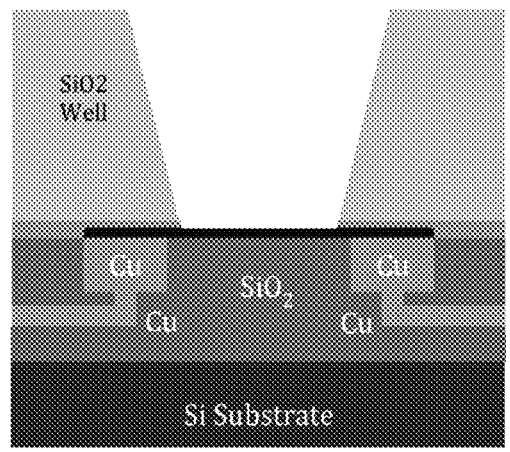

FIG. 36 is an illustration of a wet or gaseous etched thin inorganic layer for well formation on a GFET according to the invention.

Figure 37:
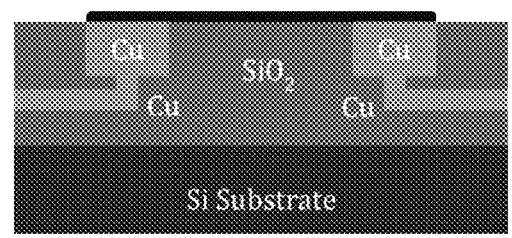

FIG. 37 is an illustration of a thin inorganic layer on a GFET according to the invention.

Figure 38:
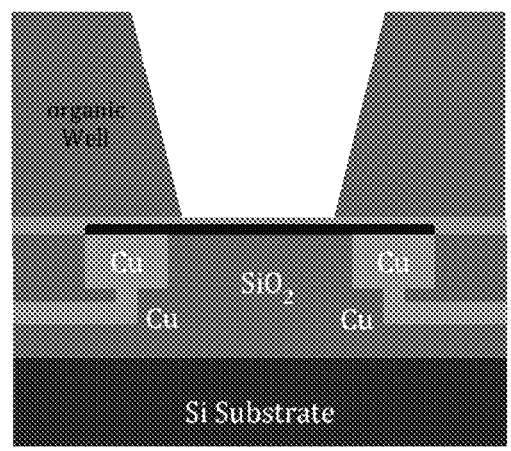

FIG. 38 is an illustration of an organic well on a GFET according to the invention.

Figure 39:
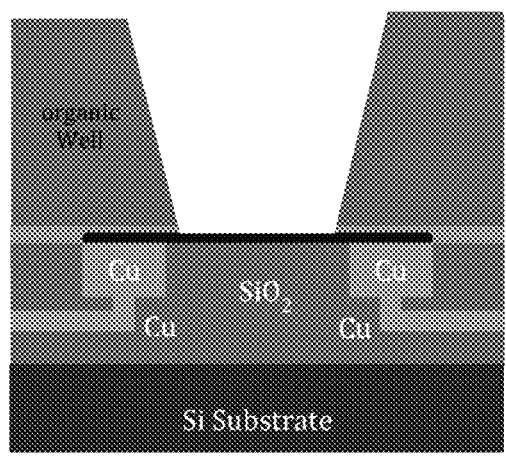

FIG. 39 is an illustration of an organic well on a GFET according to the invention.

Figure 40:
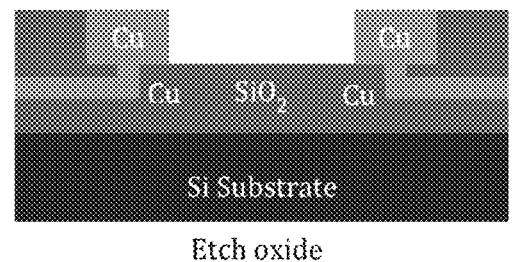

FIG. 40 is an illustration of an oxide etching step for well formation on a GFET according to the invention.

Figure 41:
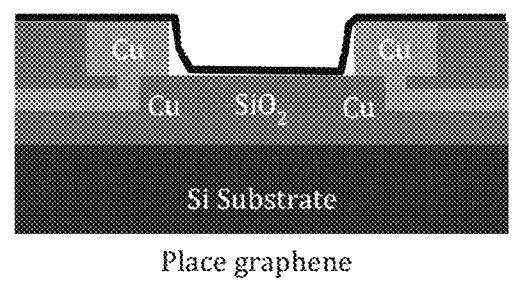

FIG. 41 is an illustration of a graphene placement step for well formation on a GFET according to the invention.

Figure 42:
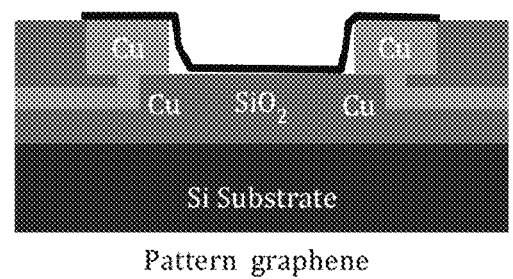

FIG. 42 is an illustration of a graphene patterning step for well formation on a GFET according to the invention.

Figure 43:
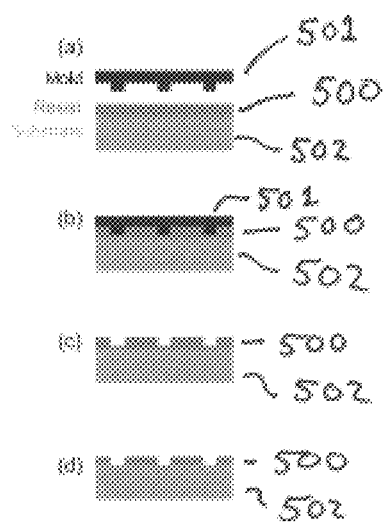

FIG. 43 is an illustration of nanoimprinting of a polymer material for well formation on a GFET according to the invention.

Figure 44:

FIG. 44 is an illustration of an ion sensitive layer or other functional layer placement on a graphene layer step for well formation on a GFET according to the invention.

Figure 45:
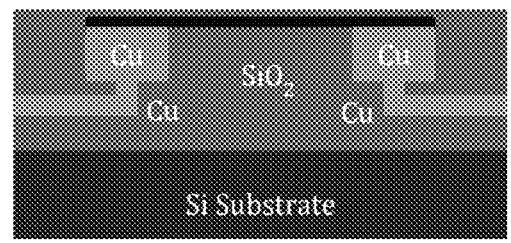

FIG. 45 is an illustration of placement of a thin inorganic layer (etch stop layer) on the functional layer step for well formation on a GFET according to the invention.

Figure 46:
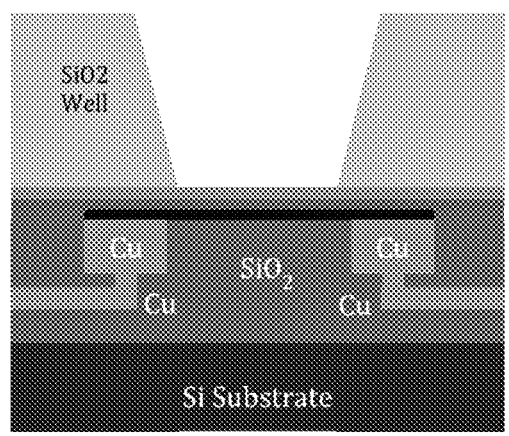

FIG. 46 is an illustration of a dry etch the thick inorganic layer step for well formation on a GFET according to the invention.

Figure 47:
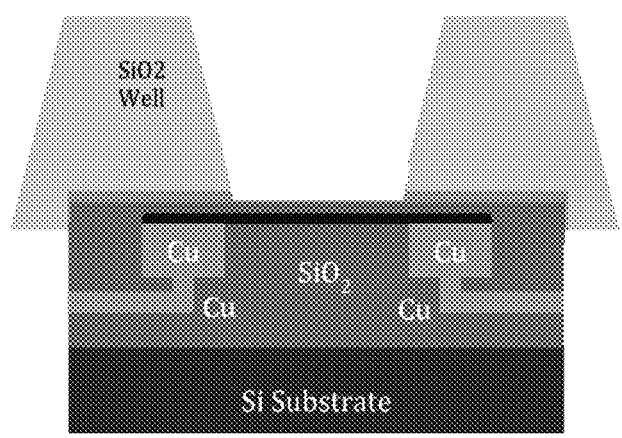

FIG. 47 is an illustration of a wet or gaseous etch the thin inorganic layer step for well formation on a GFET according to the invention.

Figure 48:
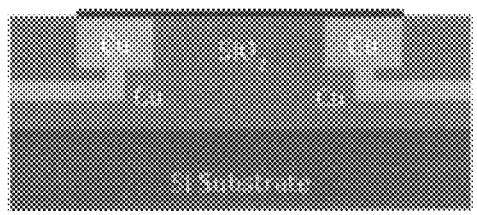

FIG. 48 is an illustration of a CMOS wafer with a graphene layer deposited thereon.

Figure 49:
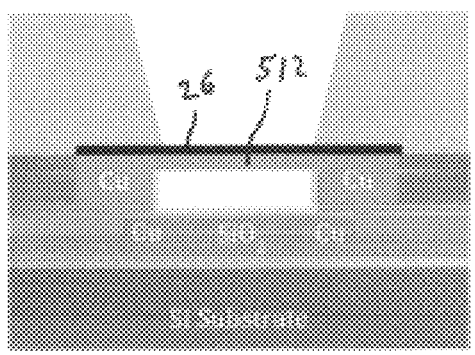

FIG. 49 is an illustration of photoresist pattern and etch step for formation of a FET.

Figure 50:
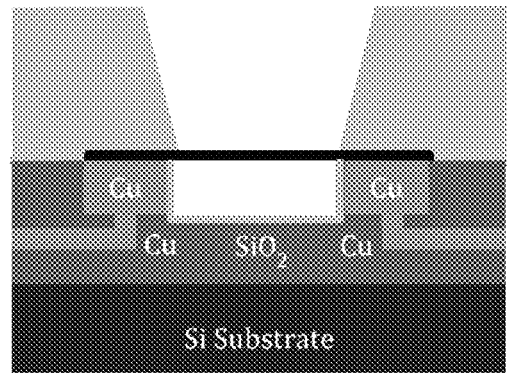

FIG. 50 is an illustration of a copper etching step for formation of a FET.

Figure 51:
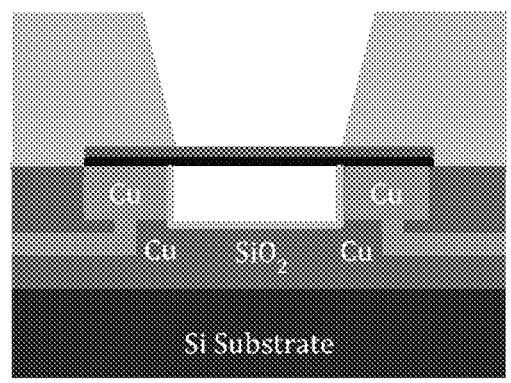

FIG. 51 is an illustration of a functional layer over the graphene layer of a FET.

Figure 52:
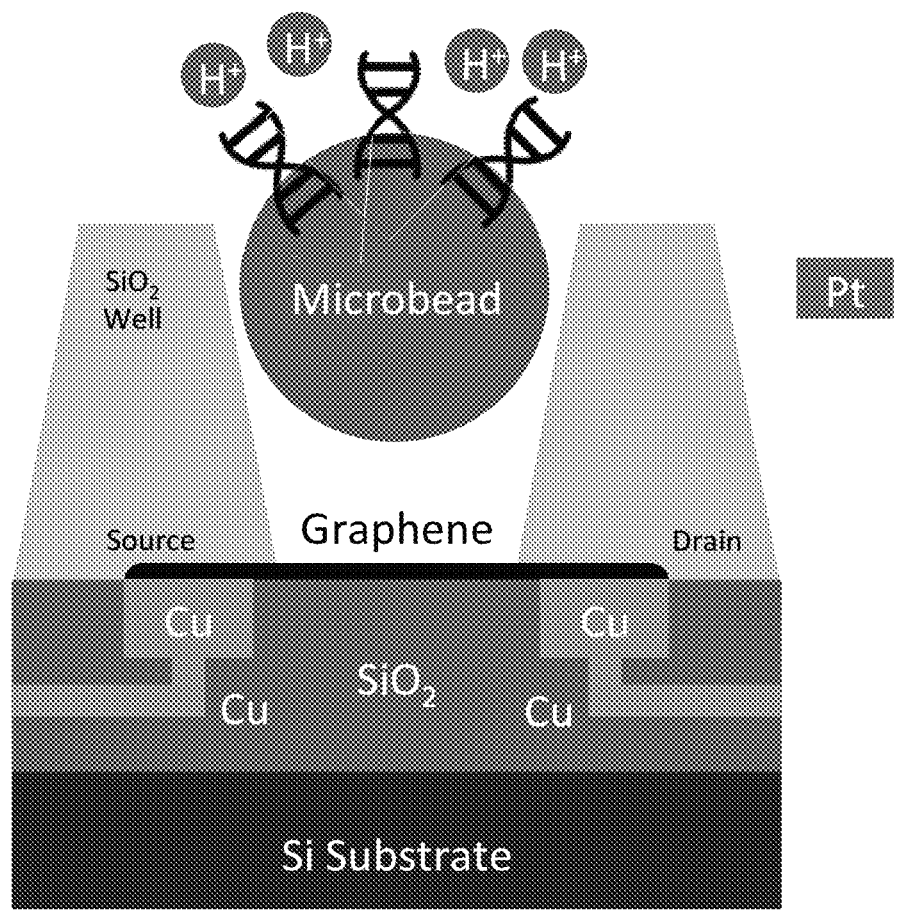

FIG. 52 is a block diagram of a chemically-sensitive field-effect transistor with a well structure and a reference electrode.

Figure 53:
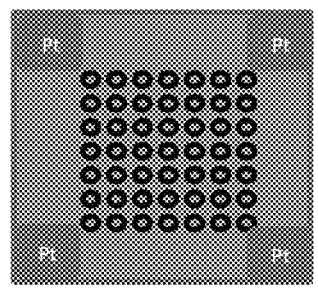

FIG. 53 is an illustration of multiple reference electrodes on a chip.

Figure 54:
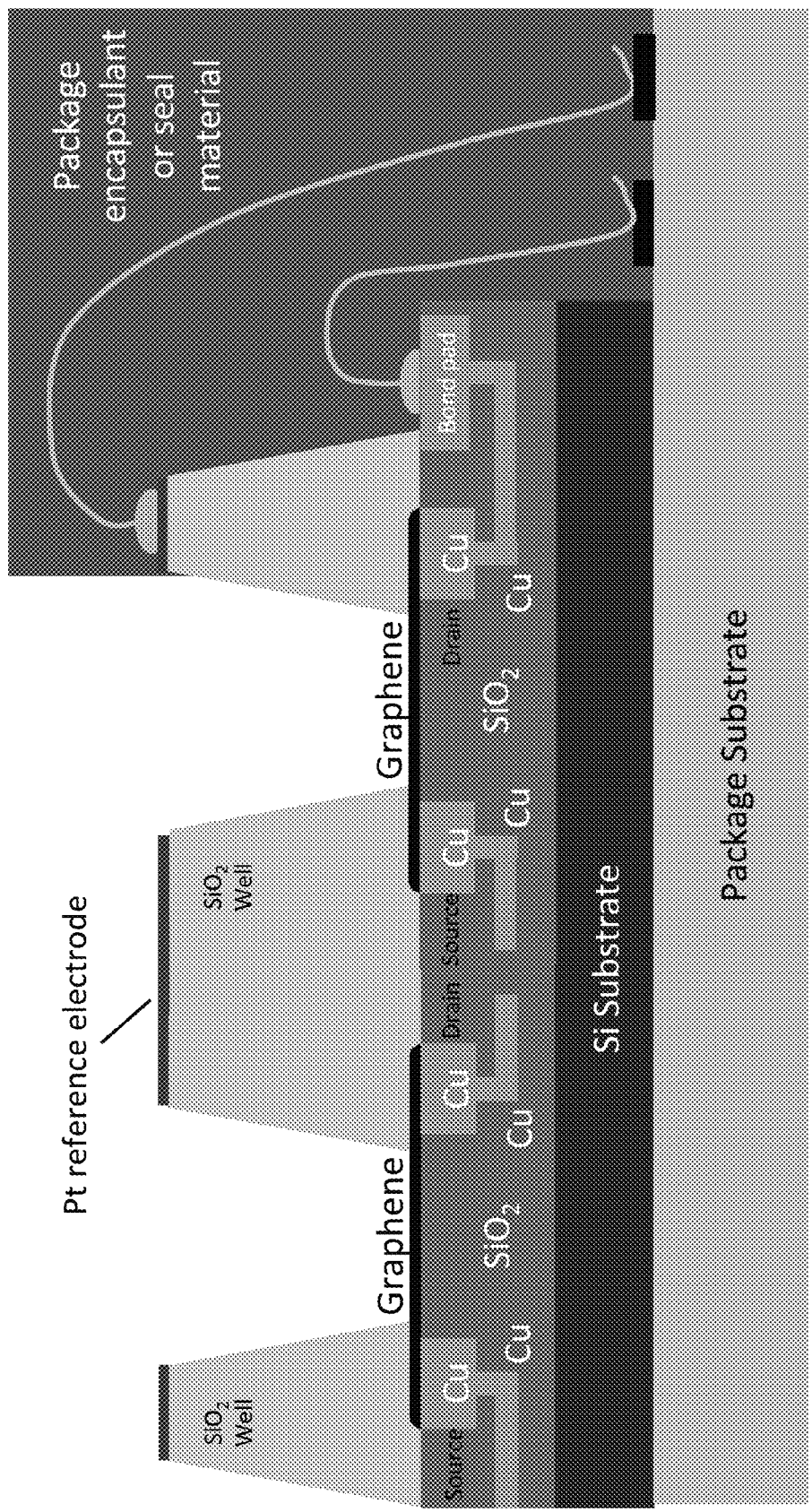

FIG. 54 is an illustration of multiple chemically-sensitive field-effect transistors with a well structures and reference electrodes on top of the wells.

DETAILED DESCRIPTION OF THE INVENTION

Overview

Provided herein are devices, systems, and methods of employing the same for the performance of genomics and/or bioinformatics analysis. The devices, systems, and methods of the invention are directed in part to field effect transistor (FET) sensors, integrated circuits, and arrays employing the same for analyte measurements. The present FET sensors, arrays, and integrated circuits may be fabricated using conventional CMOS processing techniques based on improved FET sensor and array designs that increase measurement sensitivity and accuracy, and at the same time facilitate significantly small sensor sizes and dense GFET sensor based arrays. Particularly, improved fabrication techniques, as well as improved sensor devices, and their use, employing one dimensional (1D) or two dimensional (2D) reaction layers and/or having a three-dimensional (3D) structured layer incorporated therein, provide for rapid data acquisition from small sensors to large, including dense arrays of sensors.

Such arrays may be fabricated, as described herein, and employed to detect the presence of an analyte, changes in analyte concentration, and/or the identity of various analyte types in a wide variety of chemical and/or biological processes, including DNA hybridization and/or sequencing reactions. More particularly, presented herein are FET based sensor arrays that have been configured to facilitate DNA hybridization and sequencing techniques, as well as the resultant detection of the same, which take place proximate a reaction zone that has been adapted to include a 1D or 2D or 3D surface element. Specifically, in various embodiments, complementary metal oxide semiconductor (CMOS) field effect transistor (FET) devices are provided, where the devices include a plurality of reaction zones that have been adapted to have a 1D or 2D surface characteristic associated therewith so as to decrease sensor length at the same time as increasing sensor sensitivity. Further, in various instances, a 3D structural layer may be included, such as to extend the vertical dimension of the reaction zone. In such instances, the devices may include a number of reaction zones that have been configured to receive a solution containing one or more reactants that when conditions are such to favor a reaction result in a detectable product.

Accordingly, presented herein are improved biochemical sensor devices that are configured for detecting changes in a gate region and/or solution that result from the occurrence of a binding event between two reactants proximate a reaction zone of the device, such as within the gate region. In particular instances, the detectable changes may be based on monitoring fluctuations in hydrogen ion concentration (pH), variations in analyte concentration, and/or binding events associated with chemical processes relating to DNA synthesis, such as within a gated reaction chamber of a 1D or 2D or 3D based biosensor chip. More specifically, the present invention is at least in part directed to a chemically-sensitive field-effect transistor for analysis of biological or chemical materials that solves many of the current problems associated with nucleic acid sequencing and genetic diagnostics. Methods of fabricating such devices as well as their use in the performance of biochemical reactions are also provided.

For instance, in one aspect of the present invention, a chemically-sensitive transistor, such as a field effect transistor (FET) that is fabricated on a primary structure, such as a wafer, e.g., a silicon wafer, is provided. In various instances, the primary structure may include one or more additional structures, for instance, in a stacked configuration, such as including at least an insulator material layer. For example, the primary structure may include a secondary structure, such as composed of an insulator material, which may be included on top of, or otherwise be associated with, the primary structure, and may be an inorganic material, such as a silicon oxide, e.g., a silicon dioxide, or a silicon nitride, or an organic material, such as a polyimide, BCB, or other like material.

The secondary structure and/or insulator layer may include a further structure containing one or more of a conductive source and/or a conductive drain, such as separated one from another by a space, and embedded in the primary and/or secondary structure materials and/or may be planar with a top surface of the insulator. In various instances, the structures may further include or be functionally connected to a processor, such as for processing generated data, such as sensor-derived data. Accordingly, the structures may be configured as, or otherwise include, an integrated circuit, and/or may be an ASIC, a structured ASIC, or an FPGA. In particular instances, the structures may be configured as a complementary metal-oxide semiconductor (CMOS), which in turn may be configured as a chemically-sensitive FET containing one or more of a conductive source, a conductive drain, a gate, and/or a processor. For instance, the FET may include a CMOS configuration having an integrated circuit that is fabricated on a silicon wafer, which may further be adapted to include an insulator layer. In such an instance, the insulator layer may include the conductive source and drain such as where the source and drain are composed of metal, such as a damascene copper source and a damascene copper drain.

In various instances, one or more of the structures may include a surface, e.g., a top surface, which surface may include a channel, such as where the surface and/or channel may be configured to extend from the conductive source to the conductive drain. An exemplary length of the surface and/or channel from the source to the drain may range from about 0.001 microns to about 10 microns, such as from about 0.01 microns to about 5 microns, for instance, from about 0.05 micron to 3 microns, including about 0.1 or about 0.5 microns to about 1 or about 1.5 or about 2 microns in the horizontal and/or vertical directions. An exemplary width of the surface and/or channel from side to side may range from about 0.001 microns to about 10 microns, such as from about 0.01 microns to about 5 microns, for instance, from about 0.05 microns to 3 microns, including about 0.1 or 0.5 microns to about 1 or about 1.5 or about 2 microns.

Particularly, in particular instances, it may be useful to maximize conductance, such as by decreasing the channel length, so as to increase the sensitivity of the sensors, such as in a sensor array. For instance, to achieve enhanced transistor transconductance, the channel may be configured so as to include a short channel length, e.g., as short a length as possible, while at the same time including a larger channel width, e.g., as large as width as possible, within the sensor array, in a manner adapted for keeping the overall dimensions of the array as compact as possible. For example, the equation for transconductance of a field effect transistor, such as for a transistor presented herein, is: $g_m \propto \mu C_{ov} W/L V_{sd}$; where $g_m$ is the transconductance, $\mu$ is the carrier mobility, $C_{ov}$ is the overall capacitance of the oxide or other layers over the transistor, W is the channel width, L is the channel length, and $V_{sd}$ is the voltage from the source to the drain. Since $g_m$ directly relates to the sensitivity of the sensor it may be desirable to increase gm through moderating the terms shown in the equation.

In particular increasing the W/L ratio (maximizing W and minimizing L) will increase $g_m$. In particular instances, a useful length of the channel from the source to the drain ranges is less than 1 micron, such as less than 500 nm, such as less than 50 nm, and may be as short as the fabrication process will allow without generating defects or results that render the device unusable. A particularly useful channel length may be 20 nm or less. Conversely, the width of the channel may be as wide as possible. In such instances, the width of the channel is not governed by the fabrication process as much as by the design requirements of the overall sensor chip. In various instances, many millions of sensors may be positioned on the sensor chip. With this large number of sensors the individual sensor size and pitch (e.g., which may directly affect the channel width) may be kept small, such as reasonably small, so as to prevent the chip from being so large as to be unable to be fabricated (e.g., exceeds the photolithography reticle size) or too expensive (due to the effect of defect density on a large chip size). A practical range of channel width in particular instances may be from 0.1 micron to 2 microns, e.g., for a simple rectangular channel design. In some cases, it may be desirable to increase the channel length to channel width ratio through the use of design techniques—for example, structured and/or an interdigitated 3D tooth and comb design can provide for short channel lengths and large channel widths within a relatively compact area.

In certain instances, the surface and/or channel may include a one-dimensional transistor material, a two-dimensional transistor material, a three-dimensional transistor material, and/or the like. In various instances, a one-dimensional (1D) transistor material may be included, which 1D material may be composed of, for example, a carbon nanotube or a semiconductor nanowire. In various instances, a two-dimensional (2D) transistor material may be included, which 2D material may be composed of a graphene layer, silicene, molybdenum disulfide, black phosphorous, and/or metal dichalcogenides. In particular instances, a three-dimensional (3D) structural material, such as proximate a reaction zone and/or channel layer may be provided. In various embodiments, the surface and/or channel may further include a dielectric layer. In particular instances, the surface and/or channel may include a graphene layer.

Additionally, in various instances, a reaction layer, e.g., an oxide layer, may be disposed on the surface and/or channel, such as layered or otherwise deposited on the 1D, 2D, e.g., graphene, or 3D layer, and/or an included dielectric layer. Such an oxide layer may be an aluminum oxide or a silicon oxide, such as silicon dioxide. In some embodiments, the oxide layer may have a thickness of about 100 nanometers or less, preferably about 20 nanometers or less, such as about 15 nanometers, such as 10 or 9 or 7 or 5 nanometers or less. In various instances, a passivation layer may be disposed on the surface and/or channel, such as layered or otherwise deposited on the 1D, 2D, or 3D layer and/or on an associated reaction layer on the surface and/or channel. Such a passivation layer may have a thickness of about 0.5 microns or less, such as about 0.1 microns or about 50 nanometers or about 20 nanometers, such as about 15 nanometers, such as 10 or 9 or 7 or 5 nanometers or less.

In particular instances, the primary and/or secondary and/or tertiary structures may be fabricated or otherwise configured so as to include a chamber or well structure in and/or on the surface. For instance, a well structure may be positioned on a portion of a surface, e.g., an exterior surface, of the primary and/or secondary structures. In some instances, the well structure may be formed on top of, or may otherwise include, at least a portion of the 1D, 2D, and/or 3D material, and/or may additionally include the reaction, e.g., oxide, and/or passivation layers. In various instances, the chamber and/or well structure may define an opening, such as an opening that allows access to an interior of the chamber, such as allowing direct or indirect contact with the 1D, e.g., carbon nanotube or nanowire, 2D, e.g., graphene, surface and/or channel. In such instances, the FET device may be configured as a solution gated sensor device.

Accordingly, a further aspect of the present invention is a biosensor. The bio-sensor includes a CMOS structure that may include a metal containing source, e.g., a damascene copper source, as well as a metal containing drain, e.g., a damascene copper drain, a 1D or 2D layered, e.g., a graphene layered, surface or channel extending from the source to the drain, and a well or chamber structure that may be positioned on a portion of an exterior surface of the 1D or 2D and/or 3D layered well. In particular instances, the well structure may be configured so as to define an opening that allows for direct or indirect fluidic contact with the 1D, e.g., nanotube, nanowire, and/or 2D, e.g., graphene, well or chamber surface. In various instances, the well structure is further configured to include a 3D structural element, such as incorporated into one or more of the well bounding members. Further, an oxide and/or passivation layer may be disposed in or on the chamber surfaces. Hence, in certain instances, a chemically-sensitive transistor, such as a field effect transistor (FET) including one or more nano- or micro-wells may be provided.

In view of the above, in one aspect, the present invention is directed to a method of fabricating a field effect transistor, such as a transistor having one or more of a 1D, 2D, or 3D material associated therewith, such as in proximity to a reaction zone configured within the FET. Any suitable method may be employed in such a fabrication process, however, in various instances, the method may involve the growing and/or transferring of the one-dimensional (1D0 or two-dimensional (2D) material for use as in the sensor. In such an instance, the method may include the growing of the 1D or 2D material layer, such as on a suitable growth platform, which may be a silicon platform or substrate. Particularly, the method may also include releasing the 1D and/or 2D material layer from the growth platform and/or transferring the material layer to the semiconductor structure or substrate.

Accordingly, in some embodiments, the chemically-sensitive FET may include a plurality of wells and may be configured as an array, e.g., a sensor array. Such an array or arrays may be employed such as to detect a presence and/or concentration change of various analyte types in a wide variety of chemical and/or biological processes, including nucleic acid hybridization (e.g., DNA/DNA, DNA/RNA) and/or DNA or RNA sequencing reactions. For instance, the devices herein described and/or systems including the same may be employed in a method for the analysis of biological or chemical materials, such as for whole genome analysis, genome typing analysis, microarray analysis, panels analysis, exome analysis, microbial/microbiome analysis, genotyping analysis, and/or clinical analysis, such as cancer analysis, NIPT analysis, cfDNA, blood/plasma/serum analysis, and/or UCS (upstream conserved sequence) analysis. In a particular embodiment, one or more surfaces within the wells of the field effect transistor may be configured as a reaction zone, which reaction zone may include an additional structure, such as a 1D, 2D, e.g., graphene, or 3D layer, and hence, the FET may be a graphene FET (GFET) array.

Such FET sensors as herein described may be employed to facilitate DNA hybridization and/or sequencing techniques, such as based on monitoring changes in hydrogen ion concentration (pH), changes in other analyte concentrations, and/or binding events associated with chemical processes (e.g., relating to DNA synthesis), such as within a gated reaction chamber or well of the GFET based sensor, such as proximate the reaction zone(s). For example, the chemically-sensitive field effect transistor may be configured as a CMOS biosensor and/or may be adapted to increase the measurement sensitivity and/or accuracy of the sensor and/or associated array(s), such as by including one or more surfaces or wells having a surface layered with a 1D and/or 2D and/or 3D material, a dielectric or reaction layer, a passivation layer, and the like. In particular instances, the increased sensitivity of the sensors may, in part, be due to the presence of the presence of the 1D or 2D material, and/or further enhanced by its relationship to one or more of the reaction and/or passivation layers, which in turn allows for smaller sensor configurations, therefore smaller channels and/or gates, and thus a greater density of sensors and/or arrays.

For instance, in a particular embodiment, a chemically-sensitive, graphene-containing field effect transistor (GFET), such as a GFET having a CMOS structure is provided, where the GFET sensor, e.g., biosensor, may include a substrate and at least a first insulating layer that may itself be configured so as to incorporate one or more of a 1D, 2D, and/or 3D structure therein. For example, a 1D structure may be layered within or coated on top of the insulation layer, such as via chemical vapor deposition, e.g., PVC/CNT deposition, spin coating, physical vapor deposition, and the like. Additionally, or alternatively, a 2D structure or material layer may be applied to the first insulating layer of the CMOS structure, such as by the growth, or release, and/or transfer of the 2D material thereon. Particularly, in various embodiments, the 2D material may be graphene, molybdenum disulfide ($MoS_2$), phosphorene (black phosphorous), silicene, borophene, tungsten disulfide ($WS_2$), boron nitride, $WSe_2$, stanene (2D tin), graphane, germanane, nickel HITP, and Mxenes (Ti2C, (Ti0.5, Nb0.5), V2C, Nb2C, Ti3C2, Ti3CN, Nb4C3, Ta4C3).

More particularly, in certain embodiments, the 2D material may be grown and/or transferred onto the substrate and/or insulating surface of the CMOS structure, which structure may therefore be a read-out integrated circuit (ROIC). For instance, there are several growth mechanisms that may be implemented for the growth of such a 2D material on a growth substrate, such as including the growth on a metal plate, a metal foil, a thin film metal, or a metal, e.g., silicon, wafer, and the like. Likewise, the 2D material may be applied to the material by chemical vapor deposition ("CVD") (atmospheric, low or very low pressure), PECVD, FIB, ALD, or grown in a hot wall or cold wall reactor. Once gown, the 2D material may be transferred to the CMOS/ROIC structured materials, such as by one or more of the following transfer mechanisms including direct transfer from the growth substrate to a ROIC wafer using Van der Waal's forces, fusion bonding, and/or using temporary bonding. Further, there are several release mechanisms that may be implemented for effectuating the release of the 2D material from the growth medium and/or substrate pursuant to the transfer of the 2D material to the ROIC, which release mechanisms may include aqueous electrolyte electrolysis, e.g., with the growth platform as the cathode, and separation due to hydrogen evolution. Another release mechanism may be by separating a temporary adhesive from the growth platform using a laser, a UV light, a temperature increase, or physical peeling or pulling, and the like.

Additionally, in various embodiments, the CMOS structure may additionally include a further insulating layer, such as positioned on top of the second insulating layer, which first and/or second insulating layer(s) may be positioned one on top of the other, such as with the 1D or 2D material deposited there between. In particular instances, the first and/or second insulating layers may include a well structure, such as a well or chamber having a 3D structural layer, such as within or otherwise associated with a surface of the well or chamber. Further, in various embodiments, the CMOS structure may include an oxide and/or passivation layer, such as a layer that is deposited, e.g., via CVD deposition, or may be otherwise disposed on the surface of the well or chamber so as to increase the measurement sensitivity and/or accuracy of the sensor and/or associated array(s). The oxide layer, when present, may be composed of metal oxide, for example, an aluminum oxide, a silicon oxide, a silicon dioxide, and the like. Particularly, the oxide and/or passivation layers may have a suitable thickness such as of from about 100 nm to about 75 nm, such as from about 50 nm to about 30 nm, from about 40 nm to about 25 nm, such as from about 20 nm to about 10 nm or 9 nm or less, respectively.

Accordingly, the present FET integrated circuits, sensors, and/or arrays of the description may be fabricated such as using any suitable CMOS processing techniques known in the art. In certain instances, such a CMOS processing technique may be configured to increase the measurement sensitivity and/or accuracy of the sensor and/or array, and at the same time facilitate significantly small gates having relatively smaller sensor sizes and more dense FET chamber sensor regions. Particularly, in various embodiments, the improved fabrication techniques herein described result in sensor devices containing reaction zones employing a 1D or 2D material layer, and/or may include a 3D structural layer. For instance, a 1D or 2D material layer may be grown, such as on a growth platform, and once grown may be released from the growth platform, and then be transferred to a semiconductor structure, such a CMOS substrate, so as to be employed as a sensor therein.

Additionally, during or after manufacture one or more surfaces or layers of the CMOS transistor structure may be treated so as to contain one or more additional reaction layers, such as an oxide and/or passivation layers, which structures and layers, alone or in combination provide for rapid data acquisition, such as from small sensors to large and dense arrays of sensors. In certain embodiments, one or more of such layers may be fabricated along with the manufacture of the array, such as via one or more chemical vapor deposition techniques. Further, in particular embodiments, an ion-selective permeable membrane may be included, such as where the membrane layer may include a polymer, such as a perfluorosulphonic material, a perfluorocarboxylic material, PEEK, PBI, Nafion, and/or PTFE. In some embodiments, the ion-selective permeable membrane may include an inorganic material, such as an oxide or a glass. In more particular embodiments, one or more of the various layers disclosed herein, e.g., the 1D or 2D layer, the reaction, passivation, and/or permeable membrane layers, and the like may be fabricated or otherwise applied by a spin-coating, anodization, PVD, and/or sol-gel method.

Accordingly, in a particular fabrication process, a method of forming an integrated circuit, such as for use in performing a reaction, such as a nucleic acid sequencing reaction, is provided. The method includes one or more steps of providing a semi-conducting substrate having a plurality of extended planar surfaces, such as a top and a bottom surface, that are offset from one another by a first thickness, and are surrounded by one or more side members, such as a circumferential side member, if the substrate is circular, elliptical, or round, or a plurality of opposed side members contacting each other at their edges, such as if the substrate is square, and the like. In various instances, the substrate may include one or more transistor elements and/or interconnects that may be positioned within the thickness between the plurality of surfaces.

Additionally, a second step may include depositing a first insulating dielectric layer onto the top of the planar surface of the substrate so that the dielectric layer extends at least partially across the planar surface, such as from one side portion to another side portion, e.g., edge to edge. A plurality of trenches, e.g., opposed trenches, may then be formed in the first insulating dielectric layer, such as where each trench is offset from the other by a distance, which distance may be configured so as to form a channel region.

A third step may include depositing a first layer of conductive material into each of the trenches so as to form an electrode within each trench. For instance, a first electrode in a first trench may be configured so as to serve as a source electrode, and a second electrode in a second trench may be configured to serve as a drain electrode, such as where the source and drain electrodes are offset by the channel region, and may be in contact with the one or more transistor elements.

In certain instances, once the electrodes have been formed a 1D or 2D material layer, e.g., graphene, may be positioned over the insulating layer in a manner to cover the source and drain electrodes as well as the channel region between, thereby forming the channel. However, in some instances, the first insulating dielectric layer may be conditioned prior to depositing the 1D or 2D material layer over it, such as in a manner so that a side and/or top surface of each of the plurality of electrodes is made to extend above the surface of the surrounding insulating dielectric layer, and in some instances, only after this conditioning is the 1D or 2D, e.g., graphene, layer deposited or otherwise formed over the insulating layer, such as onto the side and top surface of each of the plurality of electrodes and across the channel region to thereby form a channel between the electrodes.

In various embodiments, the conditioning may be accomplished by etching, such as wet or dry etching. Likewise, an additional plating and/or polishing, e.g., electroless chemical polishing, and/or other conditioning steps may be included, such as by being inserted between one or more of the other recited. For example, in some embodiments, after the first conductive material is added and/or the 1D or 2D material layer is to be added, one or more openings may be made in the 1D or 2D material so as to allow the conductive electrode material to push through and rise above the surface of the 1D or 2D material layer. Such a step as this may be performed in addition to or substitution for the conditioning step. In such an instance, a second layer of conductive material may then be deposited on at least a portion of the 2D material so as to contact each of the plurality of electrodes so that combined conductive material of each of the plurality of electrodes extends further above the surface of the insulating dielectric layer.

Nevertheless, where conditioning takes place, an opening of the 1D or 2D material layer may take place so as to form an opening in the 2D material layer, such as proximate each electrode, so as to expose at least the top surface of each electrode. In such an instance, a second layer of conductive material may be deposited over each opening of the 2D material layer so that the second layer of conductive material contacts the first conductive material, fills the opening, and further extends above the 2D material layer so as to contact at least one of a side and top surface of the 2D material layer. In any of these instances, a patterning step may take place, such as employing a mask and photoresist process, so as to pattern the 1D or 2D material layer forming the channel.

Additionally, in various embodiments, a second insulating material layer may be deposited over the patterned 2D material layer, which second insulating layer may itself be patterned so as to form a chamber having a bottom surface proximate the channel region. In particular instances, this chamber may be configured as a well so as to form a reaction chamber wherein a nucleic acid sequencing reaction, or other reaction, may take place.

Consequently, in various instances, the result of these methods is the production of an integrated circuit, which as indicated above, may be used in performing a nucleic acid sequencing reaction. In such an instance, the integrated circuit may include one or more of a semi-conducting substrate that includes a plurality of extended planar surfaces offset from one another by a first thickness, which are surrounded by one or more circumferential or edged side members, such as where the substrate may be configures as a CMOS-FET, and therefore may have one or more transistor elements positioned between the plurality of surfaces.

Hence, in particular embodiments, the substrate may include an array of field effect transistors that may be arranged in or on the substrate.

Accordingly, the substrate may form or otherwise include a primary layer that forms a base layer for the integrated circuit. Additionally included may be a secondary layer that is positioned over the primary layer. Such a secondary layer may be formed of a first non-conductive material, so as to be an insulator and may include a plurality of trenches, such as where each trench is offset by a distance one from the other, where that distance forms a channel region. The trench may be configured so as to include an electrically conductive material so as to form an electrode, and the trench may further be configured in such a manner that a side and top surface of the electrode extends above the top surface of the of the insulating layer. Further, each of the electrodes may be orientated with respect to one another so as to form a channel region there between, and thus, each electrode on either side of the channel region may be either a source electrode or a drain electrode.

Further, a tertiary layer may be included and positioned over the secondary layer, such as where the tertiary layer includes a 1D and/or 2D material, which may be formed over one or more of the side and top of the source and drain electrodes. In such an instance, the 2D material may be formed over the channel region so as to electrically connect the source and the drain electrodes and thereby form the channel. In some embodiments, the structure of the integrated circuit may include a fourth layer, which fourth layer may extend across the surfaces of the second and/or third layers, and may further include a surface structure that overlaps the source and the drain in the secondary layer. For example, the surface structure may rise above the second and third layers but may include a chamber that defines a well having sidewalls and a bottom, such as a bottom that corresponds with the channel region and/or extends over at least a portion of the 2D material so as to form a reaction chamber for the performance of a sequencing reaction.

Accordingly, in a further aspect, a system is provided, such as a system configured for running one or more reactions so as to detect a presence and/or concentration change of various analyte types in a wide variety of chemical and/or biological processes, including DNA hybridization and/or sequencing reactions. As such, the system may include an array including one or more, e.g., a plurality of sensors, such as where each of the sensors includes a chemically-sensitive FET having a conductive source, a conductive drain, and a reaction surface or channel extending from the conductive source to the conductive drain. In particular instances, the array may include one or more wells configured as one or more reaction chambers having the reaction surface or channel positioned therein. In some instances, the surface and/or channel of the chamber may include a one-dimensional (1D) or two-dimensional (2D) transistor material, a three-dimensional (3D) structural layer may be included, as well as a dielectric or reaction layer, a passivation layer, and/or the like.

The system may further include one or more of a fluidic component, such as for performing the reaction, a circuitry component, such as for running the reaction processes, and/or a computing component, such as for controlling and/or processing the same. For instance, a fluidics component may be included where the fluidic component is configured to control one or more flows of reagents over the array and/or one or more chambers thereof. Particularly, in various embodiments, the system includes a plurality of reaction locations, such as surfaces or wells, which in turn includes a plurality of sensors and/or a plurality of channels, and further includes one or more fluid sources containing a fluid having a plurality of reagents and/or analytes for delivery to the one or more surfaces and/or wells for the performance of one or more reactions therein. In certain instances, a mechanism for generating one or more electric and/or magnetic fields is also included.

The system may additionally include a circuitry component, such as where the circuitry component may include a sample and hold circuit, an address decoder, a bias circuitry, and/or at least one analog-to-digital converter. For instance, the sample and hold circuit may be configured to hold an analog value of a voltage to be applied to or on a selected column and/or row line of an array of a device of the invention, such as during a read interval. Additionally, the address decoder may be configured to create column and/or row select signals for a column and/or row of the array, so as to access a sensor with a given address within the array. The bias circuitry may be coupled to one or more surfaces and/or chambers of the array and include a biasing component such as may be adapted to apply a read and/or bias voltage to selected chemically-sensitive field-effect transistors of the array, e.g., to a gate terminal of the transistor. The analog to digital converter may be configured to convert an analog value to a digital value A computing component may also be included, such as where the computing component may include one or more processors, such as a signal processor; a base calling module, configured for determining one or more bases of one or more reads of a sequenced nucleic acid; a mapping module, configured for generating one or more seeds from the one or more reads of sequenced data and for performing a mapping function on the one or more seeds and/or reads; an alignment module, configured for performing an alignment function on the one or more mapped reads; a sorting module, configured for performing a sorting function on the one or more mapped and/or aligned reads; and/or a variant calling module, configured for performing a variant call function on the one or more mapped, aligned, and/or sorted reads. Other modules that may be included are alignment modules, variant modules, and any other modules useful in analyzing the results of detection or sequencing reactions. In particular instances, the base caller of the base calling module may be configured to correct a plurality of signals, such as for phase and signal loss, to normalize to a fiducial, internal nucleotide standard, and/or to a generate a plurality of corrected base calls for each flow in each sensor to produce a plurality of sequencing reads. In various instances, the device and/or system may include at least one reference electrode.

Particularly, the system may be configured for performing a nucleic acid hybridization or sequencing reaction. In such an instance, the FET device may include an array of sensors having one or more chemically-sensitive FETs associated therewith. Such transistors may include a cascade transistor having one or more of a source terminal, a drain terminal, and or a gate terminal, such as composed of a damascene copper. In such an instance, the source terminal of the transistor may be directly or indirectly connected to the drain terminal of the chemically-sensitive FET. In some instances, a one or two dimensional channel or other suitably configured surface element may be included and may extend from the source terminal to the drain terminal, such as where the 1D channel material may be a carbon nanotube or nanowire, and the two-dimensional channel material may be composed of graphene, silicene, a phosphorene, a molybdenum disulfide, and a metal dichalcogenide. The device may further be configured to include a plurality of column and row lines coupled to the sensors in the array of sensors. In such an instance, each column line in the plurality of column lines may be directly or indirectly connected to or otherwise coupled to the drain terminals of the transistors, e.g., cascade transistors, of a corresponding plurality of sensors and/or pixels in the array, and likewise each row line in the plurality of row lines may be directly or indirectly connected to or otherwise coupled with the source terminals of the transistors, e.g., cascade transistors, of a corresponding plurality of sensors in the array. Preferably, the sensors in such an array are independently addressable.

In some instances, a plurality of source and drain terminals having a plurality of reaction surfaces, e.g., channel members, extended there between may be included, such as where each channel member includes a one or two or even three dimensional material. In such an instance, a plurality of first and/or second conductive lines, and so forth, may be coupled to the first and second source/drain terminals of the chemically-sensitive FETs in respective columns and rows in the array, and so forth. Additionally, control circuitry may be provided and coupled to the plurality of column and row lines such as for reading a selected sensor connected to a selected column line and/or a selected row line. The circuitry may also include a biasing component having a bias circuitry such as is configured to apply a read voltage, while the sample and hold circuit may be configured to hold an analog value of a voltage on a selected column line of the array during a read interval. Particularly, the bias circuitry may be configured for applying a read voltage to the selected row line, and/or to apply a bias voltage such as to the gate terminal of a transistor, such as FET and/or cascade transistor of the selected sensor. In a particular embodiment, the bias circuitry may be coupled to one or more chambers of the array and be configured to apply a read bias to selected chemically-sensitive FETs via the conductive column and/or row lines. Particularly, the bias circuitry may be configured to apply a read voltage to the selected row line, and/or to apply a bias voltage to the gate terminal of the transistor, e.g., cascade transistor, such as during a read interval.

A sense circuitry may also be included and coupled to the array so as to sense a charge coupled to one or more of the gate configurations of a selected chemically-sensitive FET. The sense circuitry may be configured to read the selected sensor based on a sampled voltage level on the selected row and/or column line. In such an instance, the sense circuitry may include one or more of a pre-charge circuit, such as to pre-charge the selected column line to a pre-charge voltage level prior to the read interval; and a sample circuit such as to sample a voltage level at the drain terminal of the selected transistor, such as during the read interval. A sample circuit may further be included and contain a sample and hold circuit configured to hold an analog value of a voltage on the selected column line during the read interval, and may further include an analog to digital converter to convert the analog value to a digital value.

In particular embodiments, the computer component of the FET, e.g., CMOS, structure may include a processor configured for controlling the performance of one or more reactions involving a biological or chemical material so as to obtain reaction results, and for analyzing those results, for instance, based on detecting and/or measuring changes in a voltage (V) potential, current (I), or capacitance occurring on the chemically-sensitive FET. Particularly, the processor, such as a signal processor, may be configured so as to generate one or more current (I) vs. voltage (V) curves, such as where the current I of the I-V curve is the current applied between the source and drain of the chemically sensitive field effect transistor and/or where the gate voltage ($V_g$) of the I-$V_g$ curve is a gate or channel voltage applied to the chemically-sensitive field effect transistor. In such an instance, the gate voltage $V_g$ curve of the I-$V_g$ curve is a top and/or a back gate voltage that may be applied to the chemically sensitive field effect transistor through a top (or front) and/or back of the device, respectively. Hence, a suitably configured device of the invention may be adapted as a front and/or back-gated device, which may further be configured as a solution gate. Accordingly, in various embodiments, a device of the invention may be a field-effect transistor that includes a chamber adapted for measuring ion concentrations in a solution; such as where, when the ion concentration (such as $H^+$ or OFF in a pH scale) within the chamber changes, the current through the transistor, e.g., a gate region thereof, will change accordingly. In such an instance, the solution, when added to the chamber forms, or otherwise serves as, a gate electrode.

Hence, in specific embodiments, the gate voltage $V_g$ of the I-$V_g$ curve may be a solution gate voltage such as applied to the chemically sensitive field effect transistor through a solution flowed over a portion, e.g., a chamber, of the device. In some embodiments, the reference I-$V_g$ curve and/or a chemical reaction I-$V_g$ curve may be generated in response to the biological material and/or chemical reaction that is to be detected and/or occurs over or near the chemically-sensitive field effect transistor, such as within a chamber or well of the FET structure. In various embodiments, the processor may be configured to determine differences in relationships between a generated reference I-$V_g$ curve and/or chemical reaction I-$V_g$ curve. In certain instances, the circuitry component may include at least one analog-to-digital converter that is configured for converting analog signals, such as obtained as a result of the performance of the reaction(s) within the reaction well, or array of wells, into digital signals.

Accordingly, in another aspect, a chemically-sensitive field effect transistor device may be provided, wherein the device may include a structure having a conductive source and drain as well as having a surface or channel or other functionally equivalent surface structure extending from the conductive source to the conductive drain, such as where the surface or channel may include a one-, two-, or three-dimensional transistor material. The device may also include a processor such as where the processor is configured for generating a reference I-$V_g$ curve and/or generating a chemical reaction I-$V_g$ curve, in response to the chemical reaction occurring within a chamber of the chemically-sensitive field effect transistor, and may be configured to determine a difference between the reference I-$V_g$ curve and the chemical reaction I-$V_g$ curve.

In some instances, the difference between the reference I-$V_g$ curve measurement and the chemical reaction I-$V_g$ curve measurement is a shift in a minimum point of the $V_g$ value of the chemical I-$V_g$ curve relative to a minimum point of the $V_g$ value of the reference I-$V_g$ curve. In other instances, the difference between the reference I-$V_g$ curve and the chemical reaction I-$V_g$ curve is a shift in an ion value of the chemical reaction I-$V_g$ curve relative to an ion value of the reference I-$V_g$ curve, for instance, where the ion values are taken from a p-type or n-type section of the I-$V_g$ curve. For example, the measurements of the slopes (one type of parameter of an I-$V_g$ curve) may be taken from the steepest and/or flattest sections on the p-type and/or n-type portions of the I-$V_g$ curves. In particular instances, the difference between the reference I-$V_g$ curve and the chemical reaction I-$V_g$ curve is a shift in an $I_{off}$ value (another representative I-$V_g$ curve parameter) of the chemical reaction I-$V_g$ curve relative to an $I_{off}$ value of the reference I-$V_g$ curve. In one embodiment, the difference between the reference I-$V_g$ curve and the chemical reaction I-$V_g$ curve is a change in the slope of the chemical reaction I-$V_g$ curve relative to a change in the slope of the reference I-$V_g$ curve. In another embodiment, the difference between the reference I-$V_g$ curve and the chemical reaction I-$V_g$ curve is an overall change in shape (another I-$V_g$ curve parameter) of the chemical reaction I-$V_g$ curve relative to an overall change in shape of the reference I-$V_g$ curve. In other embodiments, the difference in overall shape of the I-$V_g$ curves is determined by first fitting a polynomial or other fitting line to each of the I-$V_g$ curves and then comparing the coefficients of those fitting lines. In other embodiments, the difference between a reference I-$V_g$ curve and the chemical reaction I-$V_g$ curve is based on more than one chemical reaction I-$V_g$ curve.

Accordingly, in particular embodiments, the FET and/or processor may be configured to respond to a shift in the I-V or I-$V_g$ curve, such as where the curve is shifted in response to the detection of a biological compound and/or the result of a reaction taking place in or on a surface of the FET device. In some instances, the I-V/I-$V_g$ curve may be produced and/or shifted in response to a chemical reaction occurring on a reaction layer and/or the surface of a 1D or 2D, e.g., graphene, surface of the field effect transistor, such as resulting from the detection of a biological compound or reaction occurring within the well structure of the device. Hence, the FET and/or processor may be configured so as to shift the reference I-V curve or chemical reaction (or "test") I-$V_g$ curve such as in response to the chemical reaction. In various embodiments, one or more elements and/or methods, as herein described, may be used to shift a reference I-V or I-$V_g$ curve and/or a chemical reaction I-$V_g$ curve so that the difference between the reference I-$V_g$ curve and a chemical reaction I-$V_g$ curve is more pronounced. For instance, the device may include a structure, such as a membrane, other surface layer, and/or other element configured for enhancing the ability of the processor to determine the difference between various I-V and/or I-$V_g$ curves.

Hence, in a further aspect, a chemically-sensitive FET transistor that is fabricated on a primary structure having a stacked configuration including an inorganic base layer, e.g., a silicon layer; a dielectric and/or an organic or inorganic insulator layer, such as a silicon dioxide layer; a 1D, 2D, or 3D material layer, such as a carbon nanotube, nanowire, or graphene layer; a reaction, e.g., oxidation, and/or passivation layer; and further having a conductive source and drain embedded in one or more of the layers, such as between and/or forming a gate structure, e.g., a solution gate region, may be provided. In various embodiments, the gate region may be configured so as to form a chamber or well and the 1D or 2D material and/or oxidation layers may be positioned between the conductive source and drain in such a manner as to form a bottom surface of the chamber. The structures may further include or otherwise be associated with an integrated circuit and/or a processor, such as for generating and/or processing generated data, such as sensor derived data.

Accordingly, in particular embodiments, a further structured layer, e.g., a secondary or tertiary structure, may also be provided, such as where the further structured layer may be included and/or present within the well or chamber, such as to enhance the ability of the processor to determine the difference between the current and/or voltages as well as their respective associated curves. More particularly, the additional structure may include an ion-selective permeable membrane, such as an ion-selective permeable membrane that allows ions of interest to pass through the membrane while blocking other ions, such as to enhance the ability of the processor to determine the difference between the reference I-V or I-$V_g$ curve and the chemical reaction I-V or I-$V_g$ curve (or corresponding parameters thereof), and thus enhance the ability of the processor to detect a desired chemical reaction. In various instances, the FET may be configured such that the I-V or I-$V_g$ curve (s) may be shifted so as to better respond to, detect, and/or otherwise determine a biological compound and/or a chemical reaction, such as a biological compound and/or a chemical reaction occurring on the 1D or 2D, e.g., graphene, surface of the chemically-sensitive field effect transistor. In particular instances, the ion-selective permeable membrane may include a 2D transistor material, e.g., graphene, which may or may not be electrically connected to the source and/or drain layer and/or channel.

Accordingly, in various instances, the ion-selective permeable membrane may be positioned within the well and/or over a passivation layer, an ion sensitive or reaction layer, a 1D and/or a 2D transistor material layer, and/or a dielectric layer that itself may be positioned over and/or otherwise form a part of the chamber or channel. In certain embodiments, the membrane layer may be or otherwise be associated with an ion getter material, such as an ion getter material that traps ions that may or may not be relevant to the biological species and/or chemical reaction to be sensed and/or determined, such as to enhance the ability of the processor to determine the difference between the reference I-V or I-$V_g$ curve and/or the chemical reaction I-V or I-$V_g$ curve (or corresponding parameters thereof), e.g., because there are fewer interfering ions, thus enhancing the ability of the processor to detect the desired biological species and/or results of the chemical reactions. Particularly, the ion getter material may be arranged within proximity to the chamber and/or surface thereof so that the action of gettering (or sequestering) the unwanted ions improves the detection capability of the chemically-sensitive FET. In some instances, one or more of the various layers herein, such as the ion getter material may be placed over one or more of the other layers, such as the dielectric layer, oxide layer, or 1D or 2D or 3D layers, positioned in proximity to one or more of the chambers, channels, or surfaces of the FET device.

In particular instances, an additional material, e.g., HMDS, may be included so as to manage the interaction of the chamber and/or channel and/or associated oxide layer and/or underlying 1D or 2D or 3D transistor layer. For instance, a chemically-sensitive FET of the invention may include a secondary or tertiary structure that includes a 2D transistor channel or surface that may include an ion-sensitive material over the channel or surface. In such an instance, the material may be sensitive to ions that are different from the ions associated with the biological molecule or chemical reaction that is to be detected. Particularly, in some instances, the action of sensing ions that are different from the ions associated with the biologics and/or chemical reactions that are to be detected allows the processor to filter out the signal from the unwanted ions from the signal of the ions of interest.

In a further aspect of the present invention, systems having a chemically-sensitive transistor, such as a field effect transistor (FET) including one or more chambers, e.g., a plurality of chambers having a well structure(s) formed therein is provided. In such an instance, the well(s) may be structured as a reaction location, wherein one or more chemical reactions may take place. In such an embodiment, the system may include a fluidics component having a fluid source, e.g., a reservoir, containing one or more fluids therein and configured for delivering the fluid from the reservoir to the reaction chamber, such as for the detection of a biologic and/or the performance of one or more chemical and/or biological reactions, such as a nucleic acid sequencing reaction. Hence, the fluidics component, e.g., the fluid source, may be in fluidic communication with the FET device configured for biological and/or chemical analysis.

Accordingly, in certain instances, the fluid may include one or more reactants, such as one or more analytes necessary for performing a sequencing and/or detection reaction, as herein described. In a particular embodiment, the fluid may include one or more, e.g., a plurality, of microbeads or particles having nucleic acid templates attached thereto, for instance, where the template is complementary to a portion of, and thus hybridizes to, a DNA or RNA molecule to be sequenced or detected, and the fluid containing the microbead is to be delivered to the well such as for carrying out the sequencing reaction. In such embodiments, one or more of, e.g., each, of the plurality of microbeads or particles may be configured so as to have electric charge and/or paramagnetic properties. The device may additionally include an electric and/or magnetic field component, e.g., having an electric and/or magnetic field generator, such as where the electric and/or magnetic field component is configured to generate an electric and/or magnetic field so as to interact with the electric and/or magnetic charge properties of each of the plurality of microbeads or particles to attract them into a reaction location, such as a reaction surface, a channel, a well, a chamber, and/or a sensor of the FET device, such as by using electrophoresis and/or magnetism.

Hence, one or more, e.g., a plurality of microbeads, may be drawn onto or into a reaction location of the plurality of reaction locations, which locations may be formed as wells, e.g., one or more thin wells. The microbeads may include an analyte such as a biological material or a chemical material, e.g., one or more nucleotide sequences. Particularly, a fluid containing the analyte containing microbeads may be introduced into the wells, such as by a fluidics component of the invention. As the analyte may be a nucleic acid sequence having negative charge properties, an electric and/or magnetic field may be applied individually or collectively to the wells, so as to draw an analyte containing microbead onto each reaction location, e.g., into each well or sensor containing channel. In various instances, the electric and/or magnetic field component generates an electric and/or magnetic field so as to interact with the electric charge properties of the microbeads, thereby drawing it to the reaction location. In certain instances, the microbeads or particles themselves may be charged and/or may have electric and/or paramagnetic properties, and thereby may be drawn to the reaction location using electrophoresis and/or magnetism.

The use of electrophoresis and/or magnetism allows for thinner reaction location structures. In particular instances, therefore, an electric and/or magnetic field generator may be configured for drawing and/or positioning a microbead or particle within the well structure, such as in proximity to a channel or chamber of the device, and in other instances, the electric and/or magnetic field generator may be configured for reversing the electrical and/or magnetic field so as to repulse the microbead from the reaction location, channel, and/or chamber. In various instances, an array of reaction locations may be provided each having a magnet that allows for selective filling of the reaction locations with different numbers and/or types of microbeads, such as at select reaction locations. In such an instance, multiple electric and/or magnetic field generators for selective filling of reaction locations, e.g., wells.

Accordingly, one aspect of the present invention concerns systems and/or methods for positioning one or more, e.g., a plurality, of microbeads, e.g., containing one or more DNA and/or RNA templates attached thereto, within a reaction or plurality of reaction locations for biological or chemical analysis, such as for nucleic acid sequencing. Such a system may include a CMOS FET device having an integrated circuit structure configured for performing a biological or chemical analysis, such as within a plurality of nano- or micro-reaction wells, as described above, having a fluidic component, a circuitry component, and/or a computing component, and the method may include one or more of the following steps.

For instance, the method may include the fluidic component introducing a fluid to be in contact with the device, such as where the fluidics component is configured to control a flow a fluid of reagents over the array, and the fluid may include one or more microbeads or particles that may have electric charge and/or paramagnetic properties. In such an instance, the device may include an integrated circuit structure, a plurality of reaction locations having one or more wells, a plurality of sensors and/or a plurality of channels, and/or an electric and/or magnetic field component. The electric field and/or magnetic field component may be configured to activate the electronic and/or magnetic field, and the method may also include activating an electric and/or magnetic field so as to interact with the electric and/or paramagnetic properties of each of the microbeads. The method may additionally include drawing the one or more microbeads or particles into a reaction location of the plurality of reaction locations using electrophoresis and/or magnetism. In certain instances, the method may include positioning the one or more microbeads within the one or more reaction locations for biological or chemical analysis.

In particular instances, the electric and/or magnetic fields may be generated by the plurality of electric and/or magnetic field generators, e.g., included in the integrated circuit structure, in all or only a subset of the plurality of reaction locations so as to only attract a plurality of microbeads to the subset of reaction locations, such as for selectively filling the plurality of reaction locations with the plurality of microbeads. In such an instance, different types of microbeads may be attracted to different reaction locations, such as by pulsing the voltage and/or magnetic generators and/or keeping the same constant. Particularly, where an electric field generator is provided the voltage applied to the device may be variable or constant and may be less than about 10V, such as about less than 8V, or less than about 6V, including less than about 4V or about 2V or 1V. The voltage may be applied between a location above the fluid and a location on or below the reaction location, such as above the package lid and/or below the metal plate below the package. In certain instances, the location below the reaction location may be a metal or conductive layer such as within the package or package substrate. The methods may also include the step of reversing the electric or magnetic field so as to eject the plurality of bead or particles from the plurality of wells, sensors, and/or channels, either entirely or selectively.

Further, as indicated, each or a subset of the plurality of reaction locations may be utilized to generate electric fields to attract a microbead or particle, thereby allowing for programmability or addressing capability to each or a subset of reaction locations, for instance, 99% or 95% or 90% or 85%, or 80% or less of the plurality of wells are occupied with a microbead or other particle.

Additionally, in another aspect of the invention, a device, system, and/or method for verifying well occupancy for a plurality of wells for analysis of biological or chemical materials may be provided. For instance, a device of the system may include a plurality of wells having a plurality of sensors, such as where each well includes a chemically sensitive FET according to the invention. In such instances, the system may include a device for receiving a fluid containing the plurality of microbeads, particles, or other carriers compatible with microfluidic fluid flow in automated chemical/biological analysis devices. Particularly, the device may include a processor, a CMOS structure having an integrated circuit, a plurality of wells, and a plurality of sensors within the CMOS structure. Each of plurality of wells may be configured to receive a microbead of the plurality of microbeads, and the CMOS structure may include a mechanism for drawing and/or ejecting the beads into or out of the wells. Hence, the method may include the step of flowing the plurality of microbeads over and/or into the plurality of reaction locations and/or wells and/or may include determining, e.g., through electrical and/or magnetic sensing if a reaction location and/or well is occupied or unoccupied and/or if a well contains one or multiple microbeads.

Consequently, the processor may be configured to determine if a well is unoccupied and/or if the well contains one or more, e.g., multiple microbeads. In certain instances, the processor may also be configured to eliminate or modify one or more of the measurements, such as based on the number of wells occupied or unoccupied, e.g., the number of wells containing none, one or multiple microbeads. For instance, the processor may be configured to eliminate from the measurement the number of wells unoccupied and the number of wells containing multiple microbeads, or compensate in the measurement for the number of wells unoccupied and the number of wells containing multiple microbeads, and the like.

DETAILED DESCRIPTION OF REPRESENTATIVE ASPECTS AND EMBODIMENTS

Accordingly, provided herein are devices, systems, and methods of employing the same for analysis of biological or chemical materials. Particularly, the devices, systems, and methods of the invention are directed in part to 1D, 2D, or 3D field effect transistor (FET) sensors, integrated circuits, and arrays employing the same for analyte measurements. The present FET sensors, arrays, and integrated circuits may be fabricated using conventional CMOS processing techniques based on improved 1D, 2D, or 3D FET sensor and array designs that increase measurement sensitivity and accuracy, and at the same time facilitate significantly smaller sensor sizes and dense sensor array designs.

More particularly, such improved fabrication techniques employing 1D, 2D (e.g., graphene), or 3D materials as a reaction layer or structure provide for rapid data acquisition from small sensors to large and dense arrays of sensors. Such arrays may be employed to detect the presence and/or concentration changes of various analyte types in a wide variety of chemical and/or biological processes, including DNA or RNA hybridization, and/or nucleotide and/or protein sequencing and/or detection reactions. Accordingly, in particularly preferred examples, chemically-sensitive graphene field effect transistor (GFET) arrays (as well as arrays made from other chemically-sensitive 1D or 2D materials) facilitate genetic and/or protein sequencing or detection techniques based on monitoring changes in various reactants within a zone associated with the array, such as changes in ion concentration, e.g., changes in hydrogen ion concentration (pH), or changes in other analyte concentrations, and/or binding events associated with chemical or biological processes such as nucleic acid synthesis (as used in NGS and other nucleic acid sequencing approaches), such as within a gated reaction chamber of the GFET based sensor. Particularly, the present invention concerns chemically-sensitive 1D or 2D material layered FETs for analysis of biological and/or chemical materials. Such chemically sensitive FETs solve many of the current problems associated with nucleic acid detection, sequencing, genetic, and/or molecular diagnostics.

Accordingly, provided herein are systems for analysis of biological and/or chemical materials. In various embodiments, the system includes a chemically-sensitive FET, preferably having a substrate that includes one or more chamber and/or channel arrangements therein, such as where the chamber and/or channel thereof may be associated with one or more sensors. In particular instances, a solution-gated well structure is provided, such as where the well structure is configured such that a biological and/or chemical reaction can take place within the well, preferably proximate a channel structure therein that is comprised of a chemically sensitive 1D or 2D transistor material. In various instances, the well is positioned on a portion of the substrate so as to align with an exterior surface of the channel of each sensor, wherein the channel is a conductive channel that extending from the conductive source to the conductive drain of the FET. The well structure typically defines an opening that allows for direct fluid contact with the channel. The well structure is preferably made of an insulator material, preferably an inorganic material such as silicon oxide or silicon nitride. Alternatively, the insulator material for the well structure can be an organic material such as a polyimide, BCB, or other like materials.

In various instances, the length of the interior surface, e.g., the channel, of the well, such as from the source to the drain, ranges from about 0.05 micron to about 3 microns, and a width of the surface and/or channel may range from about 0.5 micron to about 2 microns. In particular instances, the well structure can be configured to include or otherwise be associated with a nucleic acid template or probe, such as a nucleic acid that may be directly or indirectly immobilized (covalently or non-covalently) on a surface of the well. For instance, in certain instances, the nucleic acid template (in the context of sequencing reactions) or probe (in the context of hybridization reactions) can be bound to or otherwise immobilized on an interior surface of the well chamber, such as on the substrate itself, or a layer associated therewith, e.g., a layer composed of a 1D or 2D transistor material or a material coating or covering the 1D or 2D transistor material. In other embodiments, the nucleic acid template or probe can be bound to a secondary substrate, such as a bead or other particle positioned within the well so that it as proximate with the chemically-sensitive 1D or 2D transistor material, e.g., graphene. Alternatively, the channel can be composed of a silicene. And additional alternative materials for the channel include borophene, $WS_2$, boron nitride, stanene (2D tin), germanane, nickel HITP, and Mxenes ($Ti_2C$, ($Ti0.5$, $Nb0.5$), $V_2C$, $Nb_2C$, $Ti_3C_2$, $Ti_3CN$, $Nb_4C_3$ and $Ta_4C_3$.

Accordingly, in one aspect of the present invention, the sensor substrate is configured as a chemically-sensitive FET. Particularly, in certain embodiments, the FET includes a chamber having a channel structure incorporated therein. In particular embodiments, the chamber and/or the channel and/or a structure thereof is optimized in such a manner so as to maximize the ratio of channel width (W) to channel length (L). For instance, the channel may include a 1D or 2D or 3D structure, such as where the channel and/or the channel structure includes a geometry that has been optimized to maximize the ratio of channel width (W) to channel length (L). This can be accomplished, for example, through the use of interdigitated source and drain electrode geometries in a single plane or through the use of 2D and/or 3D electrode structures, such as a 3D interdigitated well structure.

In such embodiments, the transistor includes a conductive channel extending between, or spanning, a conductive source and a conductive drain to form the channel structure. In such embodiments, the opening of the well is positioned in relation to the channel so that the opening aligns with the source and drain, and more particularly, with the associated sensor. As indicated, in various embodiments, a bounding surface of the well includes a one-dimensional (1D) transistor material (e.g., a carbon nanotube (CNT) or a semiconductor nanowire) or a two-dimensional (2D) transistor material, such as composed of graphene, molybdenum disulfide, other metal dichalcogenides, and black phosphorous. In various instances, a three-dimensional (3D) structure may be included.

For example, the transconductance through the channel may be modified in various manners so as to modulate, e.g., increase, the sensitivity of the associated biosensors, such as in the sensor array. Particularly, in various instances, it may be useful to configure the chamber and/or well so as to have a short channel length and a wide channel width, such as the shortest channel length and largest channel width possible, given the configuration of the one or more chambers in the one or more sensor arrays. More particularly, the equation for transconductance of the field effect transistors disclosed herein is: $g_m \propto \mu\, C_{ov}\, W/L\, V_{sd}$ where $g_m$ is the transconductance, $\mu$ is the carrier mobility, $C_{ov}$ is the overall capacitance of an included oxide or other layers over the transistor, W is the channel width, L is the channel length and $V_{sd}$ is the voltage from the source to the drain. Since $g_m$ directly relates to the sensitivity of the sensor it is desirable to increase $g_m$ through the terms shown in the equation. In particular, increasing the W/L ratio (maximizing W and minimizing L) will increase $g_m$.

In particular instances, the length of the channel from the source to the drain ranges is less than about (1) micron, such as less than about 500 nm, including less than about 50 nm, and in particular instances: as short as the fabrication process will allow without generating defects or results that render the device unusable. In one particular embodiment the channel length is about (20) nm or less. Conversely, the width of the channel may be as wide as feasible and/or possible. In such an instance as this, the width of the channel need not be governed by the fabrication process as much as by the design requirements of the overall sensor chip. For instance, in specific instances, hundreds of thousands to millions of sensors may be included in an exemplary sensor chip.

Figure 11:
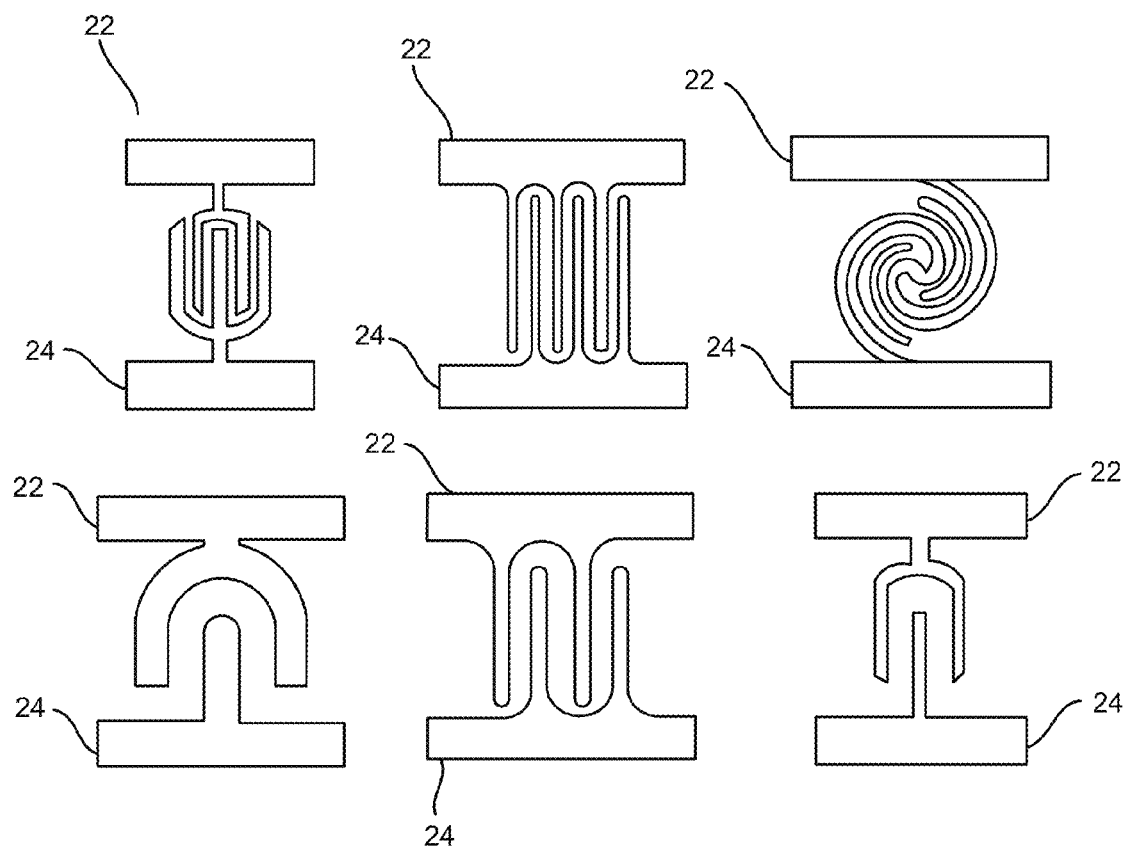
FIG. 11 is an illustration of various planar source and drain electrode designs, including interdigitated designs.

However, with such a large number of sensors, each individual sensor size and/or pitch, e.g., which may directly affect the channel width, should be kept reasonably small so as to prevent the chip from being so large as to be unable to be fabricated (e.g., such as exceeding the photolithography reticle size) or too expensive (e.g., due to the effect of defect density on a large chip size). Hence, in one implementation, e.g., of a rectangular channel design, a practical range of the channel width is from about 0.1 micron to about 2 microns. As indicated above, in some instances, it may be desirable to increase the channel length to channel width ratio, such as through the use of various design techniques. In one particular exemplary instance, a structure, such as an interdigitated tooth and comb structure, can be provided such as for short channel lengths and large channel widths, such as within a relatively compact area, such as shown in FIG. 11, which depicts various designs of interdigitated source and drain electrodes that can be implemented so as to increase the W/L of the channel within a relatively small area.

Another aspect of the present invention is the inclusion of an ion sensitive layer to the channel to improve the sensitivity of the 1D or 2D or 3D material of the FET. Hence, the 1D and/or 2D layer can further be associated with an insulator material. For instance, the insulator material for the well structure may be an organic material, such as a polyimide or BCB, and/or may be an inorganic material, such as silicon oxide or silicon nitride.), and the like.

In particular instances, a reaction layer can also be provided, such as a layer associated with the 1D or 2D, e.g., graphene, layer. For instance, in one embodiment, a thin (0.01 micron) passivation or etch stop layer (ESL) is placed over the channel layer (e.g., graphene), such as in the case where a well etch process affects the channel-forming material. In various embodiments, an oxide layer can be included, such as disposed within the chamber and/or channel thereof. Particularly, in various embodiments, a method for depositing the dielectric layer may include Atomic Layer Deposition (ALD). Another method for creating an analyte-sensitive layer is to first deposit a metal layer (e.g., by sputtering or evaporation) onto the 1D, 2D, or 3D material layer and then oxidizing the metal to form a metal oxide layer. It is further possible to combine material layers using different deposition processes to create an analyte-sensitive layer. For example, a first layer can be comprised of sputtered metal that is oxidized, followed by a layer comprised of an ALD deposited oxide. It is also possible to combine two or more analyte-sensitive layers, such as may be comprised of different materials to create an overall analyte-sensitive layer stack. For example, a first layer of metal, e.g., aluminum oxide, may be formed over the channel material and then a second layer of metal, e.g., tantalum oxide, can be formed over the aluminum oxide. In some embodiments, an analyte-sensitive dielectric layer need not be required nor used.

However, where employed, the oxide layer is configured so as to prevent the nucleic acid template or probe, e.g., present on a micro- or nano-bead, from contacting the 1D or 2D material or other reaction layer of the chamber directly. The oxide layer can be composed of an aluminum oxide, tantalum oxide, and/or a silicon oxide. In various instances, the oxide layer has a thickness of about 9 nanometers or less. In further instances, the chemically-sensitive FET can read through an oxide layer, if present. In particular instances, the well structure includes a permeable membrane associated with the channel-forming material, e.g., graphene.

One aspect of the present invention is a chemically-sensitive FET that is fabricated in a stacked configuration including a primary structure, such as a wafer, e.g., a silicon wafer, as well as one or more additional structures. For instance, an insulator material layer may also be included on top of the primary structure, and may be an inorganic material. The first and second structures include a further structure that contain one or more of a conductive source and a conductive drain separated one from another by a space and spanned by a conductive channel made of a chemically-sensitive 1D or 2D material. The source, drain, and channel can be embedded in the primary and/or secondary structures and/or may be planar with a top surface of the secondary structure or a further layer or structure associated therewith. In various preferred embodiments, the structures further include a processor, such as for processing generated data, such as sensor-derived data. Accordingly, the structures can be configured as, or otherwise include, an integrated circuit, and/or may be an ASIC, a structured ASIC, or an FPGA.

Figure 1A:
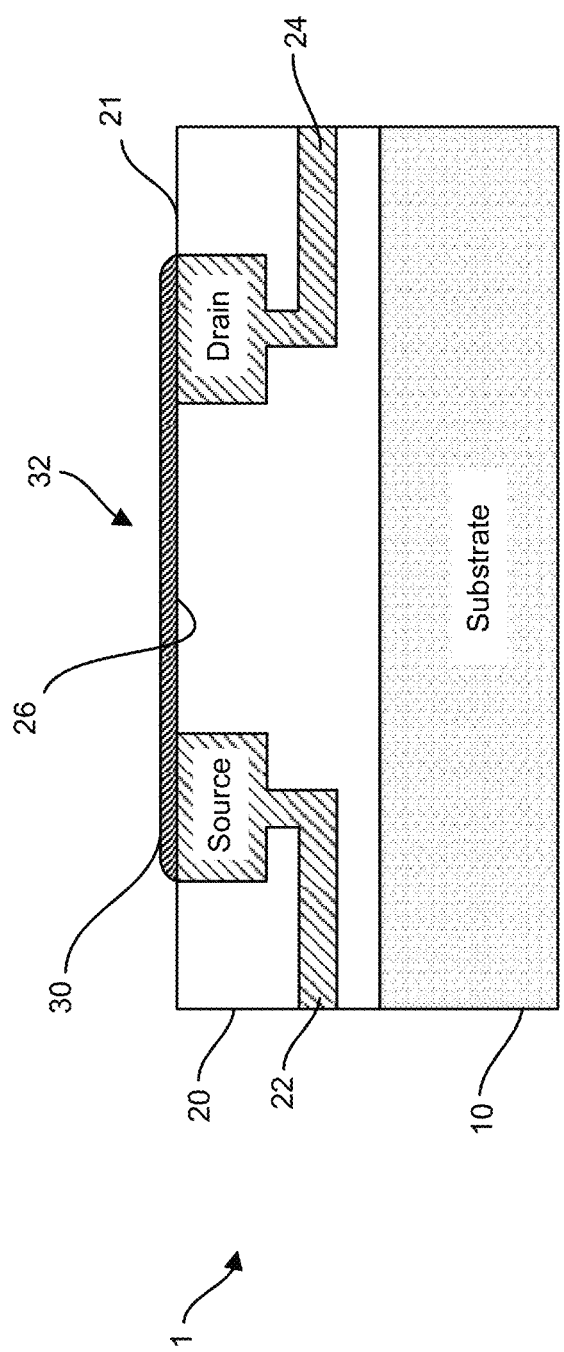
FIG. 1A is an illustration of a substrate for use in a chemically-sensitive FET, such as for a system for analysis of biological and/or chemical materials. In this instance, the substrate includes an insulating layer having a source and a drain, and further includes a reaction zone having a graphene layer associated therewith.

For instance, as can be seen with respect to FIG. 1A, a graphene layered substrate (10) for a chemically-sensitive FET, such as for a system for the analysis of chemical and/or biological materials, is provided. The substrate (10) includes a primary base structure, such as composed of silicon. In various embodiments, the silicon-based primary structure (1) can be configured as a complementary metal-oxide semiconductor (CMOS). The primary structure can include one or more additional structures such as an insulator material layer (20). For example, the substrate may be in a stacked configuration such as where a secondary structure, e.g., including an insulator material, is deposited or otherwise fabricated on top of the primary structure.

The structured primary (10) and/or insulator layers (20) may further include a chemically-sensitive conductive channel (26) that extends from the conductive source to the conductive drain, the conductive channel comprised of a 1D transistor material or a 2D transistor material, e.g., graphene. For instance, the stacked structured layers are configured to include a channel structure (26), which in turn may be adapted as the reaction layer. Particularly, in certain instances, the insulator layer (20) includes a channel (26) and a conductive source (22) and a conductive drain (24), wherein the source and drain are separated from one another by a space that is spanned by channel (26), which source and drain may be planar with a top surface (21) of the insulator layer 20. The source (22) and drain (24) are preferably made of metal, such as damascene. In various embodiments, the insulator material is an organic or an inorganic material. In some embodiments, the organic material is a polymer, polyimide, BCB, or other like material. In other embodiments, the inorganic material may be a silicon oxide, e.g., a silicon dioxide, or a silicon nitride or other metal oxide or nitride.

In particular embodiments, the structures are configured as a complementary metal-oxide semiconductor (CMOS, 1) configured as a chemically-sensitive FET containing one or more of a conductive metal source (22), a conductive metal drain (24), and a channel. In some embodiments, a processor is operably associated with the chemically-sensitive FET. For instance, the chemically-sensitive FET (1) may include a CMOS structure having an integrated circuit that is fabricated on a silicon wafer (10), which further includes a silicon dioxide insulator layer (20), including a conductive damascene copper source (22) and a conductive damascene copper drain (24), which are embedded in at least the insulator layer (20). In various instances, the structures may include a surface (21), e.g., a top surface, which surface may include the channel (26), such as where the surface and/or channel may be configured as a reaction zone (26) that extends from the conductive source (22) to the conductive drain (24). An exemplary length of the surface and/or channel (26) from the source to the drain may range from about 0.001 microns to about (10) microns, such as from about 0.01 microns to about 5 microns, for instance, from about 0.05 micron to 3 microns, including about 0.1 or about 0.5 microns to about (1) or about (1). 5 or about 2 microns. An exemplary width of the surface and/or channel from side to side may range from about 0.001 microns to about (10) microns, such as from about 0.01 microns to about 5 microns, for instance, from about 0.05 microns to 3 microns, including about 0.1 or 0.5 microns to about (1) or about (1). 5 or about 2 microns.

In certain embodiments, the surface and/or channel region may form a reaction layer (26) that include a chemically-sensitive 1D or 2D transistor layer (30). Accordingly, in various embodiments, a 1D transistor material may be included, which 1D material can be composed of a carbon nanotube or a semiconductor nanowire. In other embodiments, a 2D transistor material is included, which 2D material may be a graphene layer, silicene, molybdenum disulfide, black phosphorous, and/or metal dichalcogenides.

For instance, in various embodiments, the chemically-sensitive 1D or 2D transistor layer (30) may be a single layer or a 2D material such as a graphene. Particularly, as can be seen with respect to FIG. 1B, graphene is a two-dimensional, monolayer of carbon atoms that are arranged as a lattice structure. This lattice structure forms regular hexagons with a carbon atom at each vertex. In such a structure, the bond length between adjacent carbon atoms is about (1). 42 Å and the lattice constant is about 2.46 Å. This molecular structure is very unique in that each carbon atom shares one of its four free valence electrons with three of its adjacent and planar carbon atoms such that each of the three planar carbon atoms is orientated at about a 120° with respect to the other three carbon atoms. Such an orientation gives graphene its honeycomb, lattice structure. Additionally, the fourth valence electron forms a pi bond, perpendicular to the three planar sigma-bonded carbon atoms, which is responsible for the unique electronic characteristics of graphene.

Particularly, the single-layer, two-dimensional structure of graphene gives it at least three important characteristics with respect to its use herein: it creates the presence of a bandgap; it makes the graphene layer a semimetal; and it promotes rapid charge transport (mobility and high-field transport) at room temperature. Hence, in various instances, a graphene FET as herein described performs better as a biological sensor than a typical CMOS-FET device not having such a reaction layer. For instance, with respect to nucleic acid hybridization detection and/or sequencing, a traditional MOSFET transistor may have fundamental limitations in its sensitivity (due to channel thickness and intervening insulating layers), whereas the present GFET, with its single atom thickness, can be employed to form a solution-gated reaction zone and/or channel, wherein the graphene layer may be in direct contact with a chemical reaction zone proximate. Specifically, the channel layer may include a 1D or 2D transistor material (30) configured so as to have a much higher carrier mobility than the typical doped silicon commonly used in MOSFET or ISFET devices. This gives the instant 1D and 2D chemically-sensitive FET-based sensor devices increased sensitivity to and faster detection of chemical reactions. Further, in various embodiments, the surface and/or channel (26) may include or make up a dielectric layer, such as for further increasing sensor sensitivity and/or functioning.

Figure 1B:
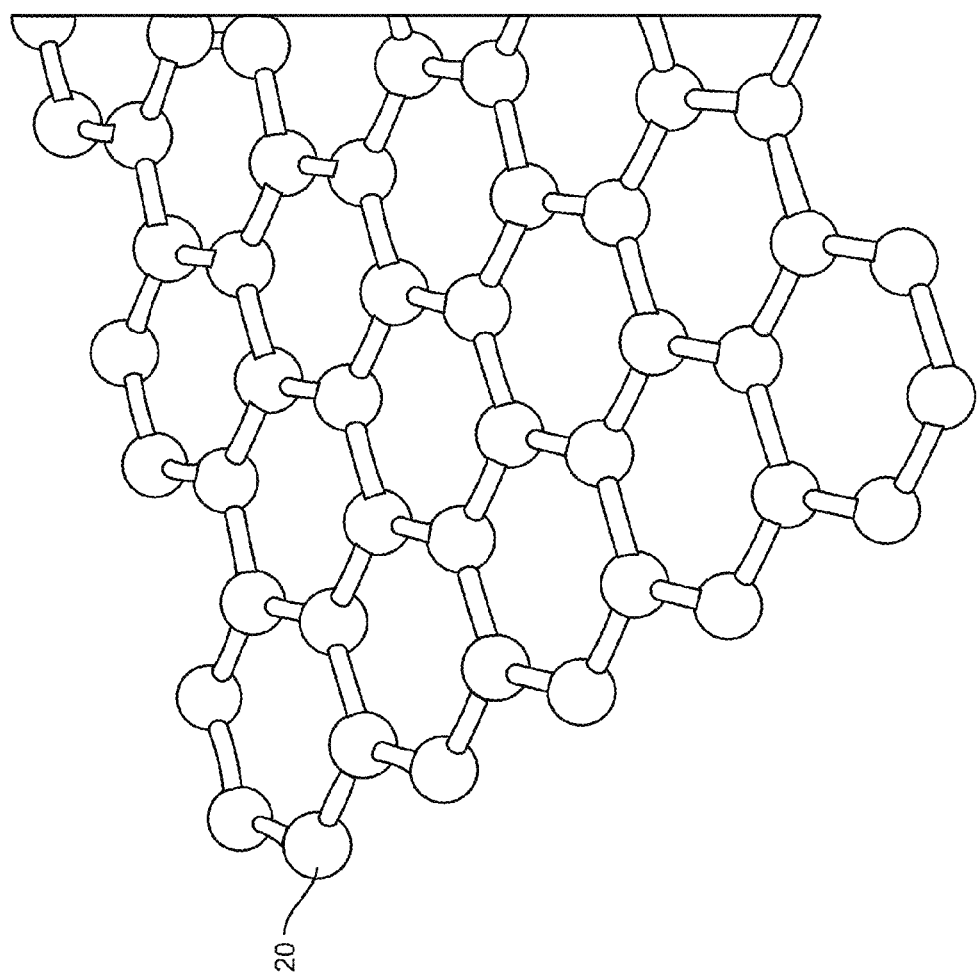
FIG. 1B is an illustration of a graphene layer, such as for use in the substrate of FIG. 1A.
Figure 1C:
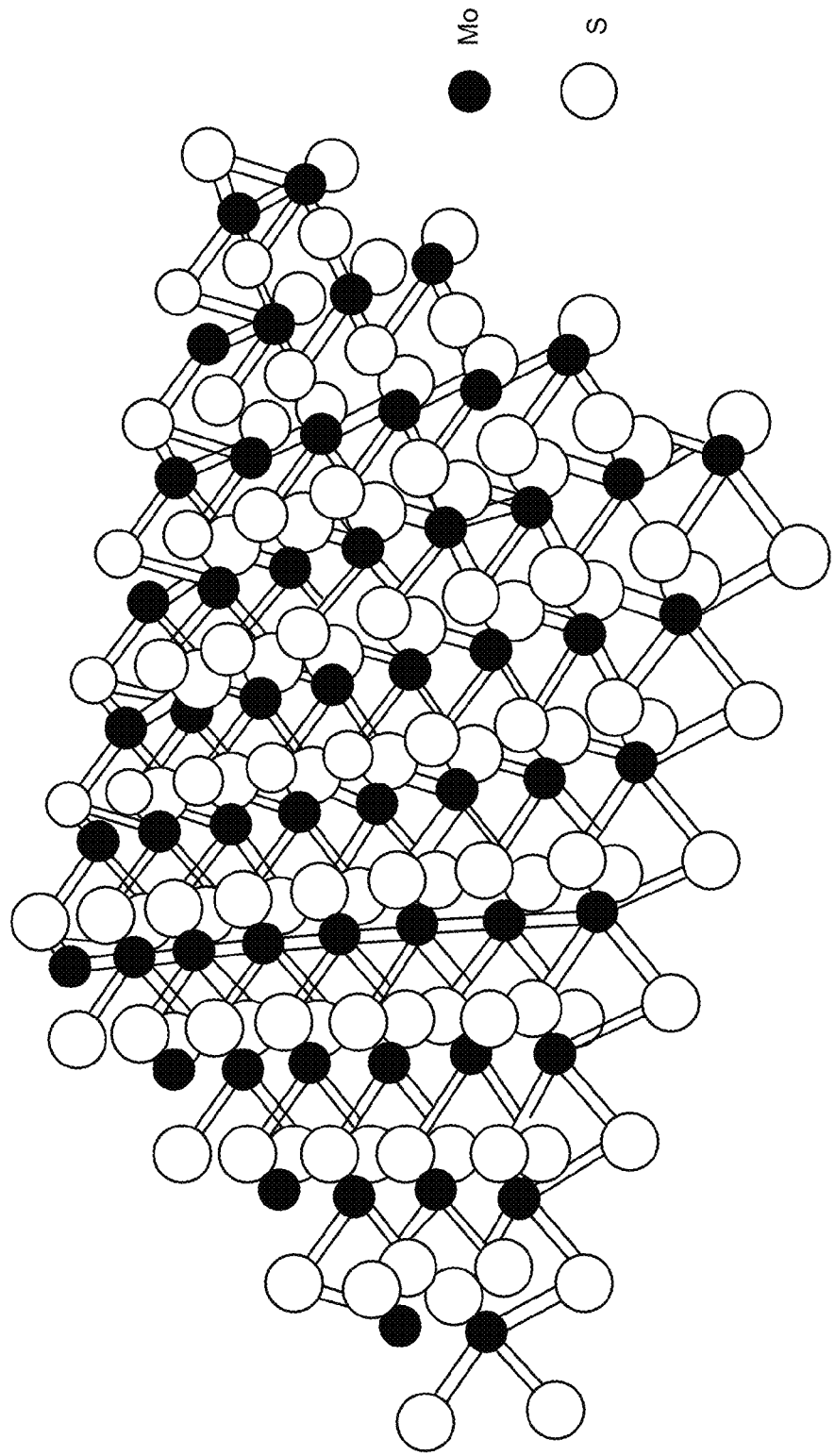
FIG. 1C is an illustration of molybdenum disulfide.
Figure 1D:
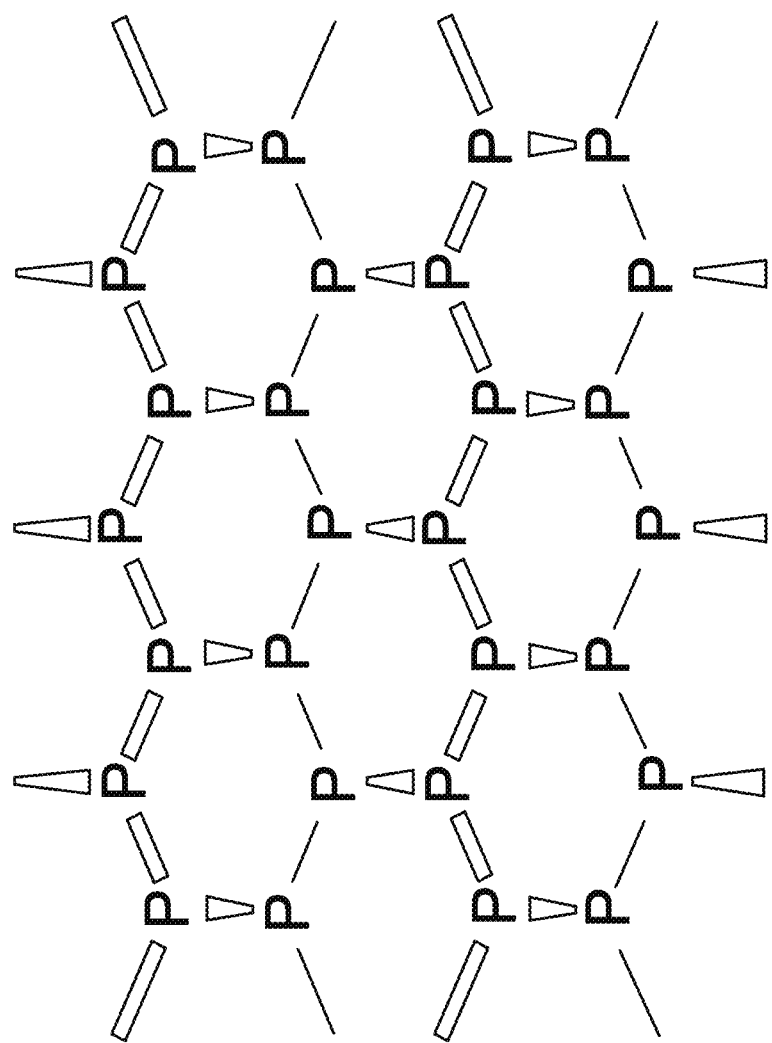
FIG. 1D is an illustration of black phosphorous.
Figure 1E:
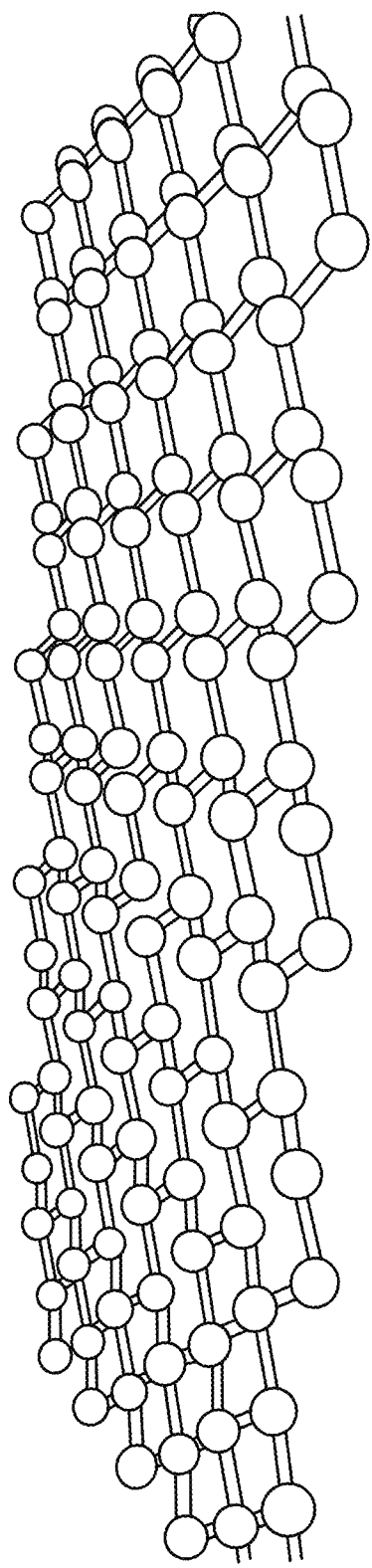
FIG. 1E is an illustration of silicone.
Figure 1F:
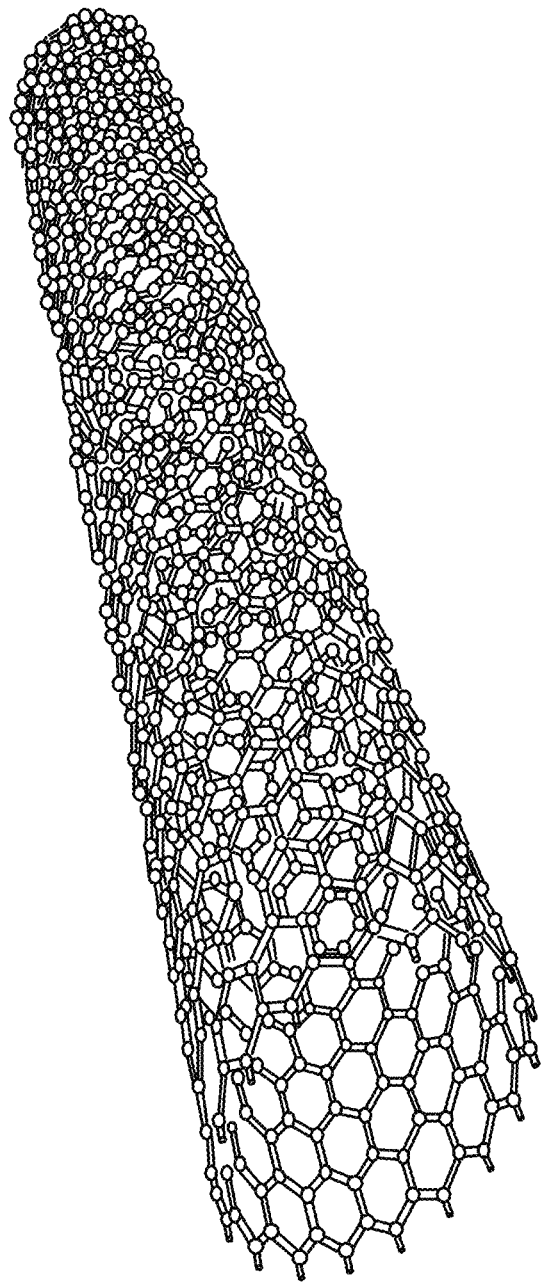
FIG. 1F is an illustration of a nanotube.
Figure 1G:
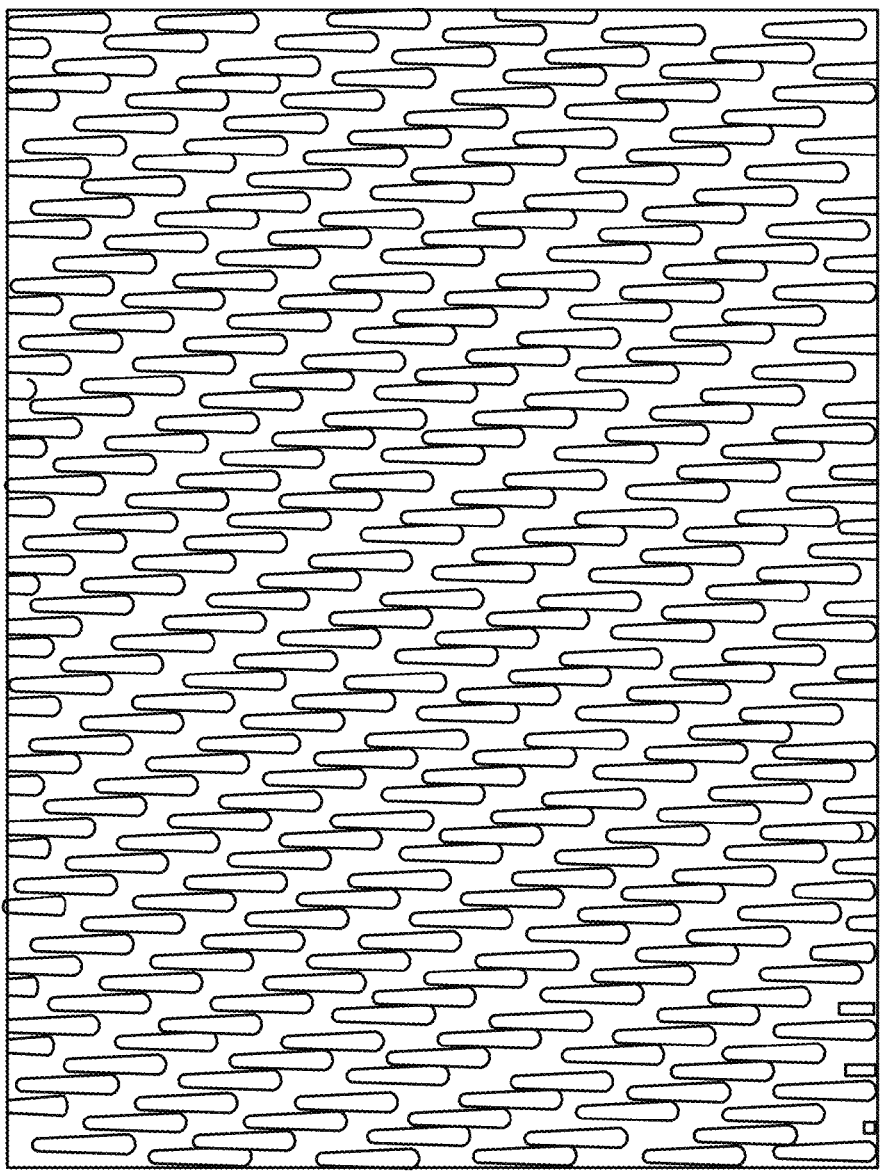
FIG. 1G is an illustration of a semiconductor nanowire structure.

Additionally, FIG. 1C depicts an alternative 2D transistor material layer (30) that can be employed so as to increase sensitivity of the sensor so as to better enable the FET (1) to determine the presence and/or identity of one or more reactants and/or products thereof that results from the occurrence of a chemical and/or biological reaction that takes place proximate to the chemically sensitive FET. As can be seen with respect to FIG. 1C, the 2D material layer in this instance is a molybdenum disulfide. Further 2D materials, as presented herein to increase sensitivity of the sensors include a black phosphorous layer, as depicted in FIG. 1D, and silicone as depicted in FIG. 1E. Alternatively, a 1D material, such as a carbon nanotube may be employed for these enhancement purposes, such as presented in FIG. 1F. A semiconductor nanowire structure, as depicted in FIG. 1G may also be used.

Figure 1H:
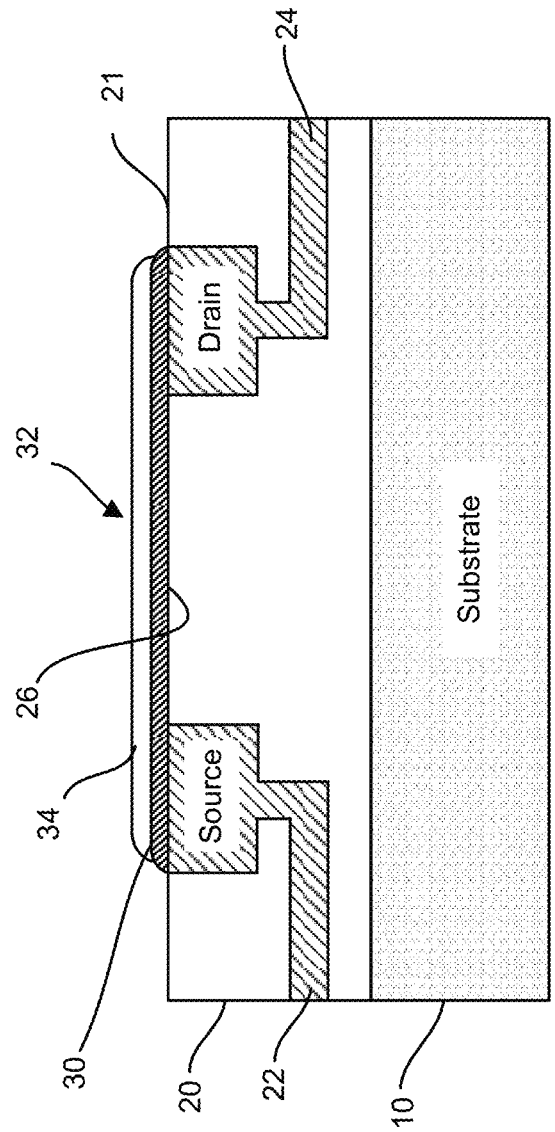
FIG. 1H is an illustration of a graphene layered substrate of FIG. 1A configured as a chemically-sensitive FET having a reaction layer associated with the graphene layer, such as for use in a system for analysis of biological and/or chemical materials.

In various embodiments, as can be seen with respect to FIG. 1H, a reaction layer (34), e.g., an oxide layer, can be disposed on the surface and/or channel (26), such as layered or otherwise deposited on the 1D or 2D (e.g., graphene) layer (30). Such an oxide layer (34) may be an aluminum oxide or a silicon oxide, such as silicon dioxide. In some embodiments, the oxide layer may have a thickness of about (20) nanometers, such as about 15 nanometers, such as 10, 9, 7, or 5 nanometers or less. Particularly, the oxide layer (34), when present, may be composed of an aluminum oxide, a silicon oxide, a silicon dioxide, and the like.

In various instances, a passivation layer (36) may be disposed or otherwise be included on the surface and/or channel (26), such as layered or otherwise deposited on the 1D or 2D (e.g., graphene) layer (30) and/or on an associated reaction or oxidation layer (34) on the surface and/or channel (26). More particularly, the oxide and/or passivation layers may have a suitable thickness such as of from about 100 nm or about 75 nm to about 10 nm or 9 nm or less, such as about 0.5 microns or about 0.1 microns or about 50 nanometers or less to about (20) nanometers, such as about 15 nanometers, such as about 7 or about 5 nanometers or less, respectively.

Figure 1I:
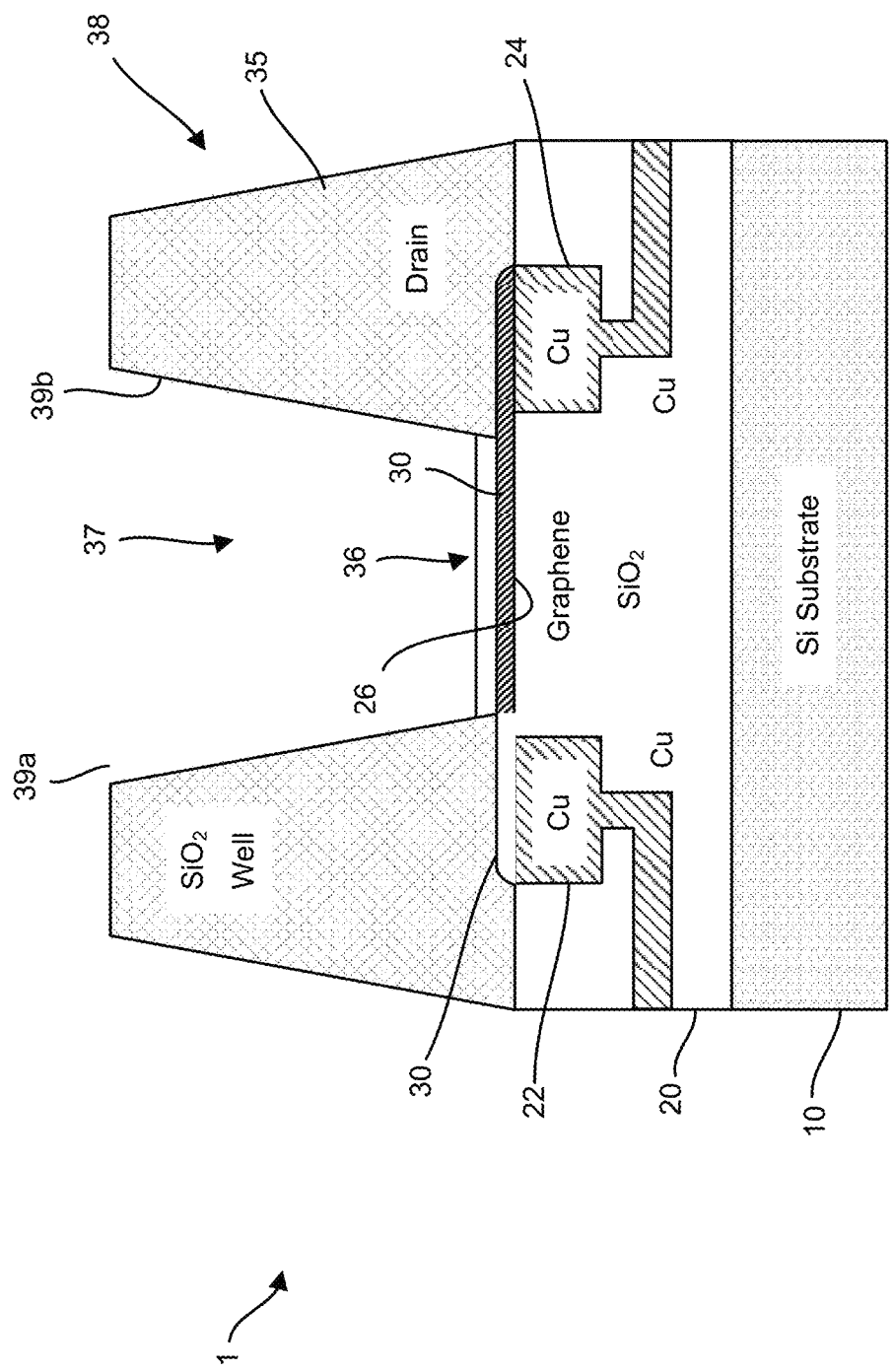
FIG. 1I is an illustration of a chemically-sensitive FET of FIG. 1A having a silicon dioxide layer positioned over the substrate and insulating layers, and further having a well structure etched into the silicon dioxide layer so as to form a chamber proximate the graphene layered reaction zone. In this instance, the chamber includes a passivation layer or etch stop layer placed over the reaction layer.

As can be seen with respect to FIG. 1I, in particular embodiments, the primary (10) and/or secondary (20) structures can be fabricated to include or otherwise be associated with a tertiary structure (35), such as may be comprised of a silicon dioxide material. In various instances, the tertiary layer can be fabricated or otherwise configured so as to include a chamber or well assembly (38) in and/or on the surface (21). For instance, FIG. 1I depicts a chemically-sensitive FET in a stacked configuration and having a well structure (38), which well structure may be positioned on a portion of a surface, e.g., an exterior surface (e.g., 21) of a primary (10) and/or secondary structure (20). In some instances, the well structure (38) may have a plurality of walls or bounding members (39a) and (39b) set apart from each other by a distance that may (or may not) be equivalent to the space between the source and drain so as to form the vertical boundaries of the chamber (38), with the bottom of the chamber forming the horizontal, bottom boundary. In particular embodiments, the bottom of the chamber (38) may be configured as a reaction zone so as to form a reaction region within the well (38). Particularly, the boundaries (39a, 39b) may be formed on top of, or may otherwise include at least a portion of the 1D or 2D (e.g., graphene) material (30), and/or may additionally include the reaction, e.g., oxide, and/or passivation layers (36). In various embodiments, the chamber and/or well structure (38) may define an opening (37), such as an opening that allows access, e.g., fluid access, to an interior of the chamber (38), thus allowing direct contact or intimate association with the 1D (e.g., carbon nanotube or nanowire) or 2D (e.g., graphene) structure associated with the surface and/or channel (26).

Certain embodiments of chemically-sensitive FETs can be fabricated in a manner to increase the contact surface area between the source and drain and the material used to form the channel. For example, a substrate can be provided, e.g., a silicon substrate. An insulating dielectric layer, e.g. an oxide layer, may then be deposited on the substrate, into which a plurality of materials may be deposited so as to form a channel region within the dielectric layer. Thus, the dielectric layer may be processed in a manner of different ways, as set forth herein, so as to produce a channel, such as a channel comprising a 1D or 2D material extending between a plurality of electrodes, such as source and drain electrodes. Accordingly, once deposited and suitably positioned above the substrate layer, the dielectric layer may be subjected to further processing so as to form a channel region, the channel region being formed between two opposed electrodes.

Figure 1J:
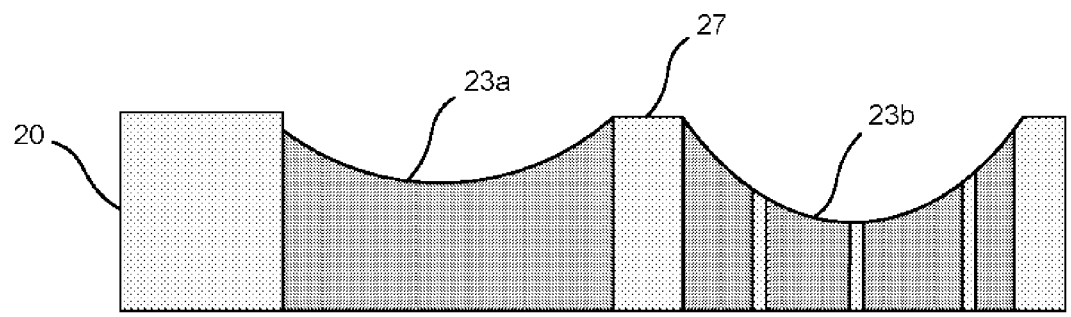
FIG. 1J shows a side sectional view of trenches formed in an insulating dielectric layer.

For instance, in an exemplary embodiment depicted in FIG. 1J, a plurality of trenches (23a, 23b) can be formed in the insulating dielectric layer (20), one trench separated from the other by a distance (27). The trenches (23a, 23b) are for receiving conductive material and forming electrodes. FIG. 1J provides a side-cutaway view of the dishing process to form the trenches in the dielectric layer of the CMOS-FET sensor of the invention. Specifically, each separate trench can be formed in a number of suitable ways, such as by cutting, carving, or etching, or otherwise cupping out, and the like. For instance, the trenches can be formed through etching, such as dry or wet etching. Additionally, once formed the trench and/or surrounding material may be planarized, so as to form a divot, such that a first part of the dielectric region is at a higher level than a second part of the dielectric material, such as surrounding where the electrode is to be present.

Following formation of trenches in the insulating dielectric layer, a conducting material, such as copper, e.g., damascene copper, or gold, or platinum, and the like may be inserted into the trenches to form the electrodes. This surface area may then be patterned before or after the application of the 1D or 2D material layer.

Figure 1K:
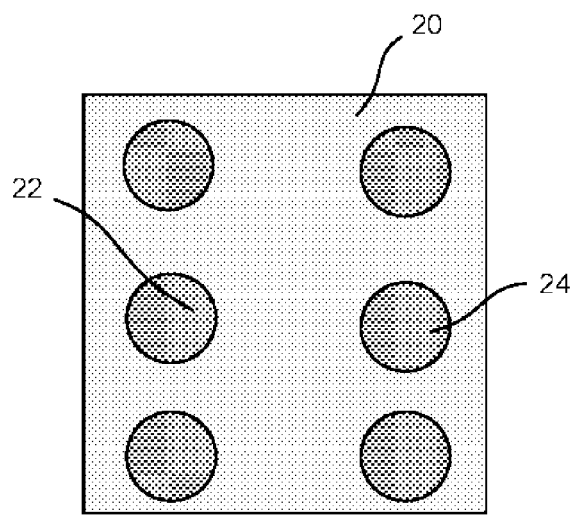
FIG. 1K shows a top view of a dielectric layer in which electrodes have been deposited.
Figure 1L:
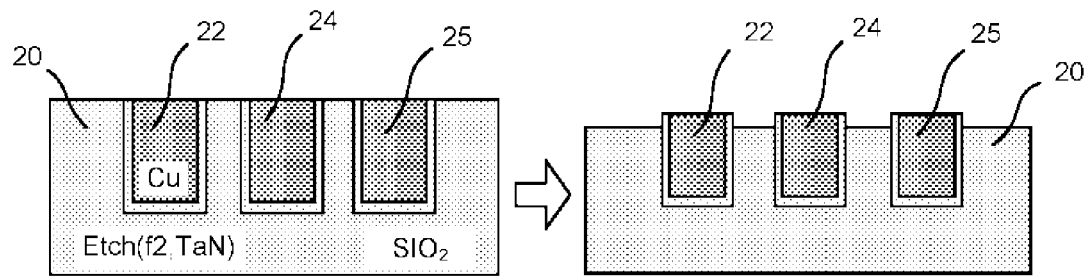
FIG. 1L shows a side sectional view of electrodes in a dielectric layer before and after chemical-mechanical planarization (CMP) process. The CMP process partially etches part of the dielectric layer to allow the electrodes to project above the surface of the dielectric layer.

It is to be noted that the configuration of the formed trench is useful for several purposes. For instance, the trench may be cupped out and the metal applied in such a manner that once deposited, a portion of the metal electrode is raised above the bounding surfaces of the trench. This exposure and/or projection above the trench is useful because it forms the contact with the 1D and/or 2D material that forms the channel structure. Hence, when applying the metal to the formed trench area, the metal should be filled so that its final structure is raised above the substantially planar surface of the oxide dielectric layer, as can be seen with respect to FIG. 1K. Accordingly, FIG. 1K provides a top-plane view of an etched out dielectric layer (20), where the electrodes (22, 24) have been deposited. Here, the electrodes (22, 24) extend upwards and stand above the surface of the dielectric layer (20). Once the electrodes have been formed, the platform surface may then be treated or otherwise processed, such as by a chemical-mechanical planarization (CMP) process, which process is partly a chemical treatment and partly a mechanical polishing treatment so as to produce a profile on the electrodes that differs from that of the surrounding insulating dielectric layer. Specifically, as can be seen with respect to FIG. 1L, the dielectric layer (20) and electrode layers (22, 24) may be treated, e.g., via CMP, so as to produce a dishing effect, which thereby allows the electrodes when deposited and processed, e.g., polished, to stand up or otherwise project above the surface of the dielectric layer (20). In this instance, the surface of dielectric layer (20) has been planarized and then has been etched down so as to allow the electrodes (22, 24) to stand up above the etched and planar surface of dielectric layer (20). This offset between the surface of the deposited electrode and the surface of the insulating dielectric layer is useful because it allows for greater contact with the 1D and/or 2D material once deposited over the electrodes in a manner so as to form the channel, such as the channel between the first electrode, serving as the source, and the second electrode serving as the drain. This exposed configuration is important, therefore, for at least in that it increases the surface area of contact and allows for better contact fabrication as well as for better transport through the contact.

Figure 1M:
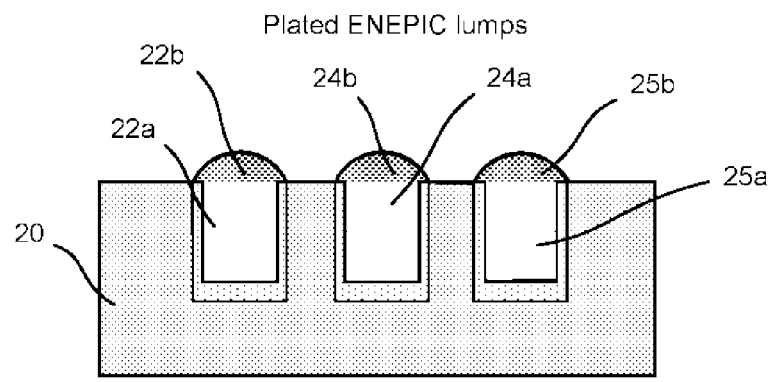
FIG. 1M shows a side sectional view of electrodes in a dielectric layer that have additional material in the form of plated bumps on the contact region of the electrodes.
Figure 1N:
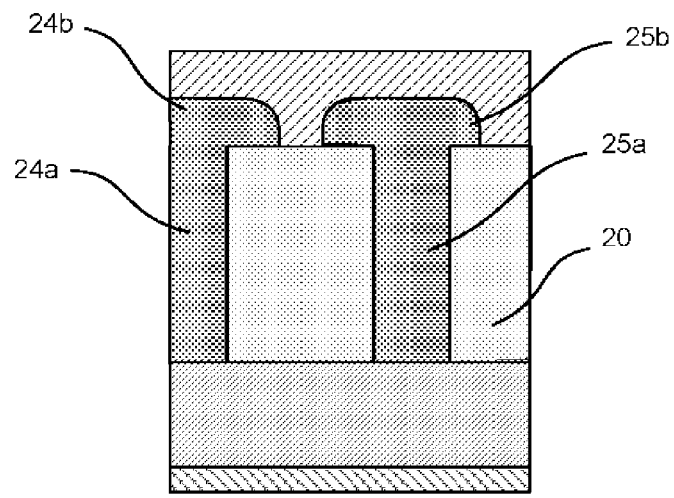
FIG. 1N illustrates a side sectional view of an embodiment of electrodes in a dielectric material with plated bumps on the electrodes that extend slightly past the edges of the electrodes.

Accordingly, in various embodiments, as seen with respect to FIGS. 1M and 1N, the processed and/or polished surface of an electrode may be further processed, such as by being subjected to a plating process so as to add additional material to the contact region, e.g., to increase its surface area and/or to give the contact region of the electrode a desired shape or configuration prior to the deposition of the 1D or 2D material layer thereon. Such plating may be performed in a variety of different ways, such as an electrolytic process and/or an electroless plating process, which allows the auto-catalytic plating on top of the deposited electrodes, so as to further build up a configuration, e.g., a bump with a more pronounced offset above the dielectric layer. FIGS. 1M and 1N show plated bumps (22b, 24b, 25b) on electrodes (22a, 24a, 25a) that extend above the surface of the oxide layer (20). In the embodiment depicted in FIG. 1N, plated bumps (24b, 25b) extend laterally slightly past the edges of the electrodes (24a, 25a). The additional material may be any form of conducting material, such as a metal. In certain embodiments, an electrode may be subjected to an additional plating process such as that described above, without an etching or other treatment to reduce the height of the insulating dielectric layer surrounding the electrode.

In various instances, once formed, the electrode may then be contacted with a 1D and/or 2D channel forming material in such a manner that a channel forms between the first and second electrodes, that is between the source and drain electrodes. In certain instances, the layering or otherwise depositing of the 1D or 2D material over the channel area, so as to form the channel between the source and drain electrodes, is performed in such a manner so as to increase the surface area of one or more edges of the channel material coming into contact with the electrode material. This is useful because carrier mobility may be increased through the interface of the electrode and the channel member at these one or more edges. Hence, it has been discovered that increasing contact efficiency increases carrier mobility through the channel. Accordingly, presented herein are field effect transistors that have optimal channel electrode interfaces that maximize this contact.

For instance, as described herein above, the 1D or 2D material layer positioned between the electrodes can be arranged in such a manner that only a bottom surface of the 1D or 2D material contacts the electrode surface, e.g., a bottom side contact. However, in some embodiments, the configuration of the contact area may be configured such that as the 1D or 2D material contacts the electrode material it does so in a manner so as to form an edged interface, which edge configuration may be particularly useful in increasing the flow efficiency of carriers through the channel. Further, this contact region may additionally be configured to include one or more of a bottom side contact, an edge side contact, a top-side contact, as well as multiple edge contacts, and interior and exterior side or edge contacts.

Figure 1O:
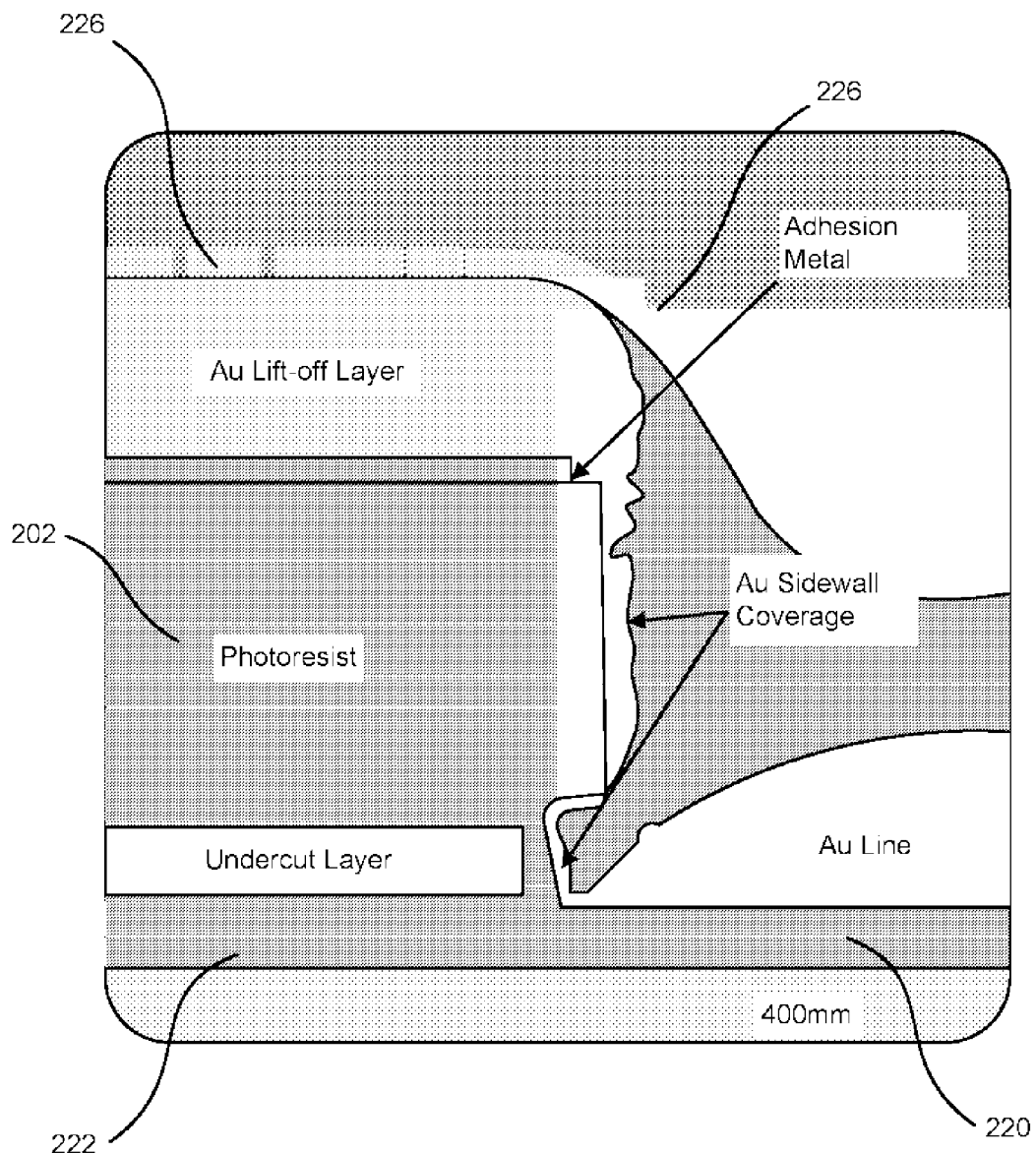
FIG. 1O shows a side sectional view of an electrode in a dielectric layer with a graphene layer on top of the electrode. The dielectric layer is in the midst of a lift-off process to create an opening in the graphene layer and thereby expose a contact region of the electrode.

In various instances, such as those shown with respect to FIG. 1O, the graphene and/or electrode layers may be additionally configured to further increase the relevant surface area of the contact. For instance, once the graphene layer (26) has been deposited, one or more openings (31) or holes or divots may be made into the material layer, which then may be subjected to another plating process to further build a metal contact surface with the graphene layer (26), thereby increasing contact between the graphene layer (26) and the electrode layer (22).

In one embodiment, the holes or openings may be formed using a lift-off process. For example, FIG. 1O shows a side sectional diagram of a graphene layer (226) and electrode layer (222) with a reverse photoresist (202) on top of the electrode layer (222). An insulating dielectric layer (220) is proximate to the electrode layer (222). The diagram of FIG. 1O shows graphene layer (226) just prior to a hole in being formed where the reverse photoresist (202) is located. The reverse photoresist (202) is destroyed, removing the portion of grapheme layer (226) associated with the reverse photoresist (202), and leaving only the portion of the graphene layer (226) in the region where the reverse photoresist is not underneath graphene layer. Accordingly, in various instances, a hole may be made through the graphene layer to the underlying metal layer of the electrode, which hole may then be filled with a secondary metal material, which material may be the same or different metal as the electrode, and thus an enlarged surface area contact is formed, as illustrated by FIG. 1O. In some embodiments, the electrode material may come up through the bottom of the holes to cover at least a portion of the top of the graphene layer, or metal may be plated on top of the graphene layer and travel downwards into the holes thereby contacting the electrode metal layer thereunder. In certain embodiments, a lift-off process may also be used to separate channels of 2D material from each other and to electrically isolate individual channels with only specific electrode pairs.

Figure 1P:
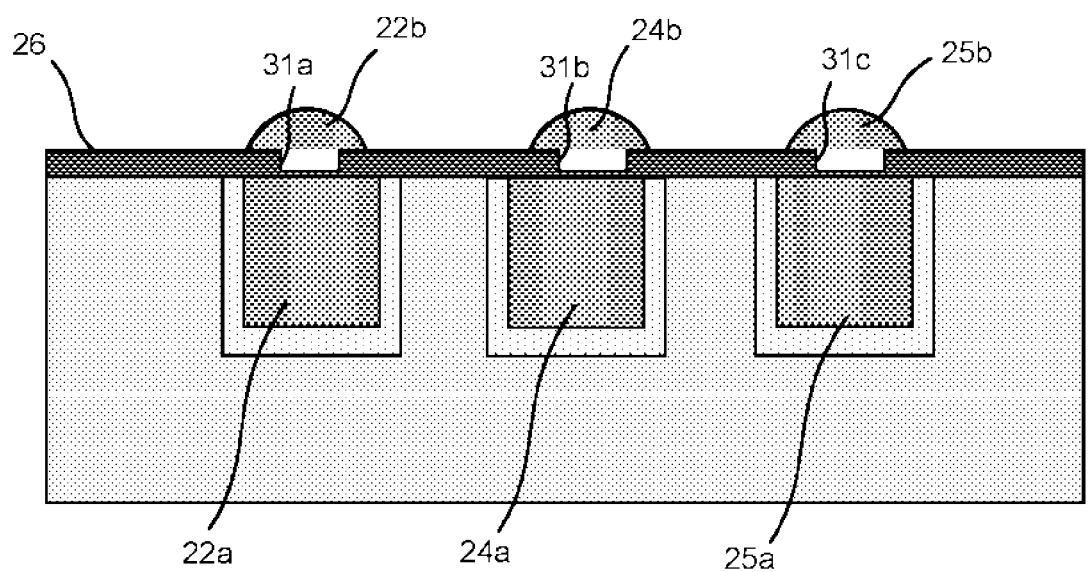
FIG. 1P shows a side sectional view of an embodiment of multiple electrodes in a dielectric layer with a graphene layer on top of the electrodes. The graphene layer has openings proximate each of the electrodes, and metal portions or cover is deposited over the openings.
Figure 1Q:
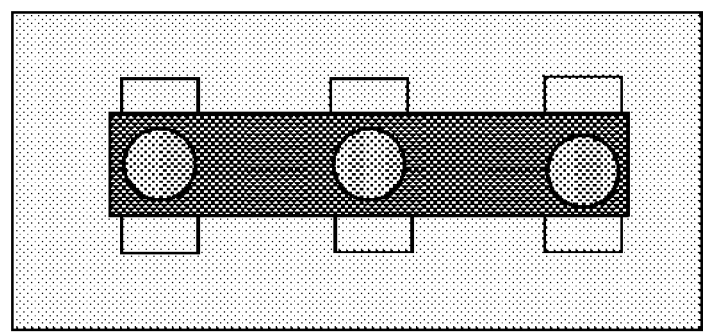
FIG. 1Q shows a top view of the multiple electrodes shown in FIG. 1P.

Accordingly, in various embodiments, once the electrodes have been fashioned and/or the 1D or 2D channel formed in conjunction therewith, e.g., such that the channel material extends between the source and drain electrodes, one or more of the contact regions between the channel material and that of the electrode material may be further processed. For instance, as can be seen with respect to FIGS. 1P and 1Q, the contact area of the channel material (26) may be patterned, e.g., one or more openings (31a, 31b, 31c) may be made in the channel and other associated material layers, to enlarge an additional surface area, and a second metal portion or cover (22b, 24b, 25b) may be deposited into the openings (31a, 31b, 31c) and/or at this area, thereby creating a further contact interface between the metal electrode material (22a, 24a, 25a) and the channel material (26).

The second metal portion may extend vertically above the surface of the 2D materials, as well as laterally on top of the 2D material a distance that is greater than the diameter of each opening. The shape of the openings (31a, 31b, 31c) may have any suitable configuration such as round, elliptical, square, rectangular, rhomboidal, and the like, so as to maximize the effect contact area. Hence, in such a configuration, the contact area between the channel material and the electrode material may include one or more of a bottom contact area, an outside contact area, an inside contact area (see FIG. 1P), and/or a top contact area (see also FIG. 1Q). Thus, once the 1D or 2D material layer is applied over the electrode layer of the dielectric layer, the 1D or 2D material may be patterned, so as to create an opening in the contact region, which opening may then be filled with another metal material layer, such as copper, silver, gold, platinum, palladium, and the like, which second metal layer may then be patterned as well, if desired.

Particularly, once the electrode area and 1D/2D material interface has been formed in the desired configuration, then, if desired, the surface thereof may be patterned. For instance, once the 2D material, e.g., graphene, is laid down, a photo-resist and/or mask having the desired configured cutouts may be placed over the channel region and/or graphene, such as where the pattern includes protected regions where patterning, e.g., etching, is not desired. Once suitably protected where desired, then an etching process, e.g., a dry or wet etching process may be employed so as to etch the surface of the 1D or 2D material and/or channel region into the desired pattern where the 1D or 2D material layer is not protected.

Figure 1R:
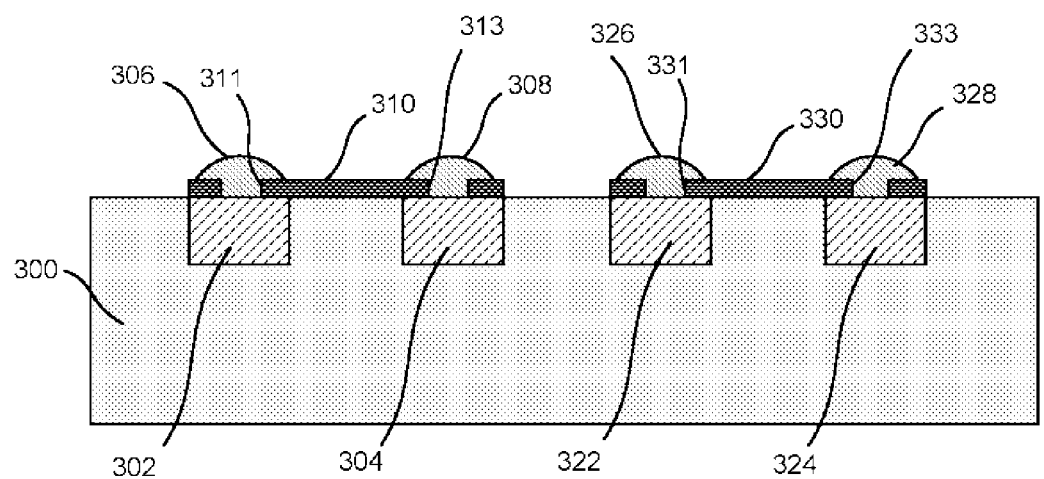
FIG. 1R illustrates a side sectional view of an embodiment of electrodes contacted by additional electrically conductive material through openings in a 2D material layer.
Figure 1S:
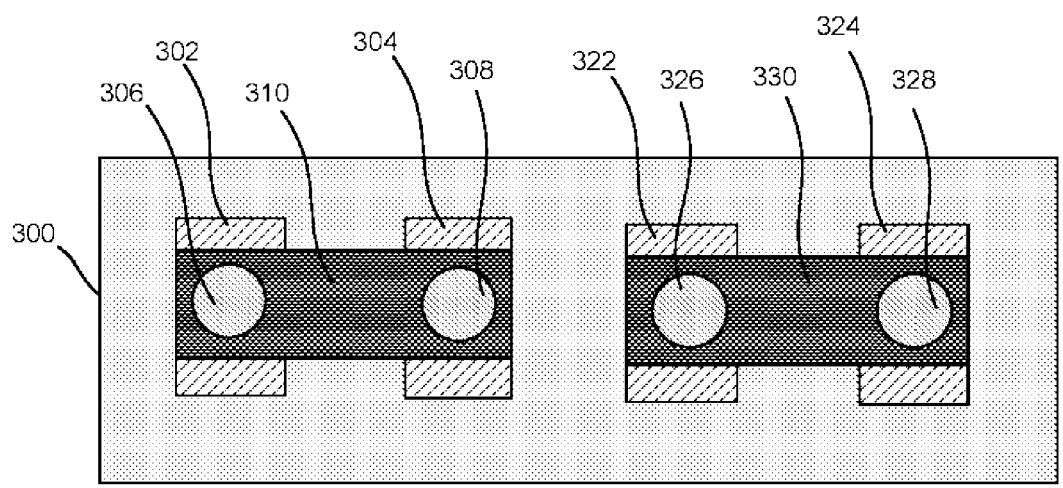
FIG. 1S shows a top view of the embodiment of electrodes, electrically conductive material, and the 2D material shown in FIG. 1R.

FIG. 1R shows another embodiment of electrodes contacted by additional plating or electrically conductive material through openings in a channel of 2D material, e.g. graphene. Electrodes (302, 304) are deposited in insulating dielectric layer (300), as well as the electrodes (322, 324). One electrode (302) may be a source electrode, and another electrode (304) may be a drain electrode. Similarly, an electrode (322) may be a source electrode and another electrode (324) may be a drain electrode. Conductive deposits (306, 308), e.g., a metal, have been deposited over openings (311, 313) in the 2D material (310), respectively, and the contact electrodes (302, 305) through their respective openings. Similarly, conductive deposits (326, 328) are deposited over respective openings (331, 333) of 2D material (330). Conductive deposits (326, 328) contact respective electrodes (322, 324) through their respective openings. FIG. 1S shows a top view of the electrodes (302, 304, 322, 324) in FIG. 1R. 2D material (310) connects electrodes (302, 304) to form a channel between the electrodes; 2D material (330) similarly connects electrodes (322, 324) to form a channel between its respective electrodes. Conductive deposits (306, 308, 326, 328) increase electrical connectivity and help maintain the 2D materials (310, 330) in place.

Figure 1T:
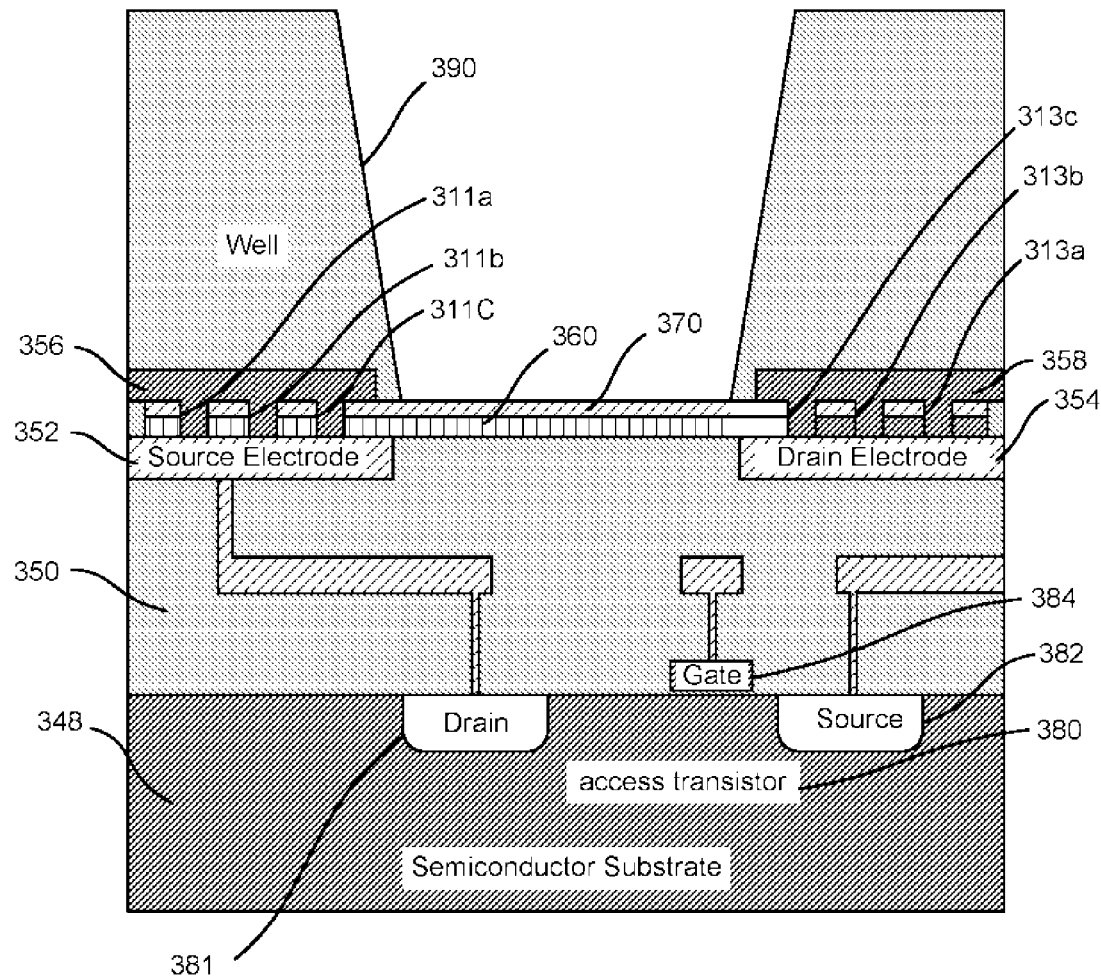
FIG. 1T illustrates a side sectional view of an integrated circuit with electrodes, a channel structure, and a well structure. The channel structure has multiple openings to allow additional conductive material to contact the electrodes.

In some embodiments, multiple openings or holes may be used to connect 1D, 2D, or even 3D material to electrodes. An exemplary embodiment of such a configuration is depicted in FIG. 1T. In the depicted embodiment, a well (390) has been patterned above 2D material (260) out of insulating dielectric material, for use in bio-sensing. Further details of exemplary bio-sensing features are described below and throughout the instant specification. In the embodiment shown in FIG. 1T, an ion sensitive layer (370) is positioned over the 2D material (260). Multiple holes or openings (311a, 311b, 311c, 313a, 313b, 313c) have been patterned through the 2D material (260) and an ion sensitive layer (370). Conductive covers or deposits (356, 358) are positioned proximate respective electrodes (352, 354) and contact respective electrodes (352, 354) through openings (311a-c, 313a-c) in the 2D material (260) and ion sensitive layer (370). In some embodiments, the electrodes (352, 354) may be positioned in trenches created in an insulating dielectric layer (350), as described above. Electrodes (352, 358) connect to a respective drain (381) and source (382) of an access transistor (380) positioned in a substrate layer (348), e.g., a silicon semiconductor. A gate (384) allows control of signals received from electrodes (352, 354) into an access transistor (380).

Figure 1U:
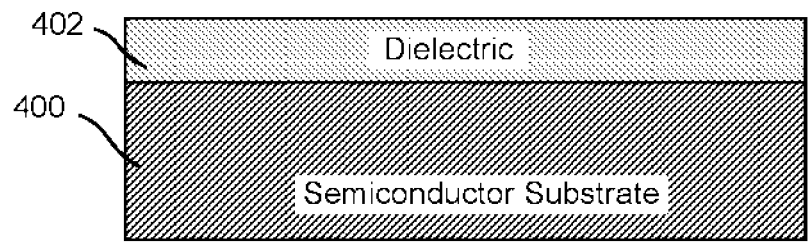
FIG. 1U shows a side sectional view of a semiconductor substrate coated with an insulated dielectric layer during fabrication of an integrated circuit of the invention.
Figure 1V:
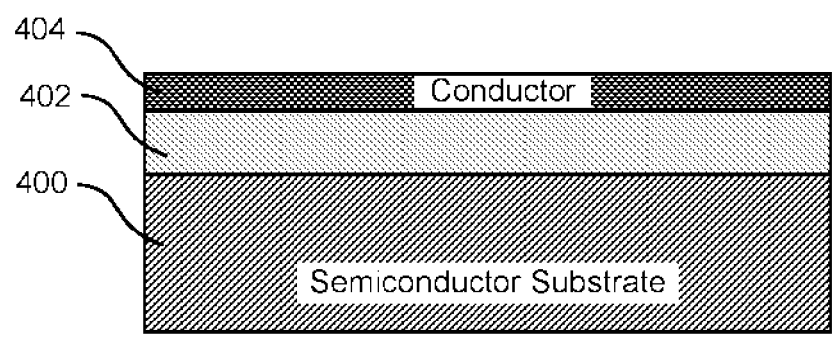
FIG. 1V illustrates a side sectional view of a conductive material layer on an insulated dielectric layer during fabrication of an integrated circuit of the invention.

FIGS. 1U-1BB provide exemplary diagrams of a semiconductor substrate at different stages of treatment to create an integrated circuits for biosensing (e.g., nucleic acid hybridization or sequencing) as described herein. At FIG. 1U, an insulated dielectric layer 402 is formed on a semiconductor substrate (400), e.g., silicon or other semiconductor. Transistors and interconnects on semiconductor substrate (400) may be present in some embodiments, but are not depicted in FIGS. 1U-1BB. A conductive material layer (404) may then be formed over insulated dielectric layer (402, see FIG. 1V). In some embodiments, the conductive material layer may be deposited in trenches formed in insulated dielectric layer (402, see, e.g. FIG. 1J-1K and description above).

Figure 1W:
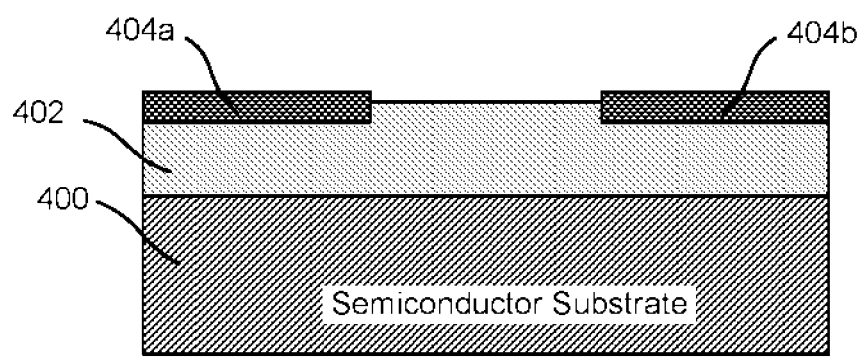
FIG. 1W shows a side sectional view of a patterned conductive material layer during fabrication of an integrated circuit of the invention.
Figure 1X:
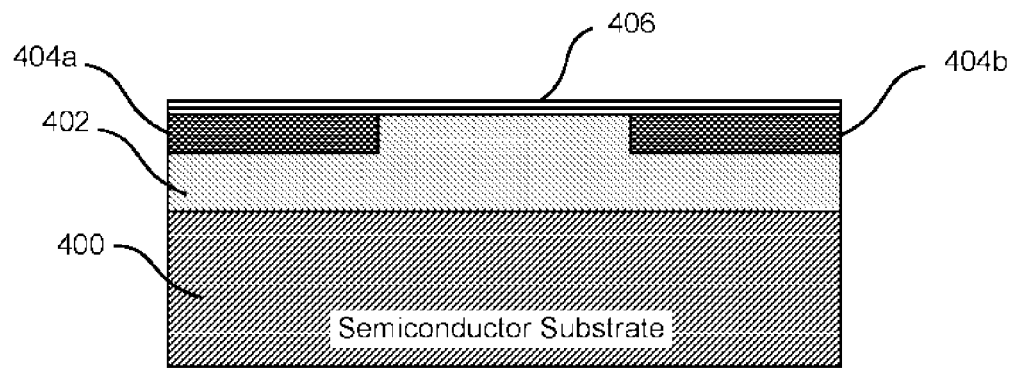
FIG. 1X illustrates a side sectional view of a 1D or 2D material layer applied over electrodes during fabrication of an integrated circuit of the invention.
Figure 1Y:
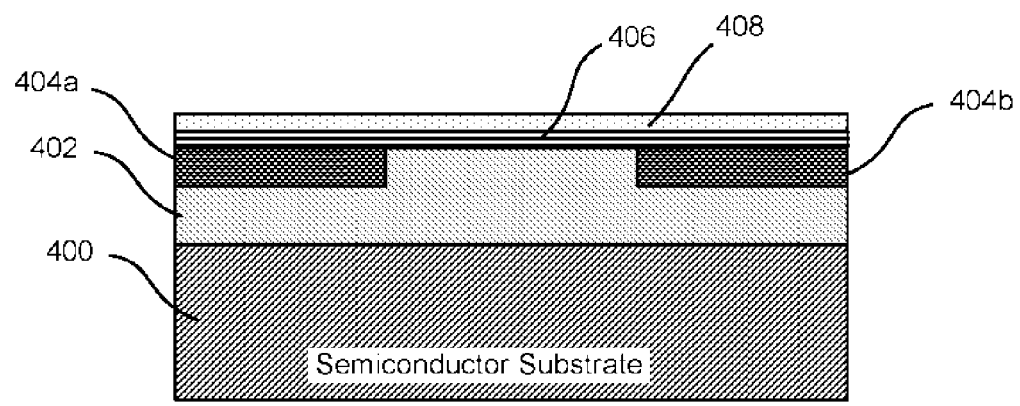
FIG. 1Y shows a side sectional view of an ion sensitive layer applied over a 1D or 2D material layer during fabrication of an integrated circuit of the invention.
Figure 1Z:
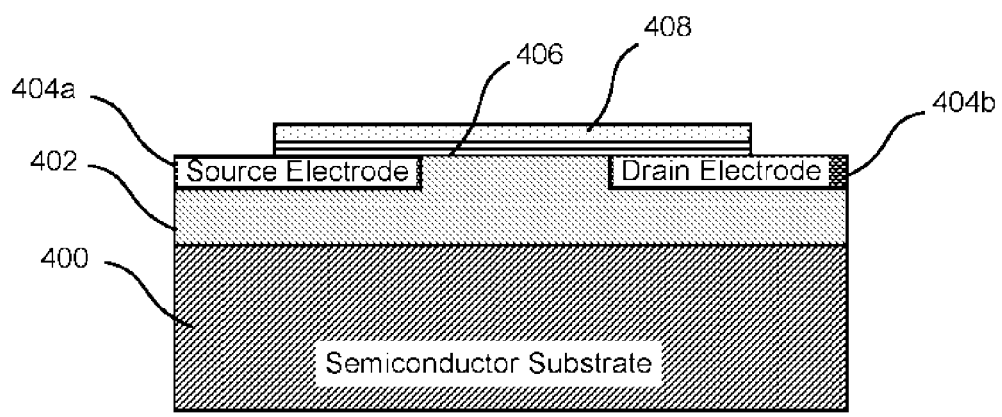
FIG. 1Z illustrates a side sectional view of ion sensitive and 1D or 2D material layers that have been patterned during fabrication of an integrated circuit of the invention.
Figure 1A:
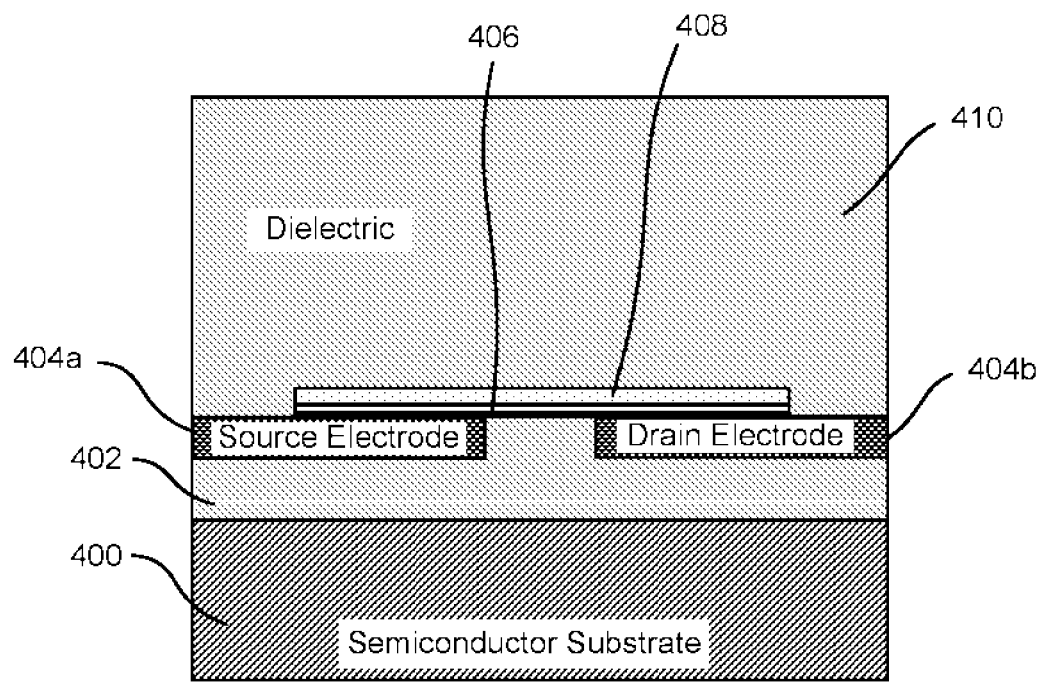
Figure 1B:
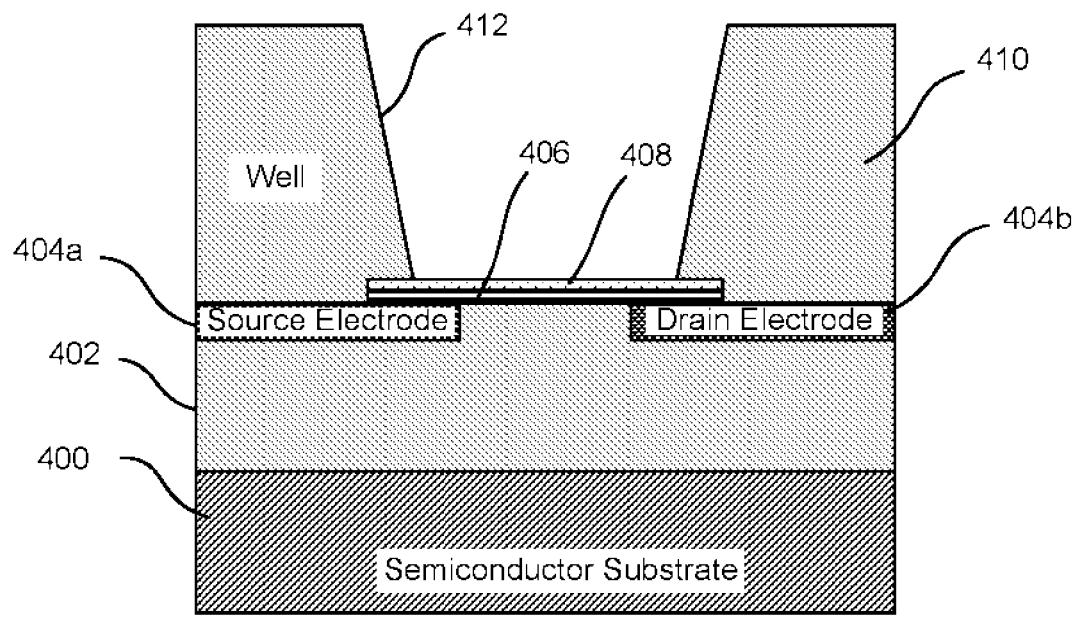

The conductive material layer (404) may then be patterned to form a source electrode (404a) and a drain electrode (404b) (FIG. 1W). A 1D or 2D material layer (406) may then be applied over the electrodes (404a, b) and insulated dielectric layer (402, FIG. 1X). An analyte or ion sensitive layer (408) may then be applied over 1D or 2D material layer (406, see FIG. 1Y). The ion sensitive layer (408) and 2D material layer (406) may then be patterned (see FIG. 1Z) using techniques described herein. In certain embodiments, holes or openings may be created in ion sensitive layer (408) and 2D material layer 406, as described above, and a second conductive layer may be placed on top of the openings or holes to electrically contact the electrodes (404a, 404b). A second insulating dielectric layer (410) may then be added on top of electrodes (404a, 404b) as well as the ion sensitive layer (408) and 2D material layer (406, see FIG. 1AA) and then patterned to form a well (412, see FIG. 1BB).

Once the appropriate electrode and channel structures have been formed proximate the dielectric insulating layer, a second insulation layer may then be deposited over the dielectric, electrodes, and channel layers, which secondary insulating layer may also be patterned, such as by etching to form one or more chambers or wells, where the opening of the chamber and/or well corresponds to the formed channel region(s). Hence, in a manner such as this, the substrate may be configured so as to include one or more nano and/or micro chambers that may further be configured to form one or more reaction wells.

Figure 2A:
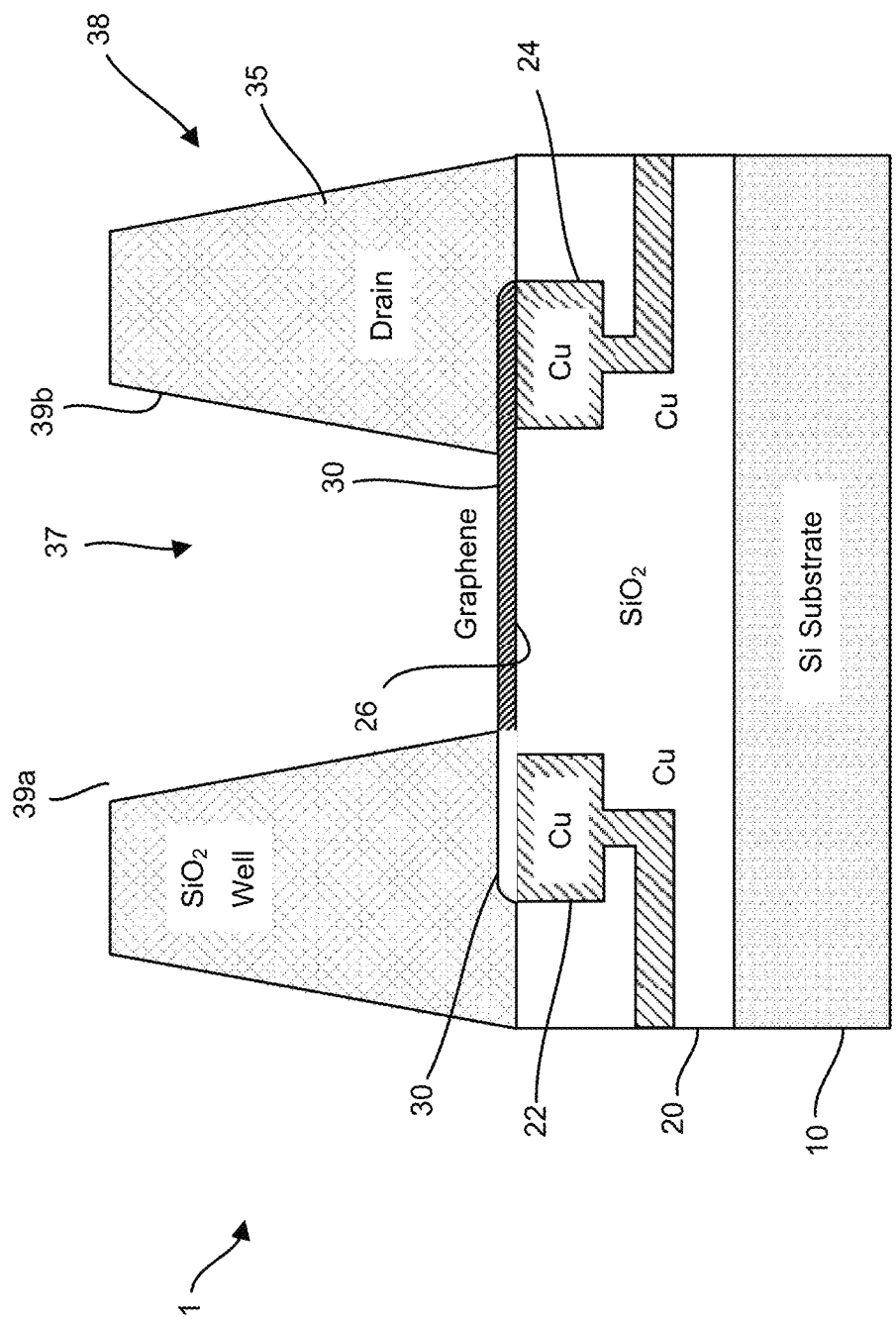
FIG. 2A is an illustration of a chemically-sensitive FET having a graphene layered well structure, such as for a system for analysis of biological and/or chemical materials.

Accordingly, as presented with respect to FIG. 2A, a further aspect of the present invention is a biosensor (1). The biosensor includes a CMOS structure (10) that may include a metal containing a source (22), e.g., a damascene copper source, as well as a metal containing a drain (24), e.g., a damascene copper drain, such as embedded within an insulating and/or dielectric layer (20), e.g., positioned on top of the structure (10). The insulating layer may be an inorganic material, such as a silicon oxide, e.g., a silicon dioxide, or a silicon nitride, or an organic material, such as a polyimide, BCB, or other like material. The biosensor may also include a 1D or 2D layered, e.g., a graphene layered, surface or channel (26) extending horizontally from the source (22) to the drain (24), so as to at least be proximate therewith and thereby form a reaction zone (26).

In this instance, the surface structure (26) completely overlaps the source (22) and drain (24) regions. A further layer of material (35) may be positioned over the surface and/or channel region (26), which layer of material may further be etched or otherwise configured to include a well or chamber structure (38) having a bottom surface that may be positioned on or proximate a portion of an exterior surface of the 1D or 2D or 3D layer, such as to be coincident with the channel region (26). In such an instance, the well structure (38) may be a layered structure and may include a plurality of surfaces, such as first (39a) and second (39b) wall structures, such as extending from or otherwise being coincident with the surface of the reaction zone (26). For instance, the wall structures (29a, 29b) may partially overlap the surface structure (26). Accordingly, FIG. 2A is an illustration of a chemically-sensitive FET having a graphene-layered well structure (38), such as for a system for analysis of biological and/or chemical materials.

Figure 2B:
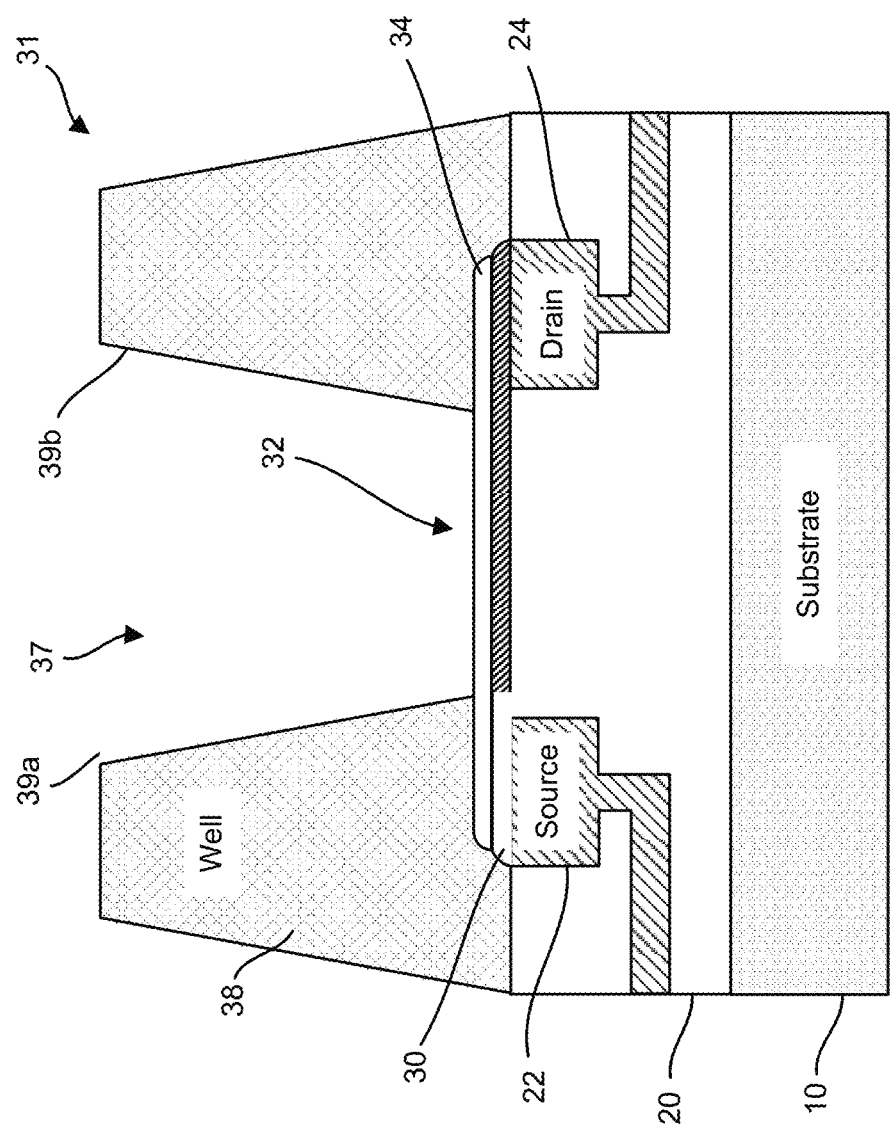
FIG. 2B is an illustration of a chemically-sensitive FET of FIG. 2A, having a graphene layered well structure that further includes a reaction layer associated with the graphene layer, such as for a system for analysis of biological and/or chemical materials.

In particular instances, the well structure (38) may be configured so as to define an opening (37) that allows for direct contact with the surface (26), and thereby contact with the 1D, e.g., nanotube, nanowire, and/or 2D, graphene, layer. Hence, in various embodiments, the cavitated FET device may be configured so as to include a plurality of graphene wells or other chamber surfaces. In various instances, the FET device may be configured as a CMOS biosensor having a well structure (38) that further includes an oxide and/or passivation layer (34), as shown in FIG. 2B, which passivation layer (34) may be disposed in or on one or more of the chamber surfaces (39). The CMOS structure (10) may additionally include the componentry typical of a CMOS semiconductor and/or transistor such as used and/or manufactured as a microchip. Hence, in certain instances, as illustrated in FIG. 2B, the CMOS FET (1) may be configured as a chemically-sensitive transistor, and may be adapted to include one or more structures, such as nano- or micro-wells (38), that are formed as a reaction chamber, into which a solution, e.g., a solution containing one or more reactants, may be deposited, such as for the performance of one or more biochemical reactions, such as a nucleic acid hybridization and/or sequencing reaction. In particular instances, the chamber (38) may include a layered surface (26) having a 1D, 2D, or 3D material, and/or one or more reaction (34) and/or passivation layers (36) deposited therein. In such instances, the chamber of the CMOS device may be configured as a solution gate and therefore the FET may be adapted so as to be an ISFET, such as configured for receiving the reactants necessary for performing an analysis of biological and/or chemical materials, for instance, a hybridization and/or sequencing reaction.

Figure 2C:
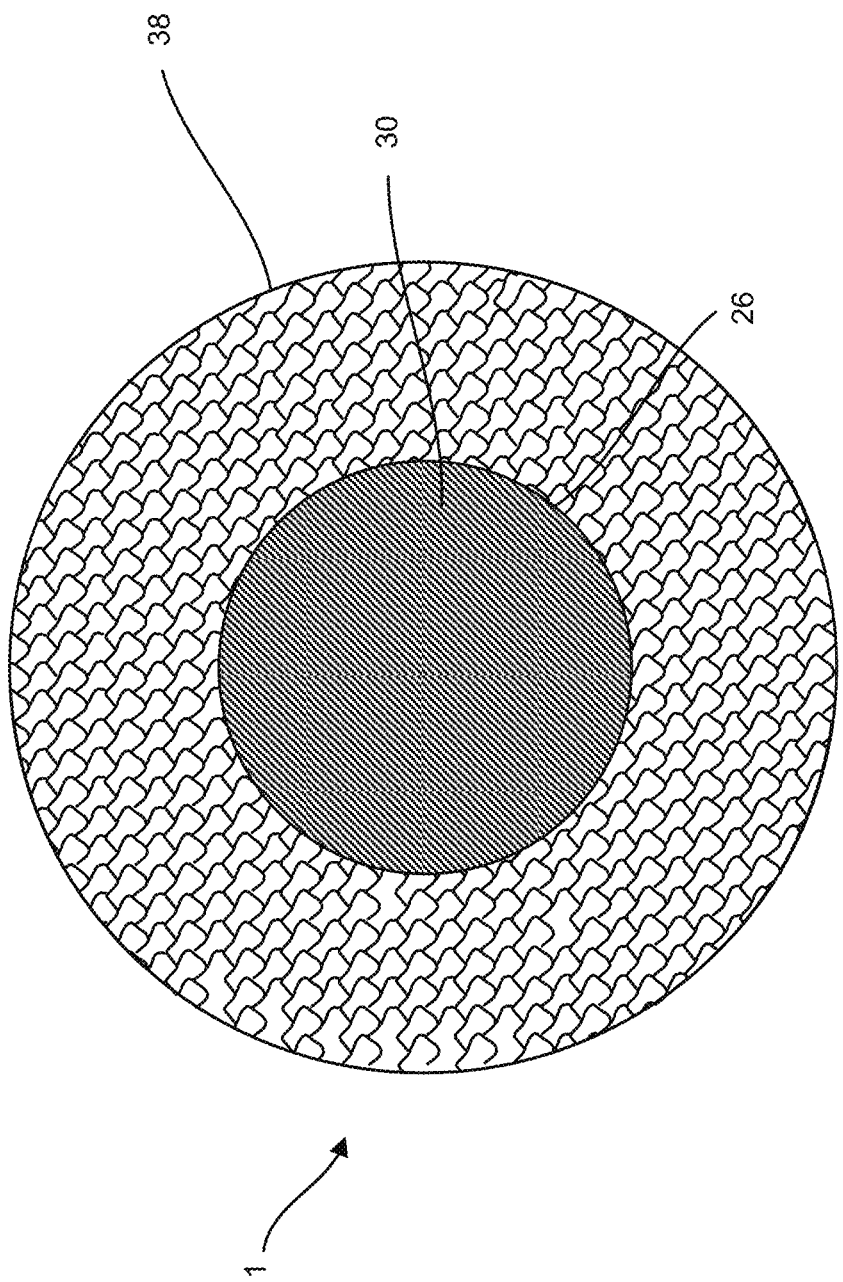
FIG. 2C is a top plan view of a chemically-sensitive FET with a well structure.
Figure 2E:
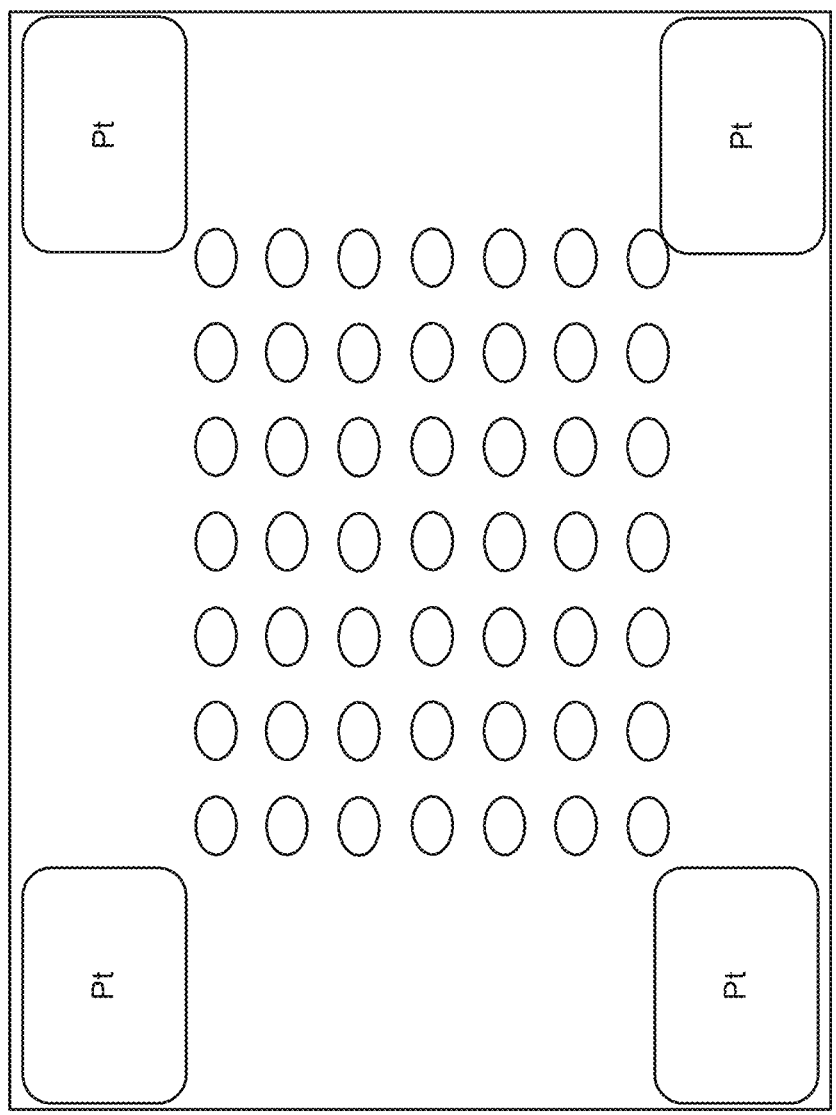
FIG. 2E is a top plan view of an array for a system for analysis of biological or chemical materials, where the array includes multiple chemically-sensitive field-effect transistors.

In some embodiments, as can be seen with respect to FIGS. 2E and 2F, the chemically-sensitive field effect transistor (1) may include a plurality of wells (38a-38e), having a plurality of openings (37a-e), where each well (38) is associated with one or more sensors, and may thus be configured as an array, e.g., a sensor array. Such an array or arrays may be employed to detect the presence and/or a change in concentration of various analyte types, such as within the wells (38), in a wide variety of chemical and/or biological processes, including DNA hybridization and/or sequencing reactions. For instance, the devices herein described and/or systems including the same may be employed in a method for the analysis of biological or chemical materials, such as for whole genome analysis, genome typing analysis, microarray analysis, panels analysis, exome analysis, microbial/microbiome analysis, genotyping analysis, and/or clinical analysis, such as cancer analysis, NIPT analysis, cfDNA, blood/plasma/serum analysis, and/or UCS analysis.

In a particular embodiment, a multiplicity of the wells (38) of the chemically-sensitive device may include a reaction zone (26) containing a graphene layer (30) so as to form a graphene FET (GFET) array (1). As herein described, the GFET array (1) can be employed to facilitate nucleic acid hybridization sequencing techniques, such as based on monitoring changes in hydrogen ion concentration (pH), changes in other analyte concentrations, and/or binding events associated with chemical processes relating to DNA synthesis and/or hybridization reactions, such as within the gated reaction chamber or well (38) of the GFET based sensor (1). For example, the chemically-sensitive FET (1) may be configured as an array of CMOS biosensors and/or may be adapted to increase the measurement sensitivity and/or accuracy of the sensor(s) and/or associated array(s), such as by including one or more surfaces (26a-e) or wells (38a-e) having a surface layered with a 1D and/or 2D and/or 3D material (30), such as graphene, a dielectric or reaction layer (34), a passivation layer (36), and the like.

For instance, in a particular embodiment, illustrated in FIGS. 2E and 2F, a chemically-sensitive graphene field effect transistor (GFET) (1), such as a GFET having a CMOS structure is provided, where the GFET sensor, e.g., biosensor, may be configured as a microchip, having a plurality of wells (38) configured therein. In such an instance, the microchip (1) may include a silicon base layer (10) within which the circuit components of the transistor may be embedded. A dielectric layer (20), which may be a silicon dioxide layer, may be included, such as where the silicon dioxide layer is embedded with a plurality of conductive sources (22a-e) and conductive drains (24a-e) that are separated from one another so as to form a plurality of gate regions (26a-e). In particular instances, the gate regions are configured as a plurality of reaction zones (26a-e), where each reaction zone may be contained within a well structure (38). In such an instance, the microchip (1) may include a plurality of gate regions (26a-e) that are configured as a plurality of solution gates (37a-e).

Particularly, in various embodiments, each sensor of the plurality of sensors includes a graphene FET. For instance, FIG. 2C depicts a top plane view of a first embodiment of a FET (1) having a channel structure (26) that is surrounded by a well structure (38), wherein a graphene layer (30) is deposited or otherwise positioned over the channel structure (26). FIG. 2D depicts a top plane view of another embodiment of the FET (1) having a channel structure (26) that is surrounded by a well structure (38), wherein an oxide layer (34) is deposited or otherwise positioned over the graphene layer (30), which in turn is positioned over the channel structure (26). Likewise, FIG. 2E depicts a top plan view of an array for a system for analysis of biological or chemical materials. In various instances, the array may include a plurality of sensors and one or more reference electrodes, such as a platinum or Ag/AGCl reference electrode. FIG. 2F depicts a portion of the wells of the array of FIG. 2E in greater detail.

In various embodiments, one or more of the solution gates may include a graphene-layered surface (30a-e), which in various instances may further include one or more oxide (34) and/or passivation (36) layers, such as layers that are disposed on the surface(s) of the bounding members of the wells or chambers (37) so as to increase the measurement sensitivity and/or accuracy of the sensors and/or associated array(s). Like above, in such instances, the solution gated chambers (37) of the arrays of the CMOS device may be configured as an ISFET, and be adapted for receiving the reactants necessary for performing various analyses of biological and/or chemical materials, for instance, one or more hybridization and/or sequencing reactions.

Accordingly, in one aspect, a system is provided, such as a system configured for running one or more reactions on biological and/or chemical materials so as to detect a presence and/or concentration change of various analyte types in a wide variety of chemical and/or biological processes. For instance, in some instances, the biological material may be a nucleic acid or other biological molecule, such as a protein, or the like. Hence, in particular instances, the system may be adapted for performing a DNA hybridization and/or sequencing reaction. In other instances, the analysis to be performed is for whole genome analysis, genome typing analysis, microarray analysis, panels analysis, exome analysis, microbial/microbiome analysis, genotyping analysis, and/or clinical analysis, such as cancer analysis, NIPT analysis, cfDNA, blood/plasma/serum analysis, and/or UCS analysis.

As such, the system may include an array (130) including one or more, e.g., a plurality of sensors, such as where each of the sensors includes or is otherwise associated with a chemically-sensitive FET having a conductive source, a conductive drain, and a reaction surface or channel extending from the conductive source to the conductive drain. In particular instances, the array (130) may include one or more wells configured as one or more reaction chambers having the reaction surface or channel positioned therein. In some instances, the surface and/or channel of the chamber may include a one-dimensional (1D) or two-dimensional (2D) transistor material, a dielectric or reaction layer, a passivation layer, and/or the like.

Figure 3A:
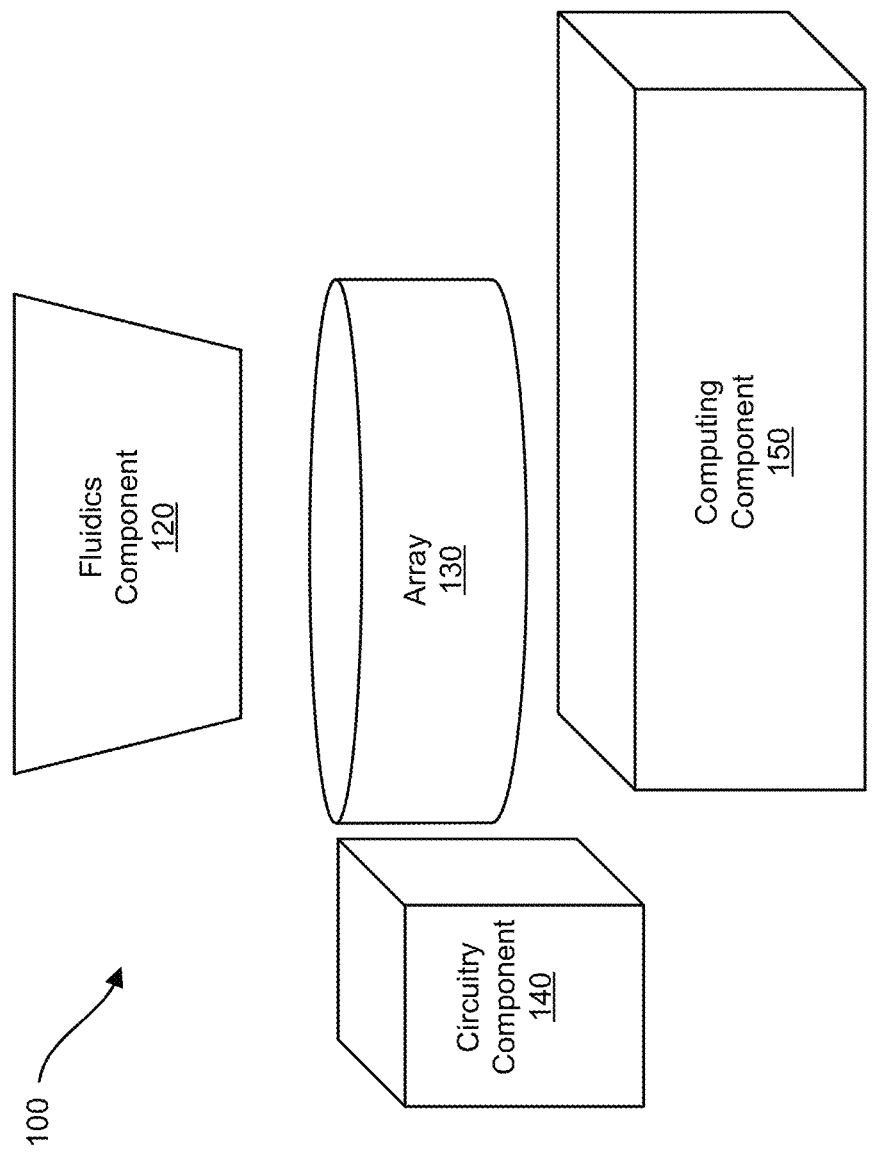
FIG. 3A is a block diagram of a system for analysis of biological or chemical materials.

As can be seen with respect to FIG. 3A, the system may include a fluidics subsystem (100) for directing and controlling the flow of various fluids throughout the system (1). The fluidics system (100) may in turn include one or more of a fluidics component (120), such as for use in performing the reaction, e.g., delivering one or more analyte containing solutions to the array (130) for the performance of the reaction thereby, a circuitry component (140), such as for running the reaction and/or detection processes, and/or a computing component (150), such as for controlling and/or processing the same. For instance, a fluidics component (120) may be included where the fluidic component is configured to control one or more flows of analytes and/or reagents over the array (130) and/or one or more chambers thereof. Particularly, in various embodiments, the system (100) includes a plurality of reaction locations, such as surfaces ($26_{a-n}$) and/or wells ($35_{a-n}$), which in turn includes a plurality of sensors and/or a plurality of channels, and further includes one or more fluid sources (120), e.g., containing a fluid having a plurality of reagents and/or analytes therein, and fluid conduits, such as for delivery of the fluids from the source (120) to the one or more surfaces (26) and/or wells (35) of the array (130) for the performance of one or more reactions thereby. In certain instances, a mechanism for generating one or more electric and/or magnetic fields is also included.

Figure 3B:
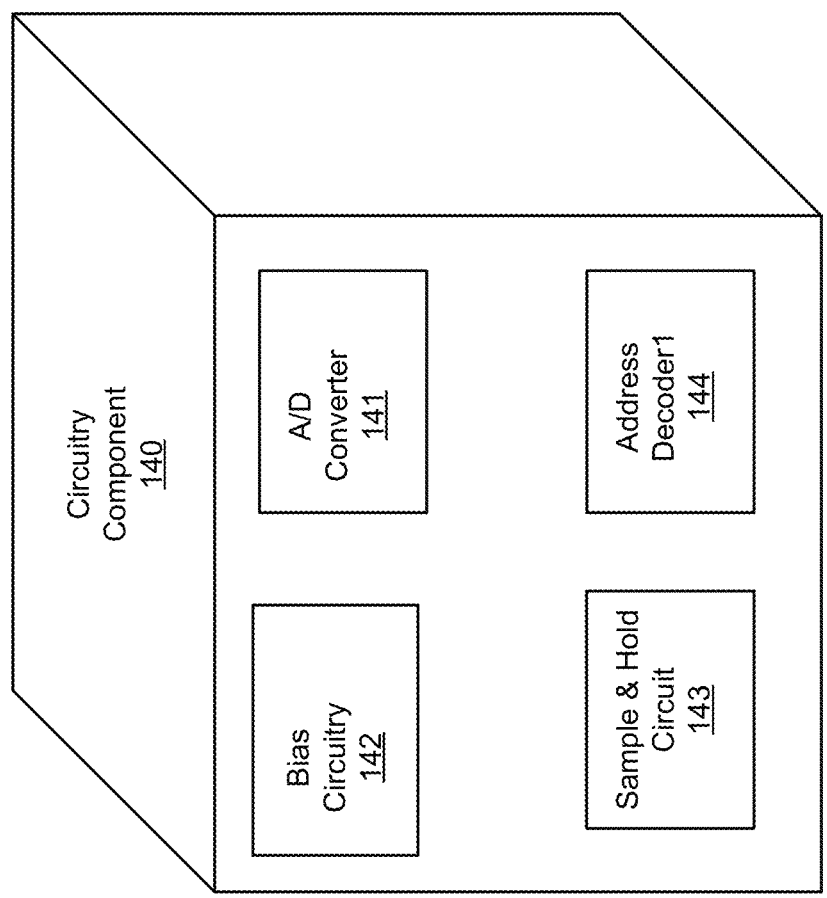
FIG. 3B is a block diagram of a circuitry component for a system for analysis of biological or chemical materials.

As can be seen with respect to FIG. 3B, the system (100) may additionally include a circuitry component (140), such as where the circuitry component may include an address decoder (144), a sample and/or hold circuit (143), a bias circuitry (142), and/or at least one analog-to-digital converter (141). For instance, the address decoder (144) may be configured to create a column and/or row address for each sensor of the array (130), such as by associating a unique identifier with each sensor, such as based upon its location within a given row and column within the array (130). It may also be configured for inputting or otherwise directing the various operations that rely upon the addressing of operations for a given well of the array. For instance, the address decoder (144) may target select signals to specific wells based on their column and/or row identifiers, so as to access a sensor and/or direct fluid flow to a given location, e.g., address within the array (130). The sample and hold circuit (143) may be configured to hold an analog value of a voltage to be applied to or on a selected well or column and/or row line of an array (130) of a device of the invention, such as during a read interval. Likewise, the bias circuitry (142) may be coupled to one or more surfaces and/or chambers of the array (130) and may include a biasing component such as may be adapted to apply a read and/or bias voltage to selected chemically-sensitive FETs of the array (130), e.g., such as to a gate terminal of the transistor. The analog to digital converter (141) may be configured to convert an analog value to a digital value (142), for instance, as a result and/or output of the reaction within an identified well (35) or selection of wells, e.g., a line of columns and rows.

Figure 3C:
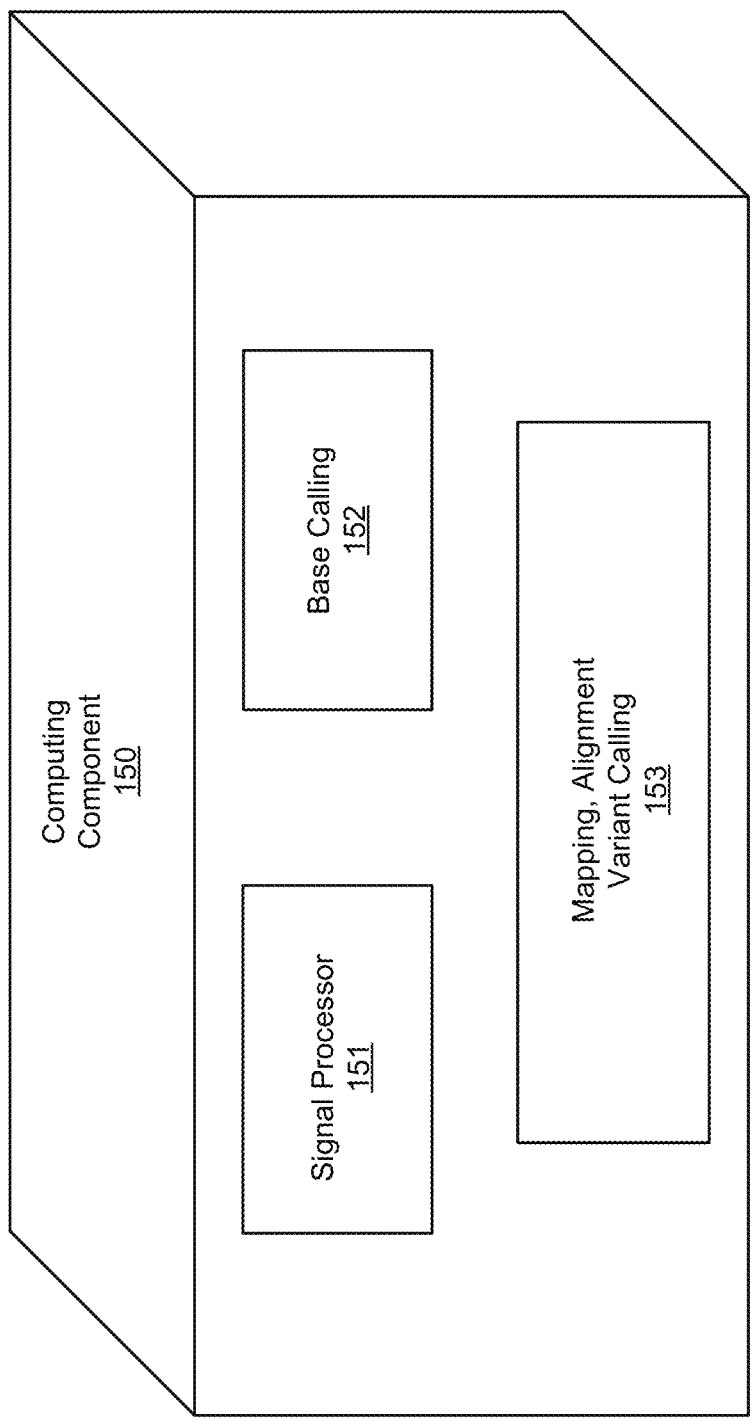
FIG. 3C is a block diagram of a computing component for a system for analysis of biological or chemical materials.

Additionally, as can be seen with respect to FIG. 3C, a computing component (150) may also be included, such as where the computing component (150) may include one or more processors, such as a signal processor (151), a base calling module (52), and an analytics module (153). The signal processor (151) may be configured for determining one or more bases of one or more reads of a sequenced nucleic acid, such as results from a sequencing reaction. The base caller of the base calling module (152) may be configured to correct a plurality of signals, such as for phase and signal loss, to normalize to a key, and/or to a generate a plurality of corrected base calls for each flow in each sensor to produce a plurality of sequencing reads. The analytics module (153) may be configured for performing one or more analytics functions on the sequenced data, and may include one or more of a mapping module, configured for generating one or more seeds from the one or more reads of sequenced data and for performing a mapping function on the one or more seeds and/or reads; an alignment module, configured for performing an alignment function on the one or more mapped reads; a sorting module, configured for performing a sorting function on the one or more mapped and/or aligned reads; and/or an variant calling module, configured for performing a variant call function on the one or more mapped, aligned, and/or sorted reads. In various embodiments, the device and/or system may include at least one reference electrode.

Particularly, the system can be configured for performing a nucleic acid hybridization or sequencing reaction. In such embodiments, the device for performing the hybridization or sequencing reaction may be adapted from a CMOS reformed to include one or more reaction chambers, e.g., micro or nano-wells, so as to form an array (130). The array (130) may be associated with one or more sensors having one or more chemically-sensitive FETs linked therewith. Such transistors may include a cascade transistor having one or more of a source terminal, a drain terminal, and or a gate terminal, such as forming a reaction zone. In such an instance, the source terminal of the transistor may be directly or indirectly connected to the drain terminal of the FET. In some instances, the gate terminal may be or may otherwise include a channel configuration, and may further include a 1D or 2D material associated with the gate. The 1D or 2D material may extend from the source terminal to the drain terminal, such as where the 1D channel material may be a carbon nanotube or nanowire, and the 2D channel material is composed of graphene, silicene, a phosphorene, a molybdenum disulfide, and a metal dichalcogenide. The device may further be configured to include a plurality of arrays, such as arranged as one or more lines of columns and rows coupled to the sensors in the array of sensors. In such an instance, each column line in the plurality of column lines may be directly or indirectly connected to or otherwise be coupled with the drain terminals of the transistors, e.g., cascade transistors, of a corresponding plurality of sensors or pixels in the array, and likewise each row line in the plurality of row lines may be directly or indirectly connected to or otherwise coupled with the source terminals of the transistors, e.g., cascade transistors, of a corresponding plurality of sensors in the array.

In some instances, a plurality of source and drain terminals having a plurality of channel members and/or associated reaction surfaces, extended there between may be included, such as where each channel member includes a one or two dimensional material. In such an instance, a plurality of first and/or second conductive lines may be coupled to the first and second source/drain terminals of the chemically-sensitive FETs in respective columns and rows in the array. Additionally, control circuitry (140) may be provided and coupled to the plurality of column and row lines such as for reading a selected sensor connected to a selected column line and/or a selected row line. The circuitry may also include a biasing component (142) such as may be configured for applying a read voltage to the selected row line, and/or to apply a bias voltage such as to the gate terminal of a transistor, such as FET and/or cascade transistor of the selected sensor. In a particular embodiment, the bias circuitry (142) may be coupled to one or more chambers of the array (130) and be configured to apply a read bias to selected chemically-sensitive FETs via the conductive column and/or row lines. Particularly, the bias circuitry (142) may be configured to apply a read voltage to the selected row line, and/or to apply a bias voltage to the gate terminal of the transistor, e.g., cascade transistor, such as during a read interval.

Sense circuitry can be included and coupled to the array so as to sense a charge coupled to one or more of the gate configurations of a selected chemically-sensitive FET. Sense circuitry can be configured to read the selected sensor based on a sampled voltage level on the selected row and/or column line. In such an instance, the sense circuitry may include one or more of a pre-charge circuit, such as to pre-charge the selected column line to a pre-charge voltage level prior to the read interval; and a sample circuit such as to sample a voltage level at the drain terminal of the selected transistor, e.g., cascade transistor, such as during the read interval. The sample circuit may also be included and contain a sample and hold circuit (143) configured to hold an analog value of a voltage on the selected column line during the read interval, and may further include an analog to digital converter (141) to convert the analog value to a digital value.

Figure 8A:
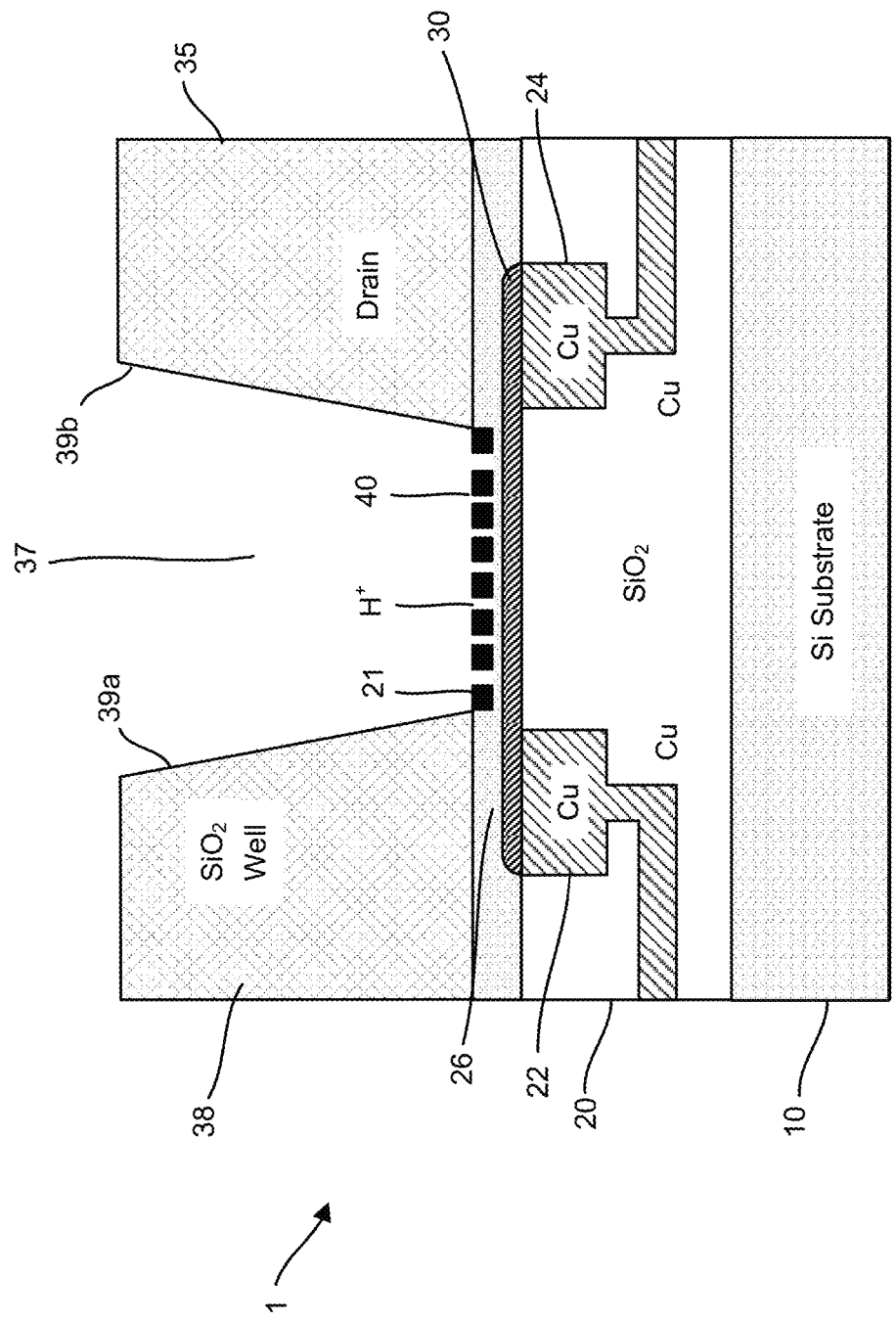
FIG. 8A is an illustration of a chemically-sensitive FET with a graphene layered well structure and having a permeable membrane associated with the graphene layer.

In a further aspect, as seen with respect to FIG. 8A, a biologically and chemically-sensitive FET sensor (1) is provided wherein the sensor includes a stacked configuration having a plurality of layers and/or structures therein. For instance, a primary structure (10) includes an inorganic base layer, e.g., a silicon layer, which is fabricated to contain or may otherwise be configured as a CMOS FET. Accordingly, stacked on top of the base layer (10) may be a secondary structure (20) that may be configured as a dielectric layer and/or another inorganic or organic insulator layer, such as a silicon dioxide layer. The primary (10) and/or secondary (20) structures may additionally include or otherwise be configured to contain a conductive source (22) and drain (24) embedded in one or more of the structured layers, such as between and/or forming a gate structure (26). In particular embodiments, an additional structure or layer (35) may be positioned above the primary and secondary layers, which layer (35) may be etched to form one or more well structures (38), which well structure may be coincident with and/or proximate to the gate structure (24) so as to form a solution gate region therewith. In various embodiments, the solution gate region may include or otherwise be formed by the gate structured layer (24) as well as the bounding wall members 39a and 39b forming the well structure (38), such as by extending laterally upwards from the surface (21) and/or structured layer (26), and having opening (37) positioned therein so as to access the gate region (26).

The well structure (38) may further include one or more additional structures and/or layers, such as a 1D or 2D or 3D material (30) and/or an oxidation (34) and/or passivation (36) layers that may be positioned between the conductive source (22) and drain (24) and/or between wall members (39a, 39b) in such a manner as to form a bottom surface and/or reaction zone (24) of the chamber (37). In various instances, one or more of the structures may further include or otherwise be associated with an integrated circuit and/or a processor, such as for generating and/or processing generated data, such as sensor derived data, e.g. indicative of a sequencing and/or hybridization reaction taking place within the well structure (38). In particular embodiments, a further structured layer (40), e.g., a secondary or tertiary or quartier structure, may also be provided, such as where the further structured layer may be included and/or present on a surface (24) or otherwise within the well or chamber (37), such as to enhance the ability of the sensor and/or the processor to determine the difference between a current and/or voltage applied across the source (22) and/or drain (24) of the transistor, as well as their respective associated charge curves, as described herein.

For instance, in the exemplary embodiment of FIG. 8A, a biologically and/or chemically-sensitive FET (1) having a graphene layered (30) well structure (37) containing a further structured layer (40) configured for enhancing the sensitivity of an associated sensor. In this embodiment, the structured well layer (40) is configured as a permeable membrane that may be associated with the graphene (30) and/or reaction (34) layers. Particularly, the chemically-sensitive FET sensor (1) includes a surface (21), which surface may be within a well chamber (37), and be configured as a reaction region (26). The surface (21) of the reaction region (26) may be coupled to or otherwise include a 1D or 2D material such as a graphene layer (30) for detecting the presence of one or more chemical and/or biological events and/or elements resulting thereby. Accordingly, the surface (21) may be configured as a reaction region (26), and the well chamber (37) may be adapted such that a chemical and/or biological reaction may take place therein. The surface (26) and/or graphene structured layer (30) may be coupled with or otherwise include an additional structure, such as the permeable membrane (40), that is configured to enhance the ability of the graphene-based sensor (1) to detect the presence of a chemical and/or biological reaction. Particularly, the additional structure (40) may be an ion-selective permeable membrane that is positioned proximate to and/or over a reaction zone (26), which may be configured as a channel, and which membrane (40) may be adapted such that it only allows ions of interest to travel through the membrane (40), while excluding those ions that might cause interference with the sensing capabilities of the sensor (1).

For example, in particular instances, the membrane material (40) may be an organic or an inorganic material. A suitable membrane may be an inorganic material such as an oxide. An alternative material may be a separate layer, such as an additional 1D or 2D material, e.g., of graphene, which is not electrically connected to the FET or its component parts, e.g., the source (22) and drain (24). Another alternative material may be a polymer, such as Nafion, PEEK, a perfluorosulphonic, and/or a perfluorocarboxylic material. Alternatively, the material may be a HMDS or other siloxane, such as positioned under a graphene layer (30). Yet another alternative may be a getter material, such as containing a positive ion, e.g., $NA^+$, which may be positioned within the chamber (37), or may be positioned elsewhere on the sensor, such as a wall (39a and/or 39b) thereof, and/or in a package that is adapted to attract unwanted ions. In another embodiment, the sensor enhancement material (40) may be an ion-selective functional layer(s) that is positioned over the sensor and adapted so as to detect contaminants, unwanted ions, or other impurities that may react with the reactants within the well (38) such that their interactions with the sensor (1) and thus the various determinations that the sensor (1) makes with respect to the reactions taking place therein, such as in relation to detecting the presence or absence of a desired ion, can be filtered out.

Accordingly, the chemically-sensitive FETs, as presented herein, for a system for analysis of biological and/or chemical materials, may be configured as solution gated field effect transistor devices having rows and columns of reaction chambers formed therein. In various instances, the FETs comprise a structure having or otherwise being associated with a channel and a processor. In such instances, the structure may include one or more of an insulating structure, a conductive source, a conductive drain, and/or a channel extending from the conductive source to the conductive drain, such as where the source and drain are embedded in the insulator and may be positioned therein so as to be planar with a top surface of the insulator. As indicated, in certain embodiments, the source and drain may each composed of a damascene copper material. Further, the channel may be composed of a one dimensional transistor material or a two-dimensional transistor material (e.g., graphene). And where desired, a reaction layer may be associated with the 1D or 2D conductive channel, and in some instances, may include a passivation layer or etch stop layer that may be placed over the conductive channel, such as between the two layers and/or above the graphene layer.

Figure 4A:
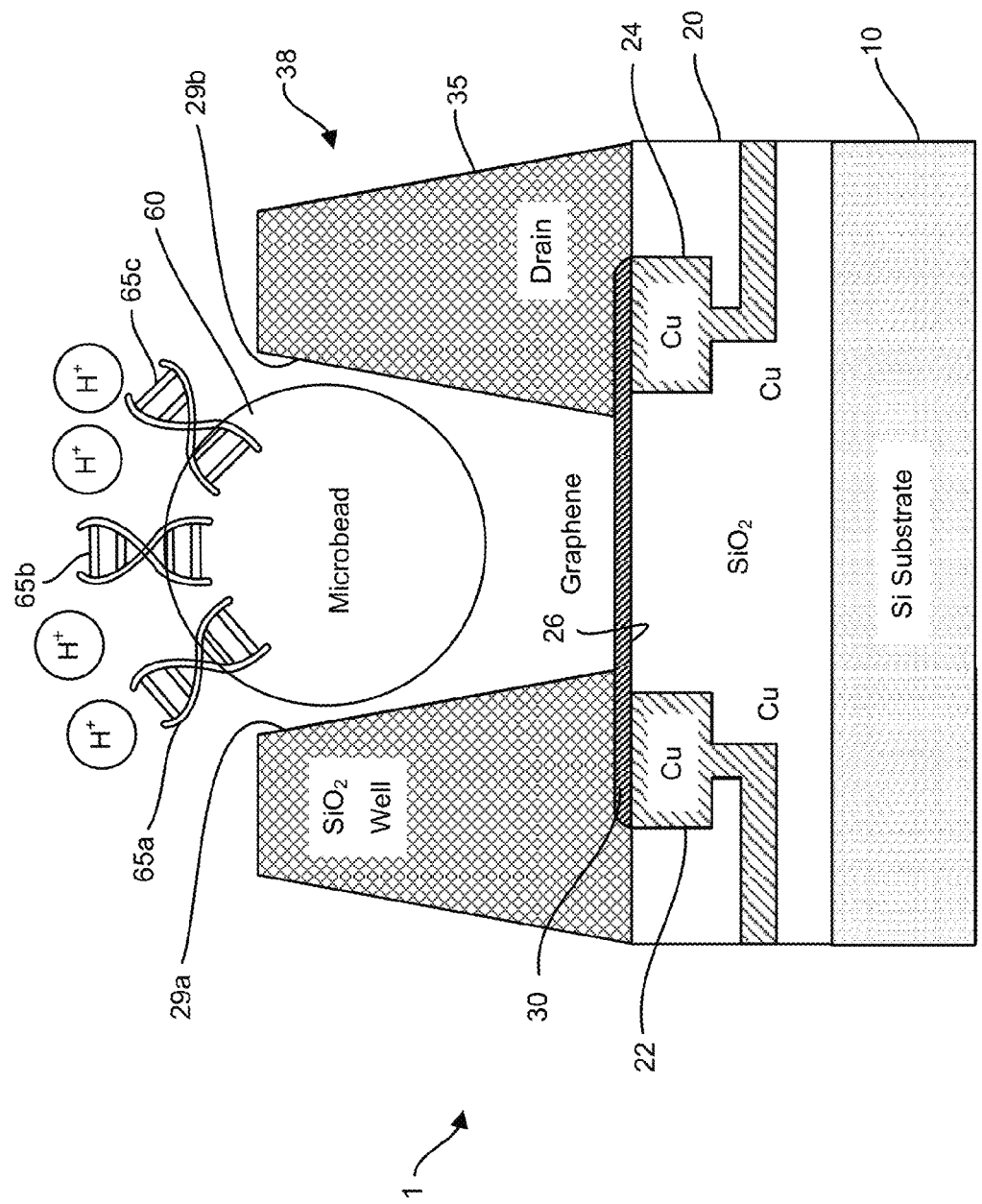
FIG. 4A is an illustration of a chemically-sensitive FET of FIG. 2A, having a graphene layered well structure that includes a nano- or micro-bead therein.
Figure 4B:
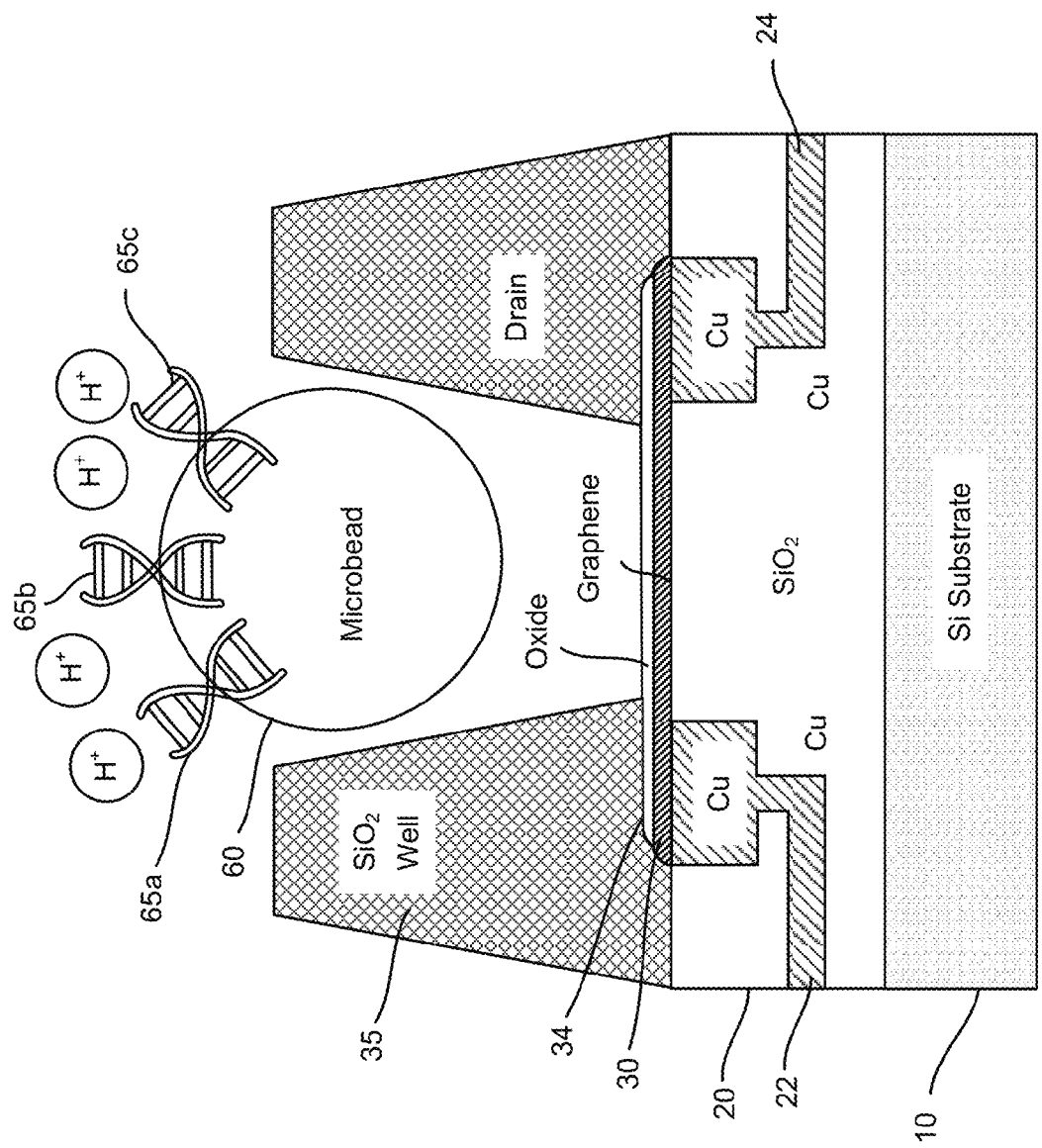
FIG. 4B is an illustration of a chemically-sensitive FET of FIG. 4A, having a graphene layered well structure that includes a reaction layer associated with the graphene layer, which further includes a nano- or micro-bead therein.
Figure 4C:
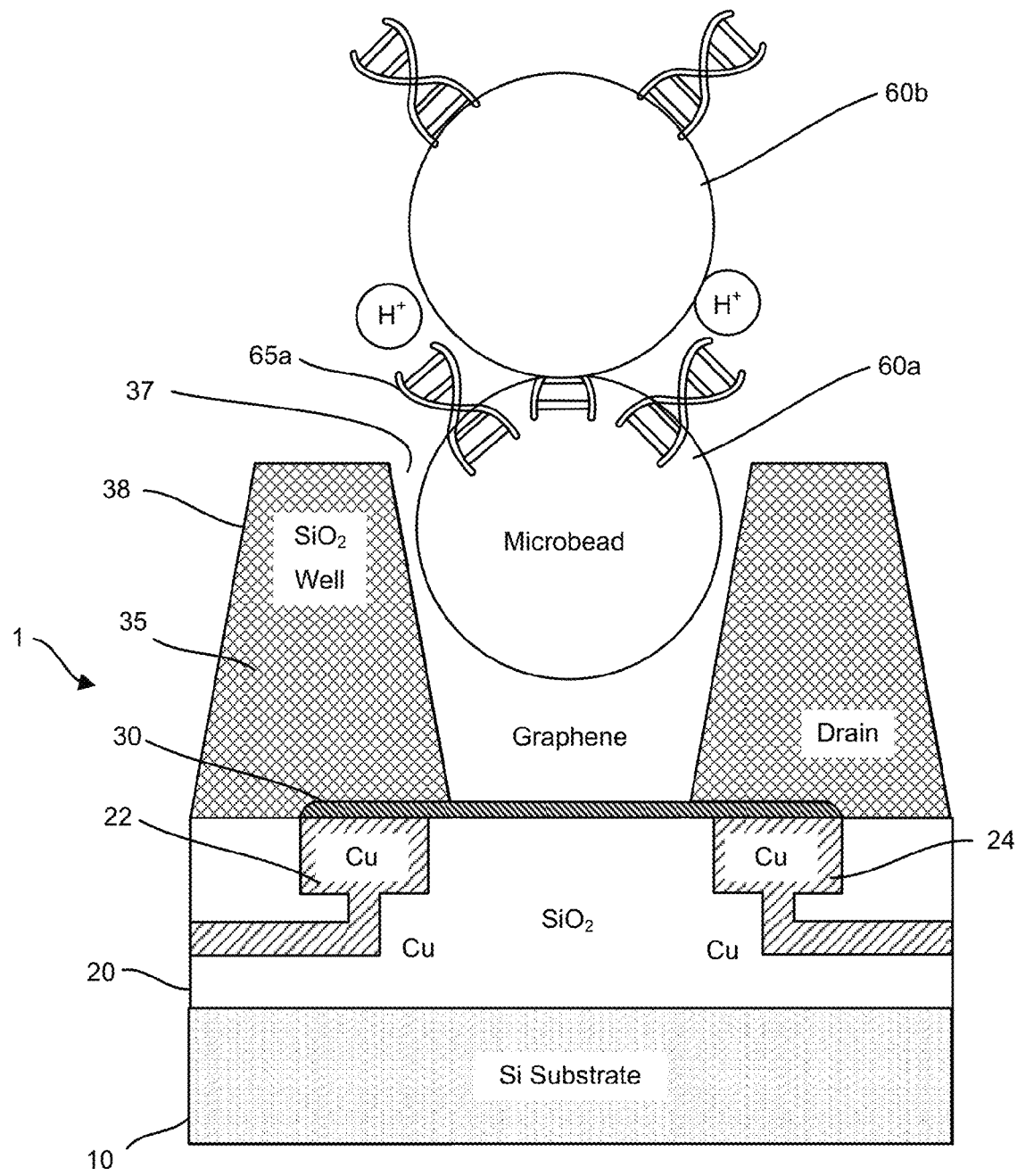
FIG. 4C is an illustration of a chemically-sensitive FET of FIG. 4A, having a graphene layered well structure that includes a plurality of nano- or micro-beads therein.

As can be seen with respect to FIGS. 4A-4C, in various embodiments, a chemically-sensitive FET (1) having a graphene layered micro- or nano-well structure (38) is provided. The FET (1) is configured as a microchip that includes a substrate layer (10) and an insulating layer (20) within which is embedded the various transistor components including a conductive source (22) and conductive drain (24) which may be adapted to form a gate region (26). In this instance, a graphene layer (30) is positioned over the insulating layer (20) and positioned so as to contact at least a proximate portion of the source (22) and a proximate portion of the drain (24). In this instance, the substrate layer (10) is composed of silicon, the insulating layer (20) is composed of silicon dioxide, and the source (22) and drain (24) are composed of a conductive metal, for example, as copper.

The source (22) and the drain (24) are separated from one another and positioned relative to the graphene layer (30) so as to form a gate structure (26). In this embodiment, the gate structure (24) is further bounded by chamber walls (29a, 29b), which together form the well (28) into which a fluid may be delivered, such as for the performance of a bio-chemical reaction, and thus, forming a solution gate configuration. Particularly, an additional layer (35), which may also be composed of silicon dioxide, may be positioned above the first silicon dioxide layer (20), and be configured, e.g., via micro etching, to form a micro- or nano-well (38) so as to form a chamber (37), which chamber (37) may be adapted to receive a solution so as to form the solution gate region. The graphene layer (30) is disposed between the first (20) and second (35) silicon dioxide layers such as to form the bottom surface of the chamber (37). In this instance, the FET sensor is configured to detect a change in ion concentration, e.g., pH, which occurs within the well (38) such as when a solution containing reactants is added to the gate region within the chamber (37), and the reactants interact with an additional element contained within the chamber, such as a bound nucleic acid template.

Particularly, one or more solutions may be added to the chamber (37), such as in the performance of a bio-chemical reaction. For instance, a first solution including a nano- or micro-bead (60) may be added to the well (38). The nano- or micro-bead may be treated so as to be associated with one or more biopolymers, such as a DNA and/or RNA template (65). Once the nano- or micro-bead containing solution is added to the well (38), in such a manner that the bead (65) is retained therein, one or more additional solutions containing reactants, such as for the performance of a biological and/or chemical reaction, may then be added to the well (38). For example, where the biological and/or chemical reaction is a nucleic acid synthesis reaction (as occurs in NGS methods), the analyte containing solution to be added to the well (38) may include a nucleotide and/or polymerase composition that if the conditions are suitable within the chamber (37) will result in a binding and/or incorporation event occurring between the template molecule (65) and the nucleotide reactant, thus resulting in the reaction taking place. Additionally, where the biological and/or chemical reaction is a hybridization reaction, the bound template molecule (65) may be configured as a probe, and the analyte containing solution to be added to the well (38) may include an additional DNA/RNA molecule of interest, which if the conditions within the chamber (37) are suitable will hybridize to the bound probe, thus resulting in the reaction taking place.

In either instance, the sensor (1) may be configured for detecting the occurrence of a chemical reaction, such as by detecting a change in the ionic concentration within the solution within the chamber (37). Particularly, if the conditions are suitable for a reaction to take place, e.g., the appropriate reactants are present, a binding and/or incorporation event will occur in such a manner that an ion, such as an $H^+$ ion, will be released into solution, such as within the chamber (37) and/or proximate the solution gate (26). In such an instance, the sensor (1) may be configured to sense the evolution of the ion, appreciate the change in pH, and detect that a reaction has taken place. In such a manner as this, a DNA/RNA molecule may be synthesized and/or a hybridization event determined.

Accordingly, as illustrated with respect to FIG. 4A, a chemically-sensitive FET (1) is provided wherein the transistor (1) includes a graphene layered well structure (38) containing a nano- or micro-bead (60) therein, such as where the graphene layer (30) may be coincident with a channel region (24) so as to form a reaction zone therewith. Further, in various instances, such as illustrated in FIG. 4B, in addition to a graphene layer (30), the reaction zone (24) within the chamber (37) of the well (38) of the transistor (1) may further include a reaction layer (340, such as a reaction layer, e.g., an oxide layer, associated with the graphene layer (30). In addition to the reaction layer (34), the reaction zone (24) may additionally include a passivation or ESL layer (36). Furthermore, as can be seen with respect to FIG. 4C, in certain embodiments, the chemically-sensitive FET (1) may include a plurality of nano- or micro-beads therein, such as within the chamber (37) of the well (38) of FET (1), so as to allow a plurality of reactions to take place at the same time involving a plurality of substrates (60a, 60b) within the well, which increases the surface area for reactions.

In some instances, it may be useful to provide a mechanism for assisting the targeting of the microbead(s) (60) to the reaction zone (24) of the FET (1). Particularly, as can be seen with respect to FIGS. 5A-E, a chemically-sensitive FET (1) is provided. In this instance, the transistor (1) may be a multi-layered structure including a primary, e.g., a substrate layer 10, a secondary structure layer, e.g., an insulator layer 20, and may further include an additional layer 35, e.g. a silicon dioxide layer, which layer may be cavitated so as to include a divot (38), such as a divot on a surface (21) of the substrate, and sized to at least partially contain a nano- or micro-bead (60) therein. In certain instances, the surface of the divot (38) may be centered such that the bead (60) rests within the divot (38) so as to be proximate the reaction zone (24) and/or a channel structure associated therewith. In particular instances, the reaction zone (24) includes a graphene layer (30) positioned at least partially between the primary and tertiary layers, and in such instances, a silicon dioxide layer (34) may be positioned above the graphene layer within the reaction zone (26). In this instance, to draw and/or attach the bead(s) (60) to the reaction zone (26), an electromagnetic field may be employed. Hence, as shown in FIG. 5A, a microbead (60) is positioned on the transistor surface 21, within the reaction zone (26), and in proximity to a channel.

More particularly, the reaction zone (24) of the FET (1) may be configured to include a channel region that is formed to correspond to the region, e.g., point, of contact between the surface of the graphene layer (30) and the bead (60). Further, to facilitate this contact, the FET (1) may include an attracting mechanism (70) that is configured to attract or otherwise draw the bead (60) in to proximity of the reaction zone and/or channel (26). For instance, in particular instances, the nano- or micro-bead (60) may include a charged and/or metallic element, and the attracting mechanism (70) may be configured so as to generate an electric and/or magnetic field, such as for drawing the bead (60) to the reaction zone (26). For example, in some embodiments, the electric field generator (70) may be a pulse generator, and in other embodiments, such as illustrated in FIG. 5A, the magnetic field generator (70) may be a magnet.

Particularly, as shown in FIG. 5A, one or more nano- or micro-bead (60) of the invention may be configured for facilitating the performance of a bio-chemical reaction such as on a reaction surface (24) of the sensor device (1). For instance, in particular embodiments, each of the one or more microbeads may include a biological material or a chemical material, associated therewith. In such an instance, the bead (60) may be introduced to the surface (24) of the sensor device (1) of the system, such as for nucleic acid sequencing, in such a manner that it is drawn or otherwise attracted to the surface (26), such as by electromagnetism. For instance, the bead (60) may be configured to include electric charge and/or paramagnetic properties so as to assist it in being drawn into proximity of a reaction location (24) positioned on a surface (21) of the device (1), such as where the nucleic acid sequencing reaction may take place. Hence, the device may include an electro-magnetic field generating component (70) that is configured to apply an electro-magnetic field that is focused within the reaction zone (24) so as to interact with the electric charge and/or paramagnetic properties of the bead (60) thereby drawing it into proximity of the surface (21) and/or in to the reaction zone (26), such as via electromagnetism. In this instance, the layers and other components of the sensor device (1) are configured in such a manner that the reaction zone (24) need not include bounding members, or if included the bounding members may be thin, allowing for a higher density of wells on the array.

Figure 5B:
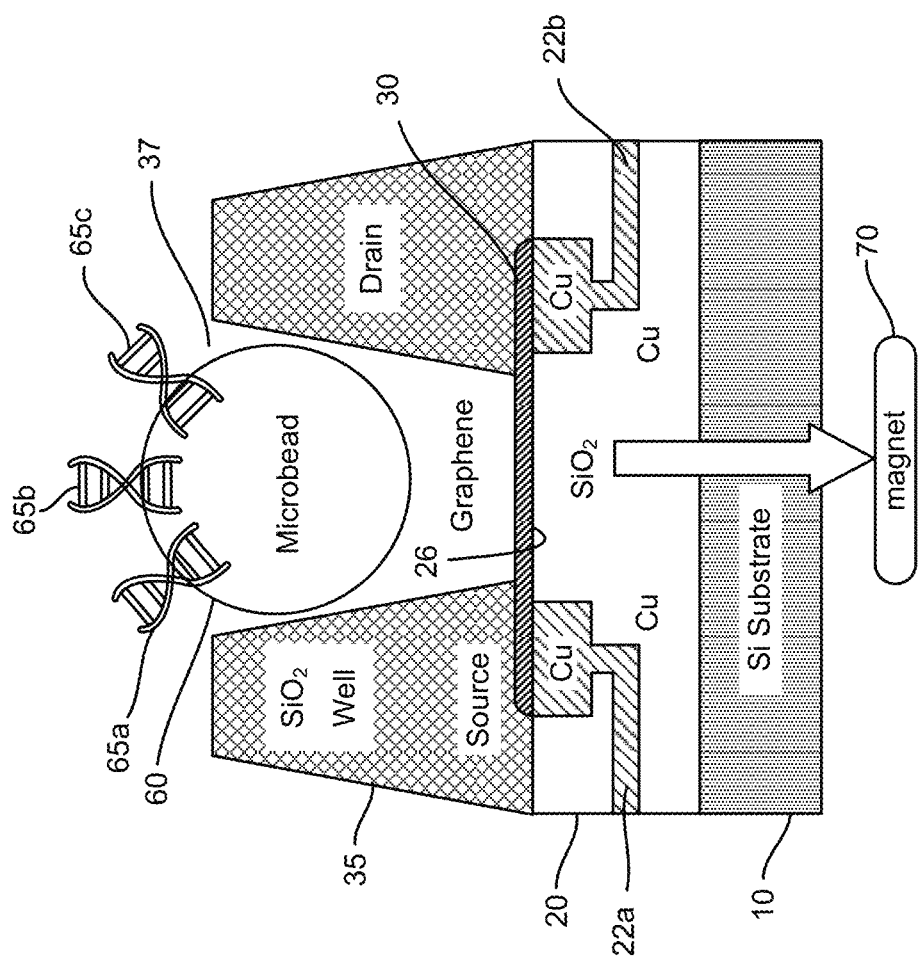
FIG. 5B is an illustration of the substrate of FIG. 1D, having a silicon dioxide layer positioned above a graphene layered reaction zone, and utilizing a magnetic field for the positioning of a nano- or micro-bead to be associated therewith.

Alternatively, in other embodiments, such as presented in FIG. 5B, the bio-chemical sensor device (1) may include a well structure (38) that is configured for receiving one or more nano- or micro-beads, such as for nucleic acid sequencing therein. For instance, each of the one or more microbeads includes an analyte and/or reactant, which is configured for participating in a reaction, such as a nucleic acid hybridization and/or sequencing reaction. Accordingly, the sensor device (1) may include a reaction location (24) that may be configured as a surface within a well (38) of the device (1), such as where the reaction location (24) is proximate a channel and/or sensor of the device (1). The nano- or micro-bead (60) may be configured for use in a system for analysis of biological and/or chemical materials such as on or within a reaction surface (26), such as within a well (38) of the sensor device (1). In this and other instances, the bead (60) may be introduced to the surface (24) of the sensor device (1) of the system in such a manner that it is drawn or otherwise attracted toward the reaction surface (26), e.g., of a well structure (38), where the nucleic acid sequencing reaction may take place, such as by electromagnetism.

For example, the bead (60) may be configured to have an electric charge property and the bead attracting mechanism (60) may be configured to emit an electric field that is opposite in nature to the charge on the bead and is thereby adapted for draw the bead (60) into proximity of the reaction surface (26). In such an instance, an electric field component generates an electric field to interact with the electric charge properties of the microbead. Hence, the microbead may be drawn to the reaction location using electrophoresis. In other instances, the bead (60) may be configured to include paramagnetic properties so as to assist it in being drawn or otherwise attracted toward reaction surface (26), e.g., into the well (38), and into proximity of the reaction zone, where the reaction may take place. The device, therefore, may include a magnetic field generating component (70) that is configured to apply an electro-magnetic field that is focused within the chamber (38) so as to interact with the paramagnetic properties of the bead (60) thereby drawing it into the chamber (38) and/or proximate the reaction surface (26), such as via magnetism. Particularly, in various embodiments, the bead or particle attracting mechanism (60) can be configured to emit a magnetic field that is opposite in polarity to the paramagnetic properties of the bead and is thereby adapted for draw the bead (60) into proximity of the reaction surface (26). In such an instance, a magnetic field component generates a magnetic field to interact with the polar properties of the microbead. The use of magnetism and/or electrophoresis allows for thinner reaction location structures.

Figure 5C:
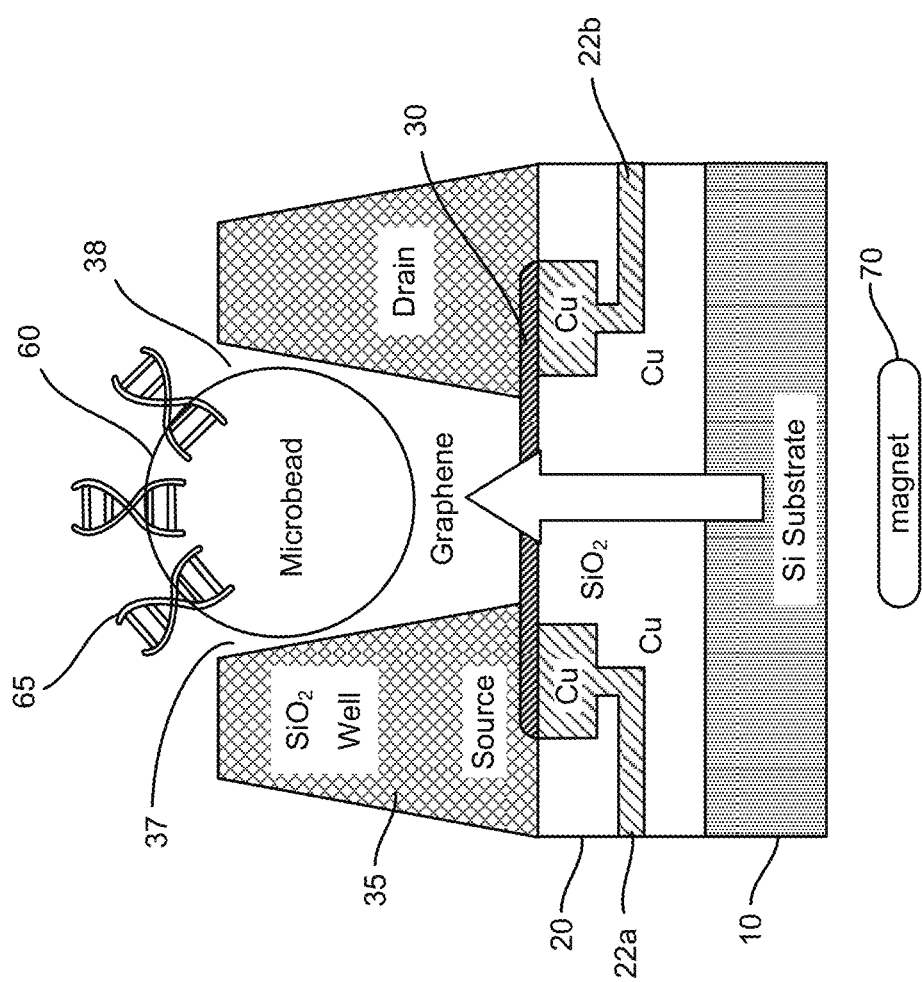
FIG. 5C is an illustration of the substrate of FIG. 5B, in an alternate configuration, such as utilizing a magnetic field reversal of a magnet to release a nano- or micro-bead.

Additionally, as illustrated in FIG. 5B, in some embodiments, the system and its components may be configured such that when the electromagnetic field is generated it interacts with the bead (60) and/or a component associated therewith so as to pull the bead toward the reaction zone (26). In other embodiments, as illustrated in FIG. 5C, the system and its components may be configured such that when the electromagnetic field is generated it interacts with the components of the bead (60) so as to push the bead away from the reaction zone (26). Accordingly, the electromagnetic fields can be generated and/or reversed so as to attract or repulse the nano-/micro-bead to or from the reaction location (26), such as to or away from a well (38), and thus utilizing an electronic and/or magnetic field, the nano- or micro-bead may be positioned within the device, such as within a well thereof.

Figure 5D:
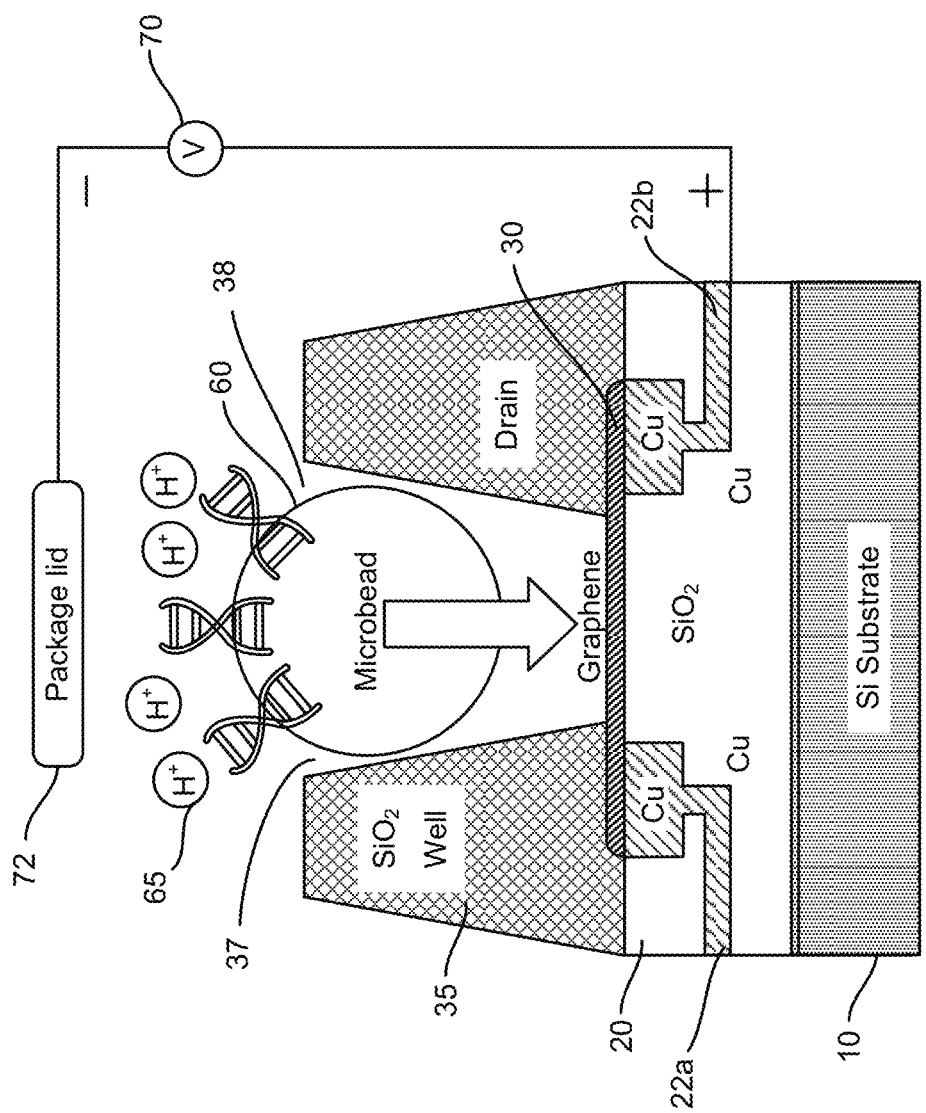
FIG. 5D is an illustration of the chemically-sensitive FET of FIG. 4A, such as for a system for analysis of biological or chemical materials, utilizing an electric field for positioning of a nano- or micro-bead.

As illustrated in FIG. 5D a chemically-sensitive FET (1) is provided, such as for a system for analysis of biological and/or chemical materials, such as by utilizing an electric and/or magnetic field generating mechanism such as for positioning of a nano- or micro-bead (60) in relation to the reaction surface (26). For instance, in particular instances, a voltage may be applied between a location above the solution of the solution gate (37) and a location on or below the reaction location (26), such as above the package lid 72 and/or below a metal component, e.g., a plate, below the package (72). In certain instances, the location below the reaction location (24) may include a metal or other conductive layer such as within the package or package substrate. Hence, in various instances, the field generating mechanism (70) may be employed to generate and/or reverse an electric or magnetic field so as to insert or eject one or more beads from one or more wells, sensors, and/or channels associated therewith, either entirely or selectively.

Figure 5E:
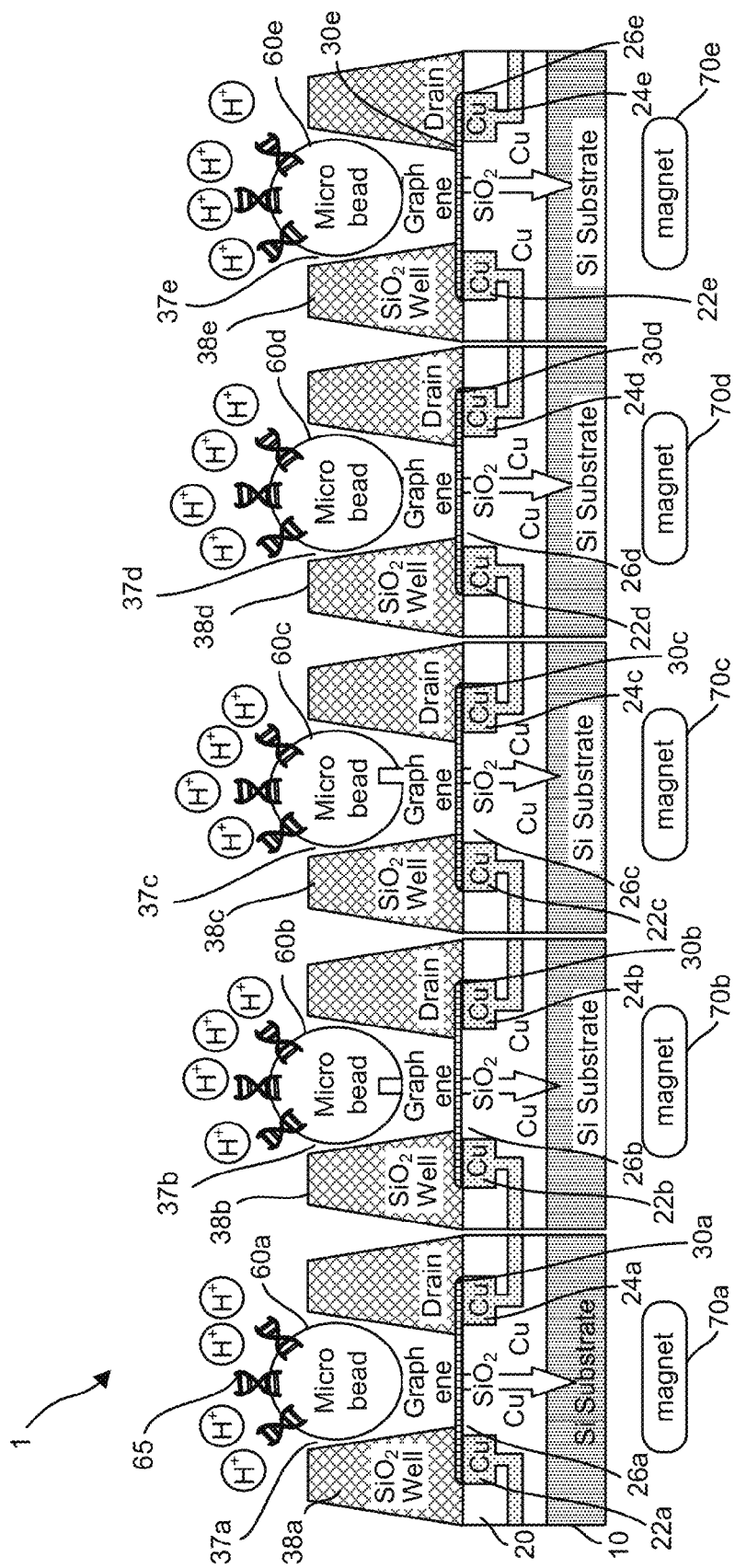
FIG. 5E is an illustration of an array of chemically-sensitive FETs for a system for analysis of biological or chemical materials utilizing multiple magnets for generating a plurality of magnetic fields for positioning of nano- or micro-beads within the wells.

Particularly, as set forth in FIG. 5E, an array (1) of chemically-sensitive FETs for a system for analysis of biological or chemical materials is provided. The array (1) includes a multiplicity of wells (38a-e) each forming a reaction location (26a-e) whereon a bio-chemical reaction may take place. Additionally, each reaction location (24) is associated with a field generator (70a-e), e.g., a magnet, which is configured so as allow for the selective filling of the reaction locations (24) with one or more types of nano- or microbeads 60a-e. Accordingly, by utilizing multiple field generators (70a-70e), e.g., multiple magnets, for generating a plurality of electro-magnetic fields, the nano- or micro-beads (60a-e) may be positioned within the plurality wells (38a-e). Such positioning may be selective such as by selecting which generators will be on, off, or reversed, so as to fill or not fill their respective wells (38a-e), as desired. In various embodiments, the electromagnetic fields for any given well (38) may be reversed so as to expel a bead (60) from the well (38) and/or reaction zone (26).

Particularly, in a further aspect of the present invention, a system having an array of chemically-sensitive FETs including a plurality of chambers (37a-e) having well structures formed therein is provided. In such an instance, the wells (38a-e) may be structured as or may otherwise include reaction locations (26a-e) wherein one or more chemical reactions may take place. In such an embodiment, the system may include one or more fluidics components having one or more fluid sources, e.g., reservoirs, containing one or more fluids therein and configured for delivering the fluid from the reservoir to the reaction chamber, such as for the detection of a biologic and/or the performance of one or more chemical and/or biological reactions, such as a nucleic acid sequencing reaction. Accordingly, the fluidics component, e.g., the fluid source, may be in fluidic communication with the FET device configured for biological and/or chemical analysis, and may be configured for controlling a flow of reagents over the array.

Accordingly, in certain instances, the fluid may include one or more reactants, such as one or more analytes necessary for performing a nucleic acid hybridization sequencing reaction, as herein described. In a particular embodiment, the fluid may include one or more, e.g., a plurality of microbeads (60), having a nucleic acid template (65) attached thereto, for instance, where the template is a DNA or RNA molecule to be sequenced, and the fluid containing the microbead (60) is to be delivered to the well (38) such as for carrying out the sequencing reaction. In such an embodiment, one or more of, e.g., each, of the plurality of microbeads may be configured so as to have electric charge and/or paramagnetic properties. The device may additionally include an electric and/or magnetic field component, e.g., having an electric and/or magnetic field generator, such as where the electric and/or magnetic field component is configured to generate an electric and/or magnetic field so as to interact with the electric and/or magnetic charge properties of each of the plurality of microbeads to attract the microbeads into a reaction location, such as a reaction surface, a channel, a well, a chamber, and/or a sensor of the FET device, such as by using electrophoresis and/or magnetism.

Hence, one or more, e.g., a plurality of microbeads (60a-e), may be drawn onto or into a reaction location of the plurality of reaction locations (37a-e), which locations may be formed as wells, e.g., one or more thin wells. The use of magnetism or electrophoresis allows for thinner reaction location structures. In particular instances, electric and/or magnetic field generator may be configured for drawing and/or positioning the microbeads within the well structure (37), such as in proximity to a channel or chamber of the device, and in other instances, the electric and/or magnetic field generator may be configured for reversing the electrical and/or magnetic field so as to repulse the microbead(s) (60) from the reaction location, channel, and/or chamber (37). In various instances, an array of reaction locations may be provided each having a magnet (70a-e) that allows for selective filling of the reaction locations with different numbers and/or types of microbeads (60), such as at select reaction locations (37a-e). In such an instance, multiple electric and/or magnetic field generators for selective filling of reaction locations, e.g., wells.

Accordingly, one aspect of the present invention is a system and/or a method for positioning one or more, e.g., a plurality, of microbeads (60) within a reaction or plurality of reaction locations (37) for biological or chemical analysis, such as for nucleic acid sequencing. The system may include a CMOS FET device having an integrated circuit structure configured for performing a biological or chemical analysis, such as within a plurality of nano- or micro-reaction wells, as described above, having a fluidic component (120), a circuitry component 140, and/or a computing component 150, and the method may include one or more of the following steps. For instance, the method may include the fluidic component (120) introducing a fluid to be in contact with the device (1), such as where the fluidics component is configured to control a flow a fluid of reagents over the array (1), and the fluid may include one or more microbeads (60) that may have electric charge and/or paramagnetic properties. In such an instance, the device may include an integrated circuit structure, a plurality of reaction locations (37) having one or more wells, a plurality of sensors and/or a plurality of channels, and/or an electric and/or magnetic field component (70). The electric field and/or magnetic field component (70) may be configured to activate the electronic and/or magnetic field, and the method may also include activating an electric and/or magnetic field so as to interact with the electric and/or paramagnetic properties of each of the microbeads (60). The method may additionally include drawing the one or more microbeads (60) into proximity with a reaction zone (24) of the plurality of reaction locations (37) using electrophoresis and/or magnetism. In certain instances, the method may include positioning the one or more microbeads within the one or more reaction locations for biological or chemical analysis.

In particular instances, the electric and/or magnetic fields may be generated by the plurality of electric and/or magnetic field generators (70), e.g., included in the integrated circuit structure, in all or only a subset of the plurality of reaction locations (37) so as to only attract a plurality of microbeads (60) to the subset of reaction locations, such as for selectively filling the plurality of reaction locations (37) with the plurality of microbeads. In such an instance, different types of microbeads may be attracted to different reaction locations, such as by pulsing the voltage and/or magnetic generators and/or keeping the same constant. Particularly, where an electric field generator (70) is provided the voltage applied to the device (1) may be variable or constant and may be less than about 10V, such as about less than 8V, or less than about 6V, including less than about 4V or about 2V or 1V. The voltage may be applied between a location above the fluid (72) and a location on or below the reaction zone (26), such as above the package lid and/or below the metal plate below the package. In certain instances, the location below the reaction location may be a metal or conductive layer such as within the package or package substrate. The method may also include the step of reversing the electric or magnetic field so as to eject the plurality of beads from the plurality of wells, sensors, and/or channels, either entirely or selectively.

Further, as indicated, each or a subset of the plurality of reaction locations may be utilized to generate electric fields to attract a microbead thereby allowing for programmability to each or a subset of reaction locations, for instance, 99% or 95% or 90% or 85%, or 80% or less of the plurality of wells are occupied with a microbead. Hence, the electric and/or magnetic field may be generated in only a subset of the plurality of wells (38a-e), sensors or channels to only attract a plurality of microbeads 60a-e to the subset. Likewise, a plurality of electric and/or magnetic field generators 70a-e for selective filling the plurality of wells (38), sensors or channels with the plurality of microbeads, and/or ejecting the plurality of beads (60) from the plurality of wells (38), sensors or channels. In such an instance, the electric and/or magnetic field generator may be an electric source, a permanent magnet and/or an electromagnet. As indicated, the plurality of magnetic field generators is configured to reverse the magnetic field to eject the plurality of microbeads (60) from the plurality of reaction locations (37) or a subset thereof.

Additionally, in one aspect of the present invention, a device, system, and/or method for verifying well occupancy for a plurality of wells (38a-e) for analysis of biological or chemical materials may be provided. The system may include a device for receiving a fluid containing the plurality of microbeads (60). Particularly, the device may include a processor, a CMOS structure having an integrated circuit, a plurality of wells (38), and a plurality of sensors within the CMOS structure. Each of plurality of wells (38) may be configured to receive a microbead (60) of the plurality of microbeads, and the CMOS structure may include a mechanism (70) for drawing and/or ejecting the beads into or out of the wells. Hence, the method may include the step of flowing the plurality of microbeads (60) over and/or into the plurality of reaction locations (26/37) and/or wells (38) and/or may include determining, e.g., through electrical and/or magnetic sensing if a reaction location (26/37) and/or well (38) is occupied or unoccupied and/or if a location (26/37) contains one or multiple microbeads (60).

Consequently, the processor (140) may be configured to determine if a well is unoccupied and/or if the well contains one or more, e.g., multiple microbeads. In certain instances, the processor (140) may also be configured to eliminate or modify one or more of the measurements, such as based on the number of wells occupied or unoccupied, e.g., the number of wells containing none, one or multiple microbeads. For instance, the processor (140) may be configured to eliminate from the measurement the number of wells unoccupied and the number of wells containing multiple microbeads, or compensate in the measurement for the number of wells unoccupied and the number of wells containing multiple microbeads, and the like. In such instances, the measurement may be a shift in an I-V or I-$V_g$ curve (or a parameter thereof), as explained below. In particular instances, the processor (140) may be configured to eliminate from the measurement the number of wells unoccupied and the number of wells containing one or multiple microbeads and/or to compensate in the measurement for the number of wells unoccupied and the number of wells containing one or multiple microbeads. Accordingly, in some embodiments, the measurement may be a shift in an I-V or I-$V_g$ curve, such as one or more of: generating a plurality of I-V or I-$V_g$ curves so as to determine a shift in response to a chemical reaction occurring on or near the chemically-sensitive FET; generating a chemically-sensitive FET I-V or I-$V_g$ curve in response to a chemical reaction occurring on or near the chemically-sensitive FET so as to detect a change in the slope of the I-V curve; and/or to sense shifts in a capacitance as a function of a gate voltage.

As indicated above, in particular embodiments, the field effect transistor can be configured as a complementary oxide semiconductor that is further adapted so as to be cavitated so as to include one or more reaction chambers that are positioned so as to align with a gate region of the FET. In such instances, the FET may be in contact with a fluidic source so as to form an ISFET. Accordingly, the CMOS-ISFET may be configured to run one or more chemical and/or biological reactions within its various chambers, such as a DNA hybridization or sequencing reaction, and the like, such as proximate a solution gated reaction zone. For these purposes, the ISFET may include a processor configured for controlling the performance of the one or more reactions, e.g., involving a biological or chemical material, so as to obtain reaction results, and for analyzing those results, for instance, based on detecting and/or measuring changes in a voltage (V) potential, current (I), or capacitance occurring within the gate region on the chemically-sensitive field effect transistor.

Figure 6A:
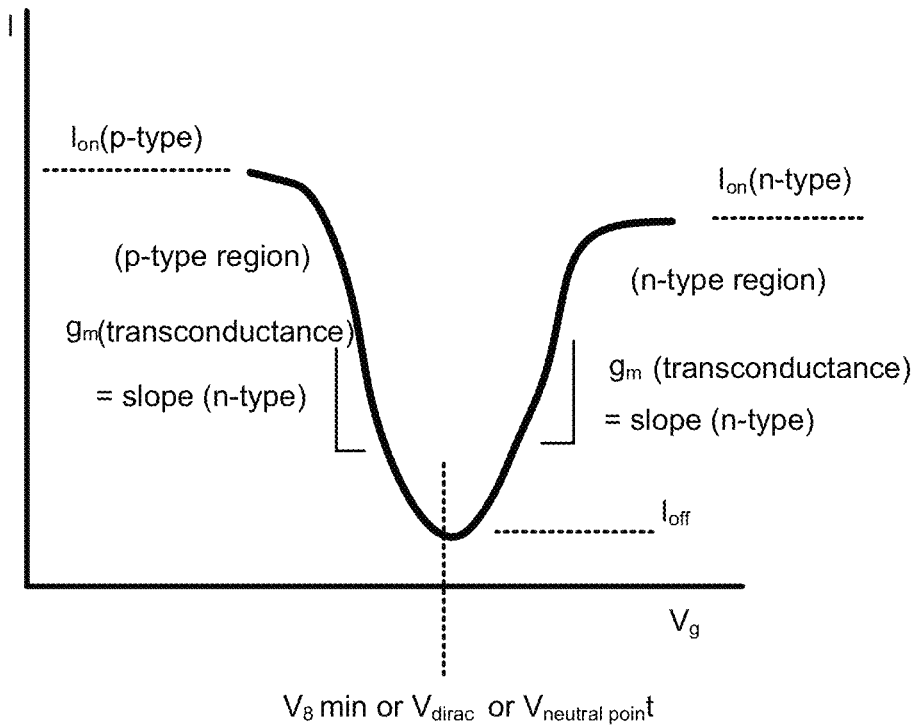
FIG. 6A is a graph of an I-$V_g$ curve with characteristics that are used to categorize I-$V_g$ curves.

Particularly, as can be seen with respect to FIG. 6A, the processor, such as a signal processor 151, may be configured so as to generate one or more current (I) vs. voltage (V) curves, such as where the current I of the I-V curve is the current applied between the source (22) and drain (24) of the chemically-sensitive solution gated FET and/or where the gate voltage (Vg) of the I-$V_g$ curve is a gate voltage applied to the chemically-sensitive field effect transistor (1). In such an instance, the gate voltage $V_g$ of the I-$V_g$ curve may be a top and/or a back gate voltage that may be applied to the chemically sensitive field effect transistor (1) through a top (or front) and/or back of the device, respectively. In particular embodiments, the gate voltage $V_g$ of the I-$V_g$ curve may be a solution gate voltage such as applied to the chemically sensitive FET through a solution flowed over a portion, e.g., a chamber (38), of the device (1). In some embodiments, the reference I-$V_g$ curve and/or a chemical reaction I-$V_g$ curve (or a corresponding parameter, e.g., a slope, of such reference and reaction curves) may be generated in response to the biological material and/or chemical reaction that is to be detected and/or occurs over or near the chemically-sensitive FET, such as within a chamber or well (38) of the FET structure. In various embodiments, the processor (150) may be configured to determine differences in relationships between a generated reference I-$V_g$ curve and/or chemical reaction I-$V_g$ curve. In certain instances, a circuitry component (140) may be included where the circuitry component may include at least one analog-to-digital converter (141) that is configured for converting analog signals, such as obtained as a result of the performance of the reaction(s) within the reaction well (38), or array of wells, into digital signals, such as may be sent back to the computing component (150) for further processing.

Accordingly, in another aspect of the invention, a chemically-sensitive field effect transistor device (1) may be provided, wherein the device may include a structure having a conductive source (22) and drain (24) as well as having a surface or channel (24) extending from the conductive source to the conductive drain, such as where the surface or channel includes a 1D or 2D transistor material (30). The device (1) may also include a computing component (150) having or otherwise being associated with a processor such as where the processor is configured for generating a reference I-$V_g$ curve and/or generating a chemical reaction I-$V_g$ curve, in response to the chemical reaction occurring within a chamber (37) of the chemically-sensitive field effect transistor (1), and may be configured to determine a difference between the reference I-$V_g$ curve and the chemical reaction I-$V_g$ curve. Specifically, FIG. 6A depicts a graph illustrating an I-$V_g$ curve calling out the various characteristics that may be used to categorize I-$V_g$ curves, and FIG. 6B depicts a graph of an I-$V_g$ curve illustrating the results of a single difference and that of multiple differences.

Figure 6B:
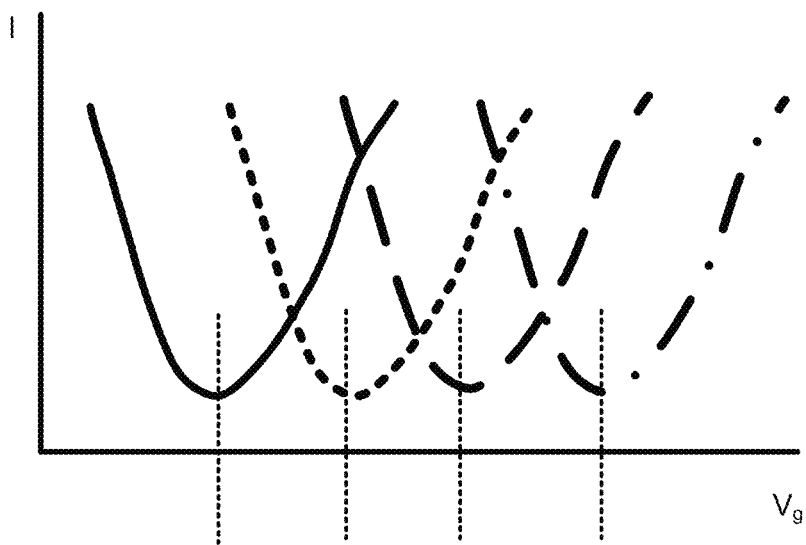
FIG. 6B is a graph of an I-$V_g$ curve illustrating a single difference or multiple differences.
Figure 6C:
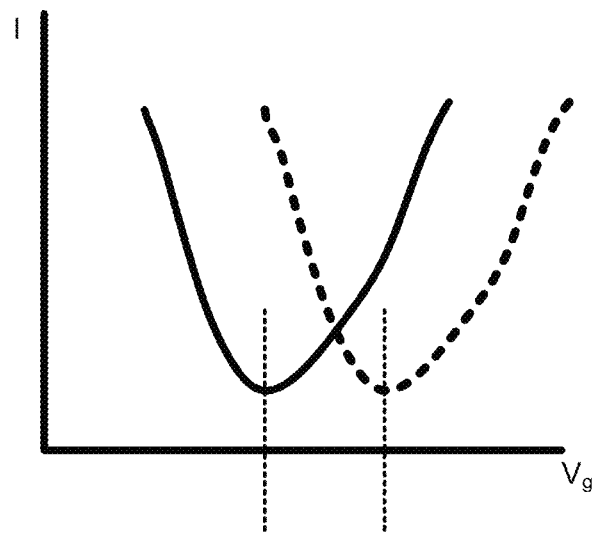
FIG. 6C is a graph of an I-$V_g$ curve illustrating a shift in the I-$V_g$ curve.
Figure 6D:
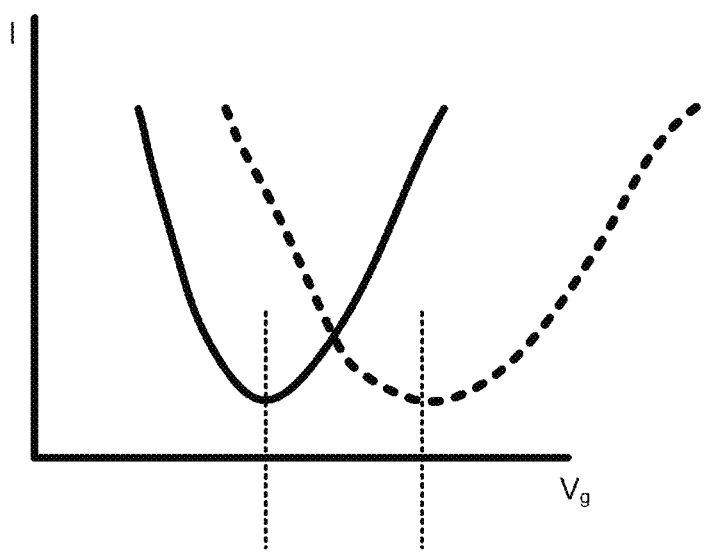
FIG. 6D is a graph of an I-$V_g$ curve illustrating a change in the shape of the I-$V_g$ curve.

Particularly, as can be seen with respect to FIG. 6B, the difference between the reference I-$V_g$ curve measurement and the chemical reaction I-$V_g$ curve (or corresponding parameters thereof) measurement is a shift in a minimum point of the $V_g$ value of the chemical reaction I-$V_g$ curve relative to a minimum point of the $V_g$ value of the reference I-$V_g$ curve. As can be seen, this shift is from left to right along the $V_g$ axis. Hence, as can be seen with respect to FIG. 6C, in some instances, a change in reaction conditions that result in a change in the I-$V_g$ curve may be demarcated by a shift in the I-$V_g$ curve, or as depicted in FIG. 6D, it may be demarcated by a change in the shape of the I-$V_g$ curve. More particularly, as exemplified in FIG. 6C, in one embodiment, the difference between the reference I-$V_g$ curve and the chemical reaction I-$V_g$ curve may be a change in the slope of the chemical reaction I-$V_g$ curve relative to a change in the slope of the reference I-$V_g$ curve. Likewise, as exemplified in FIG. 6D, the difference between the reference I-$V_g$ curve and the chemical reaction I-$V_g$ curve may be an overall change in the shape of the chemical reaction I-$V_g$ curve relative to an overall change in shape of the reference I-$V_g$ curve.

Figure 6E:
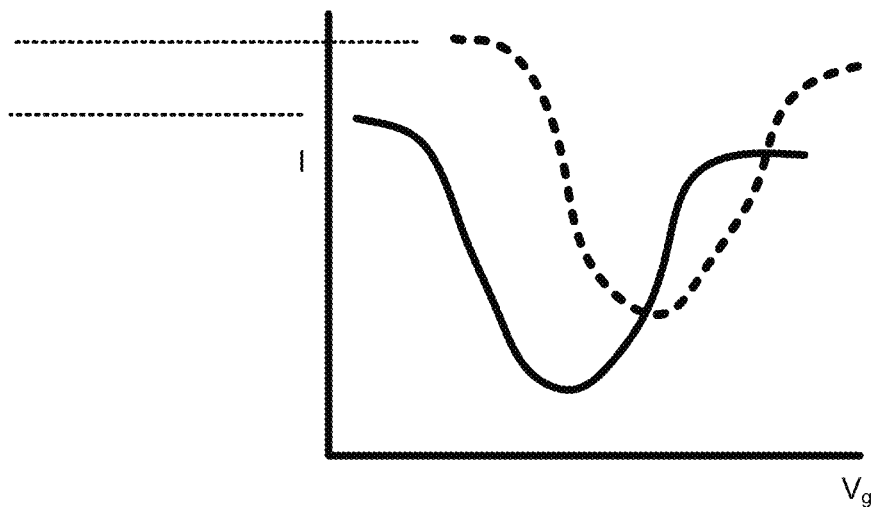
FIG. 6E is a graph of an I-$V_g$ curve illustrating a change in the level of the I-$V_g$ curve ($I_{on}$ in p-type region).
Figure 6F:
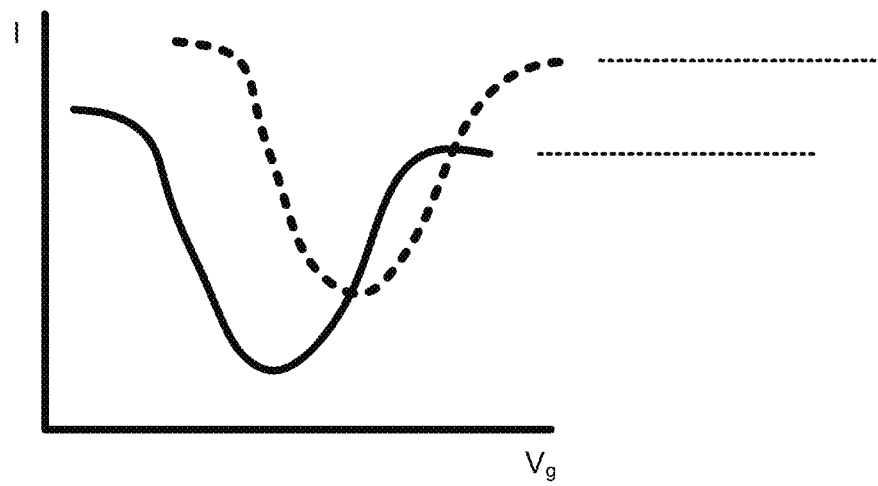
FIG. 6F is a graph of an I-$V_g$ curve illustrating a change in the level of the I-$V_g$ curve ($I_{on}$ in n-type region).

In other instances, as can be seen with respect to FIGS. 6E and 6F, the difference between the reference I-$V_g$ curve and the chemical reaction I-$V_g$ curve may be a shift in an ion value of the chemical reaction I-$V_g$ curve relative to a shift in an ion value of the reference I-$V_g$ curve, for instance, where the ion values are taken from a p-type (FIG. 6E) or n-type (FIG. 6F) section of the I-$V_g$ curve (see FIG. 6A). For example, the measurements of the slopes may be taken from the steepest and/or flattest sections on the p-type and/or n-type portions of the I-$V_g$ curves. Specifically, FIGS. 6E and 6F depict graphs of I-$V_g$ curves illustrating a change in the level of the I-$V_g$ curve where the ion is in a p-type region (FIG. 6E), and a change in the level of the I-$V_g$ curve where the ion is in a n-type region (FIG. 6F).

Figure 6G:
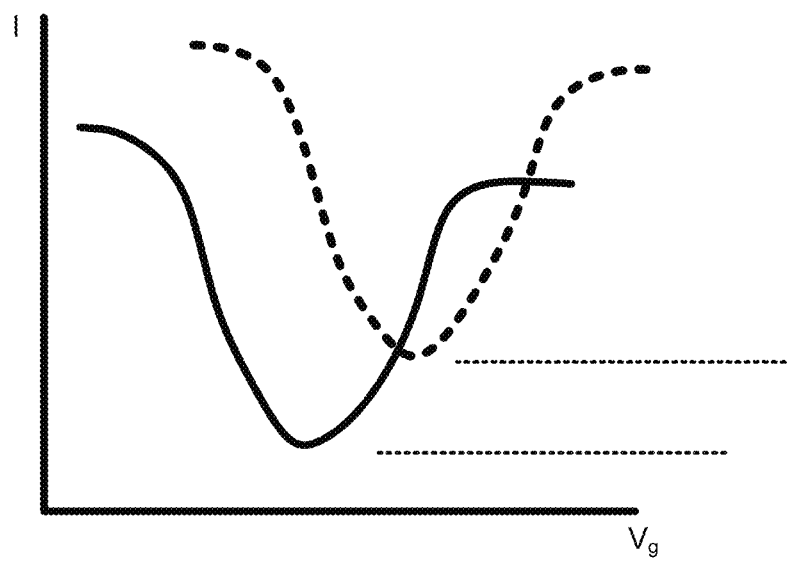
FIG. 6G is a graph of an I-$V_g$ curve illustrating a change in the level of the I-$V_g$ curve ($I_{off}$).
Figure 6H:
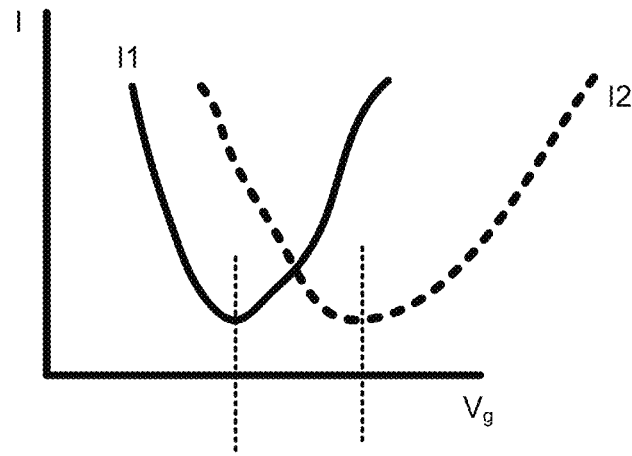
FIG. 6H is a graph of an I-$V_g$ curve illustrating a fit polynomial or other fitting line to curve and use coefficients as read criterion.
Figure 6I:
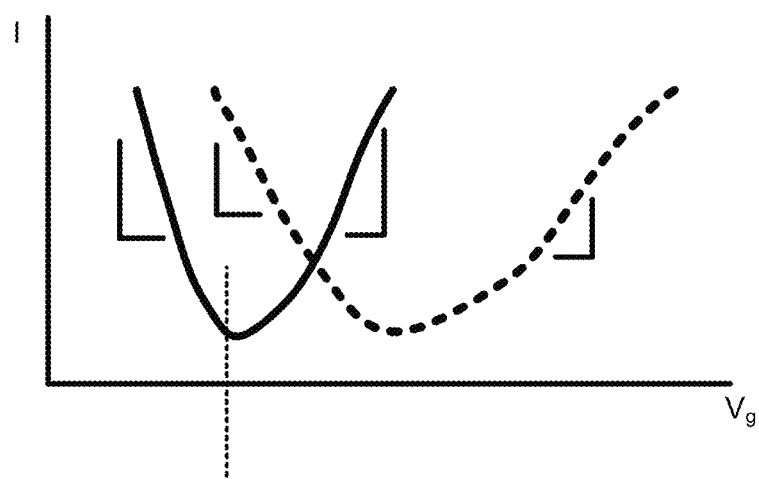
FIG. 6I is a graph of an I-$V_g$ curve illustrating a check-slope of the I-$V_g$ curve on one or both sides (Gm & proportional to mobility), and use of a solution gate and back gate in combination to improve a signal and move the curve where desired.

Additionally, in particular instances, the difference between the reference I-$V_g$ curve and the chemical reaction I-$V_g$ curve (or corresponding parameters thereof) may be a shift in an $I_{off}$ value of the chemical reaction I-$V_g$ curve relative to an $I_{off}$ value of the reference I-$V_g$ curve. Particularly, FIG. 6G depicts a graph of an I-$V_g$ curve illustrating a change in the level of the I-$V_g$ curve ($I_{off}$). More particularly, in such embodiments, as depicted in FIG. 6H, the difference in the overall shape of the I-$V_g$ curves may be determined by first fitting a polynomial or other fitting line to each of the I-$V_g$ curves and then comparing the coefficients of those fitting lines. Specifically, FIG. 6H depicts a graph of an I-$V_g$ curve illustrating a fit polynomial or other fitting line to curve and use coefficients as read criterion. In other embodiments, the difference between a reference I-$V_g$ curve and the chemical reaction I-$V_g$ curve is based on more than one chemical reaction I-$V_g$ curve. Further, FIG. 6I depicts a graph of an I-$V_g$ curve illustrating a check-slope of the I-$V_g$ curve on one or both sides ($G_m$ and proportional to mobility), and use of a solution gate and backgate in combination to improve a signal and move the curve where desired.

It is to be noted, with respect to FIGS. 5B and 5C, when no microbead (60) is present in the well structure (38), an electric signal may be transmitted to the computing component (150). In such an instance, the processor may be configured to eliminate from the measurement the number of wells (38) that are unoccupied, or at least to compensate in the measurement for the number of wells (38) that are unoccupied, such as where the measurement may be a shift in the I-$V_g$ curve and/or I-$V_g$ curve (or corresponding parameters thereof). Likewise, when two or more microbeads (60a, 60b) are present in the well structure (38), an electric signal may be transmitted to the computing component (150). In such an instance, the processor may be configured to eliminate from the measurement the number of wells (38) containing multiple microbeads 60, or at least compensate in the measurement for the number of wells (38) containing multiple microbeads (60), such as where the measurement may be recognized as a shift in the I-V curves or reference and reaction I-$V_g$ curves.

Accordingly, as can be seen with respect to FIGS. 6A-6I, in particular embodiments, the FET and/or processor may be configured to respond to a shift in the I-V or I-$V_g$ curve, such as where the curve is shifted in response to the detection of a biological compound and/or the result of a reaction taking place in or on a surface (24) of the FET device (1). In some instances, the I-V/I-$V_g$ curve may be produced and/or shifted in response to a chemical reaction occurring on a reaction layer 34/36 and/or the surface of a 1D or 2D, e.g., graphene, surface (30) of the field effect transistor (1), such as resulting from the detection of a biological compound or reaction occurring within the well structure (38) of the device. Hence, the FET and/or processor may be configured so as to shift the I-V curve or I-$V_g$ curve such as in response to the chemical reaction.

Figure 7A:
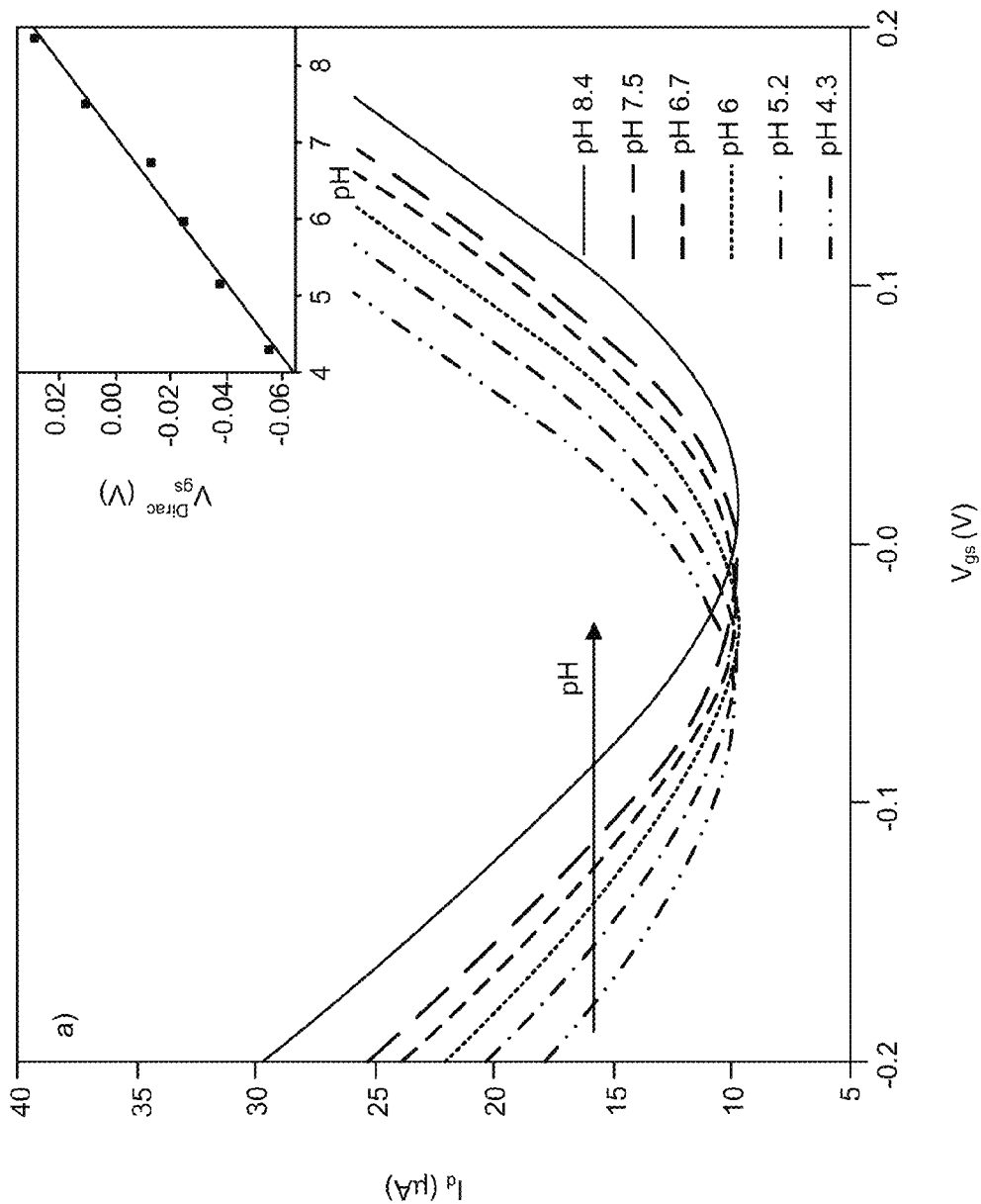
FIG. 7A is a graph of an I-$V_g$ curve for various pH values.
Figure 7B:
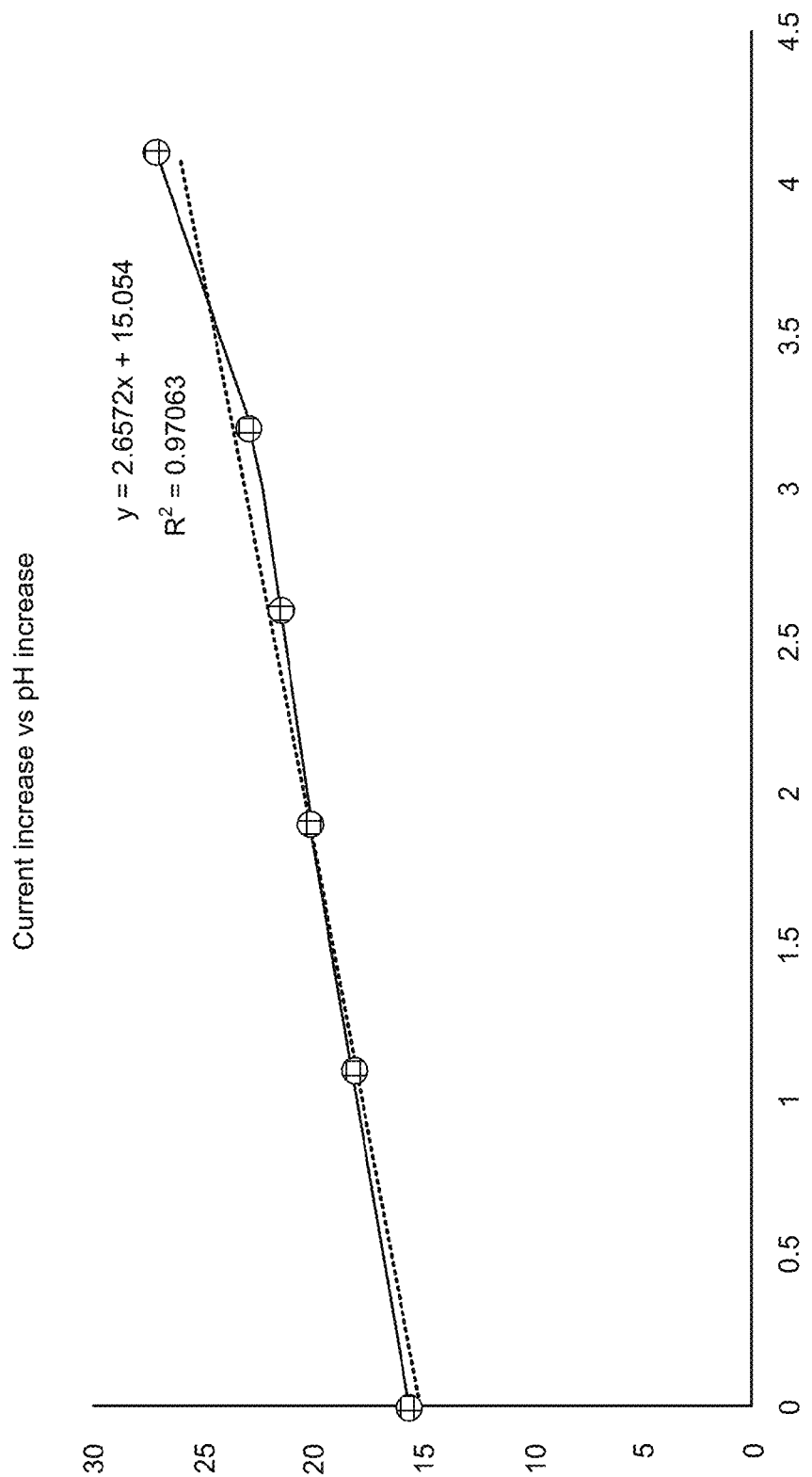
FIG. 7B is a graph of current increase vs. pH increase.
Figure 7C:
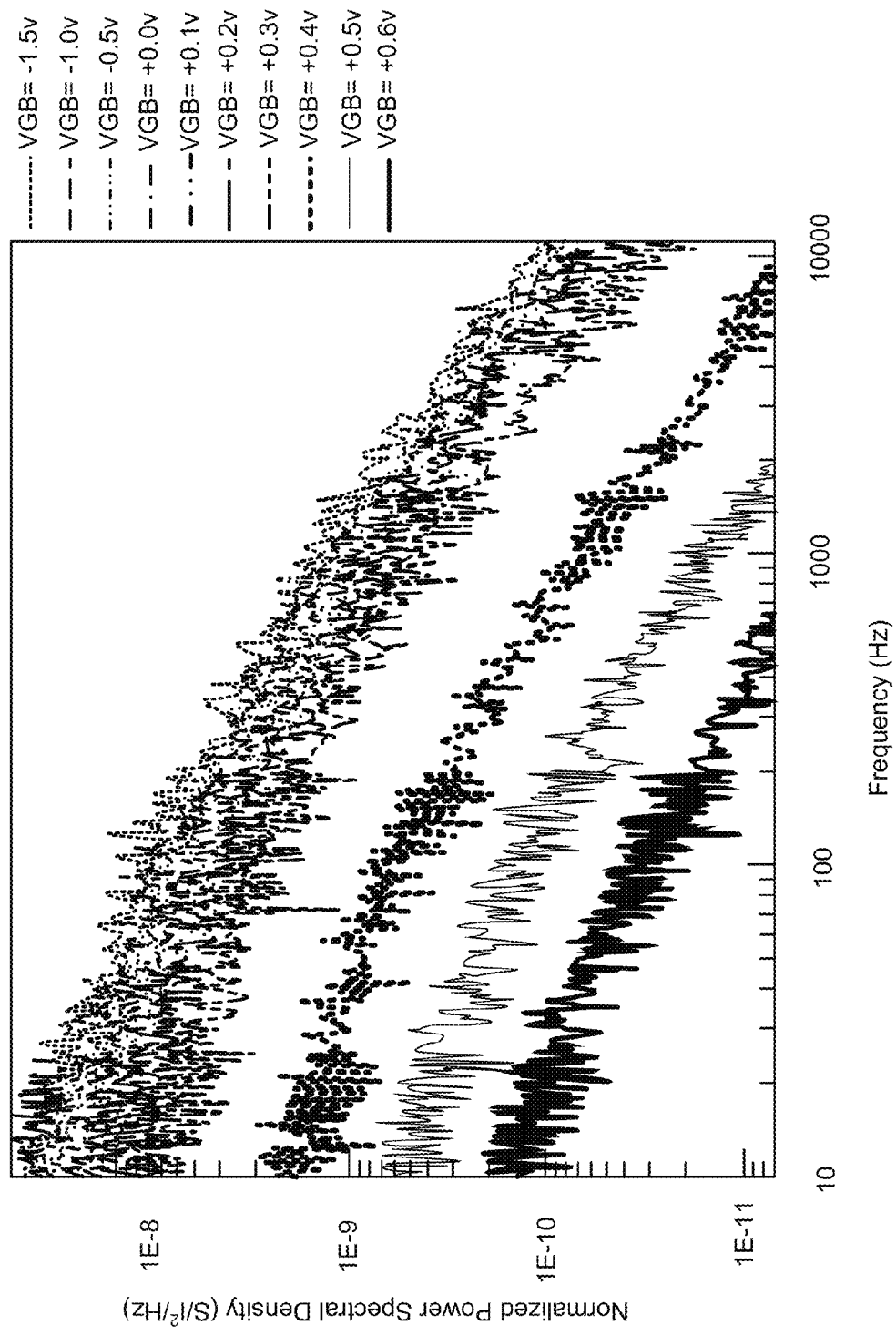
FIG. 7C is a graph of frequency vs. normalized power spectral density for silicon ISFET.
Figure 7D:
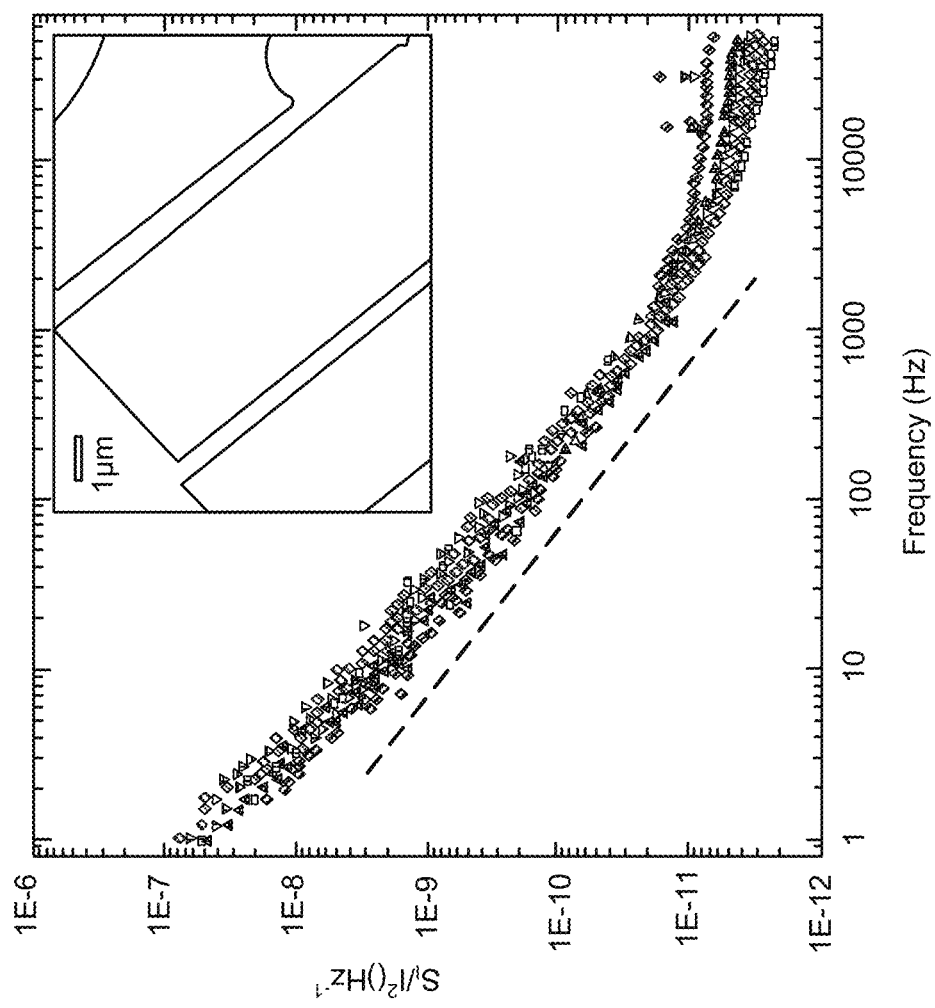
FIG. 7D is a graph of frequency vs. normalized power spectral density for a typical graphene FET.
Figure 7E:
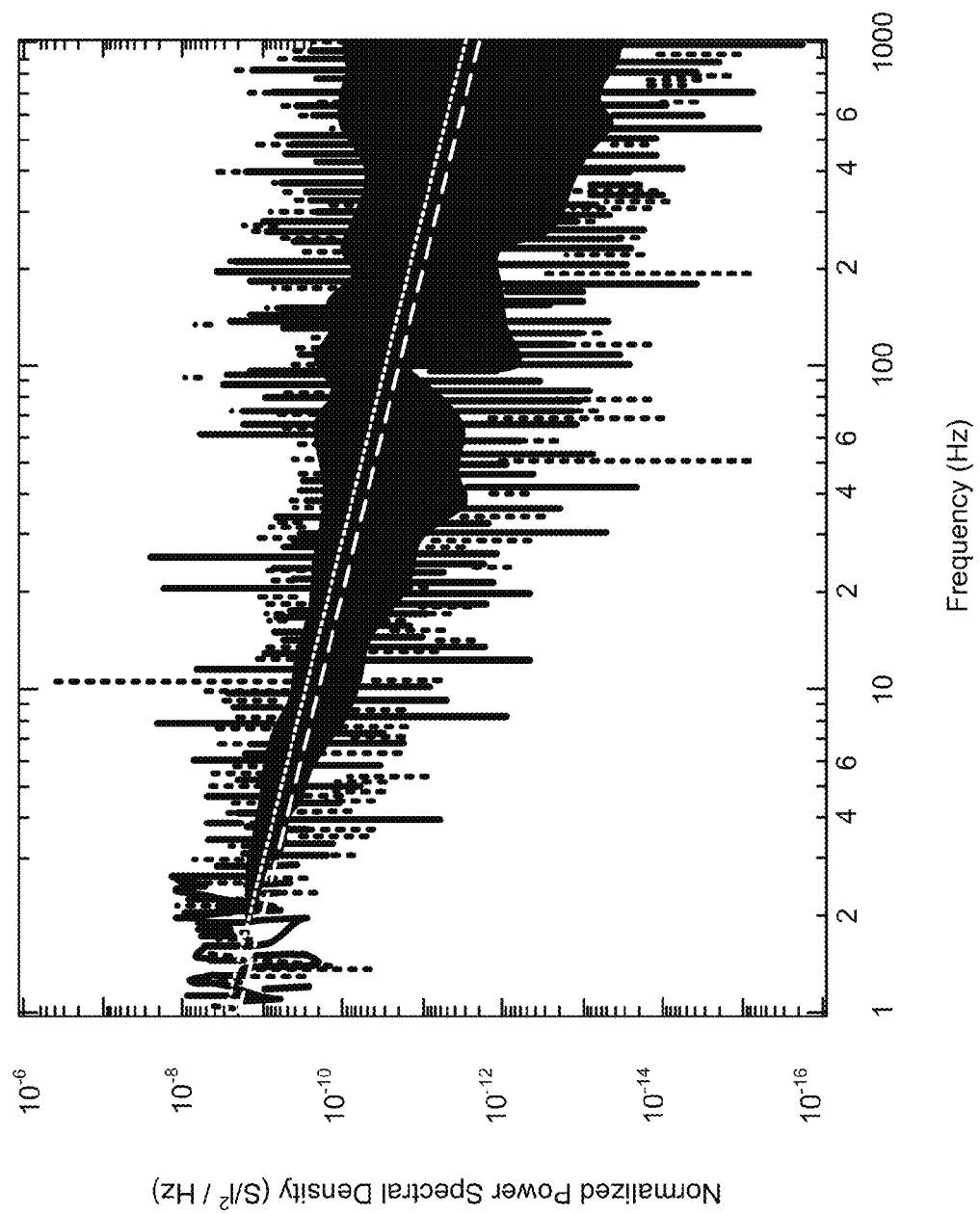
FIG. 7E is a graph of frequency vs. normalized power spectral density for a graphene FET of the present invention.
Figure 7F:
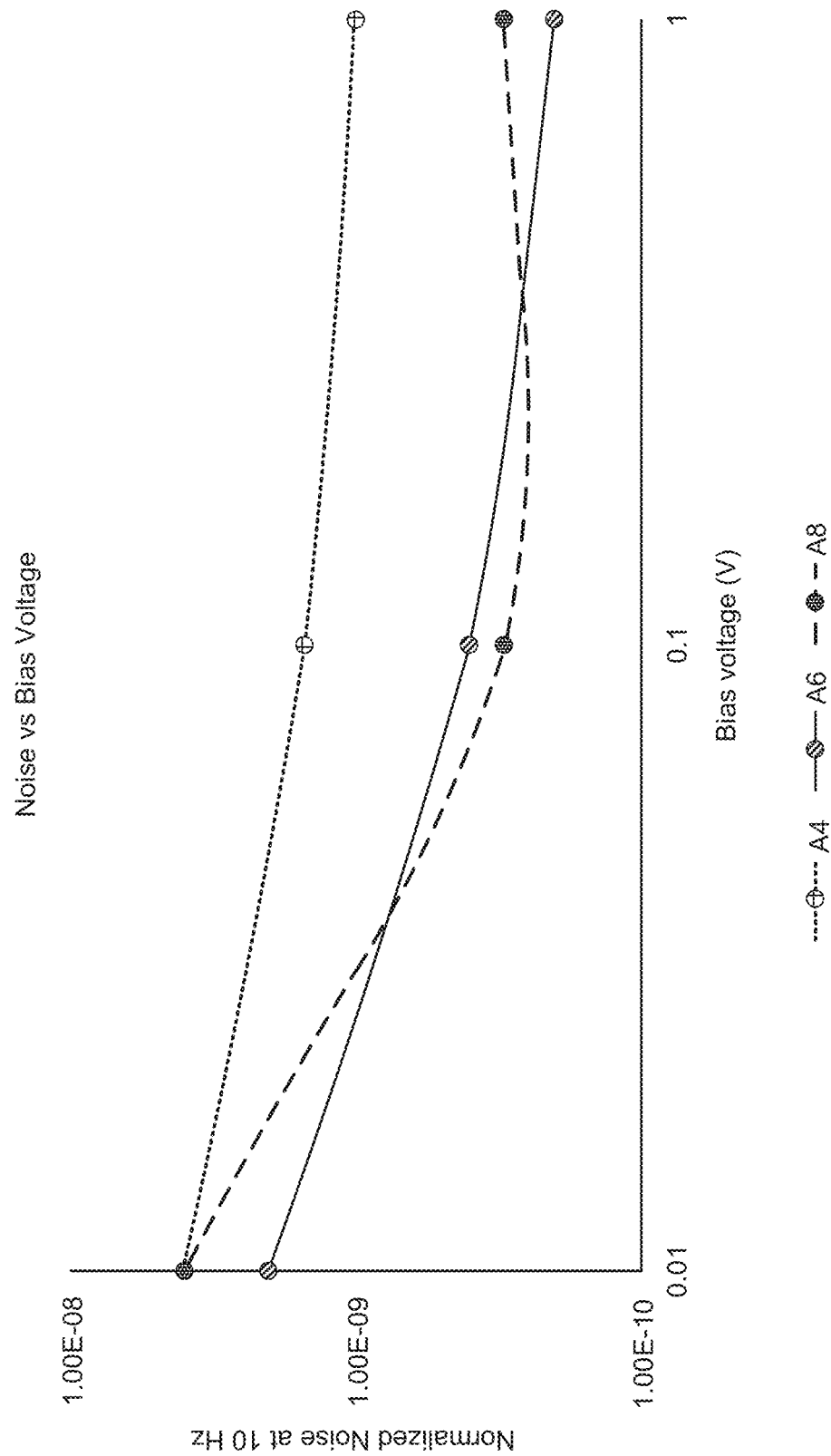
FIG. 7F is a graph of noise vs. bias voltage.
Figure 7G:
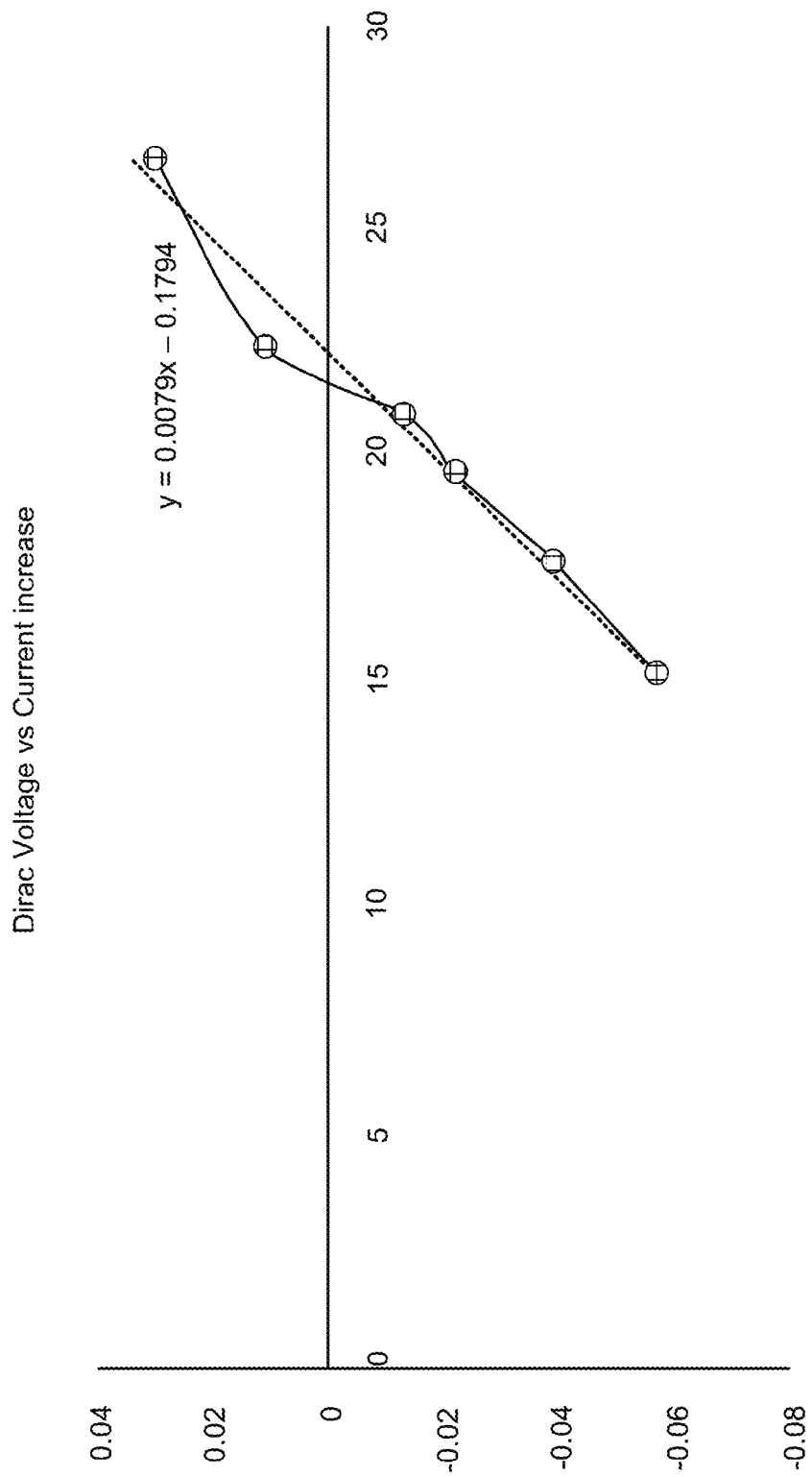
FIG. 7G is a graph of Dirac voltage vs. current increase.

For instance, FIG. 7A depicts a graph of an I-$V_g$ curve for various pH values. Particularly, FIG. 7A illustrates the transfer characteristics of a 20×40 micron graphene-on-SiO$_2$ SGFET ("solution gated FET") at a constant drain-source voltage of Vds=50 mV for different pH values. FIG. 7B depicts a graph of current increase versus pH increase. Likewise, FIG. 7C depicts a graph of frequency vs. normalized power spectral density for silicon ISFET device. FIG. 7D illustrates a graph of frequency vs. normalized power spectral density for a typical graphene FET device of the invention. Additionally, FIG. 7E depicts a graph of frequency vs. normalized power spectral density for a graphene FET of the invention. FIG. 7F depicts a graph of noise vs. bias voltage, and FIG. 7G depicts a graph of Dirac voltage vs. current increase.

Hence, in various aspects of the invention, one or more elements and/or methods, as herein described, may be used to shift a reference I-V or I-$V_g$ curve and/or a chemical reaction I-$V_g$ curve so that the difference between the reference I-$V_g$ curve and a chemical reaction I-$V_g$ curve is more pronounced. However, in various embodiments, to make such a difference more pronounced, and thus, better able to be detected, the device may include a further structure (40), such as a membrane or other element that is configured for enhancing the ability of the processor to determine the difference between various I-V and/or I-$V_g$ curves. (See, for instance, FIG. 8A). Particularly, in various embodiments, a further structured layer (4), e.g., a tertiary or quaternary structure, may also be provided, such as where the further structured layer may be included and/or present within the well or chamber, such as to enhance the ability of the processor to determine the difference between the current and/or voltages as well as their respective associated curves. Hence, in one aspect, a chemically-sensitive FET transistor (1) is provided where the FET is fabricated on a primary structure having a stacked configuration including an inorganic base layer (10), e.g., a silicon layer; a dielectric structure and/or an organic or inorganic insulator layer (20), such as a silicon dioxide layer; a 1D or 2D material layer (30), such as a carbon nanotube, nanowire, or graphene layer; an oxidation and/or passivation layer (34/36); and further having a conductive source (22) and drain (24) embedded in one or more of the layers, such as between and/or forming a gate structure (26), e.g., a solution gate region (37).

Figure 8B:
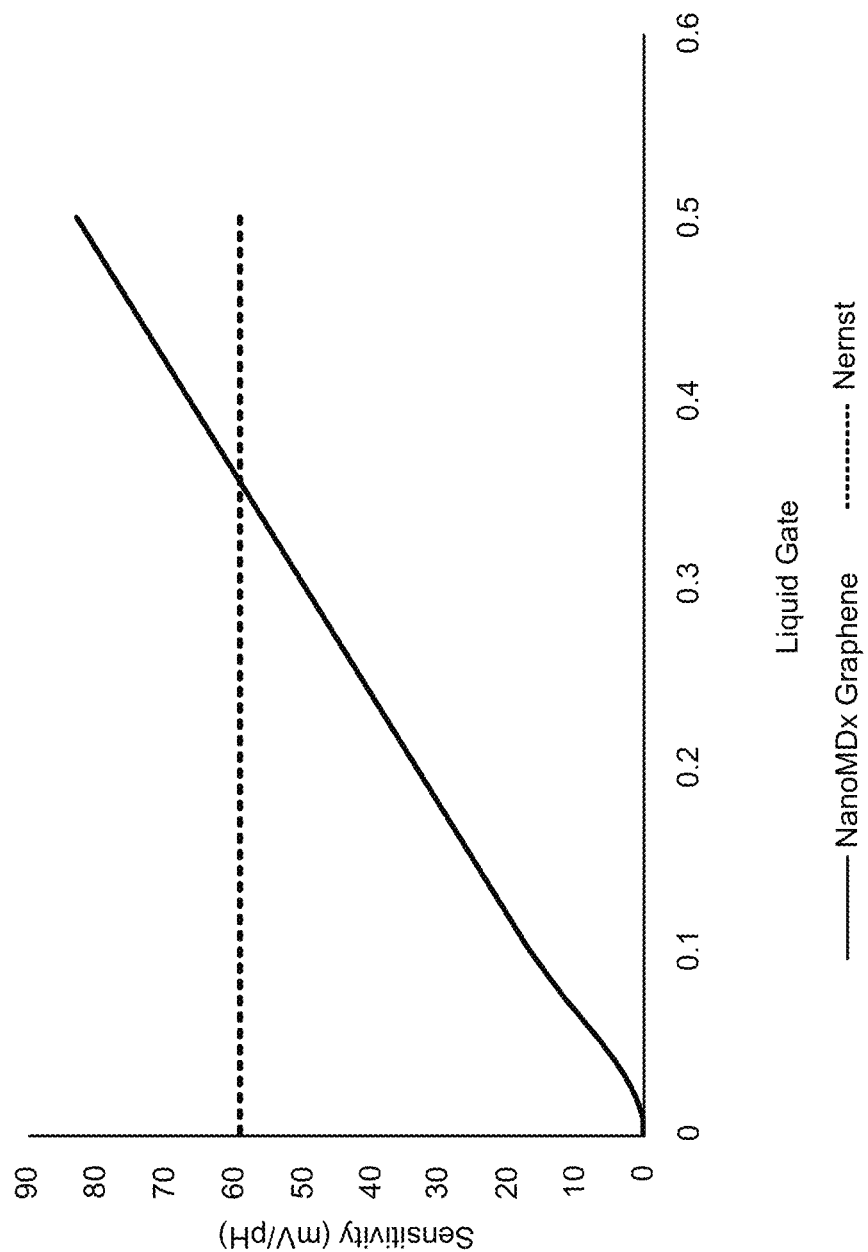
FIG. 8B is a graph of an average sensitivity of a graphene FET ("GFET") calculated as a function of liquid gate potential.

Accordingly, as can be seen with respect to FIG. 8A, in various embodiments, the gate region (24) may be configured so as to form a chamber (37) and/or well (38) and the 1D or 2D material (30) and/or oxidation layers (34) may be positioned between the conductive source (22) and drain (24) in such a manner as to form a bottom surface of the chamber (37). In various instances, the structures may further include or otherwise be associated with an integrated circuit and/or a processor, such as for generating and/or processing generated data, such as sensor derived data. And, further, in various embodiments, the chamber (37) may further include a membrane (40) or other element positioned above or between one or more of the 1D, 2D, or 3D structure layer and/or the oxidation (34) and passivation layers 36, such as where the membrane structure (40) is configured for enhancing the ability of the processor to determine the difference between various I-V and/or I-$V_g$ curves. For instance, FIG. 8B depicts a graph of an average sensitivity of a graphene FET ("GFET") calculated as a function of liquid gate potential. The GFET of the present invention surpasses the theoretical 59 mVolt maximum for an ISFET type device made of silicon. This difference is even more pronounced when an ion exclusive membrane (40) is included as part of the device.

In particular embodiments, therefore, as seen with respect to FIGS. 6 and 8, a further structured layer (40), e.g., a secondary or tertiary structure, may also be provided, such as where the further structured layer may be included and/or present within the well or chamber, such as to enhance the ability of the processor to determine the difference between the current and/or voltages as well as their respective associated curves. More particularly, the additional structure may include an ion-selective permeable membrane (40), such as an ion-selective permeable membrane that allows ions of interest to pass through the membrane (40) while blocking other indeterminate ions, such as to enhance the ability of the processor to determine the difference between the reference I-V or I-$V_g$ curve and the chemical reaction I-V or I-$V_g$ curve, and thus enhance the ability of the processor to detect a desired chemical reaction. In various instances, the FET (1) may be configured such that the I-V or I-$V_g$ curve(s) may be shifted so as to better respond to, detect, and/or otherwise determine a biological compound and/or a chemical reaction, such as a biological compound and/or a chemical reaction occurring on the 1D or 2D, e.g., graphene, surface (30) of the chemically-sensitive field effect transistor (1). In particular instances, the ion-selective permeable membrane (40) may include a 2D transistor material, e.g., graphene, which may or may not be electrically connected to the source and/or drain layer and/or channel (26).

Accordingly, in various instances, the chemically-sensitive field effect transistor (1) may be fabricated on an integrated circuit wafer that includes a primary (10) and/or secondary (20) structure as well as a channel structure (26), a processor and/or a tertiary structure (35), such as a structure forming one or more wells (38). For instance, the first and/or secondary structures may include a conductive source (22) and a conductive drain (24), which together with the other components of the FET (1) form a channel region (26). The channel (24) extends from the conductive source (22) to the conductive drain 24, with the channel (24) formed between the two, where a one-dimensional or two-dimensional transistor material layer (30) may be positioned above and/or may otherwise be in contact with the source (22) and drain (24). As indicated above, the FET (1) may include a processor, such as where the processor is configured for generating one or more of a reference I-$V_g$ curve and a chemical reaction I-$V_g$ curve, such as in response to a chemical reaction that is to be detected, for instance, a reaction occurring over or near a reaction zone (24) of the chemically-sensitive field effect transistor (1). In particular embodiments, the processor is configured for determining a difference between the reference I-$V_g$ curve and the chemical reaction I-$V_g$ curve. Hence, in various embodiments, an additional structure (40) may be included, such as a structure that is configured for enhancing the ability of the processor to determine this and other associated differences.

Particularly, in various embodiments, the additional structure may be an ion-selective permeable membrane (40) that allows one or more ions of interest to pass through the membrane (40) while blocking other ions. More particularly, the additional structure (40) may be configured so as to enhance the ability of the processor to determine the difference between the reference I-$V_g$ curve and the chemical reaction I-$V_g$ curve (or corresponding parameters thereof), and thus further enhances the ability of the processor to detect a desired chemical reaction. Accordingly, in various instances, the ion-selective permeable membrane (40) may be positioned within the well (38) and/or over a passivation layer (36), an ion sensitive or reaction layer (34), a 1D and/or a 2D transistor material layer (30), and/or a dielectric layer (35) that itself may be positioned over and/or otherwise form a part of the chamber (37) or channel (26). In certain embodiments, the membrane layer (40) may be or otherwise be associated with an ion getter material, such as an ion getter material that traps or sequesters ions that may or may not be relevant to the biological species and/or chemical reaction to be sensed and/or determined, such as to enhance the ability of the processor to determine the difference between the reference I-V or I-$V_g$ curve and/or the chemical reaction I-V or I-$V_g$ curve. This may be useful because reducing the number and/or amount of interfering ions, enhances the ability of the processor to detect the desired biological species and/or results of the chemical reactions. Particularly, the ion getter material may be arranged within proximity to the chamber (37) and/or surface (21) thereof so that the action of gettering the unwanted ions improves the detection capability of the chemically-sensitive FET (1). In some instances, one or more of the various layers herein, such as the ion getter material may be placed over or between one or more of the other layers, such as the dielectric layer (20/35), oxide layer (34), or 2D or 1D layers (30), positioned in proximity to one or more of the chambers, channels, or surfaces of the FET device (1).

In particular instances, the ion-selective permeable structure (40) may include a polymer such as perfluorosulphonic material, a perfluorocarboxylic material, PEEK, PBI, Nafion or PTFE. In other instances, the ion-selective permeable structure may be composed of an inorganic material such as an oxide or a glass. In particular instances, the ion-selective permeable structure (40) may be applied to a surface (e.g., 21) of the FET such as by being deposited thereon, such as by a spincoating, anodization, PVD, or other sol gel methods. An additional material, e.g., HMDS, may also be included so as to manage the interaction of the chamber (37) and/or channel (24) and/or associated oxide layer (20/35) and/or an underlying 2D or 1D transistor layer (30). For instance, a chemically-sensitive field effect transistor (1) of the invention may include an additional structure that includes a 2D transistor channel or surface that may include an ion-sensitive material over the channel or surface. In such an instance, the material may be sensitive to ions that are different from the ions associated with the biological molecule or chemical reaction that is to be detected. Particularly, the ion-selective permeable structure (40) may additionally be composed of an ion sensitive 1D or 2D transistor material, such as graphene, that is in addition to the 1D or 2D material layer 30, and is not electrically connected to the channel (26).

In certain instances, the ion-selective permeable structure (40) may be positioned over the ion sensitive layer (30) that itself may be positioned over the channel structure or surface (26). As indicated, the additional structure (40) may be composed of an ion getter material, wherein the ion getter material is configured to trap ions that are not relevant to the chemical reaction to be determined. Accordingly, in some instances, a suitably configured membrane (40) and/or additional structure, e.g., HMDS or other siloxane, may be useful because the action of sensing ions that are different from the ions associated with the biologics and/or chemical reactions that are to be detected allows the processor to filter out the signal from the unwanted ions from the signal of the ions of interest. In particular instances, the HMDS material may be positioned under the graphene. Accordingly, in various instances, an exemplary ion-selective permeable membrane (40) and/or an additional getter structure may be positioned over a channel structure (26), where these structures are configured so as to only allow ions of interest to travel through them. In particular instances, the getter material may be positioned within the chamber (37) or elsewhere on the chip or in the package so as to attract unwanted ions. Another alternative would be to include another ion-selective functional layer(s) over some of the sensors that can detect the presence of contaminants or unwanted ions so that their interaction with the sensor and thus the determination of the sensor reaction to the desired ion can be filtered out.

In all of these instances, the action of trapping ions that are not relevant to the chemical reaction to be determined enhances the ability of the processor to determine the difference between the reference I-$V_g$ curve and the chemical reaction I-$V_g$ curve, e.g., because there are fewer interfering ions. In such instances, the membrane (40) and/or ion getter material may be arranged within proximity to a reaction zone (24) that is in proximity to a channel region so that the action of gettering the unwanted ions improves the detection capability of the chemically-sensitive FET. Alternatively, the ion getter material may be placed over a dielectric layer that is in proximity to one or more of the reaction zones (24) and/or channels.

In another aspect, the present GFET (and other 1D and 2D-based FETs) integrated circuits, sensors, and/or arrays of the invention may be fabricated such as using any suitable complementary metal-oxide semiconductor (CMOS) processing techniques known in the art. In certain instances, such a CMOS processing technique may be configured to increase the measurement sensitivity and/or accuracy of the sensor and/or array, and at the same time facilitate significantly small sensor sizes and dense GFET chamber sensor regions. Particularly, the improved fabrication techniques herein described employing a 1D, 2D, and/or oxide as a reaction layer provide for rapid data acquisition from small sensors to large and dense arrays of sensors. In particular embodiments, where an ion-selective permeable membrane is included, the membrane layer may include a polymer, such as a perfluorosulphonic material, a perfluorocarboxylic material, PEEK, PBI, Nafion, and/or PTFE. In some embodiments, the ion-selective permeable membrane may include an inorganic material, such as an oxide or a glass. One or more of the various layers, e.g., the reaction, passivation, and/or permeable membrane layers may be fabricated or otherwise applied by a spin-coating, anodization, PVD, and/or sol gel method.

Accordingly, when using the device for sequencing a nucleic acid sample, the target nucleic acid sample may be coupled to, immobilized on, or in proximity with the reaction zone of the chemically-sensitive FET. This template sequence may then be sequenced and/or analyzed by performing one or more of the following steps. For example, a primer, and/or a polymerase, e.g., an RNA and/or DNA polymerase, and/or one or more substrates, e.g., deoxynucleotide triphosphates dATP, dGTP, dCTP, and dTTP, may be added, e.g., sequentially, to the reaction chamber, to facilitate a polymerase-mediated elongation reaction. Once the appropriate substrate is incorporated into the growing DNA strand, there will be a concomitant change in the individual electrical characteristic voltage, e.g., the source-drain voltage (Vsd), measured as a result of the new local gating effect.

Hence, for every elongation reaction with the appropriate, e.g., complementary, substrate there will be a change in the characteristic voltage. For instance, as described herein, a field-effect device for nucleic acid sequencing and/or gene detection is disposed in a sample chamber of a flow cell, and a sample solution, e.g., containing a polymerase and one or more substrates, may be introduced to the sample solution chamber. In various embodiments, a reference electrode may be disposed upstream, downstream, or in fluid contact with the FET device and/or the source and/or drain may themselves serve as electrodes, such as for hybridization detection, and gate voltage may be applied whenever needed.

Particularly, in an exemplary elongation reaction, polynucleotides are synthesized if the added substrate is complementary to the next unpaired base of the template nucleic acid. If the added substrate is not complementary to the next available base, base-pairing does not occur and there is no elongation. Since nucleic acids, such as DNAs and RNAs, have a negative charge in aqueous solutions, hybridization resulting in elongation can be incrementally determined by the change in the charge density in the reaction chamber (30). And because the substrates are added sequentially, it can readily be determined which nucleotide bound to the template to facilitate the elongation reaction. Accordingly, as a result of elongation, the negative charge on the graphene gate surface, insulating film surface, and/or the sidewall surface of the reaction chamber will be increased. This increase can then be detected, such as a change in the gate source voltage, as described in detail herein. By determining which substrate resulted in a signal of change in gate-source voltage, the base sequence identity of the target nucleic acid can be determined and/or analyzed.

More specifically, the FET, such as for nucleic acid elongation and/or hybridization detection, may be associated with a salt or analyte solution that is added to the reaction chamber, which can then be used to determine if an elongation reaction has taken place. Particularly, once the template is associated with the substrate, the reaction mixture containing a polymerase, e.g., a DNA polymerase, and a first nucleic acid substrate, e.g., dATP, is added to the buffer solution to facilitate an elongation reaction on or in proximity to the graphene gate coated insulating film of the reaction chamber surface. If the dATP is a complement to the next available reaction site in the isolated template, a binding event, i.e., base-pairing, will occur and the antisense strand of the growing sequence will be elongated, which elongation can be detected by the GFET transistor.

For example, if adenine (A) is complementary to the base thymine (T) on the target template adjacent to the 3'-terminus of the nucleic acid template, an elongation reaction occurs, resulting in the polymerase-mediated addition of one adenine base to the growing DNA strand. In such instance, an enzyme, e.g., DNA polymerase, and the substrate may be washed away from the gate portion and reaction chamber, and a buffer solution, e.g., a phosphoric acid buffer solution, e.g., having a pH of about 6, may be introduced on the graphene gate surface to measure changes in the source-drain voltage. If hybridization occurred, there will be a change in the source-drain voltage and it will be detected. However, if the dATP is not a match, there will be no hybridization, and if no hybridization, there will be no elongation and no corresponding signal detected by chemically-sensitive FET of the well in which the reaction mixture was present. Thereafter, another reaction mixture containing another, different nucleotide substrate, e.g., dCTP, the polymerase enzyme, and other necessary reagents are added to the reaction chamber under conditions suitable for polymerization if base-pairing occurs between the next nucleotide in the template and the added dCTP. If elongation occurs, it will be detected by the GFET. These steps are repeated until the nucleic acid sample has been completely sequenced. In various instances, the temperature within the reaction chamber may be controlled, for instance, it may be set to 74° C., such as by using a temperature sensor and/or a heater integrated in the field-effect device.

If an elongation reaction takes place there will be a resultant change to the threshold voltage, which will be increased, e.g., by 4 mV, from before the elongation reaction. The shift of the threshold voltage in the positive direction indicates that a negative charge was generated on the graphene gate surface. It can be understood from this that polymerization of one base to the growing DNA daughter strand caused by the elongation reaction was detectable as a change in threshold voltage. A second elongation reaction may then take place and be repeated until the entire target nucleic acid has been sequenced.

Figure 9A:
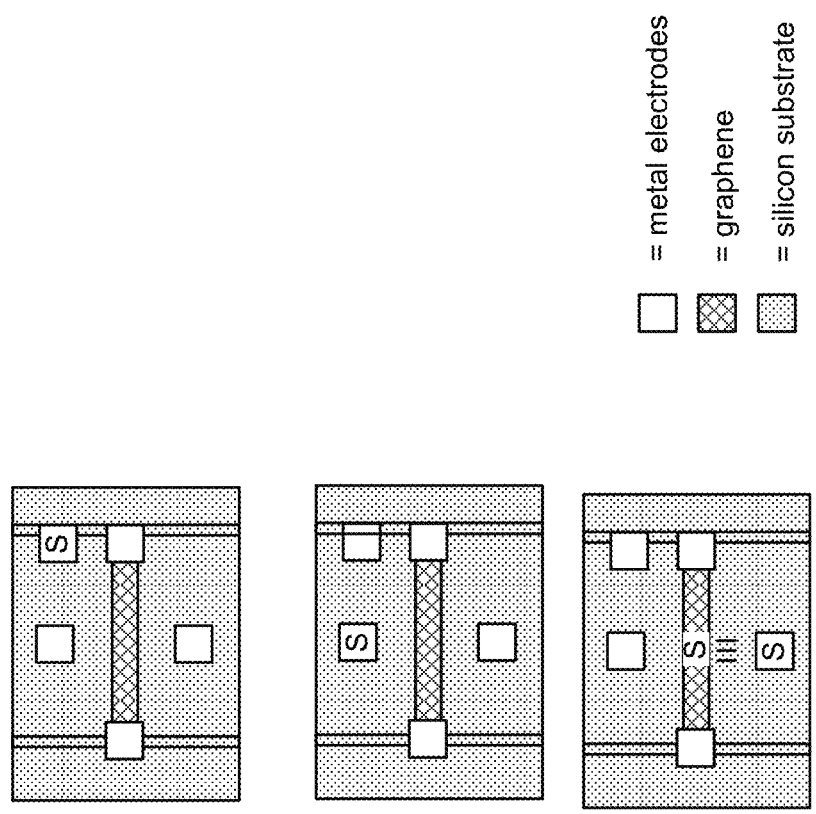
FIG. 9A is an illustration of electrowetting for biomolecule attachment.
Figure 9B:
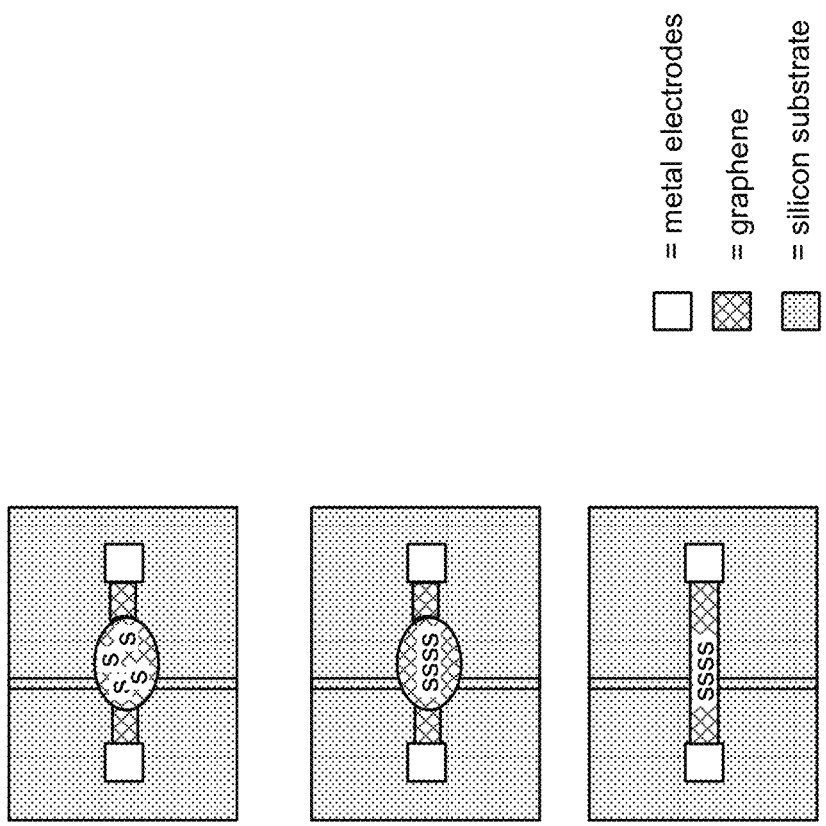
FIG. 9B is an illustration of electrophoresis for biomolecule attachment.
Figure 9C:
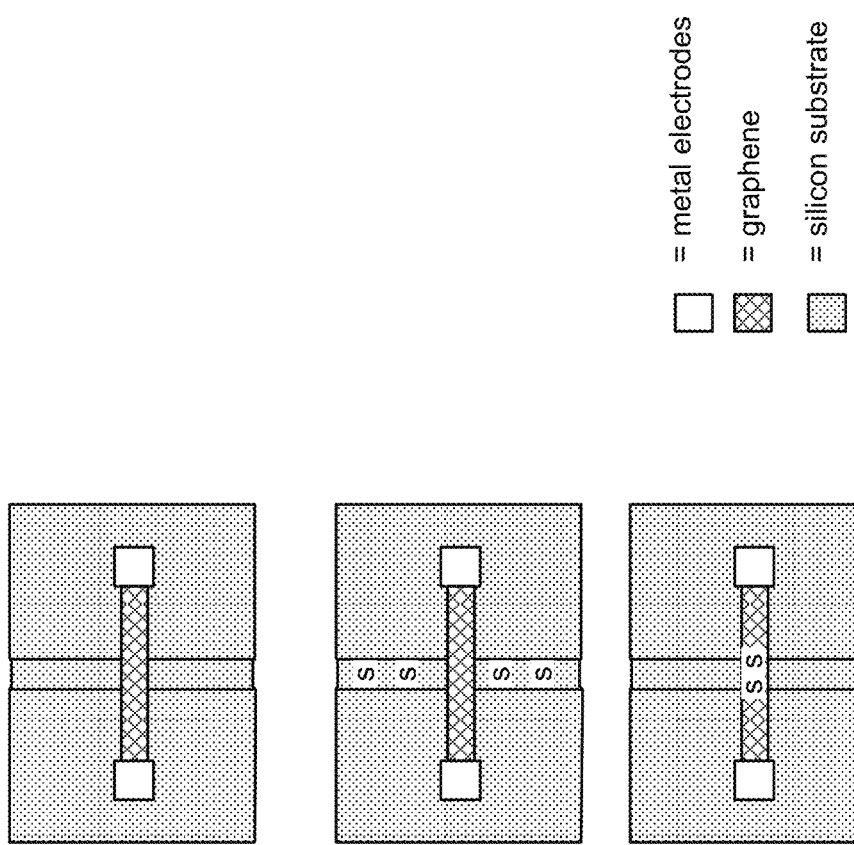
FIG. 9C is an illustration of microfluidics for biomolecule attachment.
Figure 9D:
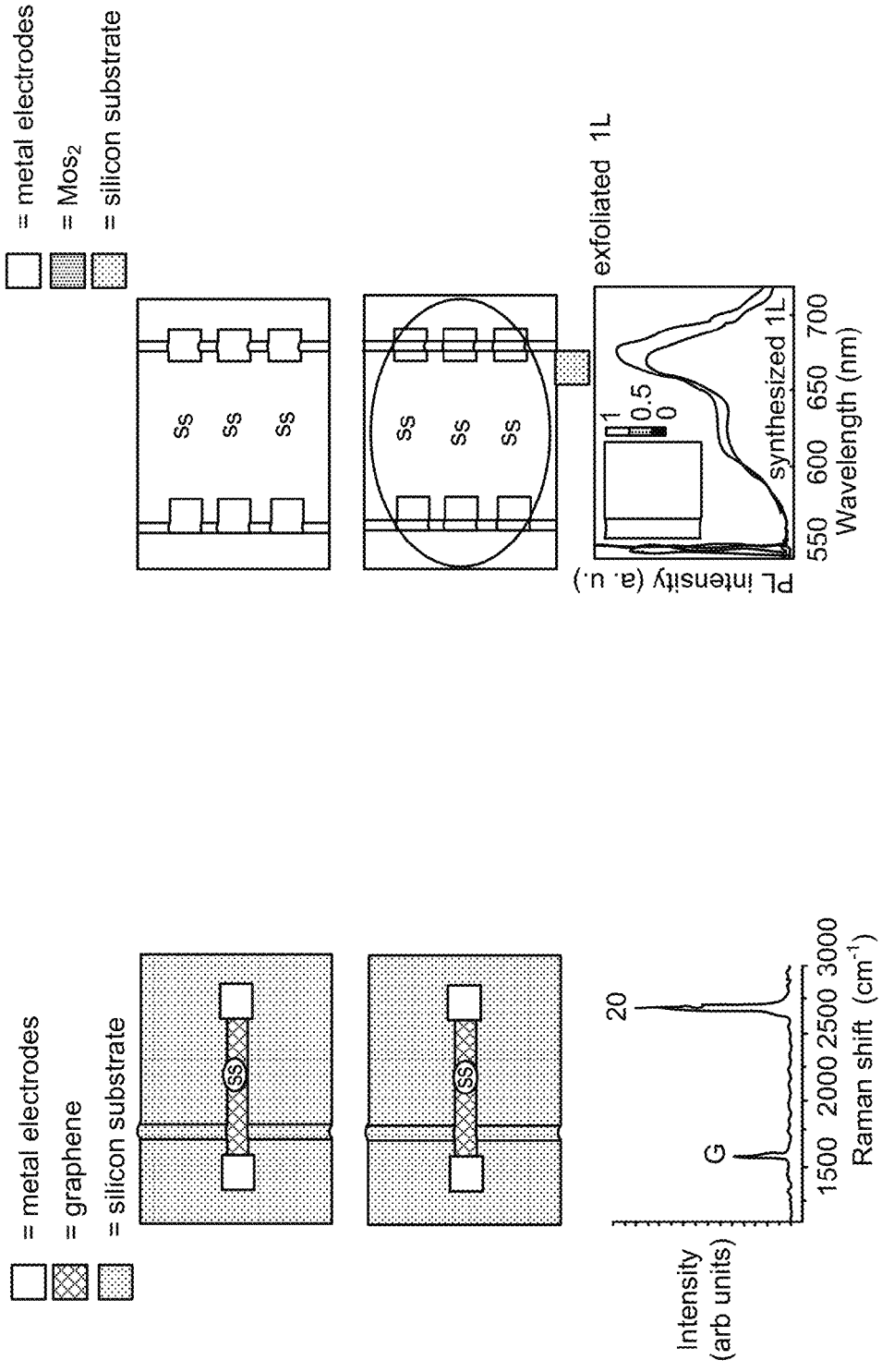
FIG. 9D is an illustration of an optical readout of DNA sequencing using nanomaterials.

Accordingly, FIG. 9A is an illustration of electrowetting for biomolecule attachment, as described herein. FIG. 9B is an illustration of electrophoresis for biomolecule attachment. FIG. 9C is an illustration of microfluidics for biomolecule attachment. And FIG. 9D is an illustration of an optical readout of DNA sequencing using nanomaterials.

More particularly, in such a configuration as represented in the figures, the drain current of the chemically sensitive FET can be modulated by the electrical charge carried by the nucleotide molecules involved in the hybridization and/or sequencing reactions. For example, in one particular configuration of the FET, after hybridization or an elongation step, the charge in the reaction zone increases resulting in a change in the output current that may be measured. This measurement, e.g., for this configuration of the FET, may be made in accordance with the following equation:

$$V_{THF} = T_{TH0} - \frac{Q_{com} + Q_0}{C_C + C_F}$$

Such as where $C_C$ represents the current at the control capacitor, and $C_F$ represents the current at the parasitic capacitor. $V_{THF}$ represents the effective threshold voltage of the transistor (20), and $V_{TH0}$ represents the native threshold voltage. $Q_0$ represents the electric charge initially trapped in the floating gate, and $Q_{DNA}$ represents the total charge of hybridization complex.

For instance, a nucleic acid from a sample to be sequenced or representative of a probe to be targeted may be immobilized on the bottom surface or the sidewall of the sample solution well chamber. A DNA polymerase (e.g., an isothermal DNA polymerase, e.g., a Bst or Bst-like DNA polymerase), a nucleotide substrate, and other necessary reagents may then be introduced to the sample solution chamber to induce an elongation reaction. As a result, DNAs may be synthesized using the immobilized nucleic acid as the template for DNA synthesis. In such an instance, as the source-drain current vs. gate voltage characteristic changes by the electrostatic interaction with the charged particles (electrons, ions, etc.) in the well, the base sequence of a template nucleic acid having a large base length can be sequenced and/or analyzed. In other embodiments, a nucleic acid probe may be immobilized on the surface of the reaction zone, as described above, and used in a hybridization reaction so as to detect, for example, genetic variation, the presence of a genetic disease, polymorphism, or pathogen.

In various instances, in order to conduct parallel analysis of a plurality of nucleic acid templates, the number of the transistors may be equal to or higher than the number and/or types of DNAs to be sequenced and/or analyzed. In certain instances, each nucleic acid template or probe may be an oligonucleotide or a fragment of DNA or RNA that may be constituted from about 100 to about 1000 bases, such as from 200 to about 800 bases, for instance, from about 300 or about 500 bases to about 600 or 700 bases or more or somewhere in between. However, in various instances, a fragment of nucleic acid having 100 bases or fewer may also be used.

Additionally, as indicated above, the present device (1) may also be used in various different DNA/RNA hybridization reactions, such as for the purpose of determining a genetic variation and/or for detecting the presence of a genetic marker for a disease or pathogen. In such an instance, a nucleic acid probe may be coupled to or immobilized on a bottom or side graphene-coated surface of the reaction chamber, per above. As indicated, the probe may be of any suitable length but in various instances from about 5 or 10 to about 1000 bases, such as from 20 or about 50 to about 700 or about 800 bases, for instance, from about 100 or about 200 bases to about 300 bases including about 400 or about 500 bases to about 600 or 700 bases or more or somewhere in between.

For instance, in one exemplary embodiment, a nucleic acid probe or template containing about 20 to 50-100 bases coding for a gene sequence of interest that has been previously amplified or otherwise synthesized (e.g., by solid state synthesis methods), may be immobilized in or proximate to the channel region and/or proximate a gate region (if included), a channel insulating film, and/or a side surface of the reaction chamber of the FET. For example, once isolated and amplified, the base of the probe may be modified so as to be attached to the graphene coated surface, and/or may be coupled to a secondary substrate, such as a glass or plastic bead that has been chemically treated so as to be coupled therewith. Once immobilized, the reaction chamber containing the probes, either on a secondary substrate or directly coupled with a chamber surface, may be reacted with a sample solution containing a number genes including a target gene of interest to be measured such that when a nucleic acid probe having a complementary base sequence to the target gene is immobilized on the gate, gate insulating film, or the sidewall surface of the sample solution well structure, or on a secondary substrate immobilized within the reaction chamber of the field-effect device for gene detection, the target gene hybridizes with the nucleic acid probe under appropriate reaction conditions and the target gene and the nucleic acid probe form a double strand, the result of which hybridization reaction may be detected.

Figure 10A:
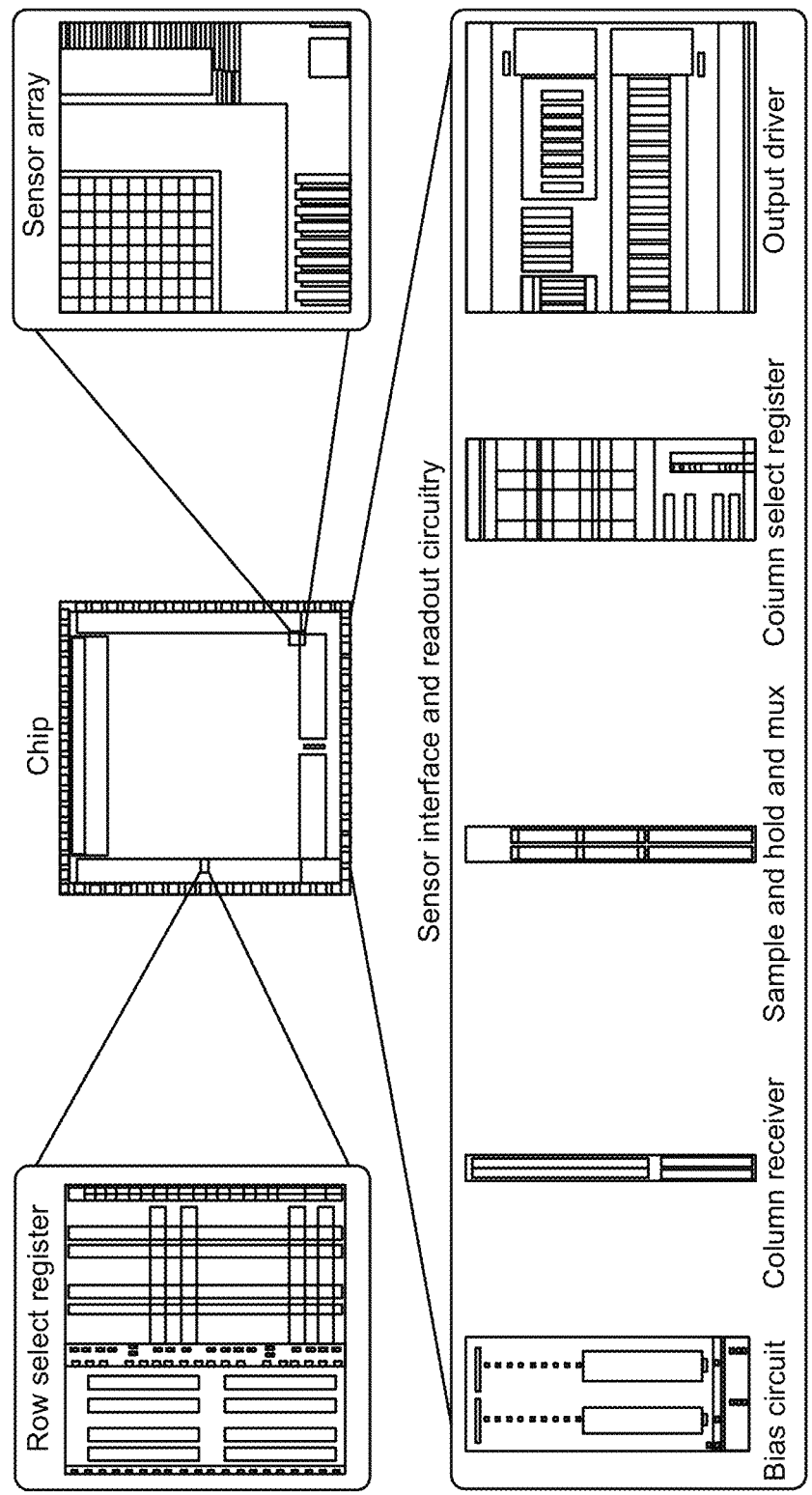
FIG. 10A is a block diagram of components for a system for analysis of biological or chemical materials.

As depicted in FIG. 10A, a GFET array sets forth a two dimensional GFET sensor array chip that in this instance is based on a column and row design, although other designs are also possible. As can be seen with respect to FIG. 10B, the system further includes a row and column decoder, as well as circuitry for performing the requisite sensing, detecting, and processing so as to measure the sensory data. Hence, also included is sensing, measurement, and other associated readout data.

Accordingly, as can be seen with respect to FIGS. 10A and 10B, in various instances, a one or two-dimensional GFET array, as described herein, may be fabricated on a microchip in accordance with the methods herein disclosed. In various instances, the array chip may include a number of GFET sensors that may be arranged in columns and/or rows. A typical number of sensors may include GFET sensor elements, described herein as "sensors," that may be arranged in a 16 sensor by 16 sensor column/row array configuration. As depicted, the array includes two columns, but typically may include sixteen columns, arranged side by side, where each column includes 16 rows. Particularly, each column of the array includes up to 16 sensors. Each column may be configured so as to include a current source $I_{SOURCE}$ that may be shared by all sensors of the column. However, in various other embodiments, each sensor may have its own current source, or the array itself may have a single current source. Additionally, each GFET sensor may include a GFET, as described above, having an electrically coupled source and/or drain and/or body, and may further include one or more switches, such as a plurality of switches S1 and S2 that may be configured so as to be responsive to one of the up to sixteen row select signals (RSEL, and it's complements). More particularly, a row select signal and its complement may be generated simultaneously to "enable" or select a given sensor of the selected column, and such signal pairs may be generated in some sequence to successively enable different sensors of the column, e.g., together or one at a time, such as sequentially.

A row decoder may also be provided as part of the system. In such an instance, the row decoder may be configured so as to provide up to sixteen pairs of complementary row select signals, wherein each pair of row select signals may be adapted so as to simultaneously or sequentially enable one sensor in each column so as to provide a set of column output signals from the array, e.g., based on the respective source voltages VSa through VSb, etc. of the enabled row of GFETs. The row decoder may be implemented as a conventional four-to-sixteen decoder (e.g., a four-bit binary input ROW1-ROW4 to select one of (24) outputs). The set of column output signals VSa through VSb for an enabled row of the array is applied to switching logic, which may be configured to include up to sixteen transmission gates Sa through Sb (e.g., one transmission gate for each output signal).

As above, each transmission gate of the switching logic may be implemented using an n-channel or p-channel MOSFET, such as where various analog and/or digital transistors and circuits may be included, such as proximate the GFET sensor array. The transmission gate may be positioned in a bottom or top gate configuration, or both to ensure a sufficient dynamic range for each of the output signals $V_{Sa}$ through $V_{Sb}$. The column decoder, like the row decoder, may be implemented as a conventional four-to-sixteen decoder and may be controlled via the four-bit binary input $COL_1$-$COL_4$ to enable one of the transmission gates Sa through Sb of the switching logic at any given time, so as to provide a single output signal $V_S$ from the switching logic. This output signal $V_S$ may be applied to a 10-bit analog to digital converter (ADC) to provide a digital representation $D_1$-$D_{10}$ of the output signal $V_S$ corresponding to a given sensor of the array.

As noted earlier, individual GFETs and arrays of GFETs such as those discussed above may be employed as sensing devices in a variety of applications involving chemistry and biology. In particular, such GFETs may be employed as pH sensors in various processes involving nucleic acids such as DNA. In general, the development of rapid and sensitive nucleic acid hybridization and sequencing methods, as herein described, e.g., utilizing automated DNA sequencers, may significantly advance the understanding of biology.

It should be noted, that with respect to the various arrays disclosed herein according to various embodiments of the present invention may be fabricated according to conventional CMOS fabrication techniques, as described above, as well as modified CMOS fabrication techniques (e.g., to facilitate realization of various functional aspects of the GFET arrays discussed herein, such as additional deposition of graphene and/or other passivation materials, process steps to mitigate trapped charge, etc.) and other semiconductor fabrication techniques beyond those conventionally employed in typical CMOS fabrication (e.g., BiCMOS).

Additionally, various lithography techniques may be employed as part of an array fabrication process. For example, in one exemplary implementation, a lithography technique may be employed in which appropriately designed blocks are "stitched" together by overlapping the edges of a step and repeat lithography exposures on a wafer substrate by approximately 0.2 micrometers. In a single exposure, the maximum die size typically is approximately (21) millimeters by (21) millimeters. By selectively exposing different blocks (sides, top & bottoms, core, etc.) very large chips can be defined on a wafer (up to a maximum, in the extreme, of one chip per wafer, commonly referred to as "wafer scale integration").

In one embodiment, the array includes 512 columns with corresponding column bias/readout circuitry (one for each column), wherein each column includes geometrically square sensors, each having a size of approximately 9 micrometers by 9 micrometers (e.g., the array may be up to 512 columns by 512 rows). In various instances, the entire array (including sensors together with associated row and column select circuitry and column bias/readout circuitry) may be fabricated on a semiconductor die as an application specific integrated circuit (ASIC), structured ASIC, or as a field gated programmable array such as having dimensions of approximately 7 millimeters by 7 millimeters.

Various power supply and bias voltages useful for array operation are provided to the array via electrical connections (e.g., pins, metal pads) and labeled for simplicity in block as "supply and bias connections." The array may also include a row select shift register, one or more, e.g., two sets of column select shift registers, and one or more, e.g., two, output drivers, which output drivers are configured to provide two parallel output signals from the array, $V_{outa}$ and $V_{outb}$, representing sensor measurements. The various power supply and bias voltages, control signals for the row and column shift registers, and control signals for the column bias/readout circuitry may be provided by an array controller, which controller may also read the output signals $V_{outa}$ and $V_{outb}$ (and other optional status/diagnostic signals) from the array. Configuring the array such that multiple regions (e.g., multiple columns) of the array may be read at the same time via multiple parallel array outputs (e.g., $V_{outa}$ and $V_{outb}$) facilitates increased data acquisition rates.

Accordingly, in various embodiments, an integrated circuit for performing a sequencing reaction is provided, such as where the sequencing reaction involves the sequencing of strands of nucleic acids, as described herein. In various embodiments, the integrated circuit may include a substrate and an array of graphene field effect transistors arranged on the substrate. In such an embodiment, one or more of, e.g., each, of the graphene field effect transistors may include a primary layer forming a base layer, and a secondary, e.g., intermediary, layer positioned over or otherwise associated with the primary layer, the secondary layer being formed of a first nonconductive material and including a source and a drain formed in the first nonconductive material, the source and drain being separated one from the other by a channel, and being formed of an electrically conductive material. In certain instances, a tertiary layer may be positioned over the secondary layer, such as where the tertiary layer includes a gate formed over the channel to electrically connect the source and the drain. In such an instance, the gate may be formed of a graphene layer. The tertiary layer may additionally include a surface structure that overlaps the source and the drain in the secondary layer, the surface structure further defining a well having side walls and a bottom that extends over at least a portion of the graphene layer of the gate so as to form a reaction chamber for the performance of the sequencing reaction. In particular embodiments, a nano- or micro-bead provided in one or more wells of the array of graphene field effect transistors, such as where one or more, e.g., each bead may be configured with one or more reactants to interact with portions of the strands of nucleic acids such that the associated chemically sensitive FET detects a change in ion concentration of the reactants by a change in current flow from the source to the drain via an activation of the graphene layer.

It should be noted that, in various embodiments of the array, one or more of the columns, e.g., the first and last columns, as well as the first and/or last sensors of each of the columns may be configured as "reference" or "dummy" sensors. For instance, the dummy sensors of an array, e.g., the topmost metal layer of each dummy sensor may be tied to the same metal layer of other dummy sensors and may be made accessible as a terminal of the chip, which in turn may be coupled to a reference voltage VREF. Such reference voltage VREF may be applied to the bias/readout circuitry of respective columns of the array. In some exemplary implementations, preliminary test/evaluation data may be acquired from the array based on applying the reference voltage VREF and selecting and reading out dummy sensors, and/or reading out columns based on the direct application of VREF to respective column buffers (e.g., via the CAL signal), to facilitate offset determination (e.g., sensor-to-sensor and column-to-column variances) and array calibration. The calibration data can be stored for each sensor location either just prior to a sequencing session, or at the end of the device manufacturing process. The calibration data can be stored on-chip, such as in non-volatile memory.

Additionally, in a further aspect of the present invention, a field effect transistor having a chamber and/or channel including a 1D or 2D and/or 3D material may be provided, such as where the 1D or 2D and/or 3D material is present within and/or proximate the chamber and/or channel and configured in such a manner so that the chamber and/or channel geometry may be optimized so as to maximize the ratio of channel width (W) to channel length (L). In various instances, this can be done through the use of interdigitated source and drain electrode geometries, such as in a single plane or, in other embodiments, such optimization may be achieved through the use of one or more 3D electrode structures, such as configured to at least partially or fully circumscribe the chamber or well. For instance, as can be seen with respect to FIG. 11, various source (22) and/or drain (24) electrodes may be configured as three-dimensional (3D) structures that are adapted so as to interact with one another in such a manner to more accurately detect the presence of a chemical reaction, e.g., the presence of a biomolecule, that occurs proximate the source and drain electrodes.

In various instances, the source (22) and drain electrodes (24), as set forth in FIG. 11 may be formed in such a manner so as to have an interdigitated configuration, such as where one or more of the electrodes, or a portion thereof, are adapted so as to be fit one within the other, such as where one electrode portion is configured as an impingement member, and the other is configured as a receiving member. In particular embodiments, the source (22) and drain (24) electrodes are configured so as to include pronged, fork-like appendages that are capable of being fitted one within the cavity of the other, such as between adjacent prong members. For example, as seen with respect to FIG. 11, the source and drain electrodes may form electrode pairs, such as where one or more of the source (22) and drain (24)

electrodes may have a planar and/or extended and/or interdigitated design, such as where one, e.g., the first, of the electrode pair forms one or more cavities and the other, e.g., the second, of the electrode pair forms an impingement member for insertion within the one or more of the cavities of the first electrode. Particularly, in various implementations, one or more of the electrode pairs may have a linear configuration, while the second of the pair may have a linear, curved, or curvilinear configuration. In particular embodiments, both the source (22) and drain (24) electrodes may both be curvilinear or curved.

Figure 12:
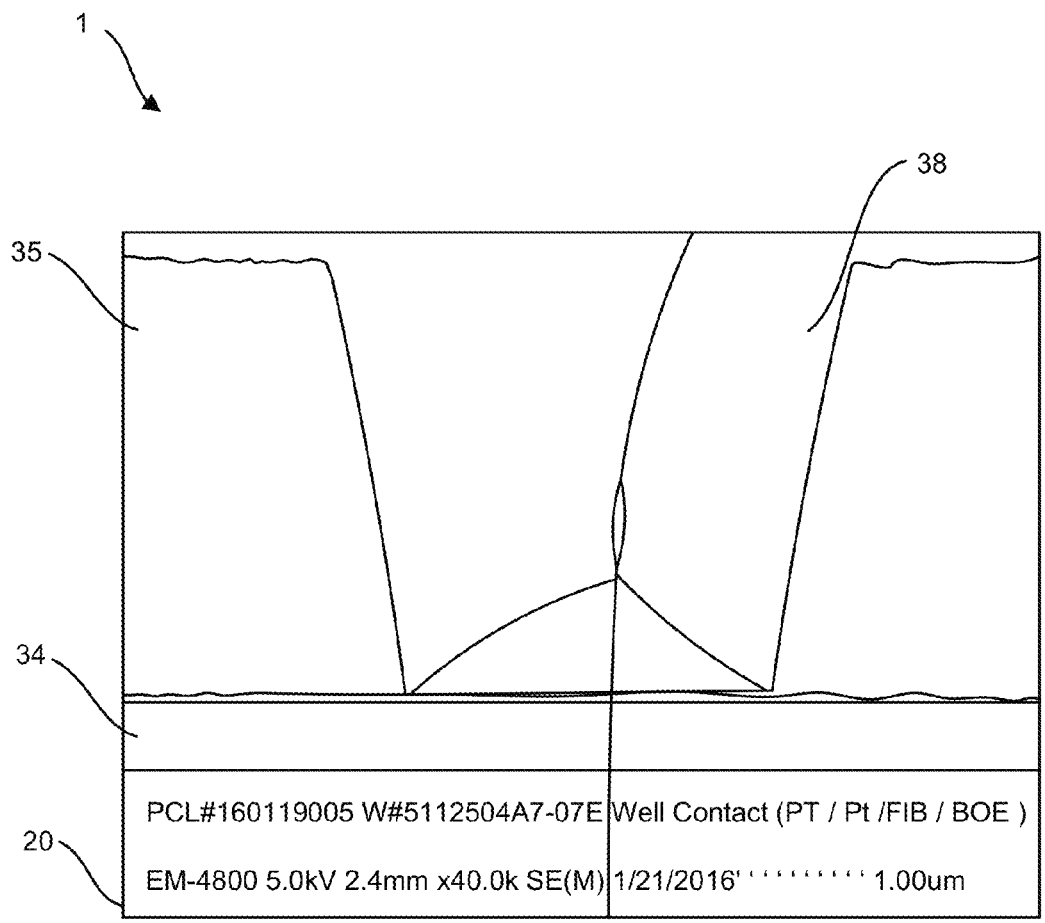
FIG. 12 is a cross-section of a well opening stopping on an analyte-sensitive layer.

More particularly, as can be seen with respect to FIG. 12, a FET sensor (1) having a well structure (38) is provided. Particularly, FIG. 12 depicts a cross-section of a well opening stopping on an analyte-sensitive layer. For instance, FIG. 12 provides a substrate, such as silicon and/or silicon dioxide substrate (10/20), where the substrate is configured so as to include a chamber, such as a chamber having a formed well (38) that may be positioned over an analyte-sensitive layer (35) that may be positioned on top of that substrate (10) and/or an associated oxide layer (20). For instance, in accordance with the methods disclosed herein, such a well (38) may be formed by any suitable method such as by a dry etching process, such as by a plasma or RIE process. In particular instances, the etching process may be selective to the well material so that the well etch can be stopped on the analyte-sensitive layer without significant damage or etching of the analyte-sensitive layer.

Figure 13:
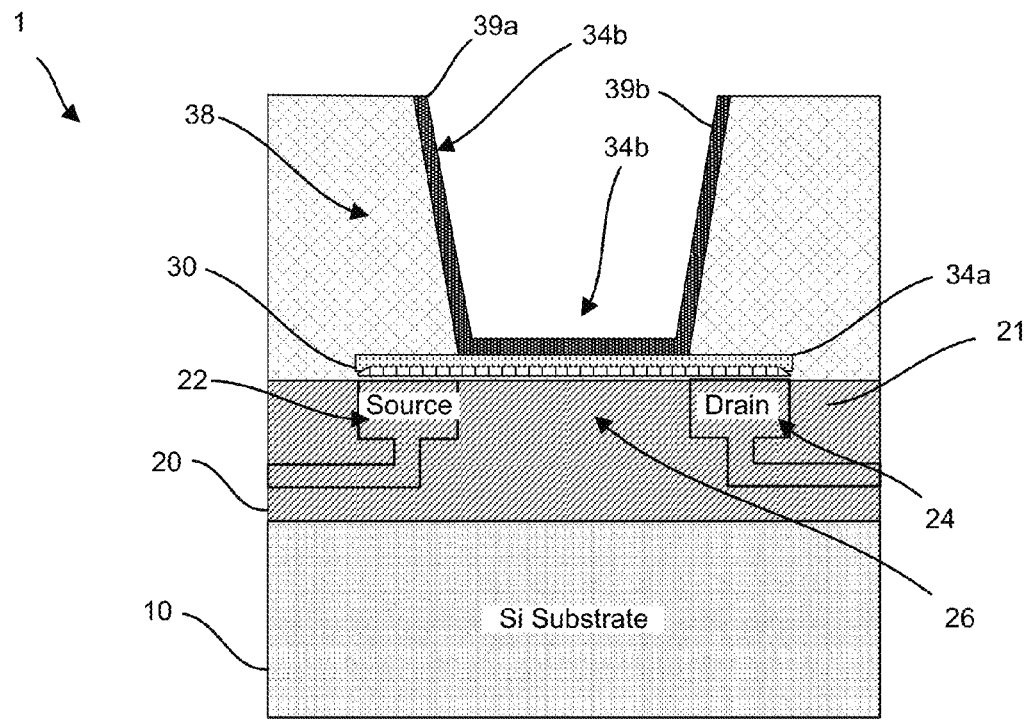
FIG. 13 is an illustration highlighting a second analyte-sensitive layer coating the walls of a well.

Additionally, as shown in FIG. 13 one or more additional analyte-sensitive layers (34) can be included in the FET, such as formed on the sidewalls (39) and bottom (21) of the well (38). For instance, FIG. 13 depicts a cut-away view of a substrate (10), wherein the substrate includes a well having a chamber therein, such as a chamber defined by one or more walls. In various instances, one or more of the walls may have an analyte-sensitive layer coating the walls of the well. Particularly, a substrate (10) may be provided such as where the substrate (10) may be formed of a silicon layer and may include one or more additional layers, such as one or more dielectric layers (20) and/or (35), which dielectric layers may be composed of silicon dioxide. Imbedded within one or more of these layers my be a pair of electrodes, such as a source electrode (22) and a drain electrode (24), which may be in one of more of the configurations set forth in FIG. 11, or other suitable configuration. As can be seen, one or more of the dielectric layers (20) and/or (35) may be configured so as to include a well structure (38), which structure may further be adapted so as to include one or more additional layers (34), such as a plurality of analyte-sensitive layers (34a, 34b). For instance, one of the analyte sensitive layers (34a) may be positioned on a bottom surface (21) of the well (38), such as layered upon a channel member (26), such as upon a graphene structure layer (30) positioned within the channel (26). Additionally, another analyte sensitive layer 34b may be layered upon one or more of the well-bounding members (39a, 39b).

Figure 14:
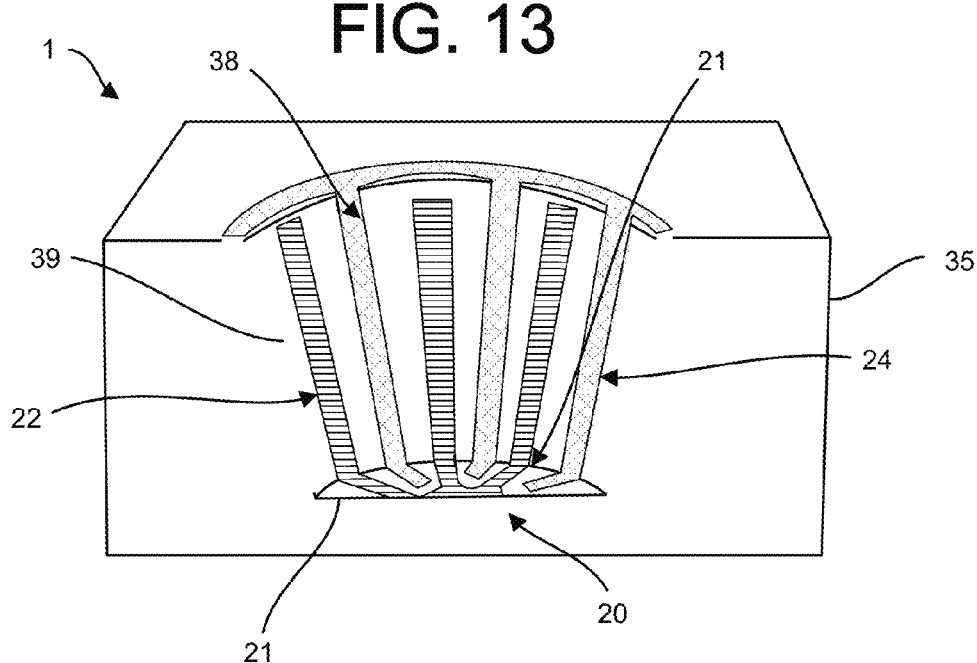
FIG. 14 is an illustration of using the well walls to create 3D interdigitated electrodes.

Further, with respect to FIG. 14, as previously noted, in various instances, it may be desirable to increase the ratio of the channel width W to the channel length L (e.g., W/L). For instance, FIG. 14 depicts a FET device, as herein described, wherein the FET includes a well having one or more walls that may be configured to produce or otherwise include a 3D interdigitated electrodes. Particularly, having a well structure, as set forth in FIGS. 12 and 13, allows the formation of source (22) and drain (24) electrodes not only on the bottom of the well (21), but also may be fabricated on the sides of the well (39), such as in one or more of the configurations set forth in FIG. 11. Specifically, FIG. 14 depicts a well structure in a cross-section view that has one or more surfaces that have been configured for allowing one or more electrodes to be fabricated therein. In this instance, the source electrodes (22) and drain electrodes (24) are interdigitated and positioned both on the bottom (21) of the well and on the sides 39 of the well. Many geometric patterns can be designed for source (22) and drain (24) electrodes to cover both the sides and bottom of the wells and the pattern shown in FIG. (14) is but one example, while FIG. 15 is another example, such as where the well includes a transistor material or an analyte-sensitive layer that may be positioned or otherwise coated over the surface of the well bounding member and/or one or more electrodes configured therein.

Figure 16:
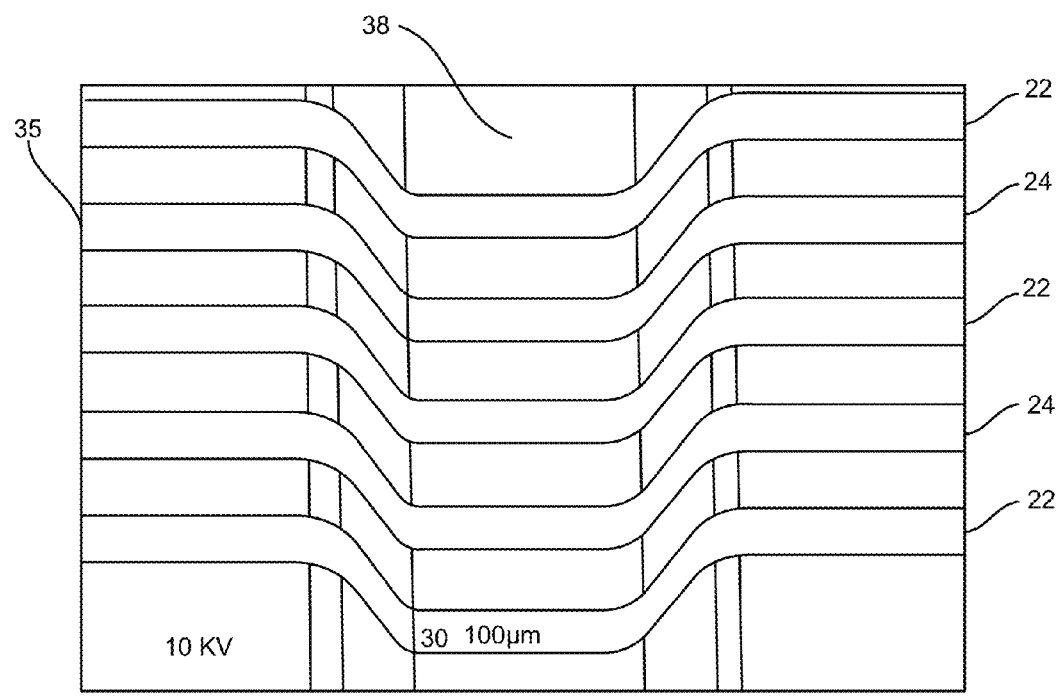
FIG. 16 is an illustration showing a metal pattern in a deep trench created by photolithography.

For example, one possibility for forming the source (22) and drain (24) electrodes in the well (38), such as in a 3D structure as set forth herein, is to use a photopatterning or photolithographic process. In such an instance, a mask with the desired pattern(s) may be used to transfer a pattern onto a photosensitive photoresist material. The pattern in the photoresist material can be used to likewise define a pattern in the conductive electrodes (e.g., by etching, lift-off, plating, and/or other processes known in the art). For instance, it is possible by employing the right optics to expose photoresist into deep trenches and/or wells so as to be able to define conductive traces in those deep trenches or wells. An example of this is shown in FIG. 16, which presents a depiction of an interdigitated well structure that has been fabricated using lithographic methods. Other techniques that can address patterning of photoresist in deep trenches or wells are laser, electron beam, and/or plasma, and the like.

Particularly, in various instances, once the source (22) and drain (24) electrodes are formed on the sides (39) of the well (38) the channel (24) may be formed over the electrodes. The process used to form the transistor channel (24) may be by any suitable process, but may depend on the materials being deposited and the presence of process limits imposed by other devices incorporated into the sensor. For instance, a silicon-based CMOS wafer with conventional transistors (e.g., formed from doped regions in the silicon and poly-silicon or metal gates) will typically have a processing temperature limit of 350 to 400 C, above which damage to those transistors may occur. So for a CMOS wafer with added sensors, the deposition of the materials making up those sensors will typically be lower than 400 C, which can be accomplished either by a low temperature in-situ deposition processes, and/or by creating the desired sensor materials separately and transferring them to the appropriate locations on the CMOS wafer.

Figure 15:
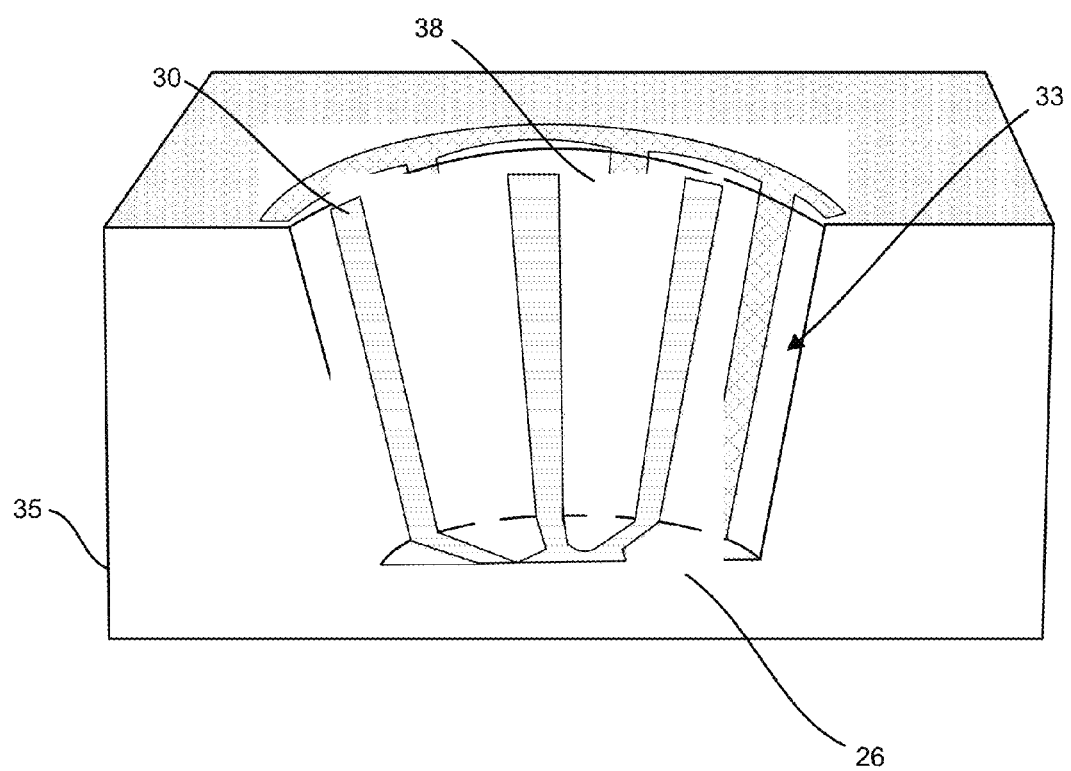
FIG. 15 is an illustration of the well structure of FIG. 14 with a transistor material or an analyte-sensitive layer.

In some instances, a 1D or 2D transistor material (30) can be formed separate from the CMOS wafer and then be transferred onto the electrode structures in the wells (38), as shown in FIG. 15. In another instance, another option may be to deposit a transistor channel material on the electrodes (22, 24) and well walls (21, 39). This may be accomplished by low temperature (e.g., below 400 degrees C.) deposition of amorphous silicon or suitable 2D material by any suitable means including, but not limited to: CVD, ALD, PVD (e.g., evaporation and/or sputtering), PECVD, and/or the like. Likewise, as depicted in FIG. 15, one or more of these methods can be used to coat the interior chamber of the well structure with a transistor material, such as an analyte-sensitive layer.

For instance, in particular embodiments, improved fabrication techniques for producing a CMOS sensor device containing reaction zones employing a 1D or 2D material layer are provided. Specifically, in certain instances, a 1D or 2D material layer may be grown, such as on a growth platform, and once grown may be released from the growth platform, and then be transferred to a semiconductor structure, such a CMOS substrate, so as to be employed as a sensor device as herein described. In particular embodiments, the 1D material may be a carbon nanotube or a semiconductor nanowire, e.g., grown on a substrate, and in other embodiments, the 2D material may be graphene, Molybdenum disulfide ($MoS_2$), Phosphorene (black phosphorous), Silicene, Borophene, Tungsten disulfide ($WS_2$), Boron Nitride, $WSe_2$, Stanene (2D tin), Graphane, Germanane, Nickel HITP, and Mxenes (Ti2C, (Ti0.5, Nb0.5), V2C, Nb2C, Ti3C2, Ti3CN, Nb4C3, Ta4C3).

There are several growth mechanisms that may be implemented for the growth of the 1D or 2D material on a substrate. In certain instances, the growth substrate may be a metal plate, a metal foil, or other thin film metal, such as a metal positioned on or over a wafer, such as a silicon wafer. The 1D or 2D material may be deposited on the growth substrate, such as for growing, by any suitable mechanism, such as by chemical vapor deposition ("CVD") (atmospheric, low or very low pressure), PECVD, ALD, submergence within a hot wall or cold wall reactor, and the like. Likewise, there are several transfer mechanisms for transferring the growing or grown 1D or 2D structure to a substrate, such as a substrate containing an integrated circuit, such as by direct transfer from the growth substrate to the wafer, e.g., a ROIC (Read-out Integrated Circuit)/CMOS wafer, such as by using Van der Waal's forces, fusion bonding, or other suitable form of temporary bonding. Additionally, there are several release mechanisms for effectuating the release of the 1D or 2D material from the growth substrate and the attachment to the ROIC wafer, including aqueous electrolyte electrolysis, where the growth platform acts as the cathode and separation is produced due to hydrogen evolution. Another release mechanism may include separation caused by use of a temporary adhesive from the growth platform, and/or by use of a laser, a UV light, a temperature increase, or physical peeling or pulling.

Figure 17:
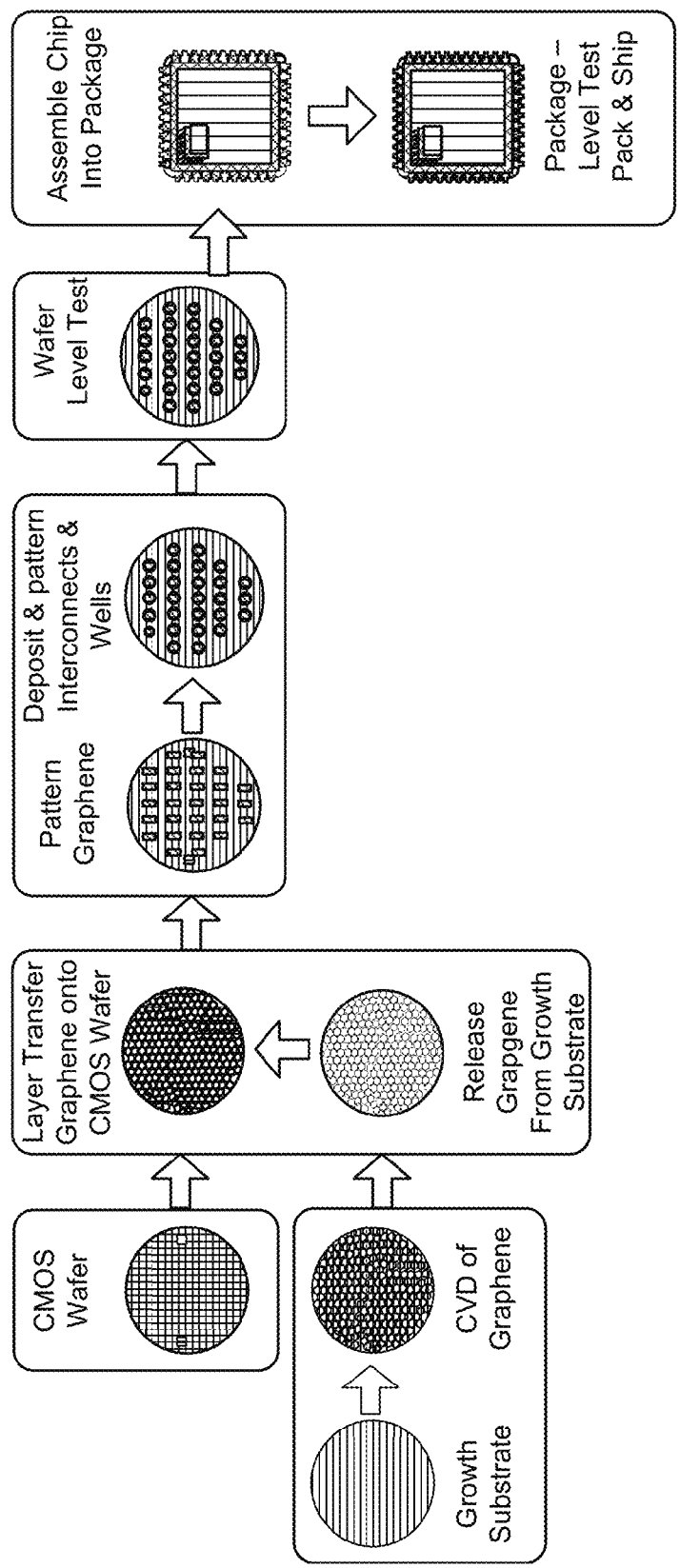
FIG. 17 is an illustration of an exemplary fabrication method as herein described.

Particularly, a direct transfer method is set forth as FIG. 17. For instance, in an exemplary sequence of steps, a growth substrate is provided. A graphene layer may then be deposited on to the growth substrate, such as by a chemical vapor deposition (CVD) process. Likewise a ROIC/CMOS wafer may be provided, such as in opposed relationship to the graphene containing substrate. Further, a release and transfer step may take place, such as where the graphene is released from the growth substrate and transferred onto the CMOS wafer. The graphene layer may then be patterned and one or more interconnects and/or wells may be deposited and/or patterned. The composition may then be tested, such as with respect to sensor operation of the underlying integrated circuit. The chip may then be assembled into a package, and a package level test may occur, and once passed the chip set may be shipped.

Figure 17A:
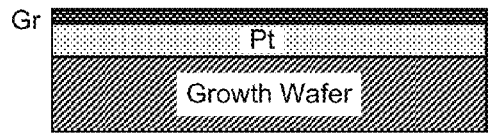
FIG. 17A illustrates a graphene growth step of direct bond transfer via Van der Waals forces, in accordance with the method steps set forth in FIG. 17.
Figure 17B:
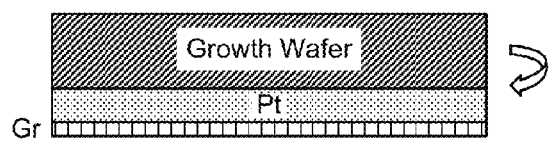
FIG. 17B illustrates a wafer-flipping step of direct bond transfer via Van der Waals forces.
Figure 17C:
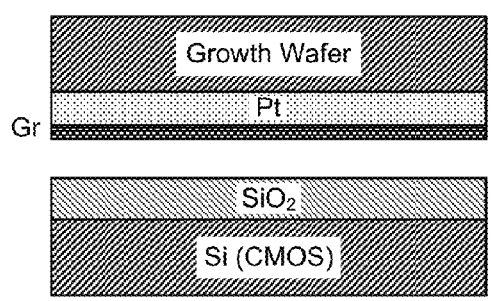
FIG. 17C illustrates a ROIC alignment step of direct bond transfer via Van der Waals forces.
Figure 17D:
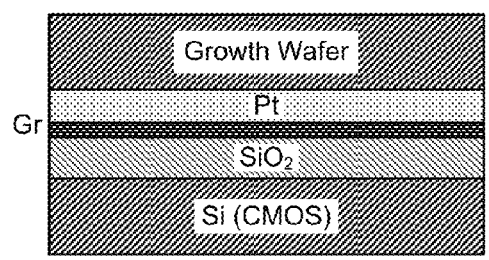
FIG. 17D illustrates a bonding graphene to an oxide on the ROIC wafer step of direct bond transfer via Van der Waals forces.
Figure 17E:
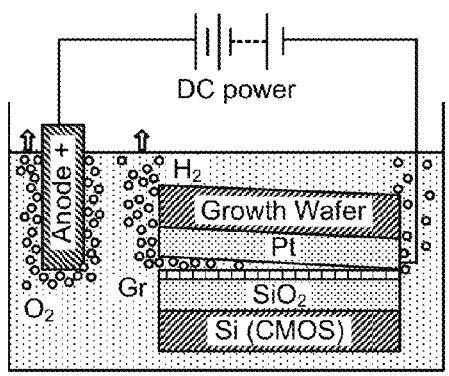
FIG. 17E illustrates a use of water electrolysis to create hydrogen bubbles to separate the graphene from the growth platform step of direct bond transfer via Van der Waals forces.
Figure 17F:
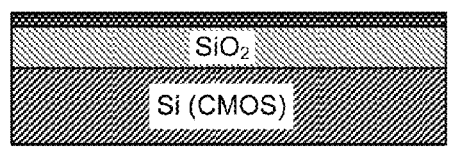
FIG. 17F illustrates a growth substrate removal step of direct bond transfer via Van der Waals forces.
Figure 18A:
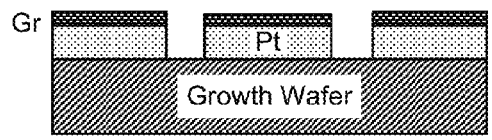
FIG. 18A illustrates a graphene with channels or divots for water access and more efficient bubble transfer growth step of direct bond transfer via Van der Waals forces, in accordance with the method steps set forth in FIG. 17.
Figure 18B:
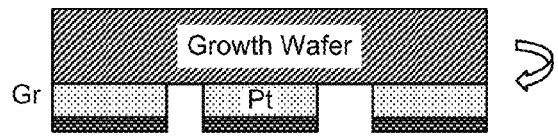
FIG. 18B illustrates a wafer-flipping step of direct bond transfer via Van der Waals forces.
Figure 18C:
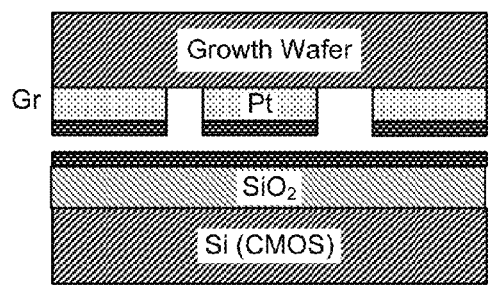
FIG. 18C illustrates a ROIC alignment step of direct bond transfer via Van der Waals forces.
Figure 18D:
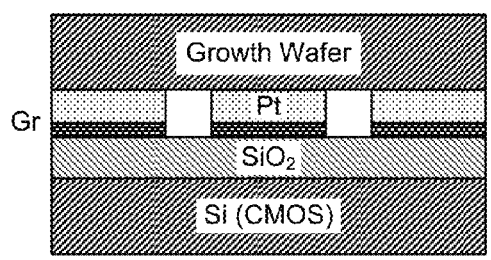
FIG. 18D illustrates a bonding graphene to an oxide on the ROIC wafer step of direct bond transfer via Van der Waals forces.
Figure 18E:
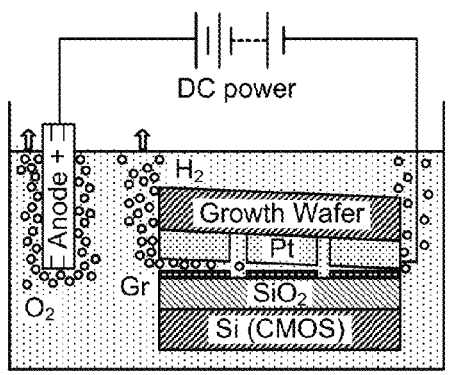
FIG. 18E illustrates a use of water electrolysis to create hydrogen bubbles to separate the graphene from the growth platform step of direct bond transfer via Van der Waals forces.
Figure 18F:
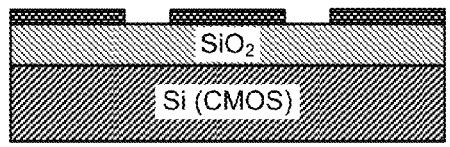
FIG. 18F illustrates a growth substrate removal step of direct bond transfer via Van der Waals forces.

More particularly, an effective method for producing such a transfer, e.g., involving a Van Der Waals Bond transfer mechanism, is illustrated in FIGS. 17A-17F. In FIG. 17A, the 2D material, e.g., graphene, is grown on a growth platform such as composed of a thin metal layer, e.g., silver, gold, or platinum layer, that is positioned on a growth wafer. In FIG. 17B, the orientation of the growth platform is flipped with respect to its fabrication process. In FIG. 17C, a silicon ROIC/CMOS wafer containing a suitably configured oxide layer, e.g., silicon dioxide, is prepared, and the flipped growth platform and the silicon wafer are aligned for bonding. In FIG. 17D, the 2D material on the growth platform is bonded to the oxide layer, e.g., silicon dioxide layer, on the ROIC wafer using Van der Waals forces. FIG. 17E shows the use of water electrolysis to create hydrogen bubbles to separate the 2D material from the metallized growth platform, which acts as a cathode in such a water electrolysis reaction. In FIG. 17F, the growth substrate is removed, leaving the 2D material on the ROIC/CMOS wafer.

FIGS. 18A-18F also depicts the same steps of direct bond transfer via Van der Waals forces as in FIGS. 17A-17F, with the distinction that FIGS. 18A-18F show the growth platform is patterned to create one or more channels or divots that allow for better water access and more efficient bubble transfer. Such openings may later be converted into one or more well or chamber boundaries as herein described.

Figure 19A:
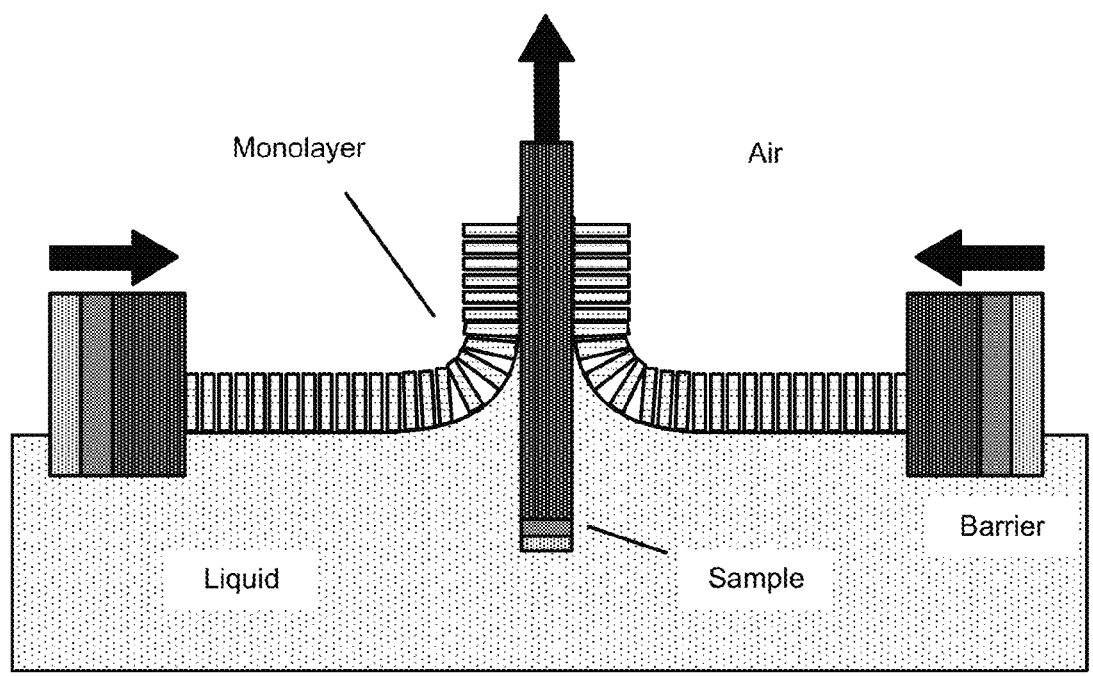
FIG. 19A illustrates a Langmuir Blodgett deposition process as an alternative option for the bubble release steps of FIGS. 17E and 18E.
Figure 19B:
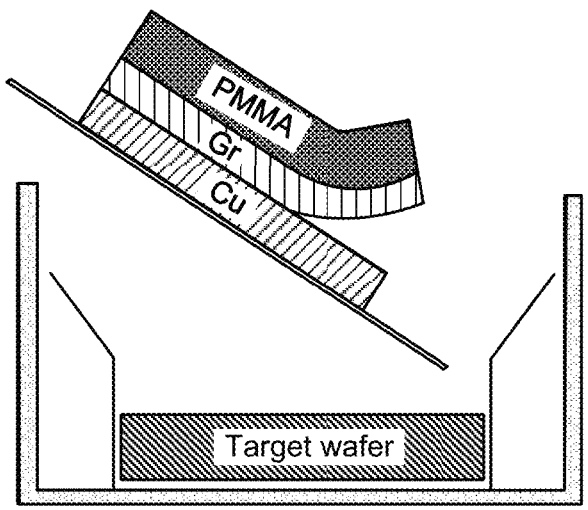
FIG. 19B illustrates a controlled immersion and bubble release step of the alternative option for the bubble release step of FIGS. 17E and 18E.
Figure 19C:
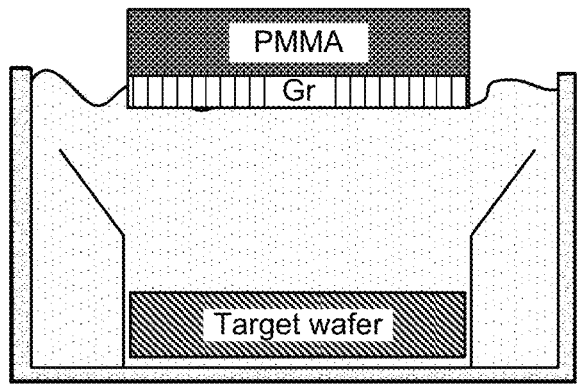
FIG. 19C illustrates a graphene and PMMA fully released step of the alternative option for the bubble release step of FIGS. 17E and 18E.
Figure 19D:
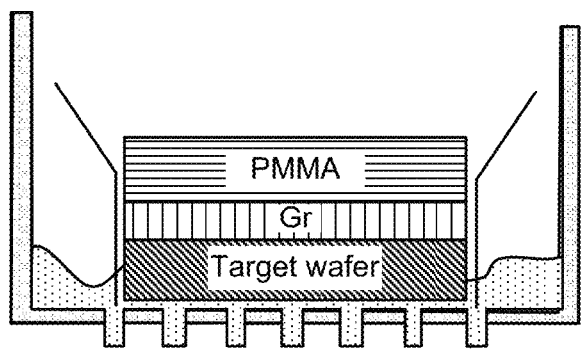
FIG. 19D illustrates a drain solution (while the graphene is aligned to the wafer) to transfer a layer onto a target step of the alternative option for the bubble release step of FIGS. 17E and 18E.

FIGS. 19A-19D illustrate an alternative method for the above described bubble elution and/or release mechanism as illustrated with respect to FIGS. 17 and 18. For instance, FIG. 19 depicts a modified Langmuir-Blodgett trough as shown in FIG. 19A. As shown in FIG. 19B, a structure composed of a PMMA substrate, a 2D material, e.g., graphene, copper, and a base layer is subjected to a controlled immersion within the trough and subjected to a bubble release protocol. As shown in FIG. 19C, the 2D material and the PMMA substrate are fully released from the copper structure. As shown in FIG. 19D, the solution is drained in such a manner that the 2D material is aligned with and becomes bonded to a target wafer, e.g., a silicon CMOS wafer, so as to transfer the 2D material layer onto the target wafer.

Figure 20A:
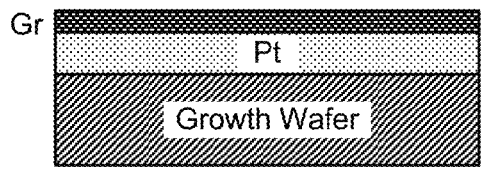
FIG. 20A illustrates a graphene growth step of direct bond transfer via fusion bonding.
Figure 20B:
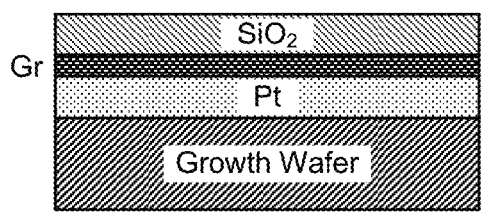
FIG. 20B illustrates a deposit cover material and CMP or polish surface step of direct bond transfer via fusion bonding.
Figure 20C:
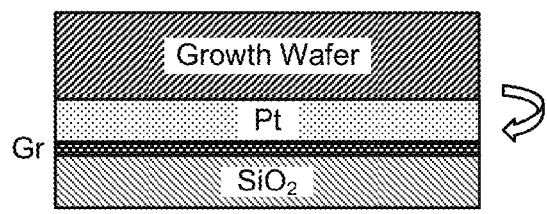
FIG. 20C illustrates a wafer-flipping step of direct bond transfer via fusion bonding.
Figure 20D:
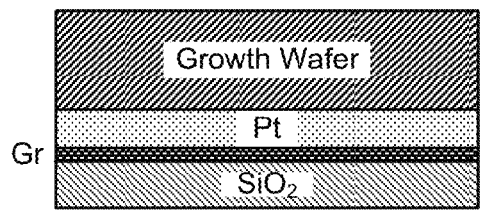
FIG. 20D illustrates a ROIC preparation and ROIC alignment step of direct bond transfer via fusion bonding.
Figure 20E:
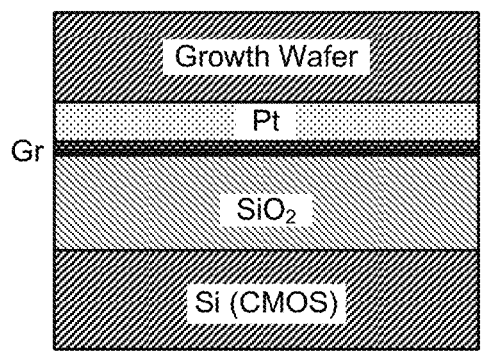
FIG. 20E illustrates a bonding a cover material to a ROIC wafer top insulator step of direct bond transfer via fusion bonding.
Figure 20F:
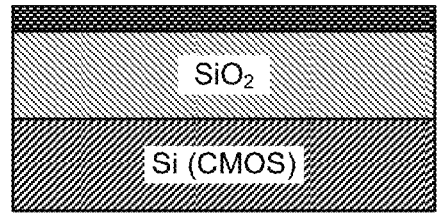
FIG. 20F illustrates a growth substrate removal from the ROIC wafer, leaving the graphene on the ROIC step of direct bond transfer via fusion bonding.

A further direct transfer method involves fusion bonding, as shown in FIGS. 20A-20F. FIGS. 20A-20F depicts the steps of direct bond transfer via fusion bonding. In FIG. 20A, the 2D material, e.g., graphene, is grown on a growth platform composed of a metal layer, e.g., a platinum layer, on a growth wafer. In FIG. 20B, a cover material, e.g., an insulating material, and CMP or polish surface is deposited on the growth platform. In FIG. 20C, the growth platform is flipped. In FIG. 20D, a ROIC wafer, such as a silicon CMOS wafer having a top insulating layer, e.g., an oxide layer, thereon is prepared, and the ROIC wafer and the growth platform are aligned for bonding. In FIG. 20E, the cover material is bonded to the top insulator layer of the ROIC wafer, and in FIG. 20F, the growth substrate is separated from ROIC wafer, leaving the 2D material on the ROIC wafer.

Accordingly, in the direct transfer fusion-bonding process, the 2D material may be encapsulated with SiO2 and then the growth wafer may be fusion bonded to the CMOS wafer. Platinum, copper, or another suitable metal may be used as the thin metal for growing the 2D material. A release or separation mechanism (e.g., the bubble process described above) may then be used to separate the 2D material from the metal layer. In such instances, the growth wafer may be composed of any suitable material upon which the 1D or 2D material may be grown, but is typically silicon, sapphire (Al2O3), or other suitable substrate that is capable of sustaining high temperatures and CTE. Alternatively, the present wafer format may be replaced with a panel or sheet, such as a thin metal panel or sheet. Various encapsulating materials may be utilized such as SiO2, Si, Si3N4. The same process may also utilize other materials that can effectuate the releasable bonding such as various polymers.

Figure 21A:
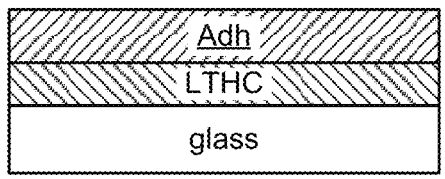
FIG. 21A illustrates a glass carrier preparation step of an adhesive temporary bond material process.
Figure 21B:
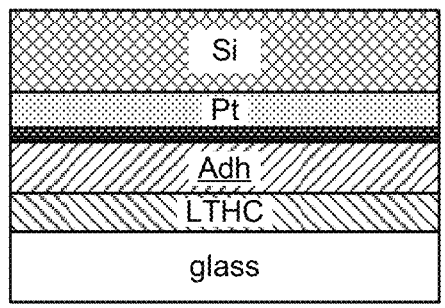
FIG. 21B illustrates room temperature ultraviolet energy bonding step of an adhesive temporary bond material process.
Figure 21C:
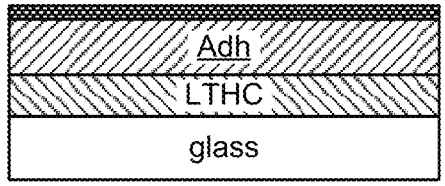
FIG. 21C illustrates an optional thin silicon wafer growth step of an adhesive temporary bond material process.
Figure 21D:
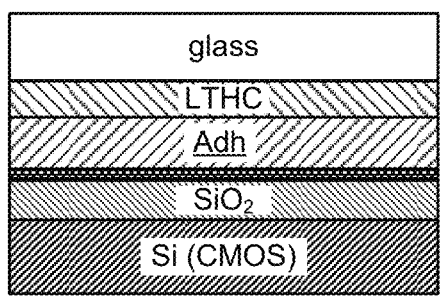
FIG. 21D illustrates a bonding the graphene layer to the target step of an adhesive temporary bond material process.
Figure 21E:
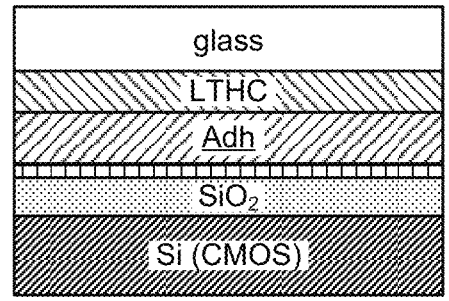
FIG. 21E illustrates a laser glass release step of an adhesive temporary bond material process.
Figure 21F:
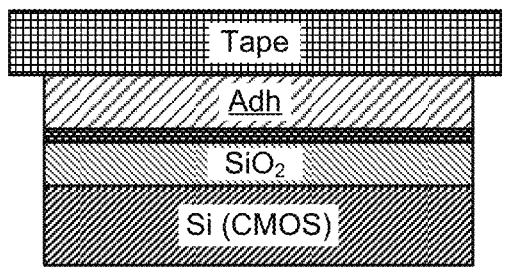
FIG. 21F illustrates an apply tape step of an adhesive temporary bond material process.
Figure 21G:
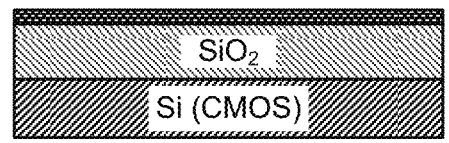
FIG. 21G illustrates a peel off the adhesive material step of an adhesive temporary bond material process.

FIGS. 21A-21G depict a process for temporary bonding that employs an adhesive material (such as an acrylate) so as to effectuate temporary bonding. In FIG. 21A, a glass carrier including an LTHC and an adhesive is prepared. In FIG. 21B, the growth platform containing the 2D material, e.g., grown in accordance with the above, is bonded to the glass carrier such as by being exposed to UV light at room temp. Optionally, a thin Si growth wafer background may be provided, such as where the Si growth wafer is approximately 100 um or less, such as 75 um or less, such as 50 um or 40 um or even 30 um or less, and positioned on top of the glass layer. In FIG. 21C, the 2D material is released from the growth platform. In FIG. 21D, the 2D material is bonded to a target wafer, and in FIG. 21E, the bond structure is exposed to a laser to release the glass. In FIG. 21F, a tape or other adhesive material-containing strip may be applied to provide an adhesive material layer. In FIG. 21G, this adhesive material layer may be peeled off and the remaining structure may be cleaned.

The glass carrier used may be transparent to UV light, which allows both for curing of the adhesive material and to effectuate release, e.g., by an infrared laser, in the glass release step. As indicated, LTHC is a useful release layer. Particularly, the adhesive material may be filled with Carbon black to absorb IR 1064 laser energy, may be heated to a high temperature, and thereby decomposed. In certain instances, LTHC may be spun on in a thin layer. In particular embodiments, the adhesive material may be an acrylate, such as PMMA. More particularly, the adhesive material may be spun on so as to form an approximately 50 um thick layer. Such adhesive materials are typically available in several different, e.g., four, different tacks, and where desired, other materials may be added to further reduce tackiness. An adhesive material 5032 4% may be employed such as a low tack material.

For bonding, the surface to be bonded may be brought in close proximity to the adhesive material layer (<1 mm) in a vacuum. A top wafer may be dropped onto the adhesive material layer on the glass carrier via gravity. UV or other high intensity light or heat may be applied until fully cured. The adhesive material may be such that it is resistant to solvents, and can be exposed up to 220 C. The 2D material may then be released, such as from a metal backing layer, e.g., composed of copper, silver, gold, or platinum, such as through a bubble bath mechanism or a mechanical peel process, as herein described. This process allows for continuous probing of the material layers to insure the presence and/or uniformity of the 2D material. After the carrier with the 2D material is placed on the target wafer, it may be adhesion baked, such as at 150 C for a short period of time, e.g., two minutes. The mechanism for the release from the glass may be to raster the structure with a UV laser for another short period of time, e.g., two minutes. The tape may be applied by a manual vacuum chuck to hold the wafer, and then a roller tape may be applied, e.g., manually. Alternatively dicing tape may be used. After peeling off the tape and the adhesive layer, anneal cleaning is performed at 400 C.

FIGS. 22A-22B illustrate an adhesive temporary bond material process using a TZNR adhesive, e.g., from TOK (Tokyo Ohka Kogyo Co., Ltd.). As shown in FIG. 6A, the process involves adhesive spin coating of a growth substrate with a 1D or 2D layer, e.g., a graphene layer, so as to deposit the graphene layer onto the growth substrate. The composition may then be subjected to a curing step, such as by pre-baking, and aligned with a support wafer, where bonding may occur. For instance, thermal bonding may be effectuated by applying heat under a vacuum, such as at a low bonding pressure (0.012 MPa). FIG. 6B illustrates the low stress debonding by dissolving the adhesive, such as in addition to solvent injection, pick up, and detachment such as by a handler. The 1D or 2D containing substrate may then be cleaned so as to remove the residue so that no residue is left on the device wafer.

Figure 23A:
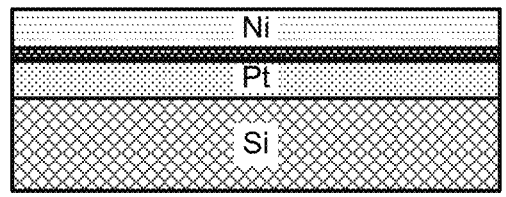
FIG. 23A illustrates a nickel deposition on a graphene layer step of an adhesive temporary bond process with a nickel deposition layer.
Figure 23B:
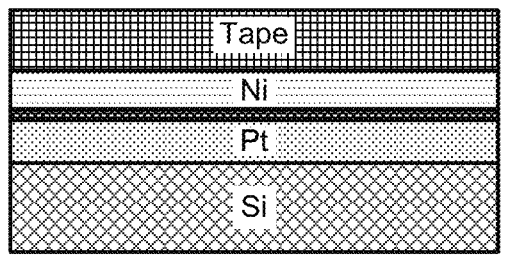
FIG. 23B illustrates a tape lamination step of an adhesive temporary bond process with a nickel deposition layer.
Figure 23C:
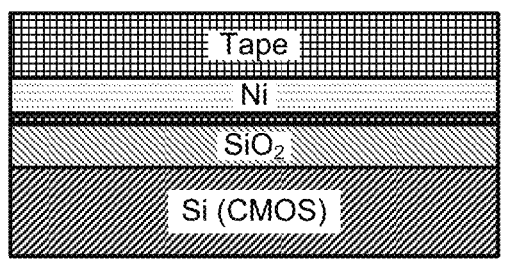
FIG. 23C illustrates a tape peel and graphene transfer step of an adhesive temporary bond material process with a nickel deposition layer.
Figure 23D:
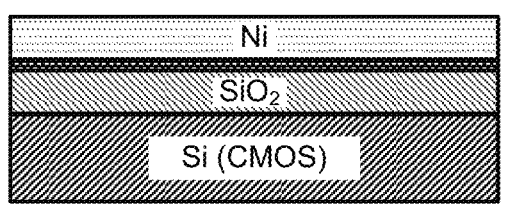
FIG. 23D illustrates a peel tape from the nickel layer step of an adhesive temporary bond material process with a nickel deposition layer.
Figure 23E:
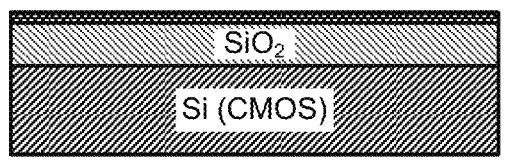
FIG. 23E illustrates a wet etch to remove the nickel layer step of an adhesive temporary bond material process with a nickel deposition layer.
Figure 24A:
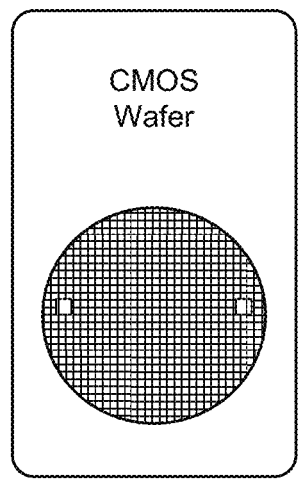
FIG. 24A is an isolated view of a CMOS wafer step for employment in the fabrication methods herein described.
Figure 24B:
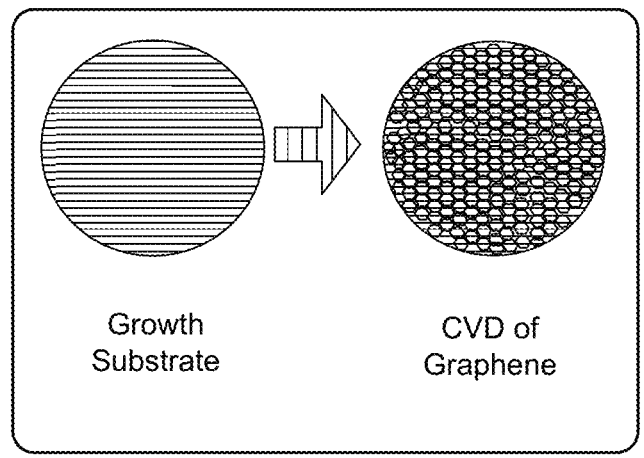
FIG. 24B is an isolated view of a graphene growth step of the method of FIG. 24A.
Figure 24C:
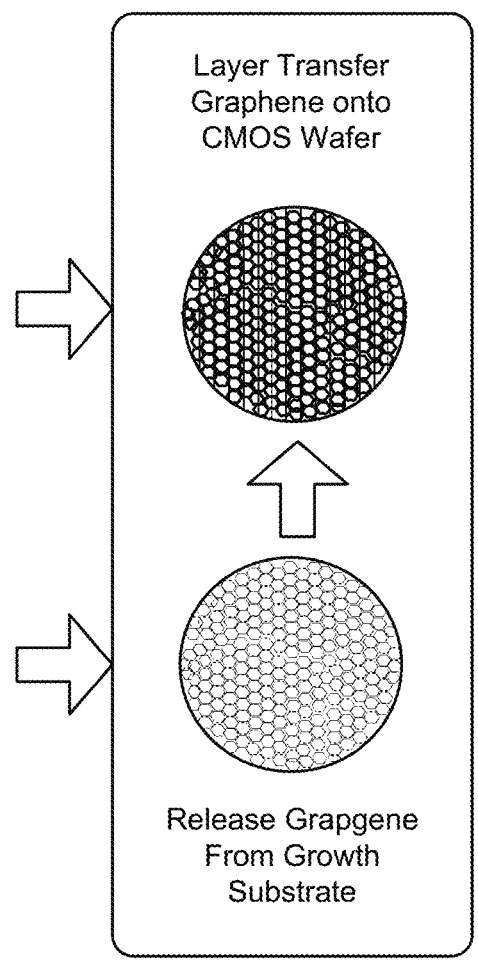
FIG. 24C is an isolated view of a graphene release and transfer step of the method.
Figure 24D:
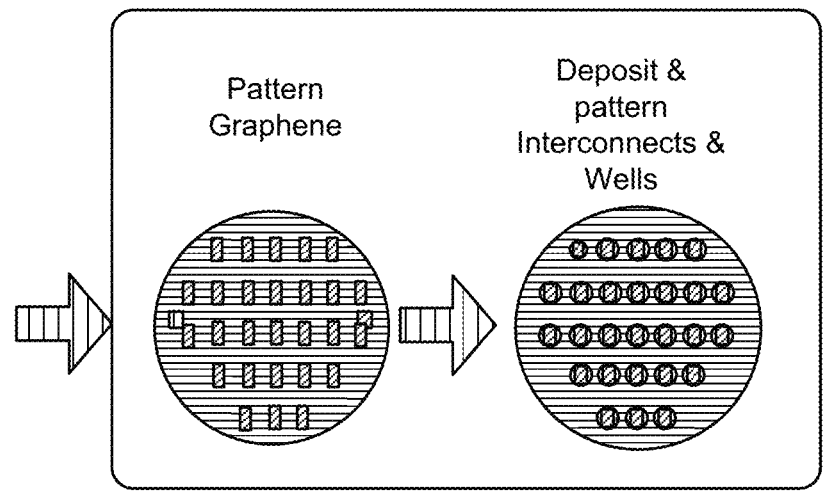
FIG. 24D is an isolated view of a CMOS integration step of the method.
Figure 24E:
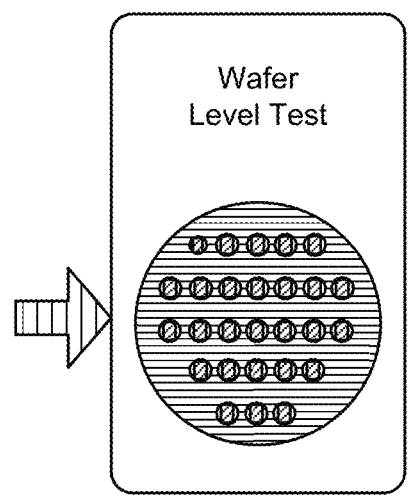
FIG. 24E is an isolated view of a CMOS wafer step of the method.
Figure 24F:
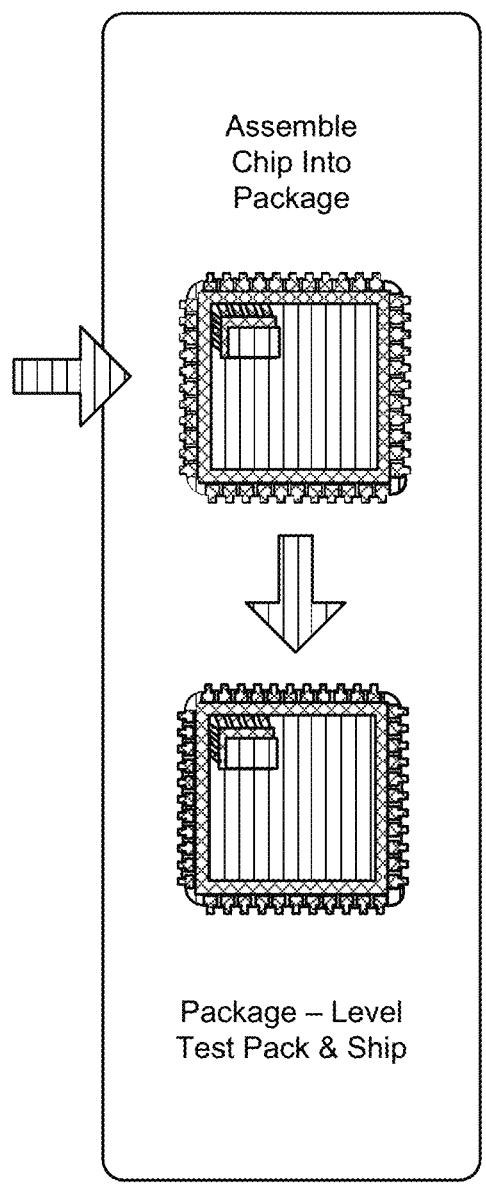
FIG. 24F is an isolated view of a packaging step of the method.

FIGS. 23A-23E illustrate the adhesive temporary bond process with a nickel ("Ni") deposition layer. As shown in FIG. 23A, a metal such as Ni may be deposited on the 2D material layer (in black). As shown in FIG. 23B, a tape lamination may be applied to the Ni layer. As shown in FIG. 23C, the tape layer may be peeled away from the growth platform and the tape layer, Ni layer, and 2D material layer may be transferred to a target wafer. Alternatively, the structure may be baked to improve the 2D material adhesion. As shown in FIG. 23D, the tape may be peeled from the Ni layer (possibly with a release mechanism). As shown in FIG. 23E, a wet etch process may be used to remove the Ni layer.

Accordingly, in one aspect of the present invention a method for forming a semiconductor wafer is provided, wherein the wafer is configured as transistor on which a 1D or 2D material layer may be positioned. The method may include providing a wafer, such as a wafer configured as or to otherwise include an integrated circuit, so as to form a semiconductor wafer. The wafer may include a substrate, such as a silicon substrate. An insulating layer may be applied to the substrate, such as via CVD of a silicon dioxide layer. A 1D or 2D material may then be applied, hence, the method may include patterning the 1D or 2D material layer so as to define 1D or 2D material channels or chambers or wells, where such channels may be aligned with interconnect lines on the semiconductor wafer.

In various instances, the method may also include depositing a first dielectric layer over the channels, chambers, or wells. The method may also include opening holes or trenches in the first dielectric layer wherein some of the holes may be aligned to the channels, chambers, or wells, and some of which may be aligned to the interconnect lines. The method may also include depositing conductive material on the 1D or 2D material layer, such as in the holes or trenches so as to create vias that contact the interconnect lines and/or the channels, chambers or wells. Additionally, the method may include depositing and patterning a set of second interconnect lines over the dielectric layer and contacting the vias. In some embodiments, the method may include depositing a second dielectric layer over the first dielectric layer and the second interconnect lines. Particularly, the method may also include patterning and opening holes or trenches in the second dielectric layer to expose portions of the second interconnect lines to be used as pads. The method may also include patterning and opening holes or trenches in the second and first dielectric layers to expose portions of the channels.

Hence, in particular embodiments, a method for forming a semiconductor wafer with transistors on which a 1D or 2D material layer may be deposited is provided. The method may include providing a semiconductor wafer having a substrate and/or insulating layer upon which a 1D and or 2D material layer is deposited. The method may then include patterning the 1D or 2D material layer to define 1D or 2D material channels, chambers, or wells, where the channels, chambers, or wells may be aligned with interconnect lines on the semiconductor wafer. The method may also include depositing an etch stop layer over or within the channels, chambers, or wells. The method may also include depositing a first dielectric layer over the etch stop layer, opening holes or trenches in the first dielectric layer, such as where some of the holes or trenches are aligned to the channels, wells, and/or chambers, and some of which are aligned to the interconnect lines.

The method may also include depositing conductive material in the holes or trenches to create vias that contact the interconnect lines and the channels. In such an instance, the method may include depositing and patterning a set of second interconnect lines over the dielectric layer and contacting the vias. The method also includes depositing a second dielectric layer over the first dielectric layer and the second interconnect lines. The method may include patterning and opening holes or trenches in the second dielectric layer to expose portions of the second interconnect lines to be used as pads. The method may additionally include patterning and opening holes or trenches in the second and first dielectric layers to expose the etch stop layer over the channels. The method also includes opening holes or trenches in the etch stop layer to expose portions of the channels, chambers, or wells.

Particularly, another aspect of the present invention is a method for forming a semiconductor wafer with transistors on which is a 2D material layer. The method may include patterning the 2D material layer to define 2D material channels, chambers, or wells, said channels, chambers, or wells being aligned with interconnect lines on the semiconductor wafer. The method also includes depositing an etch stop layer over the channels and/or depositing a first dielectric layer over the etch stop layer. Holes or trenches may be opened in the first dielectric layer and aligned to the channels, chambers, or wells and/or aligned to the interconnect lines. Conductive material may be deposited in the holes or trenches so as to create vias that may be configured to contact the interconnect lines and the channels, chambers, and/or wells. A set of second interconnect lines may be deposited and patterned over the dielectric layer so as to contact the vias. A second dielectric layer may also be deposited over the first dielectric layer and/or the second interconnect lines, and holes or trenches may be patterned to provide openings in the second dielectric layer so as to expose portions of the second interconnect lines, which may be used as pads. In such an instance, the method may also include patterning and opening holes or trenches in the second and first dielectric layers using an anisotropic etching process to expose the etch stop layer over the channels, wells, or chambers. The method may also include opening holes or trenches in the etch stop layer to expose portions of the channels, chambers, or wells.

In certain instances, a method for forming a semiconductor wafer having one or more transistors on which a 1D or 2D material layer may be deposited, as herein described. The method may include patterning the 1D or 2D material layer to define 2D material channels, said channels being aligned with interconnect lines on the semiconductor wafer. The method may also include depositing an etch stop layer over the channels. The method includes depositing a first dielectric layer over the etch stop layer and/or opening holes or trenches in the first dielectric layer, where some of which may be aligned to the channels and some of which may be aligned to the interconnect lines. In various instances, the method also includes depositing conductive material in the holes or trenches to create vias that contact the interconnect lines and the channels. In such an instance, the method may include depositing and patterning a set of second interconnect lines over the dielectric layer and contacting the vias. In certain instances, a second dielectric layer may be deposited over the first dielectric layer and the second interconnect lines. In such an instance, the method may include patterning and opening holes or trenches in the second dielectric layer to expose portions of the second interconnect lines that may be used as pads. The method may include patterning and opening holes or trenches in the second and first dielectric layers, such as by using an anisotropic etching process to expose the etch stop layer over the channels.

Accordingly, in particular instances, the semiconductor structure may include a plurality of 1D or 2D material channels, chambers, or wells composed of a 1D or 2D material, an etch stop layer, a plurality interconnect lines on a semiconductor wafer, a first dielectric layer comprising a plurality of holes or trenches, a conductive material, a second plurality of interconnect lines, and a second dielectric layer having a plurality of holes or trenches. And in some embodiments, the semiconductor structure comprises a plurality of 1D or 2D material channels, chambers, or wells composed of a 1D or 2D material, a plurality interconnect lines on a semiconductor wafer, a first dielectric layer comprising a plurality of holes or trenches, a conductive material, a second plurality of interconnect lines, and a second dielectric layer having a plurality of holes or trenches.

Figure 25A:
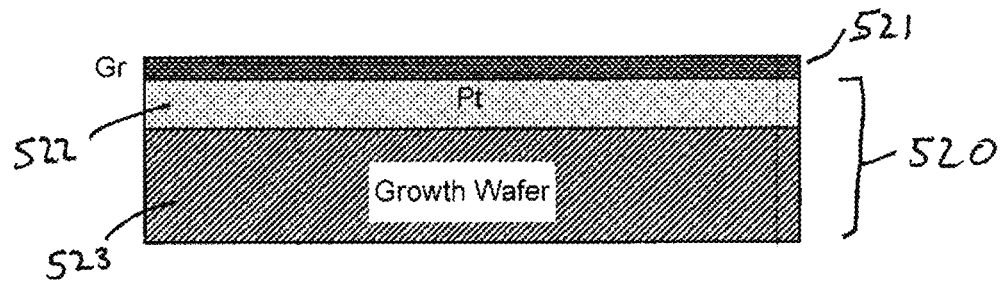
FIG. 25A illustrates a graphene growth step of direct bond transfer via fusion bonding.
Figure 25B:
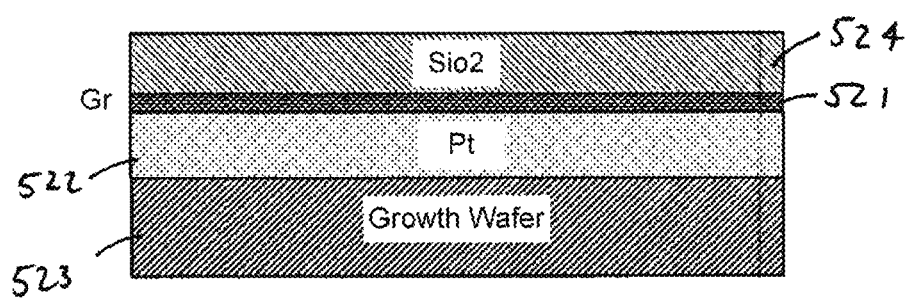
Figure 25C:
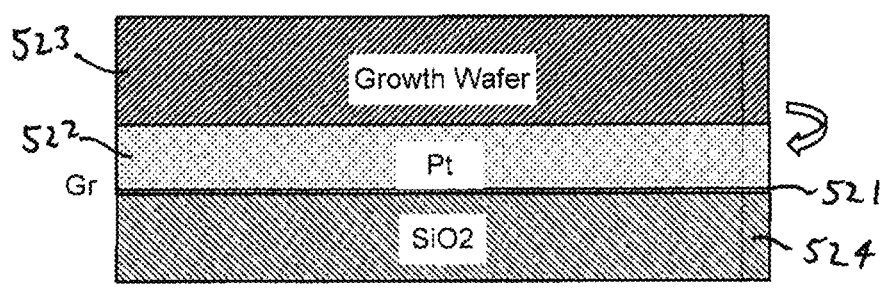
Figure 25F:
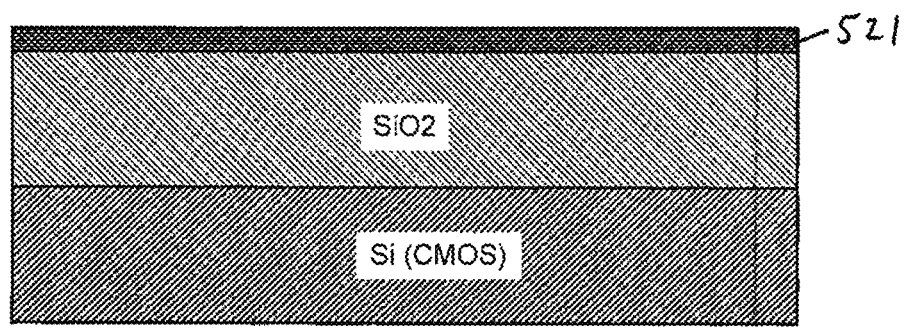

In view of the above, in various embodiments, FIG. 24 provides a flow chart of a general method of forming a semiconductor wafer with transistors with a 2D material layer in accordance with the methods set forth above. FIGS. 24A-24F illustrate the various steps. For instance, an exemplary direct transfer mechanism including direct transfer fusion bonding is provided and shown in FIGS. 25A-25F. FIGS. 25A-25F visually show the steps of direct bond transfer via fusion bonding. In FIG. 25A, the 2D material, such as graphene, is grown on a growth platform composed of a platinum layer on a growth wafer. In FIG. 25B, a cover material and CMP or polish surface is deposited on the growth platform. In FIG. 25C, the growth platform is flipped. In FIG. 25D, a ROIC wafer is prepared, the ROIC wafer and the growth platform is aligned for bonding. In FIG. 25E, the cover material is bonded to the ROIC wafer top insulator layer. In FIG. 25F, the growth substrate is separated from the ROIC wafer, leaving the 2D material on the ROIC wafer.

In the direct transfer fusion bonding process, the 2D material, e.g., graphene, may be encapsulated with $SiO_2$ and then the growth wafer may be fusion bonded to a CMOS wafer. Platinum, gold, silver, copper or another suitable metal may be used for growing the 2D material. A release or separation mechanism (e.g., bubble process) is used to separate the 2D material from the platinum or other metal. The growth wafer may be a silicon, sapphire ($Al_2O_3$), or other suitable substrate capable of sustaining high temperatures and CTE. Alternatively, a wafer format may be replaced with a panel or sheet. Various encapsulating materials may be utilized such as SiO2, Si, Si3N4. The same process may also be utilized with other materials that can be bonded such as polymers. Alternative methods for growing and transferring 2D materials are disclosed in Hoffman et al., U.S. Provisional Patent Application No. 62/175,351, filed on Jun. 14, 2015, for System And Method For Growing And Transferring Graphene For Use As A FET, which is hereby incorporated by reference in its entirety.

FIGS. 26A-26L illustrate a preferred CMOS integration method for building the interconnects, dielectric and well structures, as well as the pads for bonding the transferred 1D or 2D material to the chip. For instance, FIG. 26A illustrates a graphene material layer on a ROIC wafer. FIG. 26B illustrates patterning the graphene layer to form a channel, which may be employed as a chamber or well. FIG. 26C illustrates an etch stop layer deposited over the graphene layer. FIG. 26D illustrates a deposited, patterned, and etched thick insulator layer over the etch stop layer. FIG. 26E illustrates a wet etched etch stop layer to expose the 1D or 2D material, and wet etched etch stop layer, patterned and Deep Reactive Ion Etching (DRIE) oxide over the interconnects. FIG. 26F illustrates an optional addition of work function matching material prior to a via fill. FIG. 26G illustrates a deposit a barrier, liner, copper plate, chemical mechanical polishing (CMP). FIG. 26H illustrates a deposit of a barrier/adhesion layer, deposit of aluminum, pattern and etching of the aluminum interconnect and the pad layer. FIG. 26H illustrates a deposit of a barrier, liner, metal (copper) plate, chemical mechanical polishing (CMP). FIG. 26I illustrates a deposit of a barrier/adhesion layer, deposit of aluminum, pattern, and etching of the aluminum interconnect and the pad layer. FIG. 26J illustrates a deposit of SiO2 (e.g. CVD), CMP, and a pad open etched. FIG. 26K illustrates a DRIE of the well insulator down to the etch stop layer. FIG. 26L illustrates a wet etch of the thin etch stop layer. FIG. 26M illustrates a wet etch ESL open etch step of a CMOS integration method.

FIG. 27 depicts a top-plane view of a geometric pattern of source (22) and drain (24) electrodes that might be found at the side (39) and bottom (21) of the well structure (38) shown in cross-section view in FIG. 28. For instance, FIG. 27 depicts the use of alternating vertical metal source and drain electrode layers, which may be positioned, such as within a chamber or the bounding member(s) defining the chamber, so as to create an interdigitated type of effect and thereby maximize the of ratio channel width to channel length, as herein described. Particularly, FIGS. 27 and (28) depict a sensor (1) composed of a substrate material (e.g., 10, 20, and/or 35), and having a chamber (38) formed therein, such as by etching. The chamber (38) includes a wall 39 and/or a bottom surface (21) having a plurality of electrodes disposed therein, such as a source electrode (22) and a drain electrode (24), such as where the electrodes have been configured in an interdigitated manner. It is to be noted that although a particular electrode configuration has been depicted, any suitable configuration can be implemented, such as those depicted in FIG. 11.

To demonstrate the desirability of forming 3D electrode structures on the well surfaces (39 and/or 21), a comparison of the ratio of channel width to channel length (W/L) can be made of a device that only has electrodes 22, (24) on the well bottom (21) versus one with electrodes on the well bottom (21) and well walls (39). For instance, with respect to the well structure depicted in FIGS. 27 and 28, e.g., with a nominal 1 micron well diameter (at the well bottom (21)), the channel length of channels (24) either at the well bottom (21) or on the well walls (39) is 100 nm, for example. For the well bottom (21), the channel (24) width is given by the formula 2 OR (it is the distance of the channel defined by the gap between the source (22) and drain (24) electrodes. If one assumes the radius of the channel (24) is 150 nm, then the channel width is about 945 nm. This results in a W/L of about 9.45. Further, as depicted in FIGS. 27 and 28, there are multiple electrode layers, such as in a vertically stacked configuration that circumscribes and/or surrounds the well opening 37. In such an instance, the channel length may be about 100 nm. In this instance the channel width is contributed by the circular gap between each electrode layer times the number of such gaps.

For example, for 6 gaps, where the well diameter is 1000 nm, the channel width due to the sidewall structures is: $W_{vertical} = 2\pi r N = 6.3 \times 500$ nm×number of levels=3150 nm×6=18900 nm. Further, if the channel width at the well bottom is added, a total channel width is 19845 nm and a W/L of 198. This is more than a (20) times higher W/L than the case with an electrode structure only on the well bottom. As described above, the electrode structures (22), (24) on the well sidewalls (39) and at the well bottom (21) may be covered by a transistor material, such as depicted in FIG. 29. Furthermore, an analyte-sensitive layer (34) may be deposited over the electrodes on the well boundary walls (39) and bottom (21). Particularly, FIG. 29 depicts a well chamber (38), wherein the chamber (18) may be configured to include a transistor material or an analyte-sensitive layer.

In various instances, the source (22) and drain (24) electrodes can form electrode pairs that are separated one from the other by a distance such as to from an interdigitated source (22) and drain (24) electrode pair. As presented in FIG. 30, the source (22) and drain (24) electrode pairs may be configured so as to form a channel between the two electrodes, such as in the space between the two electrodes. In such instances, as depicted in FIG. 30, the channel may be comprised of or otherwise contain a 1D or 2D channel material, such as a carbon nanotube and/or graphene layer. Hence, an option for forming one or more channels (24) with small lengths and high effective widths is to vertically alternate not only the source (22) and drain (24) electrode layers, but also the transistor channel material (e.g., 1D or 2D material) layers, as depicted in the well structure cross-section as shown FIG. 20. In this case, the channel material 30, e.g., a series of graphene layers, is interspersed between source (22) and drain (24) electrode layers. Hence, performing the same calculation as before, but in this case using a channel length of 0.345 nm (the thickness of a single layer of graphene is 0.345 nm) results in a W/L ratio of 57,522 which is more than 290 times higher than the previous calculation and demonstrates the effectiveness of using thin channel material layers as part of the device structure.

FIG. 31 depicts one implementation of a process flow that may be employed to form the source (22) and drain (24) electrode layers as well as the 1D or 2D sensor material layer (30). For instance, FIG. 31A depicts the bottom (21) of a substrate or well material that may be configured so as to include a conductive source (22) and drain (24) electrodes. These may, for example, be fabricated and/or formed by various fabrication processes as herein described and/or known in the art, such as by using a damascene metal process. The surface of the device may be Chemically Mechanically Polished (CMP'ed), such as after the conductive source (22) and drain (24) electrodes are formed in the well bottom (21). It is to be noted, that FIG. 31A depicts the conductive source electrode (22) and conductive drain electrode (24) in different layers, and at any given level or layer of the device, where electrodes are formed, the electrodes can be formed of the same material during the same process step or different. For example the source (22) and drain (24) electrodes of FIG. 31A could be comprised primarily of copper that is deposited by an electroplating process with both types of electrodes formed in the same process step.

FIG. 31B depicts a layer of a 1D or 2D channel material (30) that has been deposited over the electrodes in the well bottom (21). The channel material (30) may be patterned so that it just covers all of the underlying conductive electrode pattern or it may be sized smaller or larger than the underlying electrode pattern—as long as it overlaps with a portion of the electrodes.

The next step, shown in FIG. 31C, is the deposition of an insulating layer (35) and then the formation of a trench in that layer.

FIG. 31D shows the trench being filled by conductive electrode material. During this step vertical electrode connections, e.g., vias, may be formed outside of the electrode patterns. Such vias may be stacked layer by layer as the process progresses allowing the vertical interconnection of source electrodes (22) on different layers, and allowing the vertical interconnection of drain electrodes (24) on different layers.

These process steps may be repeated in FIGS. 31E, 31F and 31G to create vertical layers of alternating source electrode (22), transistor channel material (30), and drain electrode (24), such as in an interdigitated configuration, as herein described. Duplicating these steps for further repetitions allows higher numbers of alternating source electrode (22), transistor channel material (30), and drain electrode (24) layers to be formed. When the selected number of layers have been formed the central portion of the well (38) can be etched (e.g., by plasma, RIE, DRIE or a similar process) as shown in FIG. 31H. This results in the fully formed layer stack depicted in FIG. 30.

FIGS. 32A and 32B depict a different embodiment for forming alternating layers of electrodes 22, (24) and transistor channel material 30. In this case vias, e.g., through-holes, trenches, and/or slots may be formed in the transistor channel material (30) as shown in FIG. 32B. In a subsequent step (not shown in the figures) the formation of the electrode material over or on the patterned channel material will also fill these vias. This allows not only a surface area connection from the electrode to the channel material but also an edge connection to the channel material (e.g., in the via the electrode material may contact the edge of the channel material). In some materials, such as graphene, it is known that edge connections from electrodes to the graphene channel material may result in lower contact resistance between the two materials and better transistor performance.

Additionally, FIG. 33 depicts an alternate well structure (1). In this instance grooves or trenches 61 may be formed in the wall boundaries of the well 39. These grooves 61 can help to align and capture the 1D and/or 2D transistor channel material—such as carbon nanotubes or silicon wires. Accordingly, FIG. 33 depicts a well that uses carbon nanotubes to create interdigitated transistors, such as in a vertical direction.

Accordingly, in various aspects of the invention, a chemically-sensitive field effect transistor (FET) having a multi-layered structure is provided. For instance, the chemically-sensitive FET may include a first layer such as a substrate layer. The substrate layer, like all layers described herein, may have an extended body including a proximal portion having a proximal end, a distal portion having a distal end, and a pair of opposed side portions, all of which together define a circumference for the substrate layer. Additionally, a second layer, e.g., a first non-conductive material layer, may be included wherein the first non-conductive material layer may be an insulating layer and be positioned above the extended body of the substrate layer. In various embodiments, a second non-conductive material layer, which may also be an insulating layer, may also be included and positioned above the first non-conductive material layer.

In various embodiments, one or more conductive elements (e.g., composed of an electrically conductive material), such as one or more electrodes, such as a source electrode and a drain electrode for a transistor, may be provided. In various instances, the conductive elements may be separated one from the other and positioned within one or more of the non-conductive layers so as to from a channel between the electrodes. In particular embodiments, the source and drain electrodes may have a planar arrangement and may be in an opposed configuration to one another, where one or both of the source and drain electrodes have a geometrical formation or pattern designed to maximize the ratio of the channel width to channel length. For instance, the source and drain electrodes may be configured, e.g., within the insulating layer such that the channel length is less than about 1000 nm, less than about 500 nm, less than about 100 nm, may be less than about 50 nm, or may be less than about (10) nm, less than about 5 or 3 nm or less.

Further, in various embodiments, the chemically-sensitive FET may include a well structure, provided at least within the first and/or second non-conductive material layers. In such an instance, the well structure may include a chamber, such as a chamber that may be bounded by one or more bounding members. For instance, the bounding member may be configured as a plurality of walls or a circular circumferential surface member. In particular embodiments, the bounding member(s) and/or the surrounding insulating layer(s) may be configured to include the source and drain electrodes. For example, one or more, e.g., both of the source and drain electrodes may be configured so as to be included within a bottom and/or a side surface on the well bounding member. In such an instance, the source and drain electrodes may be configured so as to increase the channel width to length ratio. Particularly, the source and drain electrodes may have a three-dimensional (3D) configuration and may be incorporated on or within the bottom surface member of the chamber and/or be incorporated within one or more side or circumferential surface members of the chamber. In such instances, the source and drain electrodes may be configured so as to increase the channel width to length ratio by a factor of about 10 or 20 or more, e.g., compared to an electrode pattern only at the bottom of the well, such as by a factor of 100 or more, such as a geometric electrode pattern that increases the channel width to length ratio by a factor of 1000 or more.

Particularly, in certain embodiments, the source and drain electrodes may be separated one from the other by one or more spaces, and thus, may be configured to not only have a 3D structure but to also be in an opposed but interdigitated relationship to one another. For instance, one or more of the source and drain electrodes may be formed so as to include an impingement member, and one or more of the source and drain electrodes may be formed so as to include a receiving member, such as where the impingement member is configured for being inserted within the receiving member, and the receiving member is configured for receiving the impingement member, while maintaining a distance between one another, such as to form one or more channels there between.

Hence, in various instances, the source and drain electrodes may have one or more, e.g., a plurality of, prongs or tines so as to give the electrode a fork like configuration, such as can be seen with respect to FIG. 11, where the tines are capable of being fit one within the other while maintaining a space there between. In such instances, the inter-digitated tines of the source and drain electrodes may be disposed within one or both of the first and second non-conductive material layers and be separated from one another by a distance so as to form the channel. In particular embodiments, the bounding member(s) of the chamber may be configured so as to include one or more vias, trenches, or slots that may be formed in the transistor channel material, which may then be filled with the electrode material so as to allow the formed electrodes to not only contact the well surface, but to also be in contact with the channel and/or a material layer designed to form or otherwise augment the channel conductivity. Accordingly, in various embodiments, a channel material layer may be provided, and the source and/or drain electrodes may be configured so as to contact the channel material and/or to also contact an edge of the channel material.

Thus, in various embodiments, the chemically sensitive FET may be configured to include a channel, such as a channel that includes or is otherwise composed of a transistor channel material, such as is formed over and/or between the electrodes, e.g., the source and drain electrodes. For instance, a 1D, 2D, e.g., a graphene layer, and/or 3D structured layer, may be positioned between the first and second non-conductive material layers. For example, the transistor material channel material may be a 1D material may be comprised of carbon nanotubes or semiconducting material such as in a nanowire form, such as including Si, Ge or a metal oxide. In other instances, the 2D material may be composed of one or more of graphene, molybdenum disulfide ($MoS_2$), MoSe2, phosphorene (black phosphorous), silicene, borophene, tungsten disulfide (WS2), boron nitride, WSe2, stanene (2D tin), graphane, germanane, nickel HITP, Mxenes (Ti2C, (Ti0.5, Nb0.5), V2C, Nb2C, Ti3C2, Ti3CN, Nb4C3, Ta4C3), and/or transition metal dichalcogenides. The transistor material may be a bulk transistor material such as Si, amorphous Si, Ge, and/or metal oxide. In particular instances, the channel transistor material may be configured so as to extend between a surface portion of the source electrode and a surface portion of the drain electrode. In such an instance, positioning of the transistor channel material between the source and drain electrodes is designed to form the channel and thereby control and/or regulate conductivity between the electrodes. Hence, the FET may include a gate structure.

In certain instances, as herein disclosed, the FET may be configured for performing a chemical reaction, such as for the detection of one or more analytes, such as a reactant from a chemical reaction. Accordingly, in various instances, the FET may include an analyte-sensitive layer. In various embodiments, e.g., to facilitate the performance of a chemical reaction, the field effect transistor may include a well structure, within which a chemical reaction may take place. For instance, one or more of the layers of the FET, such as the first and/or second insulating layers may include a chamber, such as a chamber to which the reactants may be added for the performance of the chemical reaction. In such an instance, the gate structure of the FET may be formed within the chamber and over the channel so as to electrically connect the source and the drain electrodes. Further, one or more solutions, such as containing one or more reactants may be added to the chamber thereby forming a solution gate. In various instances, the gate structure may include the graphene layer.

Further, in various embodiments, the chemically-sensitive FET and/or the chamber thereof may be configured such that the electrodes, e.g., the source and drain electrodes, are positioned on or in the bounding member of the chamber. For instance, in various instances, the surfaces or walls of the chamber may include one or more trenches, wherein the trench includes one or more of the electrode structures, and/or may include the 1D or 2D structure, such as the graphene layer. Hence, the electrodes of the source and drain may be included in a bottom or side or circumferential surface of the well or trench. In such an instance, an analyte-sensitive layer may be formed on the well or trench bottom and/or sidewalls and/or may cover the electrodes and/or channel material. In some instances, the 1D channel material may be a vertically-oriented 1D channel material. Consequently, the chamber may be configured for sensing and/or measuring the analyte such as a reactant that results from the reaction taking place within the chamber.

For example, one or more surfaces of the substrate and/or a well and/or a chamber thereof may be fabricated in such a manner so as incorporate the electrodes therein. Particularly, one or more of the electrodes disclosed herein may be formed by any suitable method, such as by being lithographically photopatterned, which may utilize a light source and/or optics that allow patterning of deep trenches and/or wells. More particularly, in various instances, an electron beam, laser or plasma beam may be utilized to pattern the wells and/or trenches and/or the electrodes. In various instances, the well structure is comprised of alternating vertical layers of source and drain electrodes, such as to define the channel width and the channel length. In particular embodiments, the well structure is comprised of electrodes on a well bottom and/or in conjunction with alternating vertical layers of source and drain electrodes so as to define a channel width and/or channel length. As stated above, the electrodes may have a transistor channel material and/or an analyte-sensitive material over and/or between them, such as in the alternating vertical layer configuration. In various embodiments, the analyte-sensitive material may be formed by PVD deposition of a metal and oxidization of that metal and/or the analyte-sensitive material may be formed by ALD deposition of a metal oxide, such where the PVD deposition is a sputter or e-beam deposition, and/or the oxidation is a thermal or plasma oxidation. In particular instances, the analyte-sensitive material may be comprised of multiple layers, which material may be formed by any process or a combination of processes so as to cover a bottom and/or side of the well, and in certain instances, the analyte-sensitive material at the bottom of the well may be different from the analyte-sensitive layer coating the well or trench walls.

Accordingly, in a further aspect of the invention, a method for producing a field effect transistor is provided, such as a FET that is configured for performing a chemical reaction and sensing one or more of the products thereof. In such instances, the FET may include a plurality of electrodes, and in various instances may be in an alternating, vertical and/or interdigitated layered configuration. In such an instance, the method may include forming alternating layers of source electrodes, dielectric material and drain electrodes, as well as forming a well or trench within a central portion of the source and drain electrode patterns. The method may include forming a well or trench in one or more of the layers of the FET, such as one or more of the insulating layers, such as in an etching process, such as by wet etching or plasma etching, or the like.

Hence, in various instances, the method for producing a sensor may include forming alternating and/or interdigitated layers of source electrodes, dielectric material, and/or drain electrodes, forming a well or trench within a central portion of the source and drain electrode patterns, and/or forming a transistor channel material over or between the source and drain electrodes, such as where an analyte-sensitive layer may be formed over the transistor channel layer. For instance, a first layer of transistor channel material may be formed over a first electrode layer, a dielectric layer may be formed over the first electrode layer, a trench may be patterned in the dielectric layer, a second electrode layer may then be formed within the trench. In various embodiments, the second electrode layer and dielectric layer may be planarized, a second layer of transistor channel material may then be formed over the second electrode and second dielectric layer and this process may then be repeated so as to produce the desired number of electrode and channel layers.

As described, an array according to the invention that comprises a plurality of sensors may also further include one or more reference electrodes, preferably platinum or Ag/AgCl reference electrodes.

As shown in the following figures, reference electrodes can also be utilized with the chemically sensitive FET-based sensors and devices of the invention. There are multiple reference electrode options for use with chemically sensitive sensors. For example, platinum, silver, or other biofluid-compatible reference electrodes, such as noble metal Ru, Pd, Ag, Os, Ir, Pt, Au, Rh, or Ag/AgCl, can be used. For example, the material for the reference electrodes can be deposited on (or otherwise applied to) the chip (e.g., by PVD or CVD). The reference electrodes can then be directly to the copper lines forming the other electrodes. Another approach is to plate the reference electrodes on the chip (electroless). Yet another approach is to have the reference electrodes as separate pieces adhesively attached to the chip (preferably including over active peripheral circuitry so as to conserve space and not interfere with the wells or other sensing regions of the device) and wirebond interconnected or attached to the package or the chip. Yet another embodiment includes reference electrodes as several pieces so that resistance through the fluid to the reference electrode is more normalized.

The reference electrode is preferably fabricated to as to be in contact with the solution containing the analyte to be detected.

Other embodiments have the reference electrodes incorporated as a metallization layer deposited on top of the wells (e.g., by sputtering, evaporation, or plating). The reference electrode(s) is (are) connected separately from the chip interconnect using wirebonds to the package substrate.

Thus, in some embodiments the chemically-sensitive sensor is based on a FET according to the invention fabricated on an integrated circuit wafer, which chemically-sensitive FET also includes a processor and one or more reference electrodes. The processor is configured to determine a chemical reaction based on the electrical characteristics of the chemically-sensitive field effect transistor. The reference electrode is preferably selected from the group of Ru, Pd, Ag, Os, Ir, Pt, Au, Rh, and Ag/AgCl The reference electrode is preferably in electrical communication with a chemically-sensitive FET, and is preferably used to apply a gate voltage to the chemically-sensitive FET. The reference electrode can alternatively be used to apply a gate voltage to the chemically-sensitive FET through a fluid or solution.

The reference electrode is preferably comprised of at least a portion of a metal layer over or on the integrated circuit chip.

In one embodiment, the reference electrode is incorporated in a layer of an integrated circuit chip that comprises the chemically-sensitive FET. In other embodiments, the metal layer is part of a separate piece that is attached or affixed to the integrated circuit chip.

In some embodiments, the reference electrode(s) is(are) attached or affixed to the integrated circuit chip by a material comprising a glue, adhesive, polymer, or thermoplastic.

In some preferred embodiments, the reference electrode is in electrical communication with an interconnect on the integrated circuit chip. The interconnect is integrally connected to the reference electrode through a common metal layer on the integrated circuit chip, or the interconnect is connected to the reference electrode through a wirebond, flip chip, or conductive adhesive connection. In certain embodiments, the wirebond, flip chip, or conductive adhesive connection to a portion of the reference electrode is sealed from the fluid or solution while another portion of the reference electrode is in communication with the fluid or solution.

In some embodiments, a reference electrode layer is a topmost layer of the integrated circuit.

In some embodiments, a reference electrode layer is adjacent to one or more chemically-sensitive FETs on the integrated circuit chip.

In other embodiments, the reference electrode is incorporated within the package housing the integrated circuit chip.

In certain embodiments, the reference electrode comprises at least a portion of a metal layer over or on the package substrate or package lid, while in other embodiments, the metal layer is part of a separate piece that is attached or affixed to the package substrate or package lid.

In certain embodiments, the reference electrode is attached or affixed to the package substrate or package lid by a material comprising a glue, adhesive, polymer, or thermoplastic.

In various embodiments, a reference electrode is in electrical communication with an interconnect on the package substrate or package lid.

In some embodiments, the interconnect is integrally connected to the reference electrode through a common metal layer on the package substrate or package lid.

In some embodiments, the interconnect is connected to the reference electrode through a wirebond, flip chip, solder, or conductive adhesive connection.

In certain embodiments, the wirebond, flip chip, solder, or conductive adhesive connection to a portion of the reference electrode is sealed from the fluid or solution while another portion of the reference electrode is in communication with the fluid or solution.

In various embodiments, the reference electrode layer is a topmost layer of the package substrate or a bottommost layer of the package lid. In another embodiment, the reference electrode layer is adjacent to one or more chemically-sensitive FETs on the integrated circuit chip. The metal layer is deposited by a method comprised of a PVD, CVD, printing, electroplating, or electroless plating method. In some preferred embodiments, the devices include multiple reference electrodes.

Accordingly, in one aspect, a chemically-sensitive field effect transistor (FET) may be provided. The FET may include an integrated circuit structure, such as a CMOS structure, having a conductive source and a conductive drain, which source and drain may be separated one from the other so as to form a channel region. Hence, in various embodiments, a conductive channel may be included where the channel extends at least from the conductive source to the conductive drain. In particular implementations, the conductive channel may be composed of a channel material such as a one-dimensional transistor material or a two-dimensional transistor material, such as where the conductance of the channel shifts in response to a chemical reaction occurring over or near, e.g., proximate, the channel. In various instances, the length of the channel from an inside or outside edge of the source to the drain may range from 0.05 micron to 3 microns, and may have a width of the conductive channel that ranges from 0.05 micron to 2 microns. Particularly, in certain embodiments, the channel may include a one-dimensional, e.g., nanotube or semiconductor nanowire transistor material, or a two-dimensional transistor material, such as one or more of graphene, molybdenum disulfide ($MoS_2$), phosphorene (black phosphorous), silicene, borophene, tungsten disulfide ($WS_2$), boron nitride, $WSe_2$, atanene (2D tin), graphane, germanane, nickel HITP, Mxenes (Ti2C, (Ti0.5, Nb0.5), V2C, Nb2C, Ti3C2, Ti3CN, Nb4C3, Ta4C3), and a metal dichalcogenide. Additionally, in some embodiments, a non-conductive, e.g., an oxide, layer may be disposed over the conductive channel material, which layer may be a thin layer, such as having a thickness of 50 nanometers or less.

Further, in various instances, the chemically-sensitive FET may optionally include one or more of an ion-selective permeable membrane, an HMDS, and/or a reference electrode. For instance, an ion-selective membrane may be included, such as where the membrane preferentially allows ions of interest to pass through the membrane, so as to interact with the channel, as compared to ions not of interest. Likewise, a material, e.g., a HMDS, may be included and configured to manage the interaction of the conductive channel with an underlying oxide layer. And, in various embodiments, the chemically-sensitive FET may be configured to include a gate, such as a solution gate region, and may include a reference electrode. In some embodiments, a back gate region may also be included.

In particular instances, the conductive source and the conductive drain of the chemically-sensitive FET may include a metal material, such as a copper material, e.g., a damascene copper, an aluminum material, a platinum material, a gold material, and the like. For instance, the conductive source and the conductive drain may be embedded in a dielectric and/or an insulator material, such as an oxide layer, which oxide layer may be positioned over a substrate layer. In particular embodiments, the source and drain may be configured so as to be planar with a top surface of the insulator, and in other embodiments, as described herein above, may be configured so as to extend above the insulator material layer in which they are embedded.

In certain instances, a further insulating layer, e.g., an oxide layer, may be included and positioned above the first insulating layer and/or the channel material layer. Particularly, the channel material may be at least partially covered in an oxide layer that is comprised of an ion sensitive material, e.g., a material having a high intrinsic buffer capacity, which may have a thickness of 50 nanometers or less. In one embodiments, the second oxide layer may itself include two or more oxide layers, wherein the oxide layers may be comprised of an aluminum oxide, a silicon dioxide, a hafnium dioxide, hafnium silicate, zirconium silicate, zirconium dioxide, lanthanum oxide, titanium oxide, iron oxide, or yttrium oxide.

As described herein, in various embodiments, the chemically-sensitive FET may include a well structure or chamber that is positioned on a portion of an exterior surface of the insulator, e.g., oxide, layer and may be positioned over the channel region and/or channel material. For instance, the well structure may be configured so as to define an opening allowing for direct contact with the channel and/or insulator layers, and in some instances the well structure may itself be composed of an insulator material. For example, the insulator material of the well structure may be composed of an inorganic or organic material, such as where the inorganic material may be a silicon oxide, a silicon nitride, a silicon oxynitride, a silicon carbide or other metal oxide, carbide or nitride, and the organic material may be a polymer, polyimide, BCB, or other like material. The chemically-sensitive FET, e.g., a well or chamber thereof, may be configured for chemical or biological material detection, such as where the biological material may be one or more of a nucleic acid, such as DNA or RNA, a protein, a carbohydrate, a lipid, a cell, a virus particle, an antibody, and the like.

In another aspect, a biosensor may be provided. In such an instance, the biosensor may include at least one chemically-sensitive FET that includes a well structure, as described above, where the well structure is positioned over a portion of an exterior surface of an insulation layer, e.g., a dielectric or oxide layer, of the chemically-sensitive FET(s). In certain instances, the well structure defines an opening that is configured for receiving and/or retaining reactants thereby allowing for various interactions of compounds produced in a chemical reaction within the well to occur. Accordingly, in various instances, the well may be configured as a solution well and/or may include an electrode, such as a reference electrode, and/or may otherwise be configured as a solution gate. In particular instances, the well structure may be bounded by the first dielectric or oxide layer, or may be bounded by the channel material layer, and/or a secondary oxide layer.

In particular embodiments, the biosensor may include a processor, such as proximate the substrate, which processor may be in electrical communication with the chemically-sensitive FET(s). In such an instance, the processor may be configured to perform one or more of: (i) generating a reference $I$-$V_g$ curve, such as corresponding to the conductance of the chemically-sensitive FET channel(s), e.g., in the absence of a chemical reaction occurring in the well and/or in proximity to the channel; and/or (ii) generating a chemical reaction $I$-$V_g$ curve in response to a chemical reaction occurring in the well and/or in proximity to the channel; and/or (iii) determining a difference, if any, between the reference $I$-$V_g$ curve and the chemical reaction $I$-$V_g$ curve. Particularly, the difference between the reference $I$-$V_g$ curve and the chemical reaction $I$-$V_g$ curve may be a shift in a $V_g$ value of a minimum point of the chemical reaction $I$-$V_g$ curve relative to a $V_g$ value of a minimum point of the reference $I$-$V_g$ curve.

Specifically, in one instance, the difference between the reference $I$-$V_g$ curve and the chemical reaction $I$-$V_g$ curve may be in a shift in an $I$ value of a minimum point of the chemical reaction $I$-$V_g$ curve relative to an $I$ value of a minimum point of the reference $I$-$V_g$ curve. Additionally, the difference between the reference $I$-$V_g$ curve and the chemical reaction $I$-$V_g$ curve may be a shift in a final $I$ value of the chemical reaction $I$-$V_g$ curve relative to a final $I$ value of the reference $I$-$V_g$ curve. Further, the difference between the reference $I$-$V_g$ curve and the chemical reaction $I$-$V_g$ curve may be a shift in a parameter of the reference $I$-$V_g$ curve with a corresponding parameter of the chemical reaction $I$-$V_g$ curve, such as where the parameter is a slope, optionally a steepest slope, of the reference $I$-$V_g$ and chemical reaction $I$-$V_g$ curves.

As indicated, in various instances, an ion-selective permeable membrane may be provided, such as where the ion-selective permeable membrane may be positioned within a chamber of a well and/or positioned above or otherwise proximate to the channel. In certain instances, the ion-selective permeable membrane may include a polymer, such as composed of a perfluorosulphonic material, a perfluorocarboxylic material, PEEK, PBI, Nafion, and PTFE material. Alternatively, the ion-selective permeable membrane may include an inorganic material, such as an oxide or a glass. In some instances, an additional 2D transistor material may be included, such as graphene, that need not be electrically connected to the channel material.

Further, in certain embodiments, the ion-selective permeable membrane may be applied by a spin-coating, anodization, PVD, sol gel method, and the like. Furthermore, in certain instances, the chemically-sensitive FET may include an ion getter material, such as where the ion getter material preferentially sequesters ion species that are not relevant to a particular chemical reaction to be detected, and optionally reducing noise in signals from the chemically-sensitive FET, such as where the ion getter material may placed over a dielectric layer forming the well or chamber and/or in proximity to the chamber opening and/or channel.

Additionally, as indicated, in certain instances, the chemically-sensitive FET may include a reference electrode that may be composed of Ru, Pd, Ag, Os, Ir, Pt, Au, Rh, or Ag/AgCl. In certain instances, the reference electrode may be positioned so as to be in electrical communication with the chemically-sensitive FET, such as through a fluid or solution. In such an instance, the reference electrode may be used to apply a gate voltage to the chemically-sensitive FET, optionally through the fluid or solution. Hence, the reference electrode may include at least a portion of a metal layer, such as over or on an integrated circuit structure.

Particularly, the reference electrode may be incorporated in a layer of the integrated circuit structure that comprises the chemically-sensitive FET, such as a topmost layer of the integrated circuit structure, or a layer adjacent to one or more chemically-sensitive field effect transistors on the integrated circuit structure. However, in various instances, the metal layer optionally is part of a separate piece that is attached or affixed to the integrated circuit chip, optionally using a glue, adhesive, polymer, or thermoplastic, or the like. Regardless, the reference electrode is configured so as to be in electrical communication with an interconnect on the integrated circuit structure, such as where the interconnect optionally is (i) integrally connected to the reference electrode through a common metal layer on the integrated circuit, or (ii) connected to the reference electrode through a wirebond, flip-chip, or conductive adhesive connection structure, which connection may optionally be sealed from the fluid or solution while another portion of the reference electrode may be in communication with the fluid or solution.

In certain instances, the reference electrode may be incorporated within a package and/or housing of the integrated circuit structure. For instance, the reference electrode may include at least a portion of a metal layer, e.g., over or on the package substrate or package lid, wherein the metal layer optionally is part of a separate piece that is attached or affixed to the package substrate or package lid, such as using a glue, adhesive, polymer, or thermoplastic, and/or the like. Hence, in particular instances, the reference electrode may be a metal layer deposited by a method that is a PVD, CVD, printing, electroplating, an electroless plating method, and/or the like. In some embodiments, the reference electrode may include two or more reference electrode elements.

In another aspect of the disclosure, various methods are provided. For instance, as described herein and above, a method for manufacturing a chemically-sensitive field effect transistor (FET) may be provided. The method may include depositing a conductive channel material, e.g., comprised of a one-dimensional (1D) or two-dimensional (2D) transistor material, on an exposed metal layer portion of an integrated circuit structure, such as where the integrated circuit structure includes a semiconductor substrate and/or a dielectric layer. In such an instance, the metal layer may be configured so as to form a source and drain electrode, where the source and drain electrodes are separated from one another so as to form a channel region.

Accordingly, in certain instances, the metal layer(s) may be imbedded within the dielectric layer and exposed so as to stand off therefrom. For instance, a patterned material may be used to expose a portion of the channel area and a plurality of adjacent areas. Particularly, this may be performed such as by etching the dielectric material starting with the adjacent areas thereby exposing a trench under the channel, and/or exposing the metal in the channel area. Additionally, the method may include etching the metal from underneath the channel to create a chemically-sensitive FET. In certain instances, a channel material may be provided such as before, after, or during the etching process so as to form a channel between the exposed source and drain electrodes.

Additionally, a method for manufacturing a well formation for a 1D or 2D material FET may include depositing an organic protective layer over a conductive channel of a 1D or 2D material FET of a semiconductor device structure, patterning the organic protective layer to create well formation locations over the channel, and removing the protective layer over the channel to expose the channel within the well formation.

Further, in various embodiments, the method for manufacturing a well formation for a 1D or 2D material FET may include depositing a protective layer over a conductive channel of a 1D or 2D transistor material FET of a semiconductor device structure, as described herein. Additionally, the method may include a first etching step for etching through the majority of the protective layer with a first etching method so as to create a majority of a well formation, such as over the channel. A second etching step may take place for the etching of the remaining protective layer over the channel to expose the channel within the well formation. In some instances, the depositing of the protective layer may be over a functional layer that is itself positioned over the conductive channel of 1D or 2D material.

Where one or multiple etching steps are provided, the first etching method may be a plasma method or laser method, wherein the plasma method optionally is an RIE, HDP, ICP or ECR method. The first etching method may be performed through a mask material that is patterned to shield parts of the protective dielectric layer from the first etching method while having openings that expose other parts of the protective dielectric layer to the first etching method, wherein the mask material optionally is a photoresist or a hard mask material. Additionally, a second etching method may be provided such as where the second etching step is a wet or gaseous etching method, optionally an electrochemical or chemical etching method, wherein the chemical etching method optionally comprises an acid, an aqueous acid solution, or a buffered acid solution, and wherein the second etching method optionally etches the protective layer without substantially etching or affecting the channel material. In particular embodiments, the first and/or second etching method(s) is(are) predominantly an anisotropic etching method. In such instances, the first etching method may be performed so as to etch through a controlled depth in the protective material layer wherein the control is provided by a time of etching in conjunction with the rate of etching or the control is provided by an end point detection.

When producing a well structure, the well may have any suitable shape or size of configuration. For instance, in one embodiment, the shape of the well formation when viewed from the top is a round or polygon shape. In such an instance, the largest width of the well formation when viewed from the top may be about 0.1 um to about 10 um. Further, when forming a well, in various instances, an array of two or more well formations may be formed. Hence, the ratio of the pitch of two well formations to the largest width of the well formations when viewed from the top may be greater than 1 and less than 10. Accordingly, when an array of well formations are formed, the variation of the largest widths of the well formations when viewed from the top in an array may be designed to have well formations with the same largest widths, which widths may be less than about 10%. In various instances, the well formation configuration may be chosen with respect to consideration of fluid dynamics of a fluid flowing over or into the well formation, wherein consideration of fluid dynamics includes transport of reagents or particles over or into the well formation.

In various instances, the method may include preparing a growth substrate of a 1D or 2D material. In such an instance, the method may include depositing a metal catalyst layer on a substrate, optionally a wafer or a plate and annealing the metal catalyst. The 2D material may be a transistor material selected from the group including graphene, molybdenum disulfide ($MoS_2$), phosphorene (black phosphorous), silicene, borophene, tungsten disulfide ($WS_2$), boron nitride, $WSe_2$, atanene (2D tin), graphane, germanane, nickel HITP, Mxenes (Ti2C, (Ti0.5, Nb0.5), V2C, Nb2C, Ti3C2, Ti3CN, Nb4C3, Ta4C3), and a metal dichalcogenides. Further, the metal may be Cu, Ni, or Pt, or the like. Further still, a photoresist may be included, such as where the patterned material is a photoresist, which may be patterned using a photolithographic process. Likewise, the semiconductor substrate may be a Si material, a SiGe material, or a III-V material. Therefore, in accordance with these methods, the semiconductor device structure may be configured as or otherwise based on CMOS, BiCMOS, Bipoloar, or other fabrication technology; and the integrated circuit may be configured as or based on FET, BJT, HBT, or other transistor technology.

Accordingly, the methods may include one or more of the following etching steps, which may be executed in any logical order: etching the dielectric, where the etching includes: a plasma etching process, wherein the plasma etching process optionally comprises an RIE, ICP, HDP, or ECR process; etching the dielectric, where the etching includes (i) a wet or gaseous etching method, wherein the wet or gaseous etching method optionally is an electrochemical or chemical etching method, wherein the chemical etching method optionally comprises an acid, an aqueous acid solution, or a buffered acid solution; or (ii) an isotropic etching method; and wherein the etching optionally etches the dielectric without substantially etching or affecting the channel material; etching the metal, where the etching includes a plasma etching process, optionally (i) an RIE, ICP, HDP, or ECR process; (ii) a wet or gaseous etching method, optionally an electrochemical or chemical etching method, wherein the chemical etching method optionally comprises an acid, an aqueous acid solution, or a buffered acid solution; and (iii) wherein the etching comprises predominantly an isotropic etching method; etching the metal, where the etching is predominantly an isotropic etching method; and etching the metal, where the etching etches the metal without substantially etching or affecting the channel material.

As indicated, the dielectric layer may include a first thin layer of material forming an etch stop layer under the channel to limit the extent of the dielectric etching, wherein the first thin layer of material optionally includes a silicon oxide, a silicon nitride, or a silicon carbide or a non-stoichiometric material, and wherein the first thin layer of material optionally is about 0.1 nm to 100 nm thick. Additionally, one or more functional layers may be deposited over the graphene channel prior to etching the dielectric, wherein etching the dielectric may optionally include (i) a plasma etching process, which plasma etching process optionally is an RIE, ICP, HDP, or ECR process; (ii) a wet or gaseous etching method, wherein the wet or gaseous etching method is an electrochemical or chemical etching method, wherein the chemical etching method optionally comprises an acid, an aqueous acid solution, or a buffered acid solution; and (iii) wherein etching the dielectric optionally etches the dielectric without substantially etching or affecting the channel material and without substantially etching or affecting the functional material. The one or more functional layers may be deposited over the graphene channel subsequent to etching the dielectric.

Where a protective layer is employed, the protective layer may be comprised of an inorganic material, optionally an oxide, a nitride, a carbide, an oxy-nitride, a carbon-doped oxide or a fluorine-doped oxide material. Additionally, the protective layer may be comprised of an organic material, optionally a polymer, polyimide, BCB, or other like material. Further, the protective layer may include multiple layers of material. Hence, the protective layer may be comprised of both inorganic and organic materials. In certain instances, the protective layer may be deposited by a CVD, PECVD, PVD, ALD, or spin-on dielectric process. In various instances, the protective layer may include a first thin layer of material forming an etch stop layer over the channel and a second thicker layer of material over the etch stop layer, wherein optionally (i) the first etching method has high selectivity for etching the second thicker layer of material as compared to the first thin layer of material, (ii) the first thin layer of material is about 0.1 nm to about 100 nm thick and the second thicker layer of material is about 0.1 um to about 10 um thick, (iii) the first thin layer of material is comprised of a silicon oxide, a silicon nitride or a silicon carbide, (iv) the first layer of thin material is comprised of a non-stoichiometric material, and (v) the first etching method etches through the second thicker layer of material and stops on the first thin layer of material.

Accordingly, in various embodiments, the patterning may be by an imprinting method; the protective layer may be comprised of a photosensitive material and the patterning may be by a photolithographic method; the removing may be by an etching or a developing method; the patterning method may be performed through a mask material that is patterned to shield parts of the protective dielectric layer from exposure to light energy while having openings that expose other parts of the protective dielectric layer to light energy; the removing method may be a wet or gaseous etching or developing method, wherein the wet or gaseous etching or developing method optionally is an electrochemical or chemical etching or developing method, wherein the chemical etching or developing method optionally comprises use of a base material, a photoresist developer, KOH, TMAH, or NaOH; the removing method may be predominantly an isotropic etching or developing method; the removing method may predominantly be an anisotropic etching or developing method; the removing method may etch or develop the protective layer without substantially etching or affecting the channel material; the protective layer may be comprised of a first thin layer of material forming an etch or developing stop layer over the channel and a second thicker layer of material over the etch stop layer; the first etching method may have a high selectivity for etching or developing the second thicker layer of material as compared to the first thin layer of material; the first thin layer of material is 0.1 nm to 100 nm thick and the second thicker layer of material is 0.1 um to 10 um thick; the first thin layer of material may be comprised of one polymer and the second thicker layer of material may be comprised of a different polymer; the functional layer may be comprised of an oxide; and/or the functional layer may be comprised of an ion sensitive material; the substrate may be comprised of silicon, sapphire, aluminum oxide, silicon dioxide, or a metal; the substrate includes an oxide layer; the depositing comprises an evaporation, sputtering, ALD, CVD, or ECP process, wherein the depositing optionally results in a predominantly single crystalline metal catalyst layer with a (111) crystal orientation; the annealing occurs in an environment that comprises a reducing gas, optionally hydrogen gas and either an argon or nitrogen gas, wherein the hydrogen gas optionally comprises about 1% to about 10% and the argon or nitrogen gas comprises about 90% to about 99% of the environment; the annealing is performed at a temperature of about 70% to about 98% of the melting point temperature of the metal catalyst; the annealing time is between about 15 minutes and about 90 minutes; the annealing is performed under vacuum; the annealing is performed by a laser, optionally using a process comprising scanning an excimer or other laser across the metal catalyst to re-crystalize the metal; the metal catalyst comprises Ni, Ru, Co, Cu, Pt, Pd, or Fe; the depositing comprises depositing a first layer onto the substrate that improves adhesion before depositing the metal catalyst, wherein the first layer optionally comprises Cr, Ti, Ta, tantalum nitride, W, or tungsten nitride, wherein the thickness of the first layer optionally is between about 1nm and about 15 nm; the thickness of the metal catalyst layer is between about 10 nm and about 200 nm, optionally between about 20 and about 50 nm; the metal catalyst layer is smoothed after the depositing, wherein the smoothing process optionally comprises polishing, electropolishing, or CMP; and/or the surface of the metal catalyst is activated after annealing, wherein the activating method optionally comprises a plasma process, wherein the plasma process optionally occurs in an environment that comprises a hydrogen reducing gas and a nitrogen-containing gas and is optionally performed (i) between about 300 and about 400 C and/or (ii) at a pressure between about 0.01 and about 3 Torr, optionally between about 0.05 and about 0.5 TOM The invention will be better understood by reference to the following Examples, which are intended to merely illustrate certain preferred embodiments for practicing some aspects of the invention. The scope of the invention is not to be considered limited thereto.

EXAMPLES

Example 1

Manufacture of a 2D GFET

As shown in FIGS. 34-47, in some embodiments manufacturing a well for a 2D material FET involves an organic protective layer or an inorganic protective layer.

For a well with an inorganic protective layer, PECVD oxide, LPCVD Oxide, or Nitride LPCVD are preferred, at least for the nitride, as the film has a lower stress and less tendency to crack. Most of the well depth is created by a photoresist pattern process and RIE. The final amount of well depth can be created by a wet etch process. An alternative is to deposit a thin SiN layer, then a thick $SiO_2$ layer. The $SiO_2$ is patterned and etched with a highly selective etch, in a preferred embodiment, SiN acts as an ESL. Then a final wet etch process is performed on the SiN from the bottom of the well. Yet another option is to use a low temperature TEOS oxide, which is a denser, less porous oxide. It prevents uptake of contaminants or reaction materials in the oxide that may affect results.

For organic wells, one possible material is a photoimageable organic material. In such embodiments, since organics tend to stick to graphene and are difficult to remove (and reduce the graphene carrier mobility) it is preferred to first put on a thin inorganic layer, e.g., by physical vapor deposition (PVD) or chemical vapor deposition (CVD) of an oxide or nitride. An easier and lower cost option is to spin on a thin layer of spin on glass (SOG), after which the organic material (e.g. polyimide or BCB) to form the organic layer is spun on, followed by imaging, developing, and curing. The protective oxide or nitride is then wet etched (use of dry etching may destroy or degrade the graphene component).

For organic protective layers, PECVD Oxide is preferably etched below a top copper layer to form the wells. Then, photoresist patterning and reactive-ion etching (RIE) is performed on most of the well below the wafer starting surface. Next, the graphene layer is placed. Note that it may conform somewhat to the well. Thereafter, the graphene layer is patterned to the desired size and configuration.

As shown in FIG. 43, nanoimprinting of polymer material such as SU8 epoxide photoresist (500) (or another suitable polymer material) may be used for GFET well formation. As shown in step (a) of the drawing, the mold (501) is aligned with the resist (500) and substrate (502). In step (b), the polymer material is imprinted into the resist (500). In step (c), the mold (501) is removed. In step (d), any residual resist (500) or residual polymer is removed As shown in FIGS. 44-47, there are various methods for positioning the oxide or other layer over the graphene layer. One such process is to use a plasma-timed etch or endpoint detection to stop at or near the other oxide layer, then finish with a wet etch process (FIG. 45). An alternative method is to deposit a thin SiN layer or other ESL, followed by deposition of a thick $SiO_2$ layer. The $SiO_2$ layer is then patterned and etched with a plasma anisotropic etch. In the embodiment depicted here, SiN acts as an ESL. Then, the final step involves wet etching the SiN layer or ESL from the bottom of the well with an etchant that is highly selective to the ESL used.

Preferred methods for manufacturing a well formation for a 2D material FET includes depositing a protective layer on a channel of a 2D material FET of a semiconductor device structure. Such methods also preferably include etching through the majority of the protective layer with a first etching method to create a majority of a well-disposed over the channel. These methods can also include a second etching of the remaining protective layer over the channel to expose the channel within the well.

The 2D material is selected from any suitable material, including graphene, molybdenum disulfide ($MoS_2$), phosphorene (black phosphorous), silicene, borophene, tungsten disulfide ($WS_2$), boron nitride, $WSe_2$, stanene (2D tin), graphane, germanane, nickel HITP, and mxenes (e.g., Ti2C, (Ti0.5, Nb0.5), V2C, Nb2C, Ti3C2, Ti3CN, Nb4C3, Ta4C3).

The semiconductor device structure is preferably based on FET, BJT, HBT, or any other transistor technology.

The semiconductor device structure is preferably based on CMOS, BiCMOS, bipoloar, or other semiconductor fabrication technology.

In preferred embodiments, the protective layer is comprised of an inorganic material, such as an oxide, a nitride, a carbide, an oxy-nitride, a carbon-doped oxide or a fluorine-doped oxide material. In other embodiments, the protective layer is composed of an organic material, such as a polymer. In yet other embodiments, the protective layer is composed of both inorganic and organic materials.

The protective layer is preferably deposited by a CVD, PECVD, PVD, or ALD process.

The first etching method is preferably a plasma or laser etching method. A preferred plasma method is an RIE, HDP, ICP, or ECR method. Alternatively, the first etching method is performed through a mask material that is patterned to shield parts of the protective dielectric layer from the first etching method while having openings that expose other parts of the protective dielectric layer to the first etching method. A preferred mask material is a photoresist or a hard mask material. Alternatively, the first etching method is predominantly an anisotropic etching method, and the second etching method is predominantly an isotropic etching method.

Preferably, the second etching method is a wet or gaseous etching method, such as an electrochemical or chemical etching method. An example of a chemical etching method is an acid, an aqueous acid solution or a buffered acid solution. Preferably, the second etching method etches the protective layer without substantially etching or affecting the channel material.

In one exemplary preferred embodiment, the protective layer is comprised of a first thin layer of material forming an etch stop layer (ESL) over the channel and a second thicker layer of material over the ESL. The first etching method has high selectivity for etching the second thicker layer of material as compared to the first thin layer of material. The first thin layer of material is preferably 0.1 nm to 100 nm thick and the second thicker layer of material is preferably 0.1 um to 10 um thick. The first thin layer of material is preferably comprised of a silicon oxide, a silicon nitride, or a silicon carbide. The first layer of thin material is comprised of a non-stoichiometric material. The first etching method etches through the second thicker layer of material and stops on the first thin layer of material.

Preferably, the first etching method etches through a controlled depth in the protective material layer wherein the control is provided by a time of etching in conjunction with the rate of etching. Alternatively, control can be provided by an end point detection.

Preferably, the shape of the well formation when viewed from the top is a round or polygon shape.

Preferably, the largest width of the well formation when viewed from the top is 0.1 um to 10 um.

Preferably, an array of two or more well formations are formed. The ratio of the pitch of two well formations to the largest width of the well formations when viewed from the top is greater than 1 and less than 10. The variation of the largest widths of the well formations when viewed from the top in an array designed to have well formations with the same largest widths is less than 10%.

Alternatively, the shape of the well formation is chosen with respect to consideration of fluid dynamics of a fluid flowing over or into the well formation. The consideration of fluid dynamics includes transport of reagents or particles over or into the well formation.

Other embodiments concern methods for manufacturing a well formation for a 2D material FET with an organic protective layer. These methods typically include depositing an organic protective layer on a channel of a 2D material FET of a semiconductor device structure. Such methods also include patterning the organic protective layer to create well formation locations over the channels. The methods also include removing the protective layer over each channel to expose the channel within the well formation.

The patterning of an organic protective layer is preferably by an imprinting method. The protective layer is comprised of a photosensitive material and the patterning is by a photolithographic method. The removing is preferably by an etching or a developing method.

The organic layer is preferably a polymer such as polyimide, BCB, photoresist, or parylene.

In such embodiments, the removing is preferably by an etching or a developing method such as a wet or gaseous etching or developing method. An example of wet or gaseous etching or developing method is an electrochemical or chemical etching or developing method. The chemical etching or developing method comprises a base material, a photoresist developer, KOH, TMAH, or NaOH.

In one example, the removing method is predominantly an isotropic etching or developing method. In another example, the removing method is predominantly an anisotropic etching or developing method. The removing method etches or develops the protective layer without substantially etching or affecting the channel material.

The protective layer is comprised of a first thin layer of material forming an etch or developing stop layer over the channel and a second thicker layer of material over the etch stop layer. The first etching or method has high selectivity for etching or developing the second thicker layer of material as compared to the first thin layer of material.

Example 2

Manufacture of a 2D GFET

A preferred representative method for manufacturing a FET for chemical and biological analysis is shown in FIGS. 48-51. The method includes depositing a graphene channel on an exposed metal layer of an integrated circuit structure. The integrated circuit structure comprises a semiconductor substrate, a dielectric layer, and the metal layer. The method also includes utilizing a patterned material to expose a portion of a channel area and a plurality of adjacent areas. The method also includes etching the dielectric material starting with the adjacent areas thereby exposing a trench under the channel and exposing the metal in the channel area. The method also includes etching the metal from underneath the graphene channel to create a chemically-sensitive FET.

This method uses a full CMOS wafer with top copper electrodes exposed by CMP. In this case there is also copper in the channel area (512). A graphene layer (26) is deposited (e.g., via PECVD or another suitable method) on all of the exposed copper areas. Then a pattern photoresist process is performed to expose the channel areas and some area to the side of the channel. Then $SiO_2$ is etched from the sides of the channel to expose a trench under the channel and expose the copper in the channel area. Then, the copper is wet-etched from underneath the graphene channel.

Advantages of this method include: no graphene release and layer transfer. The metal can be any suitable material (or combinations of material), for example, Ni, Cu, or Pt. The graphene layer can be deposited could be by CVD, PECVD, or any suitable process. The dielectric material can be an oxide, nitride, carbide, or low K dielectric. The dielectric layer can be etched by a dry or wet, preferably predominantly isotropic, etching process, although the selectivity of the etching process is targeted for the dielectric or metal constituents as compared to the graphene (or any functional layer placed over the graphene).

The patterned material is preferably a photoresist. The photoresist is preferably patterned using a photolithographic process.

The semiconductor substrate is preferably a Si, SiGe, or a III-V material.

The integrated circuit is preferably formed using a CMOS, BiCMOS, Bipoloar, or other fabrication technology.

The integrated circuit is preferably based on FET, BJT, HBT, or other transistor technology.

Etching the dielectric preferably comprises a plasma etching process. The plasma etching process preferably comprises an RIE, ICP, HDP, or ECR process.

Etching the dielectric preferably comprises a wet or gaseous etching method. The wet or gaseous etching method is preferably an electrochemical or chemical etching method. The chemical etching method preferably comprises an acid, an aqueous acid solution or a buffered acid solution.

Etching the dielectric preferably comprises predominantly an isotropic etching method. Etching the dielectric alternatively etches the dielectric without substantially etching or affecting the channel material.

Etching the metal preferably comprises a plasma etching process, wherein the plasma etching process comprises an RIE, ICP, HDP, or ECR process.

Etching the metal alternatively comprises a wet or gaseous etching method, wherein the wet or gaseous etching method is an electrochemical or chemical etching method, and wherein the chemical etching method comprises an acid, an aqueous acid solution or a buffered acid solution.

Etching the metal alternatively comprises predominantly an isotropic etching method.

Etching the metal alternatively etches the metal without substantially etching or affecting the channel material.

The dielectric layer is preferably composed of a first thin layer of material forming an ESL under the channel to limit the extent of the dielectric etching. The dielectric etching has high selectivity for etching the dielectric material as compared to the first thin layer of material. The first thin layer of material is preferably 0.1 nm to 100 nm thick. The first thin layer of material is preferably composed of a silicon oxide, a silicon nitride, or a silicon carbide. The first layer of thin material is alternatively composed of a non-stoichiometric material.

One or more functional layers are preferably deposited over the graphene channel prior to etching the dielectric. Alternatively, one or more functional layers are deposited over the graphene channel subsequent to etching the dielectric, wherein etching the dielectric comprises a plasma etching process, and wherein the plasma etching process comprises an RIE, ICP, HDP, or ECR process. Alternatively, etching the dielectric comprises a wet or gaseous etching method, wherein the wet or gaseous etching method is an electrochemical or chemical etching method, and wherein the chemical etching method comprises an acid, an aqueous acid solution or a buffered acid solution. Etching the dielectric preferably comprises predominantly an isotropic etching method. Etching the dielectric etches the dielectric without substantially etching or affecting the channel material and without substantially etching or affecting the functional material. Etching the metal comprises a plasma etching process, wherein the plasma etching process comprises an RIE, ICP, HDP, or ECR process. Alternatively, etching the metal comprises a wet or gaseous etching method, wherein the wet or gaseous etching method is an electrochemical or chemical etching method, and wherein the chemical etching method comprises an acid, an aqueous acid solution or a buffered acid solution.

Alternatively, etching the metal comprises predominantly an isotropic etching method. Alternatively, etching the metal etches the metal without substantially etching or affecting the channel material and without substantially etching or affecting the functional material.

Example 3

Manufacture of a Growth Substrate

FIG. 17 shows a flow chart of a general method of forming a semiconductor wafer with transistors having 2D material layers. FIGS. 25A-25F illustrate the various steps.

A preferred direct transfer mechanism, direct transfer fusion bonding, is shown in FIGS. 25A-25F. FIGS. 25A-25F visually show the steps of direct bond transfer via fusion bonding. In FIG. 25A, the 2D material (521), preferably graphene, is grown on a growth platform (520) composed of a platinum layer (522) on a growth wafer (523). In FIG. 2B, a cover material (524) and CMP or polish surface is deposited on the growth platform (523). In FIG. 25C, the growth platform (520) is flipped. In FIG. 25D, a ROIC wafer (525) is prepared, and the ROIC wafer (525) and the growth platform (520) are then aligned for bonding. In FIG. 25E, the cover material (524) is bonded to the ROIC wafer top insulator layer (526). In FIG. 25F, the growth substrate (527) is separated from the ROIC wafer, leaving the 2D material (521), preferably graphene, on the ROIC wafer. In the direct transfer fusion bonding process, the 2D material, preferably graphene, is encapsulated with $SiO_2$ and then the growth wafer is fusion-bonded to a CMOS wafer. Platinum, copper, or another suitable metal is used for growing the 2D material. A release or separation process (e.g., a bubble process) is used to separate the 2D material from the platinum or other metal. The growth wafer is preferably silicon, sapphire ($Al_2O_3$), or another suitable substrate capable of sustaining high temperatures and CTE. Alternatively, a wafer format is replaced with a panel or sheet. Various encapsulating materials are utilized such as $SiO_2$, Si, $Si_3N_4$. The same process can also be utilized with other materials that can be bonded such as polymers.

Example 4

Manufacture of a Growth Substrate

A preferred embodiment of the invention is shown in FIG. 8A. The invention provides enhancements to a graphene-based sensor. An ion-selective permeable membrane (40) over the channel (26) only allows ions of interest to travel through the membrane. One preferred ion-permeable material is an inorganic material such as an oxide. An alternative material is a separate layer of graphene that is not electrically connected to the FET. Another alternative material is a polymer such Nafion, PEEK, a perfluorosulphonic or a perfluorocarboxylic material. Another alternative is a HMDS or other siloxane under the graphene. Yet another alternative is a getter material elsewhere on the chip or in the package to attract and sequester unwanted ions. Another alternative is an ion-selective functional layer(s) over the GFET that attracts and sequesters contaminants or unwanted ions so that their interaction with the sensor and thus the determination of the sensor reaction to the desired ion can be reduced or eliminated.

In this embodiment, the chemically-sensitive field effect transistor is fabricated on an integrated circuit wafer and comprising a first structure, a channel (26), a processor (not shown), and a second structure. The first structure comprises a conductive source and a conductive drain. The channel (26) extends from the conductive source to the conductive drain, with the channel comprised of a one-dimensional transistor material or a two-dimensional transistor material. The processor is configured to generate a reference I-$V_g$ curve and a chemical reaction I-$V_g$ curve in response to a chemical reaction that is to be detected occurring over or near the chemically-sensitive field effect transistor. The processor is also configured to determine a difference between the reference and chemical reaction I-$V_g$ curve (or a parameter, e.g., slope, associated with such curves). The second structure enhances the ability of the processor to determine the difference.

The second structure is preferably comprised of an ion-selective permeable membrane (40). The ion-selective permeable membrane allows ions of interest, e.g., $H^+$ ions, to pass through the membrane while blocking the passage of other ion species. The action of passing only ions of interest through the membrane enhances the ability of the processor to determine the difference between the reference and chemical reaction I-$V_g$ curves (or a parameter, e.g., slope, associated with such curves) and thus enhances the ability of the processor to detect the desired chemical reaction (which is responsible for liberating the ion species of interest for subsequent detection).

The ion-selective permeable membrane (40) is preferably comprised of a polymer such as perfluorosulphonic material, a perfluorocarboxylic material, PEEK, PBI, Nafion or PTFE, although the membrane type will vary depending upon the chemical reaction and ion species desired to be detected.

Alternatively, the ion-selective permeable membrane (40) is composed of an inorganic material such as an oxide or a glass.

The ion-selective permeable membrane is preferably applied by a spin-coating, anodization, PVD, or sol gel method, which method may vary depending upon the chemical composition of the membrane to be applied.

Alternatively, the ion-selective permeable membrane (40) can be composed of a 2D transistor material, such as graphene, that is not electrically connected to the channel (26).

In one embodiment, an ion-selective permeable membrane (40) can be positioned over an ion sensitive layer (40) that is over the channel (26).

In an alternative embodiment, the second structure is composed of an ion getter material, wherein the ion getter material traps ions that are not relevant to the chemical reaction to be determined. The action of trapping ions that are not relevant to the chemical reaction to be determined enhances the ability of the processor to determine the difference between the reference I-$V_g$ and chemical reaction I-$V_g$ curves (or a parameter, e.g., slope, associated with such curves) because there are fewer interfering ions and thus enhances the ability of the processor to detect the desired chemical reaction. Preferably, the ion getter material is arranged proximate to the channels so that the action of "getting" the unwanted ions improves the detection capability of the chemically-sensitive FET of the invention.

Alternatively, the ion getter material can be placed over a dielectric layer in proximity to one or more of the channels.

In another embodiment, the second structure is comprised of a material to manage the interaction of the 2D transistor channel with an underlying oxide (or other suitable) layer. In such an embodiment, the material is composed of HMDS.

In another embodiment, the second structure is comprised of a 2D transistor channel with an ion-sensitive material over the channel, wherein the material is sensitive to ionic species that are different from the ions associated with the chemical reaction to be detected, and wherein the action of sensing ions that are different from the ions associated with the chemical reaction to be detected assists in filtering unwanted noise from signals sent from the biosensor.

Example 5

Analysis of I-$V_g$ Curves

As described above, the chemically-sensitive FETs of the invention will find various applications, including as biosensors. In such biosensing applications, a chemically-sensitive FET-based biosensor senses a desired reaction that can be detected, for example, by using a processor to detect an alteration, e.g., a shift, in an I-V curve, for example, an I-$V_g$ curve, or a parameter of an I-$V_g$ curve, e.g., the curve's slope, corresponding to the chemically-sensitive FET. In such applications, a processor functionally associated with the chemically-sensitive FET preferably compares a reference I-V curve for the well (or other capture region or structure) and an I-V curve generated in connection with a chemical reaction in well (or other capture region or structure associated with the chemically-sensitive FET). If the processor detects a difference between the reference and reaction-associated curves that exceeds a predetermined threshold, a positive result can be indicated. Examples of such curves are presented in FIGS. 6B-6I, while FIG. 6A illustrates various components and parameters of an I-$V_g$ curve.

In a preferred embodiment of this approach, the difference between a reference I-$V_g$ curve and the chemical reaction I-$V_g$ curve can be a shift in a minimum point of the $V_g$ value of the chemical reaction I-$V_g$ curve relative to a minimum point of the $V_g$ value of the reference I-$V_g$ curve. See FIGS. 6B, 6C.

In an alternative embodiment, the difference between the reference I-$V_g$ curve and the chemical reaction I-$V_g$ curve is a shift in an $I_{on}$ value of the chemical reaction I-$V_g$ curve relative to an $I_{on}$ value of the reference I-$V_g$ curve. See FIGS. 6E, 6F.

In an alternative embodiment, the difference between the reference I-$V_g$ curve and the chemical reaction I-$V_g$ curve is a shift in an $I_{off}$ value of the chemical reaction I-$V_g$ curve relative to an $I_{off}$ value of the reference I-$V_g$ curve. See FIG. 6G.

In an alternative embodiment, the difference between the reference I-$V_g$ curve and the chemical reaction I-$V_g$ curve is an overall change in shape of the chemical reaction I-$V_g$ curve relative to an overall change in shape of the reference I-$V_g$ curve. See FIG. 6D.

In an alternative embodiment, the difference between the reference I-$V_g$ curve and the chemical reaction I-$V_g$ curve is a change in the slope of the chemical reaction I-$V_g$ curve relative to a change in the slope of the reference I-$V_g$ curve. See FIG. 6I.

The $I_{on}$ values may be taken from the p-type section or the n-type section of an I-$V_g$ curve. In a preferred embodiment, the slopes of the reference and test curves are measured on the steepest sections on the n-type portions of the I-$V_g$ curves, whereas in another preferred embodiment, the slopes of the curves can measured on the steepest sections on the p-type portions of the I-$V_g$ curves. In yet another embodiment, the slopes are measured on the steepest sections on both the p-type and n-type portions of the reference and test I-$V_g$ curves. See FIG. 6I.

In some embodiments, the difference between a reference I-$V_g$ curve and a chemical reaction I-$V_g$ curve is an overall change in shape of the chemical reaction (or test) I-$V_g$ curve relative to an overall change in shape of the reference I-$V_g$ curve. The difference in overall shape of the I-$V_g$ curves can be determined, for example, by first fitting a polynomial or other fitting line to each of the I-$V_g$ curves and then comparing the coefficients of those fitting lines.

In some embodiments, the gate voltage, $V_g$, of the I-$V_g$ curve is a gate voltage applied to the chemically-sensitive field effect transistor of the invention.

In other embodiments, the gate voltage $V_g$ of the I-$V_g$ curve is a back gate voltage applied to a chemically-sensitive FET through the back of the device.

In some another embodiments, the gate voltage of the I-$V_g$ curve is a top gate voltage applied to the chemically-sensitive FET through the top of the device.

In yet other embodiments, the gate voltage of the I-$V_g$ curve is a solution gate voltage applied to the chemically-sensitive FET through a solution over the device.

Example 6

Preparing FETs

Alternative methods for growing and transferring 2D materials are described, for example, in Hoffman et al., U.S. Provisional Patent Application No. 62/175,351, filed on Jun. 14, 2015, for System And Method For Growing And Transferring Graphene For Use As A FET, which is hereby incorporated by reference in its entirety.

FIGS. 26A-26M illustrate a preferred CMOS integration method for building interconnects, dielectric, and well structures, as well as the pads for bonding the transferred 2D material to the chip.

FIG. 26A illustrates a graphene on a ROIC wafer step of a CMOS integration method. FIG. 26B illustrates a patterning a graphene layer to form channels step of a CMOS integration method. FIG. 26C illustrates a depositing an etch stop layer over a graphene layer to step of a CMOS integration method. FIG. 26D illustrates a deposit, pattern and etch a thick insulator layer step of a CMOS integration method. FIG. 26E illustrates a wet etch ESL, pattern and DRIE oxide over interconnects step of a CMOS integration method. FIG. 26F illustrates an optional addition of work function matching material prior to a via fill step of a CMOS integration method. FIG. 26G illustrates a deposit a barrier, liner, copper plate, CMP step of a CMOS integration method. FIG. 26H illustrates a deposit a barrier, liner, copper plate, CMP step of a CMOS integration method. FIG. 26I illustrates a deposit a barrier/adhesion layer, deposit aluminum, pattern, etch aluminum interconnect and pad layer step of a CMOS integration method. FIG. 26J illustrates a deposit $SiO_2$ (e.g. CVD), CMP, pad open etch step of a CMOS integration method. FIG. 26K illustrates a DRIE well insulator down to an etch stop layer step of a CMOS integration method. FIG. 26L illustrates a wet etch a thin etch stop layer step of a CMOS integration method. FIG. 26M illustrates a wet etch ESL open etch step of a CMOS integration method.

The substrate may be composed of at least one of Si, Si/$SiO_2$, $SiO_2$, sapphire/$Al_2O_3$, and a metal plate. An adhesion layer, as needed, is composed of at least one of Ti, Cr, Ta, W, WN, and TaN. The adhesion layer has a thickness of 5 to 15 nm and preferably approximately 10 nm. A metal catalyst layer composed of at least one of Ni, Cu, Pt, Pd, Co, Ru, and Fe, is also present. The metal layer is formed by at least one of PVD (sputtering, ebeam evaporation, thermal evaporation), CVD, electrochemical plating, and ALD. The metal catalyst layer attempts to achieve mostly single crystalline layer with (111) crystal. Annealing of the metal catalyst layer (to recrystallize and grow grains) at preferably between 750 to 1000 C in a forming gas composed of approximately 5% $H_2$/95% $N_2$ or 5% $H_2$/95% Ar for 30 minutes to 60 minutes to achieve mostly single crystalline layer with (111) crystal. Optional surface polishing, e.g., mechanical polishing, electropolishing, or CMP, after metal deposition is performed. Also, an optional plasma treatment (best done just before growth) with plasma with $H_2$ and $N_2$ or ammonia at approximately 0.1 Torr, 300-400 C can be performed.

A useful detailed description is set forth in van Rooyen et al., U.S. Patent Publication Number 20140371110 for Bioinformatics Systems, Apparatuses, and Methods Executed On An Integrated Circuit Processing Platform, which is "hereby incorporated by reference in its entirety.

A useful detailed description is set forth in van Rooyen et al., U.S. Patent Publication Number 20140309944 for Bioinformatics Systems, Apparatuses, and Methods Executed On An Integrated Circuit Processing Platform, which is hereby incorporated by reference in its entirety.

A useful detailed description is set forth in van Rooyen et al., U.S. Patent Publication Number 20140236490 for Bioinformatics Systems, Apparatuses, and Methods Executed On An Integrated Circuit Processing Platform, which is hereby incorporated by reference in its entirety.

A useful detailed description is set forth in van Rooyen et al., U.S. Patent Publication Number 20140200166 for Bioinformatics Systems, Apparatuses, and Methods Executed On An Integrated Circuit Processing Platform, which is hereby incorporated by reference in its entirety.

A useful detailed description is set forth in McMillen et al., U.S. Provisional Patent Application No. 62/127,232, filed on Mar. 2, 2015, for Bioinformatics Systems, Apparatuses, And Methods Executed On An Integrated Circuit Processing Platform, which is hereby incorporated by reference in its entirety.

A useful detailed description is set forth in van Rooyen et al., U.S. Provisional Patent Application No. 62/119,059, filed on Feb. 20, 2015, for Bioinformatics Systems, Apparatuses, And Methods Executed On An Integrated Circuit Processing Platform, which is hereby incorporated by reference in its entirety.

A useful detailed description is set forth in van Rooyen et al., U.S. Provisional Patent Application No. 61/988,128, filed on May 2, 2014, for Bioinformatics Systems, Apparatuses, And Methods Executed On An Integrated Circuit Processing Platform, which is hereby incorporated by reference in its entirety.

A useful detailed description of a GFET is set forth in van Rooyen, U.S. Provisional Patent Application No. 62/094, 016, filed on Dec. 18, 2014, for Graphene FET Devices, Systems, And Methods Of Using The Same For Sequencing Nucleic Acids, which is hereby incorporated by reference in its entirety.

A useful detailed description of a GFET is set forth in Hoffman et al., U.S. Provisional Patent Application No.

62/130,594, filed on Mar. 9, 2015, for Chemically Sensitive Field Effect Transistor, which is hereby incorporated by reference in its entirety.

A useful detailed description of a GFET is set forth in Hoffman et al., U.S. Provisional Patent Application No. 62/130,598, filed on Mar. 9, 2015, for Method And System For Analysis Of Biological And Chemical Materials, which is hereby incorporated by reference in its entirety.

A useful method for growing and transferring graphene is disclosed in Hoffman et al., U.S. Provisional Patent Application No. 62/175,351, filed on Jun. 14, 2015, for a System And Method For Growing And Transferring Graphene For Use As A FET, which is hereby incorporated by reference in its entirety.

A use for 2D materials is disclosed in Hoffman et al., U.S. Provisional Patent Application No. 62/175,384, filed on Jun. 14, 2015, for a CMOS Integration Of A Two Dimensional Material, which is hereby incorporated by reference in its entirety.

The following U.S. Patent Applications discuss the processing component of the a system for analysis of biological and chemical materials: U.S. patent application Ser. No. 14/279,063, titled, Bioinformatics Systems, Apparatuses, and Methods Executed on an Integrated Circuit Processing Platform, filed May 15, 2014; U.S. patent application Ser. No. 14/180,248, titled Bioinformatics Systems, Apparatuses, and Methods Executed on an Integrated Circuit Processing Platform, filed Feb. 13, 2014; U.S. patent application Ser. No. 14/179,513, titled Bioinformatics Systems, Apparatuses, and Methods Executed on an Integrated Circuit Processing Platform, filed Feb. 12, 2014; U.S. patent application Ser. No. 14/158,758, titled Bioinformatics Systems, Apparatuses, and Methods Executed on an Integrated Circuit Processing Platform, filed Jan. 17, 2014; U.S. patent application Ser. No. 14/279,063; U.S. Provisional Application No. 61/826,381, titled System and Method for Computation Genomic Pipeline, filed May 22, 2013; U.S. Provisional Application No. 61/943,870, titled Dynamic Genome Reference Generation For Improved NGS Accuracy And Reproducibility, filed Feb. 24, 2014; all of which are hereby incorporated by reference in their entireties herein.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

All of the devices and methods described and claimed herein can be made and executed without undue experimentation in light of the present description. While the devices and methods of this invention have been described in terms of preferred embodiments, it will be apparent to those of skill in the art that variations may be applied to the compositions and methods. All such similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

I claim:

1. A chemically-sensitive field effect transistor having a multi-layered structure, comprising:
    a substrate layer having an extended body;
    a first insulating layer positioned above the extended body of the substrate layer;
    a second insulating layer positioned above the first insulating layer;
    a source electrode and a drain electrode each having a top surface and a bottom surface, the top surface separated from the bottom surface by opposing outer and inner side portions, each of the opposed side portions and each of the bottom surfaces of the source and drain electrodes being disposed within the first insulating layer, the source electrode being separated from the drain electrode by a distance;
    a graphene layer positioned between the first and second insulating layers and extending between the outer side portion of the source electrode and the outer side portion of the drain electrode thereby forming a channel between the source and drain electrodes, the graphene layer contacting the top surface of the source and drain electrodes; and
    a well structure provided in the second insulating layer, the well structure having a bottom surface positioned above and in contact with the graphene layer, a top surface opposed to the bottom surface, and a chamber, the chamber extending from the top surface to the bottom surface of the well structure and exposing the graphene layer within the chamber, the graphene layer forming a bottom surface of the chamber.

2. The chemically-sensitive field effect transistor according to claim 1, wherein the multi-layered structure is configured so as to shift an I-V curve or an I-Vg curve in response to a chemical reaction occurring within the well of the chemically-sensitive field effect transistor.

3. The chemically-sensitive field effect transistor according to claim 1, wherein the conductive source and the conductive drain are each composed of a copper material, an aluminum material, a platinum material, or a gold material.

4. The chemically-sensitive field effect transistor according to claim 1, wherein a length of the channel from the source to the drain ranges from 0.05 micron to 3 microns, and a width of the channel ranges from 0.05 micron to 2 microns.

5. The chemically-sensitive field effect transistor according to claim 4, wherein the channel has a thickness of 50 nanometers or less.

6. The chemically-sensitive field effect transistor according to claim 2, wherein the first insulating layer comprises an analyte-sensitive dielectric layer.

7. The chemically-sensitive field effect transistor according to claim 6, wherein the analyte-sensitive dielectric layer comprises an oxide layer.

8. The chemically-sensitive field effect transistor according to claim 6, wherein the analyte-sensitive dielectric layer is comprised of one of an aluminum oxide, a silicon dioxide, a hafnium dioxide, a hafnium silicate, a zirconium silicate, a zirconium dioxide, a lanthanum oxide, a tantalum oxide, a titanium oxide, an iron oxide, or a yttrium oxide an ion sensitive material with a high intrinsic buffer capacity.

9. The chemically-sensitive field effect transistor according to claim 6, wherein the second insulating layer is composed of a polyimide, BCB, silicon oxide, a silicon nitride, a silicon oxynitride or a silicon carbide.

10. The chemically-sensitive field effect transistor according to claim 6, wherein the chemical reaction involves a biological material, and the chemically-sensitive field effect transistor is configured for detecting the biological material.

11. The chemically-sensitive field effect transistor according to claim 10, wherein the biological material is a nucleotide, nucleic acid, protein, or other biological molecule.

12. A chemically-sensitive field effect transistor having a multi-layered structure, comprising:
    a substrate layer having an extended body;
    a first insulating layer positioned above the extended body of the substrate layer;
    a source electrode and a drain electrode positioned in the first insulating layer, the source electrode separated from the drain electrode by a channel;
    a second insulating layer positioned above the first insulating layer and proximate the source and drain electrodes;
    a one-dimensional transistor material or a two-dimensional transistor material layer positioned between the first and second insulating layers and extending between the source and drain electrodes thereby forming a channel; and
    a well structure provided in the second insulating layer, the well structure having a bottom surface positioned above and in contact with the one-dimensional transistor material or two-dimensional transistor material layer, a top surface opposed to the bottom surface, and a chamber extending from the top surface to the bottom surface to expose the one-dimensional transistor material or two-dimensional transistor material layer within the chamber.

13. The chemically-sensitive field effect transistor according to claim 12, wherein the one-dimensional transistor material or two-dimensional transistor material is selected from the group consisting of a single layer planar graphene, black phosphorous, silicene, borophene, tungsten disulfide, germanane, nickel HITP, stanene and Mxenes.

14. The chemically-sensitive field effect transistor according to claim 13, wherein the multi-layered structure is configured so as to shift an I-V curve or an I-Vg curve in response to a chemical reaction occurring within the chamber of the chemically-sensitive field effect transistor.

15. A chemically-sensitive field effect transistor having a multi-layered structure, comprising:
    a substrate layer having an extended body;
    a first insulating layer positioned above the extended body of the substrate layer;
    a source electrode and a drain electrode positioned in the first insulating layer, the source electrode and the drain electrode being separated by a channel;
    a second insulating layer positioned above the first insulating layer and proximate the source and drain electrodes;
    a one-dimensional transistor material or a two-dimensional transistor material layer positioned between the first and second insulating layers and extending over the channel between the source and drain electrodes; and
    a well structure provided in the second insulating layer, the well structure having an opening therein, the opening defined by opposed side portions and a bottom formed by the one-dimensional transistor material or a two-dimensional transistor material layer.

16. The chemically-sensitive field effect transistor according to claim 15, wherein the one-dimensional transistor material or two-dimensional transistor material selected from the group consisting of a single layer planar graphene, black phosphorous, silicene, borophene, tungsten disulfide, germanane, nickel HITP, stanene and Mxenes.

17. The chemically-sensitive field effect transistor according to claim 15, wherein the multi-layered structure is configured so as to shift an I-V curve or an I-Vg curve in response to a chemical reaction occurring within the well of the chemically-sensitive field effect transistor.

18. The chemically-sensitive field effect transistor according to claim 17, wherein a length of the channel from the source to the drain ranges from 0.05 micron to 3 microns, and a width of the channel ranges from 0.05 micron to 2 microns.

19. The chemically-sensitive field effect transistor according to claim 15, wherein the first insulating layer comprises an analyte-sensitive dielectric layer.

20. The chemically-sensitive field effect transistor according to claim 15, wherein the chemical reaction involves a biological material selected from the group consisting of a nucleotide, nucleic acid, and a protein, and the chemically-sensitive field effect transistor is configured for detecting the biological material.

* * * * *

UNITED STATES PATENT AND TRADEMARK OFFICE
CERTIFICATE OF CORRECTION

PATENT NO.        : 9,857,328 B2                                    Page 1 of 1
APPLICATION NO.   : 15/239800
DATED             : January 2, 2018
INVENTOR(S)       : Paul Hoffman It is certified that error appears in the above-identified patent and that said Letters Patent is hereby corrected as shown below:

On the Title Page

Item "(72) Inventors: Paul Hoffman, La Jolla, CA (US);" ---should read "(72) Inventors; Paul Hoffman, La Jolla, CA (US); Brett R. Goldsmith, San Diego, CA (US);"

Signed and Sealed this
Second Day of June, 2020

Andrei Iancu
*Director of the United States Patent and Trademark Office*